(12) United States Patent
Hannapel et al.

(10) Patent No.: US 7,579,150 B1
(45) Date of Patent: Aug. 25, 2009

(54) MOBILE RNA ACTS AS A SIGNAL TO REGULATE PLANT GROWTH AND DEVELOPMENT

(75) Inventors: David J. Hannapel, Ames, IA (US); Anjan K. Banerjee, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 359 days.

(21) Appl. No.: 11/172,023

(22) Filed: Jun. 30, 2005

Related U.S. Application Data

(60) Provisional application No. 60/584,562, filed on Jul. 1, 2004.

(51) Int. Cl.
  C12Q 1/68 (2006.01)
  C12N 15/00 (2006.01)
  C12N 5/14 (2006.01)

(52) U.S. Cl. .......................................... 435/6; 435/69.1
(58) Field of Classification Search ........................ None
  See application file for complete search history.

(56) References Cited

U.S. PATENT DOCUMENTS 7,265,263 B1 * 9/2007 Hannapel et al. ............ 800/278

OTHER PUBLICATIONS

Niklas et al. The Bio-Logic and Machinery of Plamt Morphogenesis. Am. J. of Botany 90(4): 515-525, 2003.*
Ainger et al., "Transport and Localization Elements in Myelin Basic Protein mRNA," *J. Cell Biol.* 138(5):1077-1087 (1997).
Amador et al., "Gibberellins Signal Nuclear Import of PHOR1, a Photoperiod-Responsive Protein with Homology to *Drosophila* armadillo," *Cell* 106:343-354 (2001).
Aoki et al., "A Subclass of Plant Heat Shock Cognate 70 Chaperones Carries a Motif that Facilitates Trafficking Through Plasmodesmata," *Proc. Nat'l Acad. Sci. USA* 99:16342-16347 (2002).
Bellaoui et al., "The Arabidopsis BELL1 and Knox Tale Homeodomain Proteins Interact Through a Domain Conserved Between Plants and Animals," *Plant Cell* 13:2455-2470 (2001).
Carrera et al., "Changes in GA 20-Oxidase Gene Expression Strongly Affect Stem Length, Tuber Induction and Tuber Yield of Potato Plants," *Plant J.* 22(3):247-256 (2000).
Carrera et al., "Feedback Control and Diurnal Regulation of Gibberellin 20-Oxidase Transcript Levels in Potato," *Plant Physiol.* 119:765-773 (1999).
Chan et al., "*fatvg* Encodes a New Localized RNA that Uses a 25-Nucleotide Element (FVLE1) to Localize to the Vegetal Cortex of *Xenopus* Oocytes," *Development* 126: 4943-4953 (1999).
Chartrand et al., "Structural Elements Required For the Localization of *ASH1* mRNA and of a Green Fluorescent Protein Reporter Particle In vivo," *Curr. Biol.* 9(6):333-336 (1999).
Chen et al., "Interacting Transcription Factors from the TALE Superclass Regulate Processes of Growth in Potato," Poster presentation at ASPB meeting in Denver (2002).
Chen et al., "Interacting Transcription Factors From the Three-Amino Acid Loop Extension Superclass Regulate Tuber Formation," *Plant Physiol.* 132:1391-1404 (2003).
Chen et al., "Interacting Transcription Factors Regulate Tuber Development," Presentation at Potato Genetic Committee meeting in St. Paul, Minnesota, NCR-84 (2001).
Crété et al., "Graft Transmission of Induced and Spontaneous Post-Transcriptional Silencing of Chitinase Genes," *Plant J.* 28:493-501 (2001).
Dong et al., "*MDH1*: An Apple Homeobox Gene Belonging to the *BEL1* Family," *Plant Mol. Biol.* 42:623-633 (2000).
Fernie et al., "Molecular and Biochemical Triggers of Potato Tuber Development," *Plant Physiol.* 127:1459-1465 (2001).
Foster et al., "A Surveillance System Regulates Selective Entry of RNA into the Shoot Apex," *Plant Cell* 14:1497-1508 (2002).
Fujiwara et al., "Cell-to-Cell Trafficking of Macromolecules Through Plasmodesmata Potentiated by the Red Clover Necrotic Mosaic Virus Movement Protein," *Plant Cell* 5:1783-1794 (1993).
GenBank Accession No. AAK43836 (Apr. 30, 2001).
GenBank Accession No. AF375964 (Jun. 2, 2003).
GenBank Accession No. AF375965 (Jun. 2, 2003).
GenBank Accession No. AF375966 (Jun. 2, 2003).
GenBank Accession No. AF406697 (Jul. 14, 2003).
GenBank Accession No. AF406698 (Jul. 14, 2003).
GenBank Accession No. AF406699 (Jul. 14, 2003).
GenBank Accession No. AF406700 (Jul. 14, 2003).
GenBank Accession No. AF406701 (Jul. 14, 2003).
GenBank Accession No. AF406702 (Jul. 14, 2003).
GenBank Accession No. AF406703 (Jul. 14, 2003).
GenBank Accession No. T05281 (Jun. 30, 1993).
GenBank Accession No. U65648 (Feb. 4, 1997).
Gilbertson & Lucas, "How Do Viruses Traffic on the Vascular Highway?," *Trends Plant Science* 1(8):260-268 (1996).
Guivarc'h et al., "Local Expression of the *ipt* Gene in Transgenic Tobacco (*Nicotiana tabacum* L. cv. SR1) Axillary Buds Establishes a Role for Cytokinins in Tuberization and Sink Formation," *J Exp Bot* 53:621-629 (2002).
Hannapel, "Characterization of the Early Events of Potato Tuber Development," *Physiologia Plantarum* 83:568-573 (1991).
Hart, "Isolation and Characterization of Genes Belonging to Developmental Regulatory Gene Classes in Potato (*Solanum tuberosum* L.)," Ph.D. Dissertation, Iowa State University (1998).
Havin et al., "RNA-Binding Protein Conserved in Both Microtubule- and Microfilament-Based RNA Localization," *Genes Devel.* 12:1593-1598 (1998).

(Continued)

*Primary Examiner*—Nancy Vogel
*Assistant Examiner*—Michele K. Joike
(74) *Attorney, Agent, or Firm*—Nixon Peabody LLP

(57) ABSTRACT

The present invention relates to isolated nucleic acid molecules which encode a BEL transcription factor from potato (*Solanum tuberosum* L.) and the amino acid sequences encoded by such nucleic acid molecules. The present invention also relates to a method of screening a biomolecule for its ability to assist in mediating long-distance movement of a mobile RNA in a plant.

26 Claims, 39 Drawing Sheets

OTHER PUBLICATIONS

Haywood et al., "Plasmodesmata: Pathways for Protein and Ribonucleoprotein Signaling," *Plant Cell* S303-S325 (Suppl. 2002).

Heinlein, "The Spread of *Tobacco Mosaic Virus* Infection: Insights into the Cellular Mechanism of RNA Transport," *Cell Mol. Life Sci.* 59:58-82 (2002).

Hendriks et al., "Patatin and Four Serine Proteinase Inhibitor Genes are Differentially Expressed During Potato Tuber Development," *Plant Mol. Biol.* 17:385-394 (1991).

Hoffmann-Benning et al., "Comparison of Peptides in the Phloem Sap of Flowering and Non-Flowering *Perilla* and Lupine Plants Using Microbore HPLC Followed by Matrix-Assisted Laser Desorption/Ionization Time-of-Flight Mass Spectrometry," *Planta* 216:140-147 (2002).

Jackson et al., "Expression of Maize *Knotted1* Related Homeobox Genes in the Shoot Apical Meristem Predicts Patterns of Morphogenesis in the Vegetative Shoot," *Development* 120:405-413 (1994).

Jackson, "Multiple Signaling Pathways Control Tuber Induction in Potato," *Plant Physiol.* 119:1-8 (1999).

Jansen, "mRNA Localization: Message on the Move," *Nature Rev.* 2:247-256 (2001).

Kim et al., "Developmental Changes Due to Long-Distance Movement of a Homeobox Fusion Transcript in Tomato," *Science* 293:287-289 (2001).

Kislauskis et al., "Sequences Responsible for Intracellular Localization of β-Actin Messenger RNA Also Affect Cell Phenotype," *J. Cell Biol.* 127:441-451 (1994).

Kloc et al., "Mechanisms of Subcellular mRNA Localization," *Cell* 108:533-544 (2002).

Krusell et al., "DNA Binding Sites Recognized In vitro by a Knotted Class 1 Homeodomain Protein Encoded by the *hooded* Gene, *k*, in Barley (*Hordeum vulgare*)," *FEBS Lett.* 408:25-29 (1997).

Kühn et al., "Macromolecular Trafficking Indicated by Localization and Turnover of Sucrose Transporters in Enucleate Sieve Elements," *Science* 275:1298-1300 (1997).

Lee et al., "Selective Trafficking of Non-Cell-Autonomous Proteins Mediated by NtNCAPP1," *Science* 299:392-396 (2003).

Lincoln et al., "A *knotted1*-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994).

Lucas et al., "RNA as a Long-Distance Information Macromolecule in Plants," *Nature Rev.* 2:849-857 (2001).

Lucas et al., "Selective Trafficking of Knotted1 Homeodomain Protein and Its mRNA Through Plasmodesmata," *Science* 270:1980-1983 (1995).

Meins, "RNA Degradation and Models for Post-Transcriptional Gene-Silencing," *Plant Mol. Biol.* 43:261-273 (2000).

Müller et al., "In vitro Interactions Between Barley TALE Homeodomain Proteins Suggest a Role for Protein-Protein Associations in the Regulation of *Knox* Gene Function," *Plant J.* 27:13-23 (2001).

Nagasaki et al., "Functional Analysis of the Conserved Domains of a Rice Knox Homeodomain Protein, OSH15," *Plant Cell* 13:2085-2098 (2001).

Nakajima et al., "Intercellular Movement of the Putative Transcription Factor SHR in Root Patterning," *Nature* 413:307-311 (2001).

Okita et al., "mRNA Localization in Plants: Targeting to the Cell's Cortical Region and Beyond," *Curr. Opin. Plant Biol.* 5:553-559 (2002).

Parnis et al., "The Dominant Developmental Mutants of Tomato, *Mouse-ear* and *Curl*, Are Associated with Distinct Modes of Abnormal Transcriptional Regulation of a*Knotted* Gene," *Plant Cell* 9:2143-2158 (1997).

Ramos et al., "RNA Recognition by a Staufen Double-Stranded RNA-Binding Domain," *EMBO J.* 19:997-1009 (2000).

Reiser et al., "Knots in the Family Tree: Evolutionary Relationships and Functions of *knox* Homeobox Genes," *Plant Mol. Biol.* 42:151-166 (2000).

Reiser et al., "The *Bell1* Gene Encodes a Homeodomain Protein Involved in Pattern Formation in the *Arabidopsis* Ovule Primordium," *Cell* 83:735-742 (1995).

Rosin et al., "A Potato *knox* Gene Involved in Plant Development," Oral Presentation at the 2001 Annual Meeting of the American Society of Plant Biologists in Providence, Rhode Island (2001).

Rosin et al., "Overexpression of a *Knotted*-Like Homeobox Gene of Potato Alters Vegetative Development by Decreasing Gibberellin Accumulation," *Plant Physiol.* 132:106-117 (2003).

Rosin, "Transcription Factors Involved in the Development of Potato (*Solanum tuberosum* L.)," Ph.D. Dissertation, Iowa State University (2002).

Ruiz-Medrano et al., "Phloem Long-Distance Transport of *CmNACP* mRNA: Implications for Supracellular Regulation in Plants," *Development* 126:4405-4419 (1999).

Sessions et al., "Cell-Cell Signaling and Movement by the Floral Transcription Factors Leafy and Apetala1," *Science* 289:779-781 (2000).

Smith et al., "Selective Interaction of Plant Homeodomain Proteins Mediates High DNA-Binding Affinity," *Proc. Nat'l Acad. Sci. USA* 99:9579-9584 (2002).

Sonoda et al., "Graft Transmission of Post-Transcriptional Gene Silencing: Target Specificity for RNA Degradation is Transmissible Between Silenced and Non-Silenced Plants, But Not Between Silenced Plants," *Plant J.* 21:1-8 (2000).

Wu et al., "Modes of Intercellular Transcription Factor Movement in the *Arabidopsis* Apex," *Development* 130:3735-3745 (2003).

Xoconostle-Cázares et al., "Plant Paralog to Viral Movement Protein that Potentiates Transport of mRNA into the Phloem," *Science* 283:94-98 (1999).

* cited by examiner

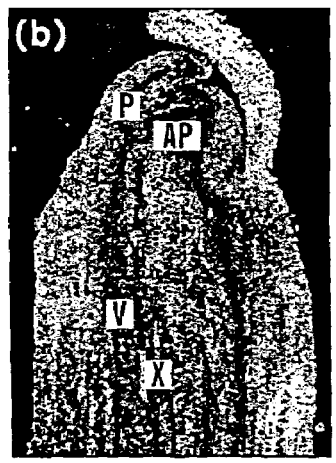
FIG. 3A  FIG. 3B  FIG. 3C
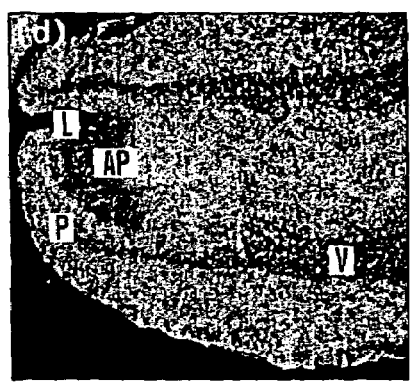
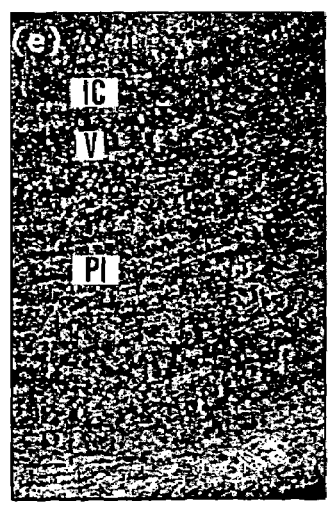
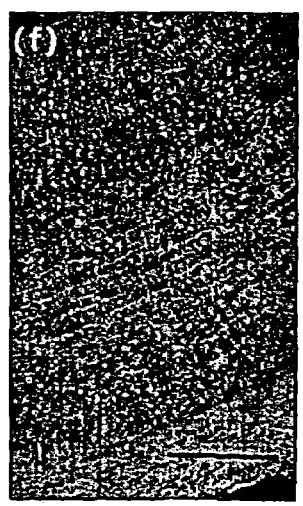
FIG. 3D  FIG. 3E  FIG. 3F

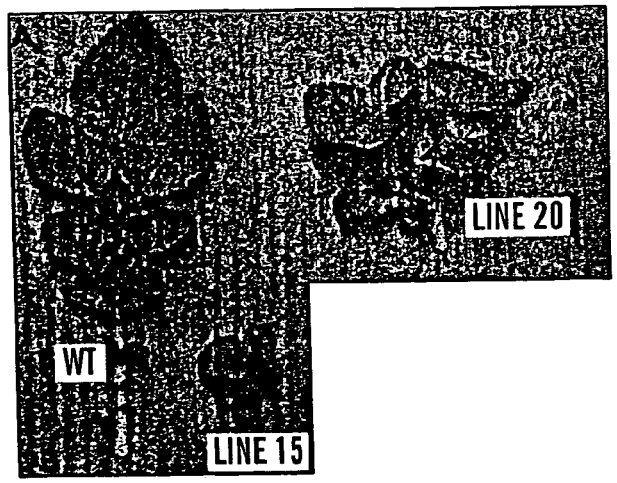
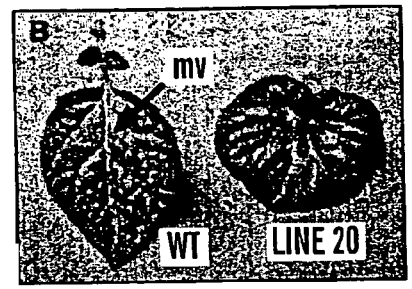
*FIG. 5B*
*FIG. 5A*
 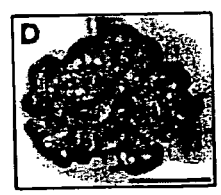 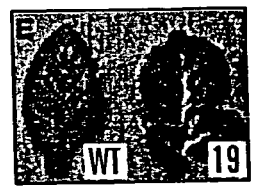
*FIG. 5C*  *FIG. 5D*  *FIG. 5E*
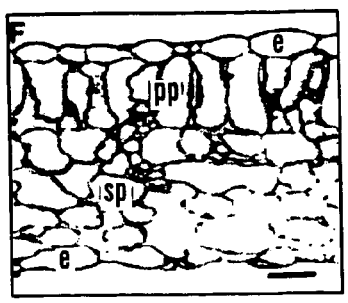 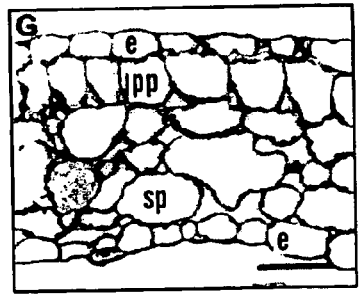 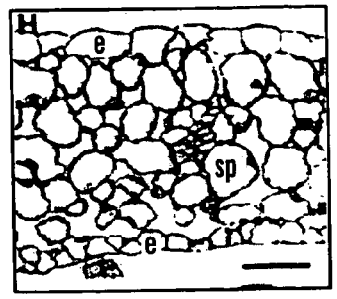
*FIG. 5F*  *FIG. 5G*  *FIG. 5H*

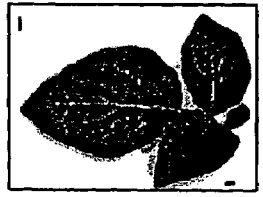
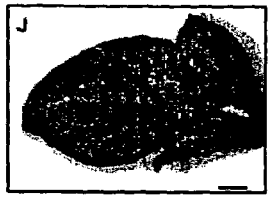
*FIG. 5I*  *FIG. 5J*  *FIG. 5K*
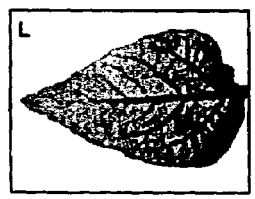
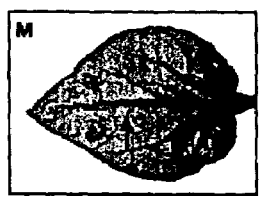
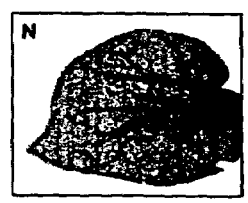
*FIG. 5L*  *FIG. 5M*  *FIG. 5N*
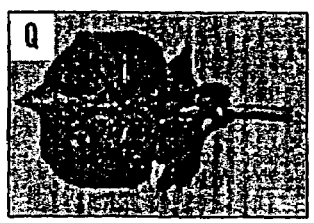
*FIG. 5O*  *FIG. 5P*  *FIG. 5Q*

| | | GROWTH ON SELECTIVE MEDIA | RELATIVE % β-gal ACTIVITY |
|---|---|---|---|
| POTH1 (345 aa) | | YES | 100 |
| pBHD1 (115-345) | | YES | 35 |
| pBHD2 (165-345) | | YES | 45 |
| pBHD3 (209-345) | | NO | 0 |
| pBHD4 (1-261) | | YES | 72 |
| pBHD5 (1-223) | | YES | 92 |
| pBHD6 (1-171) | | YES | 25 |
| pBHD9 (1-113) | | YES | 38 |

*FIG. 10A*

| | | GROWTH ON SELECTIVE MEDIA | RELATIVE % β-gal ACTIVITY |
|---|---|---|---|
| pAD5 (653 aa) | | YES | 100 |
| pAD5-1 (230-653) | | YES | 45 |
| pAD5-2 (257-653) | | NO | 0 |
| pAD5-3 (313-653) | | NO | 0 |
| pAD5-4 (348-653) | | NO | 0 |
| pAD5-5 (384-653) | | NO | 0 |
| pAD5-7 (1-487) | | YES | 97 |
| pAD5-8 (1-358) | | YES | 57 |
| pAD5-9 (1-315) | | YES | 9.1 |
| pAD5-11 (1-286) | | YES* | 0 |

*INTERACTION WITH THIS CONSTRUCT PRODUCED A FEW, SLOW GROWING COLONIES BUT NO DETECTABLE β-gal ACTIVITY.

*FIG. 10B*

FIG. 17A — STBEL5 SENSE LINES IN SOIL

FIG. 17B — STBEL5 SENSE LINES IN VITRO

FIG. 17C — POTH1 SENSE LINES IN VITRO

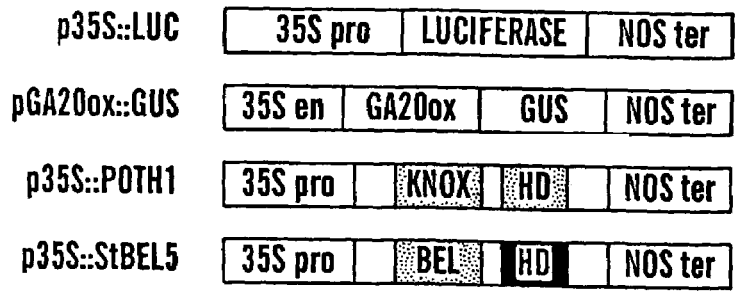
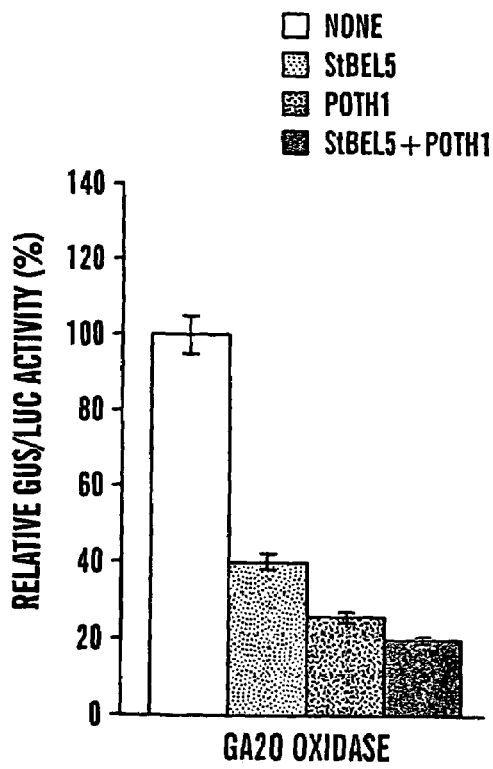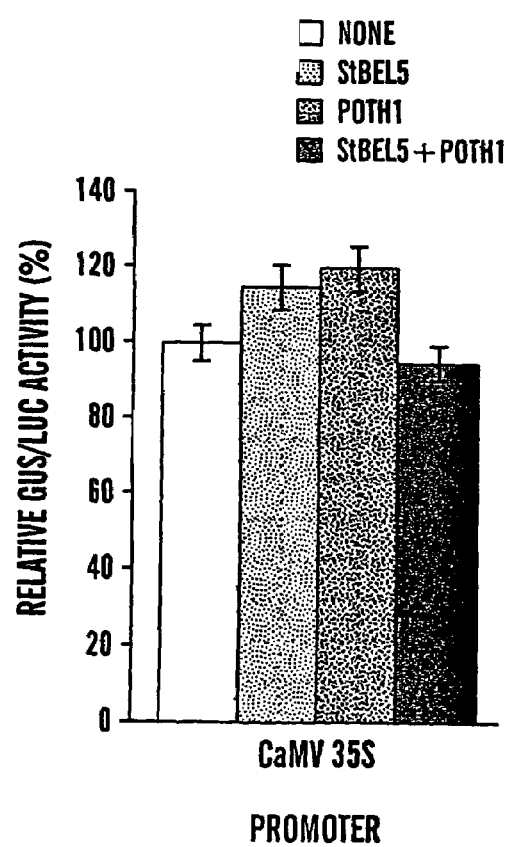
FIG. 24A
FIG. 24B
FIG. 24C

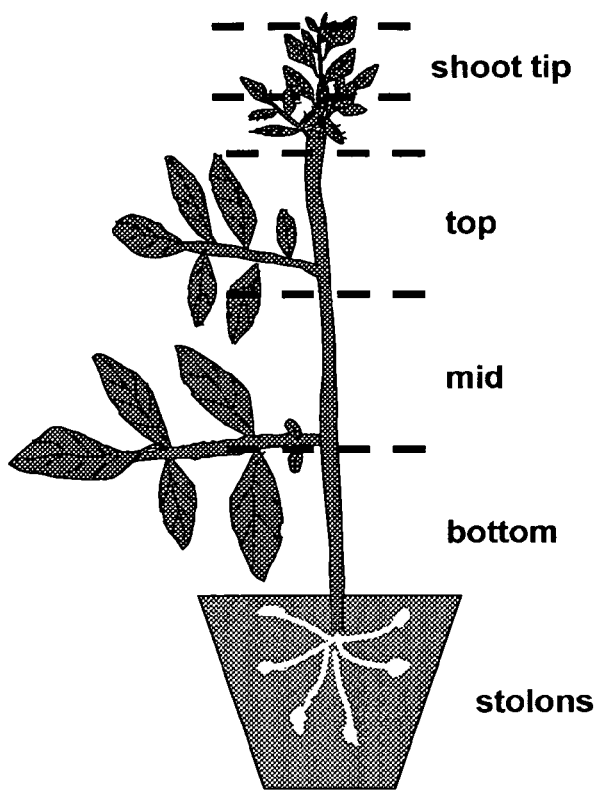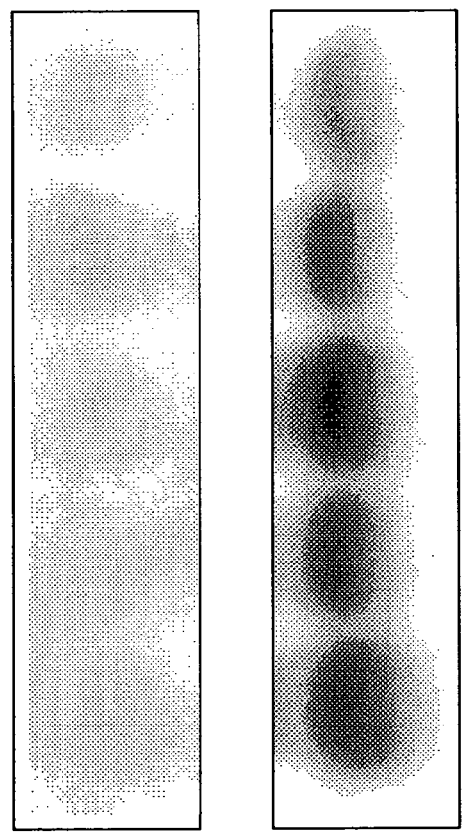
FIG. 36

```
                        SEQUENCE LISTING

<160> NUMBER OF SEQ ID NOS: 34

<210> SEQ ID NO 1
<211> LENGTH: 2735
<212> TYPE: DNA
<213> ORGANISM: Solanum tuberosum

<400> SEQUENCE: 1
catgcagaga taaaaatata gatcagtctg acaagaaggc aacttctcaa agcttagaga      60
gctaccaccc gaagatagac agttagttac atgtactgtt atagataaaa ggagaaatcc     120
gaagaagaaa gaattttttt tgcagatatg tactatcaag gaacctcgga taatactaat     180
atacaagctg atcatcaaca acgtcataat catgggaata gtaataataa taatattcag     240
acactttatt tgatgaaccc taacaattat atgcaaggct acactacttc tgacacacag     300
cagcagcagc agttactttt cctgaattct tcaccagcag caagcaacgc gctttgccat     360
gcgaatatac aacacgcgcc gctgcaacag cagcactttg tcggtgtgcc tcttccggca     420
gtaagtttgc acgatcagat caatcatcat ggactttttac agcgcatgtg gaacaaccaa     480
gatcaatctc agcaggtgat agtaccatcg tcgacggggg tttctgccac gtcatgtggc     540
gggatcacca cggacttggc gtctcaattg gcgtttcaga ggccgattcc gacaccacaa     600
caccgacagc agcaacaaca gcaaggcggt ctatctctaa gcctttctcc tcagctacaa     660
cagcaaatta gtttcaataa caatatttca tcctcatcac caaggacaaa taatgttact     720 attagggaa cattagatgg aagttctagc aacatggttt taggctctaa gtatctgaaa      780
gctgcacaag agcttcttga tgaagttgtt aatattgttg gaaaaagcat caaaggagat     840
gatcaaaaga aggataattc aatgaataaa gaatcaatgc ctttggctag tgatgtcaac     900
actaatagtt ctggtggtgg tgaaagtagc agcaggcaga aaaatgaagt tgctgttgag     960
```

-continued

```
cttacaactg ctcaaagaca agaacttcaa atgaaaaaag ccaagcttct tgccatgctt    1020
gaagaggtgg agcaaaggta cagacagtac catcaccaaa tgcaaataat tgtattatca    1080
tttgagcaag tagcaggaat tggatcagcc aaatcataca ctcaattagc tttgcatgca    1140
atttcgaagc aattcagatg cctaaaggat gcaattgctg agcaagtaaa ggcgacgagc    1200
aagagtttag gtgaagagga aggcttggga gggaaaatcg aaggctcaag actcaaattt    1260
gtggaccatc atctaaggca acaacgcgcg ctgcaacaga taggaatgat gcaaccaaat    1320
gcttggagac cccaaagagg tttacctgaa agagctgtct ctgtccttcg tgcttggctt    1380
ttcgagcatt ttcttcatcc ttacccaaag gattcagaca aaatcatgct tgctaagcaa    1440
acggggctaa caaggagcca ggtgtctaac tggttcataa atgctcgagt tcgattatgg    1500
aagccaatgg tagaagaaat gtacttggaa gaagtgaaga atcaagaaca aaacagtact    1560
aatacttcag gagataacaa aaacaaagag accaatataa gtgctccaaa tgaagagaaa    1620
catccaatta ttactagcag cttattacaa gatggtatta ctactactca agcagaaatt    1680
tctacctcaa ctatttcaac ttcccctact gcaggtgctt cacttcatca tgctcacaat    1740
ttctccttcc ttggttcatt caacatggat aatactacta ctactgttga tcatattgaa    1800
aacaacgcga aaaagcaaag aaatgacatg cacaagtttt ctccaagtag tattctttca    1860
tctgttgaca tggaagccaa agctagaaa tcatcaaata aagggtttac taatcccttta    1920 atggcagcat acgcgatggg agattttgga aggtttgatc ctcatgatca caaatgacc    1980 gcgaattttc atggaaataa tggtgtctct cttactttag acttcctcc ttctgaaaac    2040 ctagccatgc cagtgagcca acaaaattac cttctctaatg acttgggaag taggtctgaa    2100
atggggagtc attacaatag aatgggatat gaaaacattg attttcagag tgggaataag    2160
cgatttccga ctcaactatt accagatttt gttacaggta atctaggaac atgaatacca    2220
gaaagtctcg tattgatagc tgaaaagata aaggaagtt agggatactc ttatattgtg    2280
tgaggccttc tggcccaagt cggaggaccc aatttgatac aacctatcat aggagaaaag    2340
aagtggagac taaattaaag taacaaaatt ttaaagcaca ctttctagta tatatacttc    2400
ttttttttat agtatagaaa agaagagatt ttgtgcttta gtgtatagat agagtctact    2460
tagtataggt tatacttcta gttccttgag aagattgata caactagtag tattttttt    2520 cttttgggtt ggcttggagt actattttaa gttattggaa actagctata gtaaatgttg    2580
taaagttgtg atattgttcc tctcaatttg catataattt gaaatatttt gtacctacta    2640
gctagtctct aaattatgtt tccattgctt gtaattgcaa ttttatttga attttgtgct    2700
atcattatta gattagcaaa aaaaaaaaa aaaaa                                2735
```

<210> SEQ ID NO 2
<211> LENGTH: 688
<212> TYPE: PRT
<213> ORGANISM: Solanum tuberosum

<400> SEQUENCE: 2

```
Met Tyr Tyr Gln Gly Thr Ser Asp Asn Thr Asn Ile Gln Ala Asp His
  1               5                  10                  15

Gln Gln Arg His Asn His Gly Asn Ser Asn Asn Asn Asn Ile Gln Thr
             20                  25                  30

Leu Tyr Leu Met Asn Pro Asn Asn Tyr Met Gln Gly Tyr Thr Thr Ser
         35                  40                  45

Asp Thr Gln Gln Gln Gln Gln Leu Leu Phe Leu Asn Ser Ser Pro Ala
     50                  55                  60
```

-continued

```
Ala Ser Asn Ala Leu Cys His Ala Asn Ile Gln His Ala Pro Leu Gln
 65                  70                  75                  80

Gln Gln His Phe Val Gly Val Pro Leu Pro Ala Val Ser Leu His Asp
                 85                  90                  95

Gln Ile Asn His His Gly Leu Leu Gln Arg Met Trp Asn Asn Gln Asp
            100                 105                 110

Gln Ser Gln Gln Val Ile Val Pro Ser Ser Thr Gly Val Ser Ala Thr
        115                 120                 125

Ser Cys Gly Gly Ile Thr Thr Asp Leu Ala Ser Gln Leu Ala Phe Gln
130                 135                 140

Arg Pro Ile Pro Thr Pro Gln His Arg Gln Gln Gln Gln Gln Gln Gly
145                 150                 155                 160

Gly Leu Ser Leu Ser Leu Ser Pro Gln Leu Gln Gln Ile Ser Phe
                165                 170                 175

Asn Asn Asn Ile Ser Ser Ser Ser Pro Arg Thr Asn Asn Val Thr Ile
            180                 185                 190

Arg Gly Thr Leu Asp Gly Ser Ser Asn Met Val Leu Gly Ser Lys
                195                 200                 205

Tyr Leu Lys Ala Ala Gln Glu Leu Leu Asp Glu Val Val Asn Ile Val
            210                 215                 220

Gly Lys Ser Ile Lys Gly Asp Asp Gln Lys Lys Asp Asn Ser Met Asn
225                 230                 235                 240

Lys Glu Ser Met Pro Leu Ala Ser Asp Val Asn Thr Asn Ser Ser Gly
                245                 250                 255

Gly Gly Glu Ser Ser Ser Arg Gln Lys Asn Glu Val Ala Val Glu Leu
            260                 265                 270

Thr Thr Ala Gln Arg Gln Glu Leu Gln Met Lys Lys Ala Lys Leu Leu
                275                 280                 285

Ala Met Leu Glu Glu Val Glu Gln Arg Tyr Arg Gln Tyr His His Gln
            290                 295                 300

Met Gln Ile Ile Val Leu Ser Phe Glu Gln Val Ala Gly Ile Gly Ser
305                 310                 315                 320

Ala Lys Ser Tyr Thr Gln Leu Ala Leu His Ala Ile Ser Lys Gln Phe
                325                 330                 335

Arg Cys Leu Lys Asp Ala Ile Ala Glu Gln Val Lys Ala Thr Ser Lys
            340                 345                 350

Ser Leu Gly Glu Glu Glu Gly Leu Gly Gly Lys Ile Glu Gly Ser Arg
                355                 360                 365

Leu Lys Phe Val Asp His His Leu Arg Gln Gln Arg Ala Leu Gln Gln
            370                 375                 380

Ile Gly Met Met Gln Pro Asn Ala Trp Arg Pro Gln Arg Gly Leu Pro
385                 390                 395                 400

Glu Arg Ala Val Ser Val Leu Arg Ala Trp Leu Phe Glu His Phe Leu
                405                 410                 415

His Pro Tyr Pro Lys Asp Ser Asp Lys Ile Met Leu Ala Lys Gln Thr
            420                 425                 430

Gly Leu Thr Arg Ser Gln Val Ser Asn Trp Phe Ile Asn Ala Arg Val
                435                 440                 445

Arg Leu Trp Lys Pro Met Val Glu Glu Met Tyr Leu Glu Glu Val Lys
            450                 455                 460

Asn Gln Glu Gln Asn Ser Thr Asn Thr Ser Gly Asp Asn Lys Asn Lys
465                 470                 475                 480
```

```
Glu Thr Asn Ile Ser Ala Pro Asn Glu Glu Lys His Pro Ile Ile Thr
                485                 490                 495

Ser Ser Leu Leu Gln Asp Gly Ile Thr Thr Gln Ala Glu Ile Ser
            500                 505                 510

Thr Ser Thr Ile Ser Thr Ser Pro Thr Ala Gly Ala Ser Leu His His
            515                 520                 525

Ala His Asn Phe Ser Phe Leu Gly Ser Phe Asn Met Asp Asn Thr Thr
        530                 535                 540

Thr Thr Val Asp His Ile Glu Asn Asn Ala Lys Lys Gln Arg Asn Asp
545                 550                 555                 560

Met His Lys Phe Ser Pro Ser Ser Ile Leu Ser Ser Val Asp Met Glu
                565                 570                 575

Ala Lys Ala Arg Glu Ser Ser Asn Lys Gly Phe Thr Asn Pro Leu Met
            580                 585                 590

Ala Ala Tyr Ala Met Gly Asp Phe Gly Arg Phe Asp Pro His Asp Gln
            595                 600                 605

Gln Met Thr Ala Asn Phe His Gly Asn Asn Gly Val Ser Leu Thr Leu
        610                 615                 620

Gly Leu Pro Pro Ser Glu Asn Leu Ala Met Pro Val Ser Gln Gln Asn
625                 630                 635                 640

Tyr Leu Ser Asn Asp Leu Gly Ser Arg Ser Glu Met Gly Ser His Tyr
                645                 650                 655

Asn Arg Met Gly Tyr Glu Asn Ile Asp Phe Gln Ser Gly Asn Lys Arg
            660                 665                 670

Phe Pro Thr Gln Leu Leu Pro Asp Phe Val Thr Gly Asn Leu Gly Thr
        675                 680                 685

<210> SEQ ID NO 3
<211> LENGTH: 1898
<212> TYPE: DNA
<213> ORGANISM: Solanum tuberosum

<400> SEQUENCE: 3
atgactttca ggtctagtct tccactagac ctccgtgaaa tttcaacaac aaatcatcaa      60
gttggaatac tatcatcatc accattacca tcaccaggaa caaataccaa taatatcaat     120
catactcgag gattaggggc atcatcatct ttttcgattt ctaatgggat gatattgggt     180
tctaagtacc taaagttgc acaagatctt cttgatgaag ttgttaatgt tggaaaaaac     240
atcaaattat cagatggctt agagagtggt gcaaaggaga acacaaaatt ggacaatgaa     300
ttaatatctt tggctagtga tgatgttgaa agcagcagcc aaaaaaatag tggtgttgaa     360
cttacaacag ctcaaagaca agaacttcaa atgaagaaag ccaagcttgt tagcatgctt     420
gatgaggtgg atcaaaggta tagacaatac catcaccaaa tgcaaatgat tgcaacatca     480
tttgagcaaa caacaggaat tggatcatca aaatcataca cacaacttgc tttgcacaca     540
atttcaaagc aatttagatg tttaaaagat gcaatttctg ggcaaataaa ggacactagc     600
aaaactttag gggaagaaga aaacattgga ggcaaaattg aaggatcaaa gttgaaattt     660
gtggatcatc atttacgcca acaacgtgca ctacaacaat tagggatgat gcaaaccaat     720
gcatggaagc tcaaagagg tttgccagaa agagcggttt cagttctccg cgcttggctt     780
ttcgagcatt tcttcatcc gtatcccaaa gattcagata aaatcatcct tgctaagcaa     840
acagggctaa caaggagcca ggtatcaaat tggtttataa atgctagagt tagactatgg     900
aagccaatgg tagaagaaat gtacatggaa gaagtgaaga aaaacaatca agaacaaaat     960
```

-continued

```
attgagccta ataacaatga aattgttggc tcaaaatcaa gtgttccaca agagaaatta    1020
ccaattagta gcaatattat tcataatgct tctccaaatg atatttctac ttccaccatt    1080
tcaacatctc cgacgggtgg cggcggttcg attccgactc agacggttgc aggtttctcc    1140
ttcattaggt cattaaacat ggagaacatt gatgatcaaa ggaacaacaa aaaggcaaga    1200
aatgagatgc aaaattgttc aactagtact attctctcaa tggaaagaga atcataaat     1260 aaagttgtgc aagatgagac aatcaaaagt gaaaagttca acaacacaca aacaagagaa    1320
tgttactctc taatgactcc aaattacaca atggatgatc aatttggaac aaggttcaat    1380
aatcaaaatc atgaacaatt ggcaacaaca acaacttttc atcaaggaaa tggtcatgtt    1440
tctcttactt tagggcttcc accaaattct gaaaccaac acaattacat tggattggaa      1500
aatcattaca atcaacctac acatcatcca aatattagct atgaaaacat tgattttcag    1560
agtggaaagc gatacgccac tcaactatta caagattttg tttcttgatg atatatataa    1620
tttgcaggta aatcagcttg aaattacatc atgacaggtc ttgaataaaa gaaggggagt    1680
tgagatttag tgatcatata aatatgtata ggtagaaatt ttagttagta tatataggtt    1740
atacttctag tttcttaatg aagatacaag ttttgttgtt attttttgtat tgaggtaact    1800 agctagcttg gattatttaa agttggtgca tgcaactaaa gaagaagaaa aaataatcta    1860
tatatgcaaa ctacagtata ttgtaaattt tgtgcttc                             1898
```

<210> SEQ ID NO 4
<211> LENGTH: 535
<212> TYPE: PRT
<213> ORGANISM: Solanum tuberosum

<400> SEQUENCE: 4

```
Met Thr Phe Arg Ser Ser Leu Pro Leu Asp Leu Arg Glu Ile Ser Thr
  1               5                  10                  15

Thr Asn His Gln Val Gly Ile Leu Ser Ser Pro Leu Pro Ser Pro
             20                  25                  30

Gly Thr Asn Thr Asn Asn Ile Asn His Thr Arg Gly Leu Gly Ala Ser
         35                  40                  45

Ser Ser Phe Ser Ile Ser Asn Gly Met Ile Leu Gly Ser Lys Tyr Leu
     50                  55                  60

Lys Val Ala Gln Asp Leu Leu Asp Glu Val Val Asn Val Gly Lys Asn
 65                  70                  75                  80

Ile Lys Leu Ser Asp Gly Leu Glu Ser Gly Ala Lys Glu Lys His Lys
                 85                  90                  95

Leu Asp Asn Glu Leu Ile Ser Leu Ala Ser Asp Val Glu Ser Ser
            100                 105                 110

Ser Gln Lys Asn Ser Gly Val Glu Leu Thr Thr Ala Gln Arg Gln Glu
        115                 120                 125

Leu Gln Met Lys Lys Ala Lys Leu Val Ser Met Leu Asp Glu Val Asp
    130                 135                 140

Gln Arg Tyr Arg Gln Tyr His His Gln Met Gln Met Ile Ala Thr Ser
145                 150                 155                 160

Phe Glu Gln Thr Thr Gly Ile Gly Ser Ser Lys Ser Tyr Thr Gln Leu
                165                 170                 175

Ala Leu His Thr Ile Ser Lys Gln Phe Arg Cys Leu Lys Asp Ala Ile
            180                 185                 190

Ser Gly Gln Ile Lys Asp Thr Ser Lys Thr Leu Gly Glu Glu Asn
        195                 200                 205
```

```
Ile Gly Gly Lys Ile Glu Gly Ser Lys Leu Lys Phe Val Asp His His
    210                 215                 220

Leu Arg Gln Gln Arg Ala Leu Gln Gln Leu Gly Met Met Gln Thr Asn
225                 230                 235                 240

Ala Trp Lys Pro Gln Arg Gly Leu Pro Glu Arg Ala Val Ser Val Leu
                245                 250                 255

Arg Ala Trp Leu Phe Glu His Phe Leu His Pro Tyr Pro Lys Asp Ser
            260                 265                 270

Asp Lys Ile Ile Leu Ala Lys Gln Thr Gly Leu Thr Arg Ser Gln Val
        275                 280                 285

Ser Asn Trp Phe Ile Asn Ala Arg Val Arg Leu Trp Lys Pro Met Val
    290                 295                 300

Glu Glu Met Tyr Met Glu Glu Val Lys Lys Asn Asn Gln Glu Gln Asn
305                 310                 315                 320

Ile Glu Pro Asn Asn Asn Glu Ile Val Gly Ser Lys Ser Ser Val Pro
                325                 330                 335

Gln Glu Lys Leu Pro Ile Ser Ser Asn Ile Ile His Asn Ala Ser Pro
            340                 345                 350

Asn Asp Ile Ser Thr Ser Thr Ile Ser Thr Ser Pro Thr Gly Gly Gly
        355                 360                 365

Gly Ser Ile Pro Thr Gln Thr Val Ala Gly Phe Ser Phe Ile Arg Ser
    370                 375                 380

Leu Asn Met Glu Asn Ile Asp Asp Gln Arg Asn Asn Lys Lys Ala Arg
385                 390                 395                 400

Asn Glu Met Gln Asn Cys Ser Thr Ser Thr Ile Leu Ser Met Glu Arg
                405                 410                 415

Glu Ile Ile Asn Lys Val Val Gln Asp Glu Thr Ile Lys Ser Glu Lys
            420                 425                 430

Phe Asn Asn Thr Gln Thr Arg Glu Cys Tyr Ser Leu Met Thr Pro Asn
        435                 440                 445

Tyr Thr Met Asp Asp Gln Phe Gly Thr Arg Phe Asn Asn Gln Asn His
    450                 455                 460

Glu Gln Leu Ala Thr Thr Thr Thr Phe His Gln Gly Asn Gly His Val
465                 470                 475                 480

Ser Leu Thr Leu Gly Leu Pro Pro Asn Ser Glu Asn Gln His Asn Tyr
                485                 490                 495

Ile Gly Leu Glu Asn His Tyr Asn Gln Pro Thr His His Pro Asn Ile
            500                 505                 510

Ser Tyr Glu Asn Ile Asp Phe Gln Ser Gly Lys Arg Tyr Ala Thr Gln
        515                 520                 525

Leu Leu Gln Asp Phe Val Ser
    530                 535

<210> SEQ ID NO 5
<211> LENGTH: 1920
<212> TYPE: DNA
<213> ORGANISM: Solanum tuberosum

<400> SEQUENCE: 5
ggggagcgag tggttccgac aaggtatggt aatgggtgga ggtgcaagta gtcaacaatt    60
gggatatgca aaaaatcata ctcctaatgt ggcggagtcc atgcaacttt ttctaatgaa   120
tccacaacca aggtcacctt ctccatctcc tcctaattca acttcttcta cgcttcacat   180
gttgttacca aacccatcat ctacttcaac acttcaaggg tttcctaatc cggccgaagg   240
```

-continued

```
atctttcggt caattcatta catgggggaa tggaggagca agtgctgcca cagccaccca      300
tcatctcaat gcccagaatg aaatcggagg agtaaacgtt gtagaaagtc aaggcctatc      360
tctatccttg tcttcttcgt tacagcacaa ggcggaggaa ttacaaatga gcggagaagc      420
tggaggaatg atgttcttca atcaaggagg gtctagtact tccgggcagt atcgatacaa      480
gaatttgaat atgggtggat caggagtaag cccaaacatt catcaagtcc atgttgggta      540
tgggtcatca ttaggagtgg tcaatgtgtt gaggaattcc aaatacgcga aagctgccca      600
agaactactg gaagaattct gcagtgttgg aagaggtaaa ttgaagaaga ctaacaacaa      660
agcagcagcc aataacccta atacgaaccc tagtggcgct aacaatgaag cttcttcaaa      720
agatgttcct actttgtccg ctgctgatag aattgagcat cagagaagga aggtcaaact      780
tttatctatg gttgatgagg tagataggag gtacaatcat tactgtgaac aaatgcagat      840
ggttgtaaat tcgtttgatt tagtgatggg tttcggcaca gcagttccct acacagcact      900
tgcacagaag gcaatgtcaa gacatttcag gtgtttaaag gatgcaatag gagcacaatt      960
gaagcagagt tgtgagttat taggagagaa agatgcagga aattcgggat tgactaaagg     1020
agaaactccg aggcttaaga tgcttgaaca agtttgagg caacaaaggg cgtttcacca      1080
aatgggaatg atggaacaag aagcttggag accacaaaga ggcttacctg aacgttctgt     1140
caacatttta agagcttggc ttttttgagca ttttctacac ccgtatccaa gtgatgctga     1200
taaacatctg ttggcaagac agactggtct ctccagaaat caggtatcaa attggttcat     1260
taatgctagg gttcggttgt ggaaacccat ggtagaagat atgtatcaac aagaagccaa     1320
agatgaagat ggagatggag atgagaagag ccaaagccaa aacagtggca ataacataat     1380
tgcacaaaca ccaacgccta atagcctgac taacacttca tctactaata tgacgacgac     1440
aacagcccct acaactacga cagctctagc tgctgcagag acaggaacag ctgccactcc     1500
cataactgtt acctcaagca aaagatccca aatcaatgcc acggatagtg acccttcact     1560
tgtagcaatc aattccttct ctgaaaacca agctactttt ccgaccaaca ttcatgatcc     1620
cgacgattgc cgtcgcggca acttatccgg tgacgacggg accaccacac atgatcatat     1680
ggggtccacc atgataaggt ttgggaccac tgctggtgac gtgtcactca ccttagggtt     1740
acgacatgca ggaaatttac cagagaatac tcatttcttt ggttaattaa tacgtatttt     1800
ccccatagta attaattaaa actgaatttg cttgagctca tcataattta tgcattgctt     1860
tttgttataa gaaattccat aaattagctt tgtgttaaaa aaaaaaaaa aaaaaaaaa      1920
```

<210> SEQ ID NO 6
<211> LENGTH: 586
<212> TYPE: PRT
<213> ORGANISM: Solanum tuberosum

<400> SEQUENCE: 6

```
Met Val Met Gly Gly Gly Ala Ser Ser Gln Gln Leu Gly Tyr Ala Lys
  1               5                  10                  15

Asn His Thr Pro Asn Val Ala Glu Ser Met Gln Leu Phe Leu Met Asn
             20                  25                  30

Pro Gln Pro Arg Ser Pro Ser Pro Ser Pro Asn Ser Thr Ser Ser
         35                  40                  45

Thr Leu His Met Leu Leu Pro Asn Pro Ser Ser Thr Ser Thr Leu Gln
     50                  55                  60

Gly Phe Pro Asn Pro Ala Glu Gly Ser Phe Gly Gln Phe Ile Thr Trp
 65                  70                  75                  80
```

-continued

```
Gly Asn Gly Gly Ala Ser Ala Ala Thr Ala Thr His His Leu Asn Ala
                85                  90                  95

Gln Asn Glu Ile Gly Gly Val Asn Val Val Glu Ser Gln Gly Leu Ser
            100                 105                 110

Leu Ser Leu Ser Ser Ser Leu Gln His Lys Ala Glu Glu Leu Gln Met
        115                 120                 125

Ser Gly Glu Ala Gly Gly Met Met Phe Phe Asn Gln Gly Gly Ser Ser
    130                 135                 140

Thr Ser Gly Gln Tyr Arg Tyr Lys Asn Leu Asn Met Gly Gly Ser Gly
145                 150                 155                 160

Val Ser Pro Asn Ile His Gln Val His Val Gly Tyr Gly Ser Ser Leu
                165                 170                 175

Gly Val Val Asn Val Leu Arg Asn Ser Lys Tyr Ala Lys Ala Ala Gln
            180                 185                 190

Glu Leu Leu Glu Glu Phe Cys Ser Val Gly Arg Gly Lys Leu Lys Lys
        195                 200                 205

Thr Asn Asn Lys Ala Ala Ala Asn Asn Pro Asn Thr Asn Pro Ser Gly
    210                 215                 220

Ala Asn Asn Glu Ala Ser Ser Lys Asp Val Pro Thr Leu Ser Ala Ala
225                 230                 235                 240

Asp Arg Ile Glu His Gln Arg Arg Lys Val Lys Leu Leu Ser Met Val
                245                 250                 255

Asp Glu Val Asp Arg Arg Tyr Asn His Tyr Cys Glu Gln Met Gln Met
            260                 265                 270

Val Val Asn Ser Phe Asp Leu Val Met Gly Phe Gly Thr Ala Val Pro
        275                 280                 285

Tyr Thr Ala Leu Ala Gln Lys Ala Met Ser Arg His Phe Arg Cys Leu
    290                 295                 300

Lys Asp Ala Ile Gly Ala Gln Leu Lys Gln Ser Cys Glu Leu Leu Gly
305                 310                 315                 320

Glu Lys Asp Ala Gly Asn Ser Gly Leu Thr Lys Gly Glu Thr Pro Arg
                325                 330                 335

Leu Lys Met Leu Glu Gln Ser Leu Arg Gln Gln Arg Ala Phe His Gln
            340                 345                 350

Met Gly Met Met Glu Gln Glu Ala Trp Arg Pro Gln Arg Gly Leu Pro
        355                 360                 365

Glu Arg Ser Val Asn Ile Leu Arg Ala Trp Leu Phe Glu His Phe Leu
    370                 375                 380

His Pro Tyr Pro Ser Asp Ala Asp Lys His Leu Leu Ala Arg Gln Thr
385                 390                 395                 400

Gly Leu Ser Arg Asn Gln Val Ser Asn Trp Phe Ile Asn Ala Arg Val
                405                 410                 415

Arg Leu Trp Lys Pro Met Val Glu Asp Met Tyr Gln Gln Glu Ala Lys
            420                 425                 430

Asp Glu Asp Gly Asp Gly Asp Glu Lys Ser Gln Ser Gln Asn Ser Gly
        435                 440                 445

Asn Asn Ile Ile Ala Gln Thr Pro Thr Pro Asn Ser Leu Thr Asn Thr
    450                 455                 460

Ser Ser Thr Asn Met Thr Thr Thr Ala Pro Thr Thr Thr Ala
465                 470                 475                 480

Leu Ala Ala Ala Glu Thr Gly Thr Ala Ala Thr Pro Ile Thr Val Thr
                485                 490                 495

Ser Ser Lys Arg Ser Gln Ile Asn Ala Thr Asp Ser Asp Pro Ser Leu
```

```
                500             505             510
Val Ala Ile Asn Ser Phe Ser Glu Asn Gln Ala Thr Phe Pro Thr Asn
            515                 520                 525

Ile His Asp Pro Asp Asp Cys Arg Arg Gly Asn Leu Ser Gly Asp Asp
        530                 535                 540

Gly Thr Thr Thr His Asp His Met Gly Ser Thr Met Ile Arg Phe Gly
545                 550                 555                 560

Thr Thr Ala Gly Asp Val Ser Leu Thr Leu Gly Leu Arg His Ala Gly
                565                 570                 575

Asn Leu Pro Glu Asn Thr His Phe Phe Gly
            580                 585

<210> SEQ ID NO 7
<211> LENGTH: 2103
<212> TYPE: DNA
<213> ORGANISM: Solanum tuberosum
<220> FEATURE:
<221> NAME/KEY: unsure
<222> LOCATION: (5)
<223> OTHER INFORMATION: N at position 5 is a, c, t, or g
<220> FEATURE:
<221> NAME/KEY: unsure
<222> LOCATION: (1768)
<223> OTHER INFORMATION: N at position 1768 is a, c, t, or g
<220> FEATURE:
<221> NAME/KEY: unsure
<222> LOCATION: (1780)
<223> OTHER INFORMATION: N at position 1780 is a, c, t, or g
<220> FEATURE:
<221> NAME/KEY: unsure
<222> LOCATION: (1783)
<223> OTHER INFORMATION: N at position 1783 is a, c, t, or g
<220> FEATURE:
<221> NAME/KEY: unsure
<222> LOCATION: (1785)
<223> OTHER INFORMATION: N at position 1785 is a, c, t, or g
<220> FEATURE:
<221> NAME/KEY: unsure
<222> LOCATION: (1794)
<223> OTHER INFORMATION: N at position 1794 is a, c, t, or g
<220> FEATURE:
<221> NAME/KEY: unsure
<222> LOCATION: (1802)
<223> OTHER INFORMATION: N at position 1802 is a, c, t, or g
<220> FEATURE:
<221> NAME/KEY: unsure
<222> LOCATION: (1805)
<223> OTHER INFORMATION: N at position 1805  is a, c, t, or g
<220> FEATURE:
<221> NAME/KEY: unsure
<222> LOCATION: (1811)
<223> OTHER INFORMATION: N at position 1811 is a, c, t, or g
<220> FEATURE:
<221> NAME/KEY: unsure
<222> LOCATION: (1813)
<223> OTHER INFORMATION: N at position 1813 is a, c, t, or g
<220> FEATURE:
<221> NAME/KEY: unsure
<222> LOCATION: (1818)
<223> OTHER INFORMATION: N at position 1818 is a, c, t, or g
<220> FEATURE:
<221> NAME/KEY: unsure
<222> LOCATION: (1831)
<223> OTHER INFORMATION: N at position 1831 is a, c, t, or g
<220> FEATURE:
<221> NAME/KEY: unsure
<222> LOCATION: (1862)
<223> OTHER INFORMATION: N at position 1862 is a, c, t, or g
<220> FEATURE:
<221> NAME/KEY: unsure
<222> LOCATION: (1869)
<223> OTHER INFORMATION: N at position 1869 is a, c, t, or g
<220> FEATURE:
```

-continued

```
<221> NAME/KEY: unsure
<222> LOCATION: (1872)
<223> OTHER INFORMATION: N at position 1872 is a, c, t, or g
<220> FEATURE:
<221> NAME/KEY: unsure
<222> LOCATION: (1896)
<223> OTHER INFORMATION: N at position 1896 is a, c, t, or g
<220> FEATURE:
<221> NAME/KEY: unsure
<222> LOCATION: (1911)
<223> OTHER INFORMATION: N at position 1911 is a, c, t, or g
<220> FEATURE:
<221> NAME/KEY: unsure
<222> LOCATION: (1926)
<223> OTHER INFORMATION: N at position 1926 is a, c, t, or g
<220> FEATURE:
<221> NAME/KEY: unsure
<222> LOCATION: (1932)
<223> OTHER INFORMATION: N at position 1932 is a, c, t, or g
<220> FEATURE:
<221> NAME/KEY: unsure
<222> LOCATION: (1960)
<223> OTHER INFORMATION: N at position 1960 is a, c, t, or g
<220> FEATURE:
<221> NAME/KEY: unsure
<222> LOCATION: (1967)
<223> OTHER INFORMATION: N at position 1967 is a, c, t, or g
<220> FEATURE:
<221> NAME/KEY: unsure
<222> LOCATION: (1988)
<223> OTHER INFORMATION: N at position 1988 is a, c, t, or g
<220> FEATURE:
<221> NAME/KEY: unsure
<222> LOCATION: (2002)
<223> OTHER INFORMATION: N at position 2002 is a, c, t, or g
<220> FEATURE:
<221> NAME/KEY: unsure
<222> LOCATION: (2022)
<223> OTHER INFORMATION: N at position 2022 is a, c, t, or g
<220> FEATURE:
<221> NAME/KEY: unsure
<222> LOCATION: (2034)
<223> OTHER INFORMATION: N at position 2034 is a, c, t, or g
<220> FEATURE:
<221> NAME/KEY: unsure
<222> LOCATION: (2036)
<223> OTHER INFORMATION: N at position 2036 is a, c, t, or g
<220> FEATURE:
<221> NAME/KEY: unsure
<222> LOCATION: (2039)
<223> OTHER INFORMATION: N at position 2039 is a, c, t, or g
<220> FEATURE:
<221> NAME/KEY: unsure
<222> LOCATION: (2041)
<223> OTHER INFORMATION: N at position 2041 is a, c, t, or g
<220> FEATURE:
<221> NAME/KEY: unsure
<222> LOCATION: (2049)
<223> OTHER INFORMATION: N at position 2049 is a, c, t, or g
<220> FEATURE:
<221> NAME/KEY: unsure
<222> LOCATION: (2057)
<223> OTHER INFORMATION: N at position 2057 is a, c, t, or g
<220> FEATURE:
<221> NAME/KEY: unsure
<222> LOCATION: (2068)
<223> OTHER INFORMATION: N at position 2068 is a, c, t, or g
<220> FEATURE:
<221> NAME/KEY: unsure
<222> LOCATION: (2072)
<223> OTHER INFORMATION: N at position 2072 is a, c, t, or g
<220> FEATURE:
<221> NAME/KEY: unsure
<222> LOCATION: (2076)
<223> OTHER INFORMATION: N at position 2076 is a, c, t, or g
<220> FEATURE:
<221> NAME/KEY: unsure
<222> LOCATION: (2091)
<223> OTHER INFORMATION: N at position 2091 is a, c, t, or g
```

<400> SEQUENCE: 7

```
aaccnaaaaa agagatcgaa ttcggcacga gtgatcatgg tccttcgtct tctaagaaca        60
ttattagtga acaattttac caacatggta gtcatgaaaa tatgttgaca caacaacta        120
ctcatcatga tgatcatcaa ggctcgtggc atcacgataa aacagaaca ttacttgttg        180
atgatccatc tatgagatgt gttttcccctt gtgaaggaaa tgaaaggcca agtcatggac      240
tttcattatc tctttgttcc tcaaatccat caagtattgg tttacaatct tttgaactta      300
gacatcaaga tttgcaacaa ggattaatac atgatggatt tttgggtaaa tctacaaata      360
tacaacaagg tattttcat catcatcatc aagttaggga ctcgaaatat ttaggtccgg       420
ctcaagagtt gctcagtgag ttctgtagtc tcggaataaa aagaataat gatcattctt       480
cttcaaaagt acttctaaag caacatgaga gtactgctag tacttcaaaa aagcaacttt      540
tacagtctct tgaccttttg gaacttcaaa aagaaagac aaaattgctt caaatgcttg       600
aagaggtgga tagaaggtac aagcattatt gtgatcaaat gaaggctgtt gtatcatcat      660
ttgaagcagt ggctggaaat ggagcagcaa cagtttactc agccttagca tcaagggcta     720
tgtcaaggca ttttagatgt ttaagagatg gaattgtggc acaaattaag gccacaaaaa      780
tggctatggg agaaaaagac agtactagta ctcttattcc tggttcaaca agaggtgaaa     840
caccaagact cagacttctt gatcaaactt aaggcaaca aaaggctttc caacagatga      900
atatgatgga gactcatcca tggagaccgc aacgtggtct cccagaaaga tcagtctccg     960
ttctccgcgc ttggctcttt gaacactttc ttcacccgta cccaagtgat gttgataaac    1020
acattttagc tcgccaaact ggtctttcaa gaagccaggt gtctaattgg ttcattaatg    1080
caagggtaag gctatggaag ccaatggtgg aagaaatgta cttagaagaa acaaaagaag   1140
aagaaaatgt tggatctcca gatggatcaa aagccctaat tgatgacatg acaattcatc    1200
aatcacacat tgatcatcat caagctgatc aaaagccaaa tcttgtaaga attgactctg    1260
aatgcatatc ttccatcata aatcatcaac ctcatgagaa aaatgatcaa actatggag    1320
taattagagg tggagatcaa tcgtttggcg cgattgagct agattttca acaaatattg     1380
cttatggtac tagtggtggt gaccatcatc atcatggagg gggtgtttct ttaacattgg    1440
gattacaaca acatggtgga agtggtggat catcaatggg gttaactaca ttttcatcac    1500
aaccatctca taatcaaagt tcactttttt atccaagaga tgatgatcaa gttcaatatt    1560
catcactttt ggatagtgaa atcagaatt tgccatatag aaaccttgat ggggcacaa     1620
cttcttcatg atttggctgg ttaaaaatg acagagattc ttcattttgg accttattat     1680
atactctaat tttaatatat attggtgatg aatgatgata aaaaaaaaa aaaaaaaaa     1740
aaaaaaaaa aaaaaaaaa acctcgancc cggtcgactn tananccca tagngagtcg      1800
tnttnctgca nanatctntg aatcgtaaat nctgaaaaac cccgcaagtt cacttcaact    1860
gngcatcgng cnccatctca atttcttca tttatncatc gttttgcctt nttttatgta    1920
actatnctcc tntaagtttc aatcttggcc atgtaaccctn tgatctntaa aatttttaa    1980
atgactanaa ttaatgccca tnttttttt ggacctaaat tnttcatgaa aatntnttnc    2040
nagggcttnt tcaaaancct tggacttntt cnccanaggt ttggtcaagt ntccaatcaa    2100
ggt                                                                  2103
```

<210> SEQ ID NO 8
<211> LENGTH: 589
<212> TYPE: PRT

<213> ORGANISM: Solanum tuberosum

<400> SEQUENCE: 8

```
Met Val Asn His Gln Leu Gln Asn Phe Glu Thr Asn Pro Glu Met Tyr
 1               5                  10                  15

Asn Leu Ser Ser Thr Thr Ser Ser Met Asp Gln Met Ile Gly Phe Pro
            20                  25                  30

Pro Asn Asn Asn Pro His His Val Leu Trp Lys Gly Asn Phe Pro
        35                  40                  45

Asn Lys Ile Asn Gly Val Asp Asp Asp His Gly Pro Ser Ser Ser
     50                  55                  60

Lys Asn Ile Ile Ser Glu Gln Phe Tyr Gln His Gly Ser His Glu Asn
 65                  70                  75                  80

Met Leu Thr Thr Thr Thr His His Asp Asp His Gln Gly Ser Trp
            85                  90                  95

His His Asp Asn Asn Arg Thr Leu Leu Val Asp Asp Pro Ser Met Arg
            100                 105                 110

Cys Val Phe Pro Cys Glu Gly Asn Glu Arg Pro Ser His Gly Leu Ser
            115                 120                 125

Leu Ser Leu Cys Ser Ser Asn Pro Ser Ser Ile Gly Leu Gln Ser Phe
            130                 135                 140

Glu Leu Arg His Gln Asp Leu Gln Gln Gly Leu Ile His Asp Gly Phe
145                 150                 155                 160

Leu Gly Lys Ser Thr Asn Ile Gln Gln Gly Tyr Phe His His His
                165                 170                 175

Gln Val Arg Asp Ser Lys Tyr Leu Gly Pro Ala Gln Glu Leu Leu Ser
            180                 185                 190

Glu Phe Cys Ser Leu Gly Ile Lys Lys Asn Asn Asp His Ser Ser Ser
            195                 200                 205

Lys Val Leu Leu Lys Gln His Glu Ser Thr Ala Ser Thr Ser Lys Lys
210                 215                 220

Gln Leu Leu Gln Ser Leu Asp Leu Leu Glu Leu Gln Lys Arg Lys Thr
225                 230                 235                 240

Lys Leu Leu Gln Met Leu Glu Glu Val Asp Arg Arg Tyr Lys His Tyr
                245                 250                 255

Cys Asp Gln Met Lys Ala Val Val Ser Ser Phe Glu Ala Val Ala Gly
                260                 265                 270

Asn Gly Ala Ala Thr Val Tyr Ser Ala Leu Ala Ser Arg Ala Met Ser
                275                 280                 285

Arg His Phe Arg Cys Leu Arg Asp Gly Ile Val Ala Gln Ile Lys Ala
            290                 295                 300

Thr Lys Met Ala Met Gly Glu Lys Asp Ser Thr Ser Thr Leu Ile Pro
305                 310                 315                 320

Gly Ser Thr Arg Gly Glu Thr Pro Arg Leu Arg Leu Leu Asp Gln Thr
                325                 330                 335

Leu Arg Gln Gln Lys Ala Phe Gln Gln Met Asn Met Met Glu Thr His
                340                 345                 350

Pro Trp Arg Pro Gln Arg Gly Leu Pro Glu Arg Ser Val Ser Val Leu
            355                 360                 365

Arg Ala Trp Leu Phe Glu His Phe Leu His Pro Tyr Pro Ser Asp Val
            370                 375                 380

Asp Lys His Ile Leu Ala Arg Gln Thr Gly Leu Ser Arg Ser Gln Val
385                 390                 395                 400
```

-continued

```
Ser Asn Trp Phe Ile Asn Ala Arg Val Arg Leu Trp Lys Pro Met Val
            405                 410                 415

Glu Glu Met Tyr Leu Glu Glu Thr Lys Glu Glu Asn Val Gly Ser
        420                 425                 430

Pro Asp Gly Ser Lys Ala Leu Ile Asp Asp Met Thr Ile His Gln Ser
            435                 440                 445

His Ile Asp His His Gln Ala Asp Gln Lys Pro Asn Leu Val Arg Ile
    450                 455                 460

Asp Ser Glu Cys Ile Ser Ser Ile Ile Asn His Gln Pro His Glu Lys
465                 470                 475                 480

Asn Asp Gln Asn Tyr Gly Val Ile Arg Gly Asp Gln Ser Phe Gly
                485                 490                 495

Ala Ile Glu Leu Asp Phe Ser Thr Asn Ile Ala Tyr Gly Thr Ser Gly
            500                 505                 510

Gly Asp His His His Gly Gly Gly Val Ser Leu Thr Leu Gly Leu
        515                 520                 525

Gln Gln His Gly Gly Ser Gly Gly Ser Ser Met Gly Leu Thr Thr Phe
    530                 535                 540

Ser Ser Gln Pro Ser His Asn Gln Ser Ser Leu Phe Tyr Pro Arg Asp
545                 550                 555                 560

Asp Asp Gln Val Gln Tyr Ser Ser Leu Leu Asp Ser Glu Asn Gln Asn
                565                 570                 575

Leu Pro Tyr Arg Asn Leu Asp Gly Gly Thr Thr Ser Ser
            580                 585
```

<210> SEQ ID NO 9
<211> LENGTH: 1939
<212> TYPE: DNA
<213> ORGANISM: Solanum tuberosum

<400> SEQUENCE: 9

| | |
|---|---|
| acgagcgttt atgagacagc cgggttgttg tctgaaatgt tcaatttca gacaacatcc | 60 |
| acggctgcaa ctgaattgtt gcagaatcaa ttgtcaaata actatagaca cccgaatcaa | 120 |
| cagccacatc atcaacctcc gaccagggag tggtttggta acagacaaga gatcgtagtt | 180 |
| ggtggaagtt tgcaggtaac atttggggat acaaaagatg atgtgaatgc gaaggtatta | 240 |
| ttgagtaacc gtgatagtgt aactgattat tatcagcgtc aacacaatca agtaccaagt | 300 |
| ataaataccg cggagtccat gcaactttt cttatgaatc cacaaccaag ttcaccatca | 360 |
| caatctactc cttcaactct tcatcaaggg ttttctagcc cggtcggagg cattttagt | 420 |
| caattcatgt gtggaggagc aagtacttct tcaaatccaa ttggaggagt aaatgtgatt | 480 |
| gatcaagggc aaggtctttc attgtccttg tcatctactt tacaacattt ggaagcatcc | 540 |
| aaagtggaag atttgaggat gaatagtgga ggagaaatgt tgttttcaa tcaagaaagt | 600 |
| caaaatcatc ataatattgg ttttgggtca tcactaggac tagtcaatgt gttgaggaat | 660 |
| tcaaagtatg tcaaagcaac acaagagttg ttggaagagt tttgttgtgt tgggaagggt | 720 |
| caattgttca agaaaatcaa caaagtttct aggaataaca acacaagtac atcacccatt | 780 |
| attaacccta gtggaagtaa taacaataat tcatcttctt caaaggctat tatccctcct | 840 |
| aatttgtcaa ctgcagagag acttgatcat caaagaagga aggtcaaact tttatccatg | 900 |
| cttgatgagg tagagaaaag atacaaccac tattgtgaac aaatgcagat ggtagtaaac | 960 |
| tcattcgatc tagtgatggg ttttggagct gcagttcctt acacagcact agcacagaaa | 1020 |
| gccatgtcta ggcatttcaa gtgtttaaaa gatggcgtgg cggcgcaatt gaagaagaca | 1080 |

```
tgtgaggcac taggtgaaaa agatgcaagc agtagttcag gactgactaa aggagaaaca  1140
ccaaggctta aggtgcttga acaaagcttg aggcaacaaa gagcttttca acaaatggga  1200
atgatggaac aagaagcttg gaggccacaa agaggattgc ctgaacgatc tgtcaatatt  1260
ttaagagctt ggcttttcga acattttcta catccgtatc caagtgatgc agataagcat  1320
cttttggcac gacagactgg tctctccaga aaccaggtag caaactggtt cataaatgcg  1380
agggtgagat tgtggaaacc catggtagaa gaaatgtatc aaagagaggt taatgaagat  1440
gatgttgatg acatgcaaga aaccaaaac agtacaaata cacaaatacc aacgcctaat  1500
attattatta caaccaattc taacattaca gaaacaaaat cagctgccac tgccacaatt  1560
gcttcagaca aaaaacccca aatcaatgtc tctgaaattg acccttcaat tgtcgcaatg  1620
aatacacatt attcttcctc tatgccaact caattaacca atttccccac tattcaagat  1680
gagtccgacc acatcttata tcgccgcagt ggagcggaat atgggaccac aaatatggct  1740
agtaattctg aaattggatc caacatgata acatttggga ccactacggc tagtgatgtt  1800
tcacttacct taggactgcg ccatgcgggt aatttacctg agaatactca ttttccggt  1860 taattaagat agtgtattca aacactgcta cataaattat gattttatat atatatat  1920 tgtcatccga ttagtttat                                              1939
```

<210> SEQ ID NO 10
<211> LENGTH: 620
<212> TYPE: PRT
<213> ORGANISM: Solanum tuberosum

<400> SEQUENCE: 10

```
Thr Ser Val Tyr Glu Thr Ala Gly Leu Leu Ser Glu Met Phe Asn Phe
 1               5                  10                  15

Gln Thr Thr Ser Thr Ala Ala Thr Glu Leu Leu Gln Asn Gln Leu Ser
            20                  25                  30

Asn Asn Tyr Arg His Pro Asn Gln Gln Pro His His Gln Pro Pro Thr
        35                  40                  45

Arg Glu Trp Phe Gly Asn Arg Gln Glu Ile Val Val Gly Gly Ser Leu
    50                  55                  60

Gln Val Thr Phe Gly Asp Thr Lys Asp Val Asn Ala Lys Val Leu
65                  70                  75                  80

Leu Ser Asn Arg Asp Ser Val Thr Asp Tyr Tyr Gln Arg Gln His Asn
                85                  90                  95

Gln Val Pro Ser Ile Asn Thr Ala Glu Ser Met Gln Leu Phe Leu Met
           100                 105                 110

Asn Pro Gln Pro Ser Ser Pro Ser Gln Ser Thr Pro Ser Thr Leu His
       115                 120                 125

Gln Gly Phe Ser Ser Pro Val Gly Gly His Phe Ser Gln Phe Met Cys
   130                 135                 140

Gly Gly Ala Ser Thr Ser Ser Asn Pro Ile Gly Gly Val Asn Val Ile
145                 150                 155                 160

Asp Gln Gly Gln Gly Leu Ser Leu Ser Leu Ser Ser Thr Leu Gln His
                165                 170                 175

Leu Glu Ala Ser Lys Val Glu Asp Leu Arg Met Asn Ser Gly Gly Glu
            180                 185                 190

Met Leu Phe Phe Asn Gln Glu Ser Gln Asn His His Asn Ile Gly Phe
        195                 200                 205

Gly Ser Ser Leu Gly Leu Val Asn Val Leu Arg Asn Ser Lys Tyr Val
```

-continued

```
            210                 215                 220
Lys Ala Thr Gln Glu Leu Leu Glu Glu Phe Cys Cys Val Gly Lys Gly
225                 230                 235                 240

Gln Leu Phe Lys Lys Ile Asn Lys Val Ser Arg Asn Asn Asn Thr Ser
                245                 250                 255

Thr Ser Pro Ile Ile Asn Pro Ser Gly Ser Asn Asn Asn Asn Ser Ser
                260                 265                 270

Ser Ser Lys Ala Ile Ile Pro Pro Asn Leu Ser Thr Ala Glu Arg Leu
            275                 280                 285

Asp His Gln Arg Arg Lys Val Lys Leu Leu Ser Met Leu Asp Glu Val
290                 295                 300

Glu Lys Arg Tyr Asn His Tyr Cys Glu Gln Met Gln Met Val Val Asn
305                 310                 315                 320

Ser Phe Asp Leu Val Met Gly Phe Gly Ala Ala Val Pro Tyr Thr Ala
                325                 330                 335

Leu Ala Gln Lys Ala Met Ser Arg His Phe Lys Cys Leu Lys Asp Gly
                340                 345                 350

Val Ala Ala Gln Leu Lys Lys Thr Cys Glu Ala Leu Gly Glu Lys Asp
            355                 360                 365

Ala Ser Ser Ser Ser Gly Leu Thr Lys Gly Glu Thr Pro Arg Leu Lys
370                 375                 380

Val Leu Glu Gln Ser Leu Arg Gln Gln Arg Ala Phe Gln Gln Met Gly
385                 390                 395                 400

Met Met Glu Gln Glu Ala Trp Arg Pro Gln Arg Gly Leu Pro Glu Arg
                405                 410                 415

Ser Val Asn Ile Leu Arg Ala Trp Leu Phe Glu His Phe Leu His Pro
                420                 425                 430

Tyr Pro Ser Asp Ala Asp Lys His Leu Leu Ala Arg Gln Thr Gly Leu
            435                 440                 445

Ser Arg Asn Gln Val Ala Asn Trp Phe Ile Asn Ala Arg Val Arg Leu
450                 455                 460

Trp Lys Pro Met Val Glu Glu Met Tyr Gln Arg Glu Val Asn Glu Asp
465                 470                 475                 480

Asp Val Asp Asp Met Gln Glu Asn Gln Asn Ser Thr Asn Thr Gln Ile
                485                 490                 495

Pro Thr Pro Asn Ile Ile Ile Thr Thr Asn Ser Asn Ile Thr Glu Thr
                500                 505                 510

Lys Ser Ala Ala Thr Ala Thr Ile Ala Ser Asp Lys Lys Pro Gln Ile
            515                 520                 525

Asn Val Ser Glu Ile Asp Pro Ser Ile Val Ala Met Asn Thr His Tyr
530                 535                 540

Ser Ser Ser Met Pro Thr Gln Leu Thr Asn Phe Pro Thr Ile Gln Asp
545                 550                 555                 560

Glu Ser Asp His Ile Leu Tyr Arg Arg Ser Gly Ala Glu Tyr Gly Thr
                565                 570                 575

Thr Asn Met Ala Ser Asn Ser Glu Ile Gly Ser Asn Met Ile Thr Phe
                580                 585                 590

Gly Thr Thr Thr Ala Ser Asp Val Ser Leu Thr Leu Gly Leu Arg His
            595                 600                 605

Ala Gly Asn Leu Pro Glu Asn Thr His Phe Ser Gly
610                 615                 620

<210> SEQ ID NO 11
```

```
<211> LENGTH: 2128
<212> TYPE: DNA
<213> ORGANISM: Solanum tuberosum
<220> FEATURE:
<221> NAME/KEY: unsure
<222> LOCATION: (2078)
<223> OTHER INFORMATION: N at position 2078 is a, c, t, or g

<400> SEQUENCE: 11
caagggcttt cacttagcct gtcctcgtcc cagcagccgg ggtttgggaa cttcacggcg      60
gcgcgtgagc ttgtttcttc gccttcgggt tcggcttcag cttcagggat acaacaacaa     120
caacagcaac aacagagtat tagtagtgtg cctttgagtt ctaagtacat gaaggctgca     180
caagagctac ttgatgaagt tgtaaatgtt ggaaaatcaa tgaaaagtac taatagtact     240
gatgttgttg ttaataatga tgtcaagaaa tcgaagaata tgggcgatat ggacggacag     300
ttagacggag ttggagcaga caaagacgga gctccaacaa ctgagctaag tacaggggag     360
agacaagaaa ttcaaatgaa gaaagcaaaa cttgttaaca tgcttgacga ggtggagcag     420
aggtatagac attatcatca ccaaatgcag tcagtgatac attggttaga gcaagctgct     480
ggcattggat cagcaaaaac atatacagca ttggctttgc agacgatttc gaagcaattt     540
aggtgtctta aggacgcgat aattggtcaa atacgatcag caagccagac gttaggcgaa     600
gaagatagtt tgggagggaa gattgaaggt tcaaggctta aatttgttga taatcagcta     660
agacagcaaa gggctttgca acaattggga atgatccagc ataatgcttg gagacctcag     720
agaggattgc ccgaacgagc tgtttctgtt cttcgcgctt ggcttttga acatttcctc      780 catccttatc ccaaggattc agacaaaatg atgctagcaa acaaacagg actaactagg      840 agtcaggtgt cgaattggtt catcaatgct cgagttcgtc tttggaagcc aatggtggaa     900
gagatgtact tggaagagat aaaagaacac gaacagaatg ggttgggtca agaaaagacg     960
agcaaattag gtaacagaa cgaagattca acaacatcaa gatccattgc tacacaagac    1020
aaaagccctg gttcagatag ccaaaacaag agttttgtct caaaacagga caatcatttg    1080
cctcaacaca accctgcttc accaatgccc gatgtccaac gccacttcca taccoctatc    1140 ggtatgacca tccgtaatca gtctgctggt ttcaacctca ttggatcacc agagatcgaa    1200
agcatcaaca ttactcaagg gagtccaaag aaaccgagga acaacgagat gttgcattca    1260
ccaaacagca ttccatccat caacatggat gtaaagccta acgaggaaca aatgtcgatg    1320
aagtttggtg atgataggca ggacagagat ggattctcac taatgggagg accgatgaac    1380
ttcatgggag gattcggagc ctatcccatt ggagaaattg ctcggtttag caccgagcaa    1440
ttctcagcac catactcaac cagtggcaca gtttcactca ctcttggcct accacataac    1500
gaaaacctct caatgtctgc aacacaccac agtttccttc caattccaac acaaaacatc    1560
caaattggaa gtgaaccaaa tcatgagttt ggtagcttaa acacaccaac atcagctcac    1620
tcaacatcaa gcgtctatga aaccttcaac attcagaaca gaaagaggtt cgccgcaccc    1680
ttgttaccag attttgttgc ctgatcacaa aaacaaaaac aggttttggc aacagacaaa    1740
cttctgtcgc taaacaagga catgatttag cgacagataa cttcagtcgc taacttagcg    1800
actgaaaact tctgtcgcta agcatgaaca tgtattagcg acatacagta tgcaactgta    1860
tgtcactaaa caagaacatg atgaattagt gacggacaac ttctgtcgct aaacaacaaa    1920
aaaaaatcca tgttttagta tattgtttct cattctatca tatcatggta gtgtaaagaa    1980
tcaagaaaca agttttacat agtaacagtc tttatacatt ggagatgaag aaccatttaa    2040
gttcttcaaa atagatagat tttctaggtt acttctanaa gatatatata tggttgaggg    2100
```
tttgtatatt aaaaaaaaaa aaaaaaaa                                          2128

<210> SEQ ID NO 12
<211> LENGTH: 567
<212> TYPE: PRT
<213> ORGANISM: Solanum tuberosum

<400> SEQUENCE: 12

Gln Gly Leu Ser Leu Ser Leu Ser Ser Gln Gln Pro Gly Phe Gly
 1               5                  10                  15

Asn Phe Thr Ala Ala Arg Glu Leu Val Ser Pro Ser Gly Ser Ala
                20                  25                  30

Ser Ala Ser Gly Ile Gln Gln Gln Gln Gln Gln Gln Ser Ile Ser
                35                  40                  45

Ser Val Pro Leu Ser Ser Lys Tyr Met Lys Ala Ala Gln Glu Leu Leu
        50                  55                  60

Asp Glu Val Val Asn Val Gly Lys Ser Met Lys Ser Thr Asn Ser Thr
65                  70                  75                  80

Asp Val Val Asn Asn Asp Val Lys Lys Ser Lys Asn Met Gly Asp
                85                  90                  95

Met Asp Gly Gln Leu Asp Gly Val Gly Ala Asp Lys Asp Gly Ala Pro
                100                 105                 110

Thr Thr Glu Leu Ser Thr Gly Glu Arg Gln Glu Ile Gln Met Lys Lys
                115                 120                 125

Ala Lys Leu Val Asn Met Leu Asp Glu Val Glu Gln Arg Tyr Arg His
                130                 135                 140

Tyr His His Gln Met Gln Ser Val Ile His Trp Leu Glu Gln Ala Ala
145                 150                 155                 160

Gly Ile Gly Ser Ala Lys Thr Tyr Thr Ala Leu Ala Leu Gln Thr Ile
                165                 170                 175

Ser Lys Gln Phe Arg Cys Leu Lys Asp Ala Ile Ile Gly Gln Ile Arg
                180                 185                 190

Ser Ala Ser Gln Thr Leu Gly Glu Glu Asp Ser Leu Gly Gly Lys Ile
                195                 200                 205

Glu Gly Ser Arg Leu Lys Phe Val Asp Asn Gln Leu Arg Gln Gln Arg
                210                 215                 220

Ala Leu Gln Gln Leu Gly Met Ile Gln His Asn Ala Trp Arg Pro Gln
225                 230                 235                 240

Arg Gly Leu Pro Glu Arg Ala Val Ser Val Leu Arg Ala Trp Leu Phe
                245                 250                 255

Glu His Phe Leu His Pro Tyr Pro Lys Asp Ser Asp Lys Met Met Leu
                260                 265                 270

Ala Lys Gln Thr Gly Leu Thr Arg Ser Gln Val Ser Asn Trp Phe Ile
                275                 280                 285

Asn Ala Arg Val Arg Leu Trp Lys Pro Met Val Glu Glu Met Tyr Leu
                290                 295                 300

Glu Glu Ile Lys Glu His Glu Gln Asn Gly Leu Gly Gln Glu Lys Thr
305                 310                 315                 320

Ser Lys Leu Gly Glu Gln Asn Glu Asp Ser Thr Thr Ser Arg Ser Ile
                325                 330                 335

Ala Thr Gln Asp Lys Ser Pro Gly Ser Asp Ser Gln Asn Lys Ser Phe
                340                 345                 350

Val Ser Lys Gln Asp Asn His Leu Pro Gln His Asn Pro Ala Ser Pro
                355                 360                 365

```
Met Pro Asp Val Gln Arg His Phe His Thr Pro Ile Gly Met Thr Ile
        370                 375                 380

Arg Asn Gln Ser Ala Gly Phe Asn Leu Ile Gly Ser Pro Glu Ile Glu
385                 390                 395                 400

Ser Ile Asn Ile Thr Gln Gly Ser Pro Lys Lys Pro Arg Asn Asn Glu
                405                 410                 415

Met Leu His Ser Pro Asn Ser Ile Pro Ser Ile Asn Met Asp Val Lys
                420                 425                 430

Pro Asn Glu Glu Gln Met Ser Met Lys Phe Gly Asp Asp Arg Gln Asp
            435                 440                 445

Arg Asp Gly Phe Ser Leu Met Gly Gly Pro Met Asn Phe Met Gly Gly
        450                 455                 460

Phe Gly Ala Tyr Pro Ile Gly Glu Ile Ala Arg Phe Ser Thr Glu Gln
465                 470                 475                 480

Phe Ser Ala Pro Tyr Ser Thr Ser Gly Thr Val Ser Leu Thr Leu Gly
                485                 490                 495

Leu Pro His Asn Glu Asn Leu Ser Met Ser Ala Thr His His Ser Phe
                500                 505                 510

Leu Pro Ile Pro Thr Gln Asn Ile Gln Ile Gly Ser Glu Pro Asn His
            515                 520                 525

Glu Phe Gly Ser Leu Asn Thr Pro Thr Ser Ala His Ser Thr Ser Ser
        530                 535                 540

Val Tyr Glu Thr Phe Asn Ile Gln Asn Arg Lys Arg Phe Ala Ala Pro
545                 550                 555                 560

Leu Leu Pro Asp Phe Val Ala
                565

<210> SEQ ID NO 13
<211> LENGTH: 2065
<212> TYPE: DNA
<213> ORGANISM: Solanum tuberosum

<400> SEQUENCE: 13
atctccaagt aaaaggtta ttgagaaaag taacacagat ggcgacttat tttcctagtc      60
caaacaatca aagagatgct gatcagacat ttcaatattt taggcaatct ttgcctgagt     120
cttattcaga agcttcaaat gctccagaaa acatgatggt attcatgaac tattcttctt     180
ctggggcata ttcagatatg ttgacgggta cttcccaaca acaacacaac tgcatcgata     240
tcccatctat aggagccacg cctttcaaca catcccaaca agaaatattg tcaaatcttg     300
gaggatcgca gatggggatt caggattttt cttcatggag agatagcaga aatgagatgc     360
tagctgataa tgtctttcaa gttgcacaaa atgtgcaggg tcaaggatta tccctcagtc     420
ttggctccaa tataccatct ggaattggaa tttcacatgt ccaatctcag aatcctaacc     480 aagtggcgg ttttaacatg tcctttggag atggtgataa ttcccaacca aaagaacaaa     540
gaaatgcaga ttatttcct ccggataatc ctggaaggga cttggatgct atgaaagggt     600
ataattctcc atatggtacg tcgagtattg caaggaccat tcccagctcg aagtatttga     660
aagcagctca atatttgctt gatgaggttg ttagtgtcag aaaggccatc aaggagcaaa     720
attctaagaa agagttgaca aaggattcca gagagtctga tgtggactcg aaaaatatat     780
catcagatac tcctgcaaat gggggttcaa atcctcatga gtccaaaaac aaccaaagtg     840
aactttcacc taccgagaag caagaagtgc agaacaaact ggccaaactt ctgtcaatgc     900
tggatgagat tgatagaagg tacagacaat attatcatca gatgcaaata gtggtttcat     960
```

-continued

```
catttgatgt ggtagctgga gaaggagcag ctaaaccata cacagctctt gctctccaga    1020
caatttcccg acacttccgt tgcttgcgtg atgcaatctg cgatcagatt cgagcatcac    1080
gaagaagtct tggagagcaa gatgcttcag aaaacagcaa agcgattgga atatcacgcc    1140
tgcgttttgt ggatcatcat attagacagc agagagccct gcagcagctt ggtatgatgc    1200
aacaacatgc ctggaggcct cagaggggat tgcctgaaag ctctgtttca gttttgcgtg    1260
cttggctctt tgagcacttt cttcatccct acccgaaaga ttctgacaaa attatgctag    1320
caaggcaaac tggcttaacg agaagtcagg tatcaaattg gttcataaat gcacgggtgc    1380
gtctttggaa acccatggtt gaggaaatgt acaagaaga ggctggtgat gctaaaatag    1440
actcaaattc ttcatcggat gttgccccca gacttgcaac aaaagactca aaagttgaag    1500
aaagaggaga attgcaccag aatgcagctt cagaatttga gcagtacaat agtggccaaa    1560
tcctggagtc aaaatctaac catgaagctg atgtagaaat ggagggagca agtaatgcag    1620
aaactcaaag tcaatctgga atggaaaacc aaacaggcga accctgcct gctatggata    1680 attgcaccct ttttcaggac gcatttgttc aaagcaacga tagattctca gaatttggta    1740
gttttggaag tggaaatgta ctacccaatg gagtttcact tacattgggg ctgcagcaag    1800
gtgaaggaag caacctacct atgtccatcg aaactcacgt tagttatgta ccattaaggg    1860
cagatgacat gtatagtaca gcacctacta ctatggtccc tgaaacagca gaattcaact    1920
gcttggattc tgggaatagg cagcaaccat tttggctcct accatctgct acatgatttt    1980
gtatgtgttg tagaattaaa ctgcaagttt tgagtacatc aacattcatc ttcaaaaaaa    2040
aaaaaaaaaa aaaaaaaaaa aaaaa                                          2065
```

<210> SEQ ID NO 14
<211> LENGTH: 645
<212> TYPE: PRT
<213> ORGANISM: Solanum tuberosum

<400> SEQUENCE: 14

```
Met Ala Thr Tyr Phe Pro Ser Pro Asn Asn Gln Arg Asp Ala Asp Gln
 1               5                  10                  15

Thr Phe Gln Tyr Phe Arg Gln Ser Leu Pro Glu Ser Tyr Ser Glu Ala
             20                  25                  30

Ser Asn Ala Pro Glu Asn Met Met Val Phe Met Asn Tyr Ser Ser Ser
         35                  40                  45

Gly Ala Tyr Ser Asp Met Leu Thr Gly Thr Ser Gln Gln Gln His Asn
     50                  55                  60

Cys Ile Asp Ile Pro Ser Ile Gly Ala Thr Pro Phe Asn Thr Ser Gln
 65                  70                  75                  80

Gln Glu Ile Leu Ser Asn Leu Gly Gly Ser Gln Met Gly Ile Gln Asp
             85                  90                  95

Phe Ser Ser Trp Arg Asp Ser Arg Asn Glu Met Leu Ala Asp Asn Val
            100                 105                 110

Phe Gln Val Ala Gln Asn Val Gln Gly Gln Gly Leu Ser Leu Ser Leu
        115                 120                 125

Gly Ser Asn Ile Pro Ser Gly Ile Gly Ile Ser His Val Gln Ser Gln
    130                 135                 140

Asn Pro Asn Gln Gly Gly Gly Phe Asn Met Ser Phe Gly Asp Gly Asp
145                 150                 155                 160

Asn Ser Gln Pro Lys Glu Gln Arg Asn Ala Asp Tyr Phe Pro Pro Asp
                165                 170                 175
```

-continued

Asn Pro Gly Arg Asp Leu Asp Ala Met Lys Gly Tyr Asn Ser Pro Tyr
            180                 185                 190

Gly Thr Ser Ser Ile Ala Arg Thr Ile Pro Ser Ser Lys Tyr Leu Lys
        195                 200                 205

Ala Ala Gln Tyr Leu Leu Asp Glu Val Val Ser Val Arg Lys Ala Ile
    210                 215                 220

Lys Glu Gln Asn Ser Lys Lys Glu Leu Thr Lys Asp Ser Arg Glu Ser
225                 230                 235                 240

Asp Val Asp Ser Lys Asn Ile Ser Ser Asp Thr Pro Ala Asn Gly Gly
                245                 250                 255

Ser Asn Pro His Glu Ser Lys Asn Asn Gln Ser Glu Leu Ser Pro Thr
            260                 265                 270

Glu Lys Gln Glu Val Gln Asn Lys Leu Ala Lys Leu Leu Ser Met Leu
        275                 280                 285

Asp Glu Ile Asp Arg Arg Tyr Arg Gln Tyr His Gln Met Gln Ile
    290                 295                 300

Val Val Ser Ser Phe Asp Val Val Ala Gly Glu Gly Ala Ala Lys Pro
305                 310                 315                 320

Tyr Thr Ala Leu Ala Leu Gln Thr Ile Ser Arg His Phe Arg Cys Leu
                325                 330                 335

Arg Asp Ala Ile Cys Asp Gln Ile Arg Ala Ser Arg Arg Ser Leu Gly
            340                 345                 350

Glu Gln Asp Ala Ser Glu Asn Ser Lys Ala Ile Gly Ile Ser Arg Leu
        355                 360                 365

Arg Phe Val Asp His His Ile Arg Gln Gln Arg Ala Leu Gln Gln Leu
    370                 375                 380

Gly Met Met Gln Gln His Ala Trp Arg Pro Gln Arg Gly Leu Pro Glu
385                 390                 395                 400

Ser Ser Val Ser Val Leu Arg Ala Trp Leu Phe Glu His Phe Leu His
                405                 410                 415

Pro Tyr Pro Lys Asp Ser Asp Lys Ile Met Leu Ala Arg Gln Thr Gly
            420                 425                 430

Leu Thr Arg Ser Gln Val Ser Asn Trp Phe Ile Asn Ala Arg Val Arg
        435                 440                 445

Leu Trp Lys Pro Met Val Glu Glu Met Tyr Lys Glu Glu Ala Gly Asp
    450                 455                 460

Ala Lys Ile Asp Ser Asn Ser Ser Ser Asp Val Ala Pro Arg Leu Ala
465                 470                 475                 480

Thr Lys Asp Ser Lys Val Glu Glu Arg Gly Glu Leu His Gln Asn Ala
                485                 490                 495

Ala Ser Glu Phe Glu Gln Tyr Asn Ser Gly Gln Ile Leu Glu Ser Lys
            500                 505                 510

Ser Asn His Glu Ala Asp Val Glu Met Glu Gly Ala Ser Asn Ala Glu
        515                 520                 525

Thr Gln Ser Gln Ser Gly Met Glu Asn Gln Thr Gly Glu Pro Leu Pro
    530                 535                 540

Ala Met Asp Asn Cys Thr Leu Phe Gln Asp Ala Phe Val Gln Ser Asn
545                 550                 555                 560

Asp Arg Phe Ser Glu Phe Gly Ser Phe Gly Ser Gly Asn Val Leu Pro
                565                 570                 575

Asn Gly Val Ser Leu Thr Leu Gly Leu Gln Gln Gly Glu Gly Ser Asn
            580                 585                 590

```
Leu Pro Met Ser Ile Glu Thr His Val Ser Tyr Val Pro Leu Arg Ala
        595                 600                 605

Asp Asp Met Tyr Ser Thr Ala Pro Thr Thr Met Val Pro Glu Thr Ala
        610                 615                 620

Glu Phe Asn Cys Leu Asp Ser Gly Asn Arg Gln Gln Pro Phe Trp Leu
625                 630                 635                 640

Leu Pro Ser Ala Thr
                645

<210> SEQ ID NO 15
<211> LENGTH: 7
<212> TYPE: PRT
<213> ORGANISM: Solanum tuberosum

<400> SEQUENCE: 15

Val Ser Leu Thr Leu Gly Leu
 1               5

<210> SEQ ID NO 16
<211> LENGTH: 1383
<212> TYPE: DNA
<213> ORGANISM: Solanum tuberosum

<400> SEQUENCE: 16
```

| | | |
|---|---|---|
| gagtttctct cccttttaaa aaagaaaaaa aaaacacaac acccacttca aatatcaaac | 60 |
| aaatttctca tttgattatt tctaagtgat ttacactact ttgtattttt gtttgttttt | 120 |
| ttttagatat atatatggat gatgaaatgt atggttttca ttcaacaaga gacgattacg | 180 |
| cggataaagc tttgatgtca ccggagaatt tgatgatgca aactgagtac aacaatttcc | 240 |
| acaactatac caactcgtcc atcttgactt ctaatccgat gatgtttgga tccgatgata | 300 |
| ttcaattatc atcggaacaa actaattctt tcagtactat gactcttcaa ataatgata | 360 |
| atatttatca aattagaagt ggaaattgtg gcggaggcag tggcagtggt ggtagcagta | 420 |
| aggatcataa tgataataac aataataatg aagattatga tgaagatggt tcaaatgtta | 480 |
| tcaaggctaa aatcgtctca catccttatt atcctaaatt actcaacgct tatattgatt | 540 |
| gccaaaaggt tggagcacca gcgggtatag taaatctgct ggaagaaata aggcaacaaa | 600 |
| ctgattttcg taaaccaaac gctacttcta tatgtatagg agctgatcct gaacttgatg | 660 |
| agtttatgga aacgtattgt gatatattgt tgaagtataa gtccgatctg tctaggcctt | 720 |
| ttgatgaagc aacaacgttc ctcaacaaga ttgaaatgca actaggtaat ctttgcaaag | 780 |
| atgatggtgg tgtatcatca gatgaggagt taagttgtgg tgaggcagat gcatcaatga | 840 |
| gaagtgagga taatgaactc aaagatagac tcctacgtaa gtttggaagt catttaagta | 900 |
| gtctaaagtt ggaattttca aagaaaaaga agaaagggaa gctaccaaaa gaggcaaggc | 960 |
| aaatgttact tgcatggtgg gatgatcact ttagatggcc ttaccctacg gaggctgata | 1020 |
| agaattcact agcagaatca acaggacttg atccaaagca gatcaacaat tggtttataa | 1080 |
| atcaaaggaa gagacattgg aaaccatcag agaatatgca gttagctgtt atggataatc | 1140 |
| taagctctca gttcttctca tcagatgatt gagtttgaat ggaaattgtg aaaatactgc | 1200 |
| tcttcatttc tctttttatt atatataata tataaatagt atattttgg gaaagaaaga | 1260 |
| agttattta ttaatcaaaa tctctataaa taatggtaga gattaattaa tgttgaattc | 1320 |
| ttcttgatca tgtaaatatt caatctagct aattgtcaaa attaatgctt acctaaaaaa | 1380 |
| aaa | 1383 |

<210> SEQ ID NO 17
<211> LENGTH: 345
<212> TYPE: PRT
<213> ORGANISM: Solanum tuberosum

<400> SEQUENCE: 17

```
Met Asp Asp Glu Met Tyr Gly Phe His Ser Thr Arg Asp Asp Tyr Ala
 1               5                  10                  15

Asp Lys Ala Leu Met Ser Pro Glu Asn Leu Met Met Gln Thr Glu Tyr
            20                  25                  30

Asn Asn Phe His Asn Tyr Thr Asn Ser Ser Ile Leu Thr Ser Asn Pro
        35                  40                  45

Met Met Phe Gly Ser Asp Asp Ile Gln Leu Ser Ser Glu Gln Thr Asn
    50                  55                  60

Ser Phe Ser Thr Met Thr Leu Gln Asn Asn Asp Asn Ile Tyr Gln Ile
65                  70                  75                  80

Arg Ser Gly Asn Cys Gly Gly Ser Gly Ser Gly Ser Ser Lys
                85                  90                  95

Asp His Asn Asp Asn Asn Asn Asn Glu Asp Tyr Asp Glu Asp Gly
               100                 105                 110

Ser Asn Val Ile Lys Ala Lys Ile Val Ser His Pro Tyr Tyr Pro Lys
           115                 120                 125

Leu Leu Asn Ala Tyr Ile Asp Cys Gln Lys Val Gly Ala Pro Ala Gly
       130                 135                 140

Ile Val Asn Leu Leu Glu Glu Ile Arg Gln Gln Thr Asp Phe Arg Lys
145                 150                 155                 160

Pro Asn Ala Thr Ser Ile Cys Ile Gly Ala Asp Pro Glu Leu Asp Glu
                165                 170                 175

Phe Met Glu Thr Tyr Cys Asp Ile Leu Leu Lys Tyr Lys Ser Asp Leu
            180                 185                 190

Ser Arg Pro Phe Asp Glu Ala Thr Thr Phe Leu Asn Lys Ile Glu Met
        195                 200                 205

Gln Leu Gly Asn Leu Cys Lys Asp Asp Gly Val Ser Ser Asp Glu
    210                 215                 220

Glu Leu Ser Cys Gly Glu Ala Asp Ala Ser Met Arg Ser Glu Asp Asn
225                 230                 235                 240

Glu Leu Lys Asp Arg Leu Leu Arg Lys Phe Gly Ser His Leu Ser Ser
                245                 250                 255

Leu Lys Leu Glu Phe Ser Lys Lys Lys Gly Lys Leu Pro Lys
            260                 265                 270

Glu Ala Arg Gln Met Leu Leu Ala Trp Trp Asp Asp His Phe Arg Trp
        275                 280                 285

Pro Tyr Pro Thr Glu Ala Asp Lys Asn Ser Leu Ala Glu Ser Thr Gly
    290                 295                 300

Leu Asp Pro Lys Gln Ile Asn Asn Trp Phe Ile Asn Gln Arg Lys Arg
305                 310                 315                 320

His Trp Lys Pro Ser Glu Asn Met Gln Leu Ala Val Met Asp Asn Leu
                325                 330                 335

Ser Ser Gln Phe Phe Ser Ser Asp Asp
            340                 345
```

<210> SEQ ID NO 18
<211> LENGTH: 20
<212> TYPE: DNA
<213> ORGANISM: Artificial Sequence

```
<220> FEATURE:
<223> OTHER INFORMATION: Description of Artificial Sequence:  Primer

<400> SEQUENCE: 18
aagaagaaga agaaagggaa                                              20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:  Primer

<400> SEQUENCE: 19
atgaaccagt tgttgat                                                 17

<210> SEQ ID NO 20
<211> LENGTH: 10
<212> TYPE: DNA
<213> ORGANISM: Solanum tuberosum

<400> SEQUENCE: 20
ttgacttgac                                                         10

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 21
ggatccttga agtggctctt ctct                                         24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:  Primer

<400> SEQUENCE: 22
aatctagaga cactctcttt ttcgt                                        25

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 23
ctatttgact tcacacggtt attt                                         24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 24
aaataaccgt gtgaagtcaa atag                                         24

<210> SEQ ID NO 25
```

-continued

```
<211> LENGTH: 8
<212> TYPE: DNA
<213> ORGANISM: Solanum tuberosum

<400> SEQUENCE: 25 tgacagst                                                              8

<210> SEQ ID NO 26
<211> LENGTH: 9
<212> TYPE: DNA
<213> ORGANISM: Solanum tuberosum

<400> SEQUENCE: 26 tgacttgac                                                             9

<210> SEQ ID NO 27
<211> LENGTH: 9
<212> TYPE: DNA
<213> ORGANISM: Solanum tuberosum

<400> SEQUENCE: 27 tgaswtgac                                                             9

<210> SEQ ID NO 28
<211> LENGTH: 10
<212> TYPE: DNA
<213> ORGANISM: Solanum tuberosum

<400> SEQUENCE: 28
tgattgacag                                                           10

<210> SEQ ID NO 29
<211> LENGTH: 290
<212> TYPE: DNA
<213> ORGANISM: Solanum tuberosum

<400> SEQUENCE: 29
tgatatatat aatttgcagg taaatcagct tgaaattaca tcatgacagg tcttgaataa     60
aagaagggga gttgagattt agtgatcata taaatatgta taggtagaaa ttttagttag    120
tatatatagg ttatacttct agtttcttaa tgaagataca agttttgttg ttattttgt     180 attgaggtaa ctagctagct tggattattt aaagttggtg catgcaacta agaagaaga    240 aaaaataatc tatatatgca aactacagta tattgtaaat tttgtgcttc               290

<210> SEQ ID NO 30
<211> LENGTH: 134
<212> TYPE: DNA
<213> ORGANISM: Solanum tuberosum

<400> SEQUENCE: 30
ttaatacgta ttttccccat agtaattaat taaaactgaa tttgcttgag ctcatcataa     60
tttatgcatt gcttttttgtt ataagaaatt ccataaatta gctttgtgtt aaaaaaaaaa   120
aaaaaaaaaa aaaa                                                      134

<210> SEQ ID NO 31
<211> LENGTH: 130
<212> TYPE: DNA
<213> ORGANISM: Solanum tuberosum

<400> SEQUENCE: 31
tttggctggt taaaaaatga cagagattct tcatttttgga ccttattata tactctaatt    60
```

-continued

```
ttaatatata ttggtgatga atgatgataa aaaaaaaaaa aaaaaaaaaa aaaaaaaaaa      120
aaaaaaaaaa                                                             130

<210> SEQ ID NO 32
<211> LENGTH: 76
<212> TYPE: DNA
<213> ORGANISM: Solanum tuberosum

<400> SEQUENCE: 32
ttaagatagt gtattcaaac actgctacat aaattatgat tttatatata tatatattgt       60
catccgatta gtttat                                                       76

<210> SEQ ID NO 33
<211> LENGTH: 424
<212> TYPE: DNA
<213> ORGANISM: Solanum tuberosum
<220> FEATURE:
<221> NAME/KEY: unsure
<222> LOCATION: (374)
<223> OTHER INFORMATION: N at position 374 is a, c, t, or g

<400> SEQUENCE: 33
tcacaaaaac aaaaacaggt tttggcaaca gacaaacttc tgtcgctaaa caaggacatg       60
atttagcgac agataacttc agtcgctaac ttagcgactg aaaacttctg tcgctaagca      120
tgaacatgta ttagcgacat acagtatgca actgtatgtc actaaacaag aacatgatga      180
attagtgacg gacaacttct gtcgctaaac aacaaaaaaa aatccatgtt ttagtatatt      240
gtttctcatt ctatcatatc atggtagtgt aaagaatcaa gaaacaagtt ttacatagta      300 acagtctttta tacattggag atgaagaacc atttaagttc ttcaaaatag atagattttc      360
taggttactt ctanaagata tatatatggt tgagggtttg tatattaaaa aaaaaaaaaa      420
aaaa                                                                   424

<210> SEQ ID NO 34
<211> LENGTH: 89
<212> TYPE: DNA
<213> ORGANISM: Solanum tuberosum

<400> SEQUENCE: 34
ttttgtatgt gttgtagaat taaactgcaa gttttgagta catcaacatt catcttcaaa       60
aaaaaaaaaa aaaaaaaaaa aaaaaaaaa                                        89
```

MOBILE RNA ACTS AS A SIGNAL TO REGULATE PLANT GROWTH AND DEVELOPMENT

This application claims the benefit of U.S. Provisional Patent Application Ser. No. 60/584,562, filed Jul. 1, 2004.

This invention was made with government support under grant numbers 6269590-0344850 and 0305647 awarded by NSF, and grant numbers 2002-31100-06019 and 2001-31100-06019 awarded by USDA/CSREES. The government has certain rights in this invention.

FIELD OF THE INVENTION

The present invention relates to isolated BEL transcription factors from *Solanum tuberosum*, a method of enhancing tuber development in plants, and methods of regulating flowering and growth in plants. The present invention also relates to a method of screening a biomolecule for its ability to assist in mediating long-distance movement of a mobile RNA in a plant.

BACKGROUND OF THE INVENTION

The primary developmental events of plants originate from the shoot apical meristem (SAM) (Clark, "Organ Formation at the Vegetative Shoot Meristem," *Plant Cell* 9:1067-1076 (1997); Kerstetter et al., "Shoot Meristem Formation in Vegetative Development," *Plant Cell* 9:1001-1010 (1997)). The shoot apical meristem (SAM) is responsible for the formation of vegetative organs such as leaves, and may undergo a phase change to form the inflorescence or floral meristem. Many of these events are controlled at the molecular level by transcription factors. Transcription factors (TFs) are proteins that act as developmental switches by binding to the DNA (or to other proteins that bind to the DNA) of specific target genes to modulate their expression. An important family of TFs involved in regulating the developmental events in apical meristems is the knox (knotted-like homeobo) gene family (Reiser et al., "Knots in the Family Tree Evolutionary Relationships and Functions of Knox Homeobox Genes," *Plant Mol Biol* 42:151-166 (2000)). Knox genes have been isolated from several plant species (reviewed in Reiser et al., "Knots in the Family Tree: Evolutionary Relationships and Functions of knox Homeobox Genes," *Plant Mol. Biol.* 42:151-166 (2000)) and can be divided into two classes based on expression patterns and sequence similarity (Kerstetter et al., "Sequence Analysis and Expression Patters Divide the Maize knotted1-like Homeobox Genes into Two Classes," *Plant Cell* 6:1888-1887 (1994)). Class I knox genes have high similarity to the kn1 homeodomain and generally have a meristem-specific mRNA expression pattern. Class II knox genes usually have a more widespread expression pattern.

Knox genes belong to the group of TFs known as the TALE superclass (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997)). These TFs are distinguished by a very high level of sequence conservation in the DNA-binding region, designated the homeodomain, and consisting of three α-helices similar to the bacterial helix-loop-helix motif (Kerstetter et al., "Sequence Analysis and Expression Patterns Divide the Maize knotted1-like Homeobox Genes into Two Classes," *Plant Cell* 6:1877-1887 (1994)). The third helix, the recognition helix, is involved in DNA-binding (Mann et al., "Extra Specificity From extradenticle: the Partnership Between HOX and PBX/EXD Homeodomain Proteins," *Trends in Genet.* 12:258-262 (1996)). TALE TFs contain a three amino acid loop extension (TALE), proline-tyrosine-proline, between helices I and II in the homeodomain, that has been implicated in protein interactions (Passner et al., "Structure of DNA-Bound Ultrabithorax-Extradenticle Homeodomain Complex," *Nature* 397:714-719 (1999)). There are numerous TFs from plants and animals in the TALE superclass and the two main groups in plants are the KNOX and BEL types (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997)). Related genes in animal systems play an important role in regulating gene expression.

Expression patterns and functional analysis of mutations support the involvement of knox genes in specific developmental processes of the shoot apical meristem. Kn1 from maize, the first plant homeobox gene to be discovered (Vollbrecht et al., "The Developmental Gene Knotted-1 is a Member of a Maize Homeobox Gene Family," *Nature* 350:241-243 (1991)), is involved in maintenance of the shoot apical meristem and is implicated in the switch from indeterminate to determinate cell fates (Chan et al., "Homeoboxes in Plant Development," *Biochim Biophys Acta* 1442:1-19 (1998); Kerstetter et al., "Loss-of-Function Mutations in the Maize Homeobox Gene, knotted1, are Defective in Shoot Meristem Maintenance," *Development* 124:3045-3054 (1997); Clark et al., The CLAVATA and SHOOT MERISTEMLESS Loci Competitively Regulate Meristem Activity in *Arabidopsis*," *Development* 122:1567-1575 (1996)). Transcripts of kn1 in maize (Jackson et al., "Expression of Maize KNOTTED1 Related Homeobox Genes in the Shoot Apical Meristem Predicts Patterns of Morphogenesis in the Vegetative Shoot," *Development* 120:405-413 (1994)), OSH1 in rice (Sentoku et al., "Regional Expression of the Rice KN1-type Homeobox Gene Family During Embryo, Shoot, and Flower Development," *Plant Cell* 11:1651-1663 (1999)), and NTH15 in tobacco (Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997)) were localized by in situ hybridization to undifferentiated cells of the corpus and the developing stem, but were not detected in the tunica or leaf primordia. Overexpression of kn1 in *Arabidopsis* (Lincoln et al., "A knotted1-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994)) and in tobacco (Sinha et al., "Overexpression of the Maize Homeobox Gene, KNOTTED-1, Causes a Switch From Determinate to Indeterminate Cell Fates," *Genes Dev* 7:787-795 (1993)), resulted in plants with altered leaf morphologies including lobed, wrinkled or curved leaves with shortened petioles and decreased elongation of veins. Plants were reduced in size and showed a loss of apical dominance. In plants with a severe phenotype, ectopic meristems formed near the veins of leaves indicating a reversion of cell fate back to the indeterminate state (Sinha et al., "Overexpression of the Maize Homeobox Gene, KNOTTED-1, Causes a Switch From Determinate to Indeterminate Cell Fates," *Genes Dev* 7:787-795 (1993)). Overexpression of OSH1 or NTH15 in tobacco resulted in altered morphologies similar to the 35S-kn1 phenotype (Sato et al., "Abnormal Cell Divisions in Leaf Primordia Caused by the Expression of the Rice Homeobox Gene OSH1 Lead to Altered Morphology of Leaves in Transgenic Tobacco," *Mol Gen Genet.* 251:13-22 (1996); Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997)).

Alterations in leaf and flower morphology in 35S-NTH15 or OSH1 transgenic tobacco were accompanied by changes in hormone levels. Whereas levels of all the hormones measured were changed slightly, both gibberellin and cytokinin levels were dramatically altered (Kusaba et al., "Alteration of Hormone Levels in Transgenic Tobacco Plants Overexpressing the Rice Homeobox Gene OSH1," *Plant Physiol* 116:471-476 (1998); Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997)). RNA blot analysis revealed that the accumulation of GA 20-oxidase1 mRNA was reduced several fold in transgenic plants (Kusaba et al., "Decreased $GA_1$ Content Caused by the Overexpression of OSH1 is Accompanied by Suppression of GA 20-oxidase Gene Expression," *Plant Physiol* 117:1179-1184 (1998); Tanaka-Ueguchi et al., "Overexpression of a Tobacco Homeobox Gene, NTH15, Decreases the Expression of a Gibberellin Biosynthetic Gene Encoding GA 20-oxidase," *Plant J* 15:391-400 (1998)). A KNOX protein of tobacco binds to specific elements in regulatory regions of the GA 20-oxidase1 gene of tobacco to repress its activity (Sakamoto et al., KNOX Homeodomain Protein Directly Suppresses the Expression of a Gibberellin Biosynthesis Gene in the Tobacco Shoot Apical Meristem," *Genes Dev* 15:581-590 (2001)). GA 20-oxidase is a key enzyme in the GA biosynthetic pathway necessary for the production of the physiologically inactive $GA_{20}$ precursor of active $GA_1$ (Hedden et al., "Gibberellin Biosynthesis: Enzymes, Genes and Their Regulation," *Annu Rev Plant Physiol Plant Mol Biol* 48:431-460 (1997)). $GA_1$ and other active GA isoforms are important regulators of stem elongation, the orientation of cell division, the inhibition of tuberization, flowering time, and fruit development (Jackson et al., "Control of Tuberisation in Potato by Gibberellins and Phytochrome," *B. Physiol Plant* 98:407-412 (1996); Hedden et al., "Gibberellin Biosynthesis: Enzymes, Genes and Their Regulation," *Annu Rev Plant Physiol Plant Mol Biol* 48:431-460 (1997); Rebers et al., "Regulation of Gibberellin Biosynthesis Genes During Flower and Early Fruit Development of Tomato," *Plant J* 17:241-250 (1999)).

Another plant homeobox gene family that is closely related to the knox genes is the BEL (BELL) family (Chan et al., "Homeoboxes in Plant Development," *Biochim Biophys Acta* 1442:1-19 (1998); Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997)). BEL TFs have been implicated in flower and fruit development (Reiser et al., The BELL1 Gene Encodes a Homeodomain Protein Involved in Pattern Formation in the *Arabidopsis* Ovule Primordium," *Cell* 83:735-742 (1995); Dong et al., "MDH1: an Apple Homeobox Gene Belonging to the BEL1 Family," *Plant Mol Biol* 42:623-633 (2000)). Genetic analysis of BEL1 in *Arabidopsis* showed that expression of this TF regulated the development of ovule integuments and overlaps the expression of AGAMOUS (Ray et al., "*Arabidopsis* Floral Homeotic Gene BELL (BEL1) Controls Ovule Development Through Negative Regulation of AGAMOUS Gene (AG)," *Proc Natl Acad Sci USA* 91:5761-5765 (1994); Reiser et al., The BELL1 Gene Encodes a Homeodomain Protein Involved in Pattern Formation in the *Arabidopsis* Ovule Primordium," *Cell* 83:735-742 (1995); Western et al., "BELL1 and AGAMOUS Genes Promote Ovule Identity in *Arabidopsis thaliana*," *Plant J* 18:329-336 (1999)). In COP1 mutants, the photoinduced expression of ATH1, another BEL TF of *Arabidopsis*, was elevated, indicating a possible role in the signal transduction pathway downstream of COP1 (Quaedvlieg et al., "The Homeobox Gene ATH1 of *Arabidopsis* is Depressed in the Photomorphogenic Mutants cop1 and det1," *Plant Cell* 7:117-129 (1995)).

Plants must maintain a great deal of flexibility during development to respond to environmental and developmental cues. Responses to these signals, which include day length, light quality or quantity, temperature, nutrient and hormone levels, are coordinated within the meristem (Kerstetter et al., "Shoot Meristem Formation in Vegatative Development," *Plant Cell* 9:1001-1010 (1997)). In potato, there is a specialized vegetative meristem called the stolon meristem that develops as a horizontal stem and under inductive conditions will form the potato tuber (Jackson, "Multiple Signaling Pathways Control. Tuber Induction in Potato," *Plant Physiol.* 119:1-8 (1999); Fernie et al., "Molecular and Biochemical Triggers of Potato Tuber Development," *Plant Physiol.* 127: 1459-1465 (2001)). Potato offers an excellent model system for examining how vegetative meristems respond to external and internal factors to control development at the molecular level. In model tuberization systems, synchronous tuber formation occurs under inductive conditions and shoot or stolon formation occurs under noninductive conditions. The cellular and biochemical processes that occur in these model systems have been examined extensively (Vreugdenhil et al., "Initial Anatomical Changes Associated with Tuber Formation on Single-Node Potato (*Solanum tuberosum* L.) Cuttings: A Re-evaluation," *Ann. Bot.* 84:675-680 (1999); Xu et al., "The Role of Gibberellin, Abscisic Acid, and Sucrose in the Regulation of Potato Tuber Formation *In vitro*," *Plant Physiol.* 117:575-584 (1998); Hannapel, "Characterization of Early Events of Potato Tuber Development," *Physiol. Plant* 83:568-573 (1991); Wheeler et al., "Comparison of Axillary Bud Growth and Patatin Accumulation in Potato Leaf Cuttings as Assays for Tuber Induction," *Ann. Bot.* 62:25-30 (1988)). In addition to being good systems to examine integration of signals at the meristem, understanding the molecular processes controlling tuberization in potato is important. Potato is the fourth largest crop produced in the world, ranking after maize, rice, and wheat, and is a major nutritional source in many countries (Jackson, "Multiple Signaling Pathways Control Tuber Induction in Potato," *Plant Physiol.* 119:1-8 (1999); Fernie et al., "Molecular and Biochemical Triggers of Potato Tuber Development," *Plant Physiol.* 127:1459-1465 (2001)); therefore, research focusing on the process of tuber initiation and development is very important.

Tuber formation in potatoes (*Solanum tuberosum* L.) is a complex developmental process that requires the interaction of environmental, biochemical, and genetic factors. Several important biological processes like carbon partitioning, signal transduction, and meristem determination are involved (Ewing et al., "Tuber Formation in Potato: Induction, Initiation and Growth," *Hort. Rev.* 14:89-198 (1992)). Under conditions of a short-day photoperiod and cool temperature, a transmissible signal is activated that initiates cell division and expansion and a change in the orientation of cell growth in the subapical region of the stolon tip (Ewing et al., "Tuber Formation in Potato: Induction, Initiation and Growth," *Hort. Rev.* 14:89-198 (1992); Xu et al., "Cell Division and Cell Enlargement During Potato Tuber Formation," *J. Expt. Bot.* 49:573-582 (1998)). In this signal transduction pathway, perception of the appropriate environmental cues occurs in leaves and is mediated by phytochrome and gibberellins (van den Berg et al., "Morphology and (14C) gibberellin A-12 Metabolism in Wild-Type and Dwarf *Solanum tuberosum* ssp. *Andigena* Grown Under Long and Short Photoperiods,"

J. Plant Physiol. 146:467-473 (1995); Jackson et al., "Phytochrome B Mediates the Photoperiodic Control of Tuber Formation in Potato," Plant J. 9:159-166 (1996); Jackson et al., "Control of Tuberisation in Potato by Gibberellins and Phytochrome," B. Physiol Plant 98:407-412 (1996)). Tuber development at the stolon tip is comprised of biochemical and morphological processes. Both are controlled by differential gene expression (Hannapel, "Characterization of Early Events of Potato Tuber Development," Physiol. Plant 83:568-573 (1991); Bachem et al., "Analysis of Gene Expression During Potato Tuber Development," Plant J. 9:745-753 (1996); Macleod et al., "Characterisation of Genes Isolated from a Potato Swelling Stolon cDNA Library," Pot. Res. 42:31-42 (1999)) with most of the work focusing on the biochemical processes, including starch synthesis (Abel et al., "Cloning and Functional Analysis of a cDNA Encoding a Novel 139 kDa Starch Synthase from Potato (Solanum tuberosum L.)," Plant J. 10:981-991 (1996); Preiss, "ADP-glucose Pyrophosphorylase: Basic Science and Applications in Biotechnology," Biotech. Annu. Rev. 2:259-279 (1996); Geigenberger et al., "Overexpression of Pyrophosphatase Leads to Increased Sucrose Degradation and Starch Synthesis, Increased Activities of Enzymes for Sucrose-Starch Interconversions, and Increased Levels of Nucleotides in Growing Potato Tubers," Planta 205:428-437 (1998)) and storage protein accumulation (Mignery et al., "Isolation and Sequence Analysis of cDNAs for the Major Potato Tuber Protein, Patatin," Nucl. Acid Res. 12:7989-8000 (1984); Hendriks et al., "Patatin and Four serine Protease Inhibitor Genes are Differentially Expressed During Potato Tuber Development," Plant Mol. Biol. 17:385-394 (1991); Suh et al., "Proteinase-Inhibitor Activity and Wound-Inducible Expression of the 22-kDa Potato-Tuber Proteins," Planta 184:423-430 (1991)).

Much less is known about the morphological controls of tuberization, although it is clear that phytohormones play a prominent role (Koda et al., "Potato Tuber-Inducing Activities of Jasmonic Acid and Related Compounds," Phytochemistry 30:1435-1438 (1991); Xu et al., "The Role of Gibberellin, Abscisic Acid, and Sucrose in the Regulation of Potato Tuber Formation In vitro," Plant Physiol. 117:575-584 (1998), Sergeeva et al., "Tuber Morphology and Starch Accumulation are Independent Phenomena: Evidence from ipt-transgenic Potato Lines," Physiol. Plant 108:435-443 (2000)). Gibberellins (GA), in particular, play an important role in regulating tuber development. High levels of GA are correlated with the inhibition of tuberization, whereas low levels are associated with the induction of tuber formation (Jackson et al., "Control of Tuberisation in Potato by Gibberellins and Phytochrome," B. Physiol Plant 98:407-412 (1996); Xu et al., "The Role of Gibberellin, Abscisic Acid, and Sucrose in the Regulation of Potato Tuber Formation In vitro," Plant Physiol. 117:575-584 (1998)). Specific genes, such as lipoxygenases (Kolomiets et al., "Lipoxygenase is Involved in the Control of Potato Tuber Development," Plant Cell 13:613-626 (2001)) and MADS box genes (Kang et al., "Nucleotide Sequences of Novel Potato MADS-box cDNAs and their Expression in vegetative Organs," Gene 166:329-330 (1995)) that are involved in regulating tuber formation have been identified.

Three independent research groups have recently confirmed that BEL-like TFs interact via protein binding with their respective knox-types in three separate species (Bellaoui et al., "The Arabidopsis BELL1 and KNOX TALE Homeodomain Proteins Interact Through a Domain Conserved Between Plants and Animals," Plant Cell 13:2455-2470 (2001); Muiller et al., "In vitro Interactions Between Barley TALE Homeodomain Proteins Suggest a Role for Protein-Protein Associations in the Regulation of Knox Gene Function," Plant J. 27:13-23 (2001); Smith et al., "Selective Interaction of Plant Homeodomain Proteins Mediates High DNA-Binding Affinity," Proc. Nat'l. Acad. Sci. USA 99:9579-9584 (2002)), but to date, there is no published report on the function of this interaction. Moreover, nothing is known about the role of either KNOX or the BEL TFs in the regulation of development of tuberous plants, such as potato.

Plants adapt to their environment through the perception of external cues and the activation of signaling pathways. Two of the most important environmental cues to which plants respond are light quality and duration. Length of day or photoperiod is an example of an external cue that elicits developmental responses like germination, flowering, tuber formation, the onset of bud dormancy, leaf abscission, and cambial activity. Despite the significance of photoperiod in regulating growth responses, the precise signaling mechanism is unknown.

For communicating throughout the body of the organism, plants have evolved complex systems of signaling that may be transmitted in a volatile form or carried through the non-circulatory vascular system, the phloem and xylem. Signaling molecules include salts, sugars, carbohydrates, oxylipins, peptides, proteins, RNAs, and phytohormones. Little is known about this mechanism of long-distance transport in plants but exciting, innovative research is in progress (Lucas et al., "Selective Trafficking of KNOTTED1 Homeodomain Protein and its mRNA Through Plasmodesmata," Science 270:1980-1983 (1995)). A model for intracellular RNA localization in the cell has been established for a number of animal and plant systems. Subcellular RNA movement in plants and animals is mediated by a complex transport system (Okita et al., "mRNA Localization in Plants: Targeting to the Cell's Cortical Region and Beyond," Curr. Opin. Plant Biol. 5:553-559 (2002); Kloc et al, "Mechanisms of Subcellular mRNA Localization," Cell 108:533-544 (2002)). Components of this system include a large ribonucleprotein (RNP) complex, facilitated movement of this RNP along microtubule or microfilament strands, and the anchoring of the RNA at its destination. Recognition and delivery of the RNA requires "zip code" elements and zip code proteins (Jansen, "mRNA Localization: Message on the Move," Nat. Rev. Mol. Cell. Biol. 2:247-256 (2001)).

RNA transport in plants. Phloem sap contains a unique set of transcripts and proteins (Hoffmann-Benning et al., "Comparison of Peptides in the Phloem Sap of Flowering and Non-Flowering Perilla and Lupine Plants Using Microbore HPLC Followed by Matrix-Assisted Laser Desorption/Ionization Time-of-Flight Mass Spectrometry," Planta 216:140-147 (2002)). Analysis of pumpkin sap revealed the presence of an enriched, diverse population of RNAs. From a sap cDNA library, RNAs for transcription factors, cell cycle proteins, sucrose transporters, and proteins involved in intracellular vesicular trafficking and defense were identified (Ruiz-Medrano et al., "Phloem Long-Distance Transport of CmNACPmRNA: Implications for Supracellular Regulation in Plants," Development 126:4405-4419 (1999)). Three of these RNAs present in phloem sap moved selectively into apical tissues of heterografted scions. Two were transcription factors and one was a putative phloem transport protein. Experiments with phloem sap also showed that some ingredient in phloem exudate protected RNAs from degradation (Ruiz-Medrano et al., "Phloem Long-Distance Transport of CmNACPmRNA: Implications for Supracellular Regulation in Plants," Development 126:4405-4419 (1999)). These studies clearly establish the presence of a system for the delivery of specific transcripts through the phloem to the shoot apical meristem.

There are numerous other examples of long-distance RNA movement in plants. Plant RNA viruses produce diverse proteins that facilitate cell-to-cell and long-distance movement by a variety of mechanisms (Gilbertson & Lucas, "How Do Viruses Traffic on the Vascular Highway?," *Trends Plant Science* 1:260-268 (1996)). The RNA of sucrose transporter1 moves from companion cells through the plasmodesmata into the adjacent sieve elements (Kühn et al., "Macromolecular Trafficking Indicated by Localization and Turnover of Sucrose Transporters in Enucleate Sieve Elements," *Science* 275:1298-1300 (1997)). There are several experimental examples demonstrating that cosuppression of expression mediated by systemic acquired gene silencing involves RNA transport within the phloem (Sonoda et al., "Grafi Transmission of Post-Transcriptional Gene Silencing: Target Specificity for RNA Degradation is Transmissible Between Silenced and Non-Silenced Plants, but not Between Silenced Plants," *Plant J.* 21:1-8 (2000); Crete et al., "Graft Transmission of Induced and Spontaneous Post-Transcriptional Silencing of Chitinase Genes," *Plant J.* 28:493-501 (2001)). This post-transcriptional epigenetic process is mediated by the sequence-specific degradation of targeted mRNAs (Meins, "RNA Degradation and Models for Post-Transcriptional Gene-Silencing," *Plant Mol. Biol.* 43:261-273 (2000)).

Experiments involving heterografting showed that specific RNAs can move long distances through the phloem. Scions of cucumber grafted onto pumpkin stocks (lower portion of the graft) provided direct evidence that specific pumpkin mRNAs were translocated through the heterograft (Ruiz-Medrano et al., "Phloem Long-Distance Transport of CmNACPmRNA: Implications for Supracellular Regulation in Plants," *Development* 126:4405-4419 (1999); Xoconostle-Cazares et al., "Plant Paralog to Viral Movement Protein that Potentiates Transport of mRNA into the Phloem," *Science* 283:94-98 (1999)). The discovery of the RNA-binding protein, CmPP16, provided additional support for the long-distance transport of RNA in pumpkin (Xoconostle-Cazares et al., "Plant Paralog to Viral Movement Protein that Potentiates Transport of mRNA into the Phloem," *Science* 283:94-98 (1999)). Microinjection and grafting studies demonstrated that CMPP16 moved from cell to cell, mediated the transport of RNA, and moved together with its mRNA into the sieve elements of scion tissue. One of the best examples of long-distance movement of RNA was reported for a KNOTTED-1-like homeobox gene of tomato, LeT6 (Kim et al., "Developmental Changes Due to Long-Distance Movement of a Homeobox Fusion Transcript in Tomato," *Science* 293:287-289 (2001)). Heterografts were made with overexpression mutants exhibiting the characteristic Mouse-ear phenotype of KNOX gain-of-function mutants (Parnis et al., "The Dominant Developmental Mutants of Tomato, Mouse-ear and Curl, are Associated with Distinct Modes of Abnormal Transcriptional Regulation of a Knotted Gene," *Plant Cell* 9:2143-2158 (1997)). The transport of this Knox RNA occurred in an acropetal direction and induced developmental changes in the wild-type scion consistent with the Mouse-ear phenotype. These results confirmed that the translocated RNA was functional. This mobile RNA accumulated in patterns specific to those observed for the native RNA, indicating that transport, and not promoter activity, may determine spatial expression. Remarkably, there are several examples of transcription factors, functional in meristems, with RNA that can be transported from cell to cell or over long distances (Kim et al., "Developmental Changes Due to Long-Distance Movement of a Homeobox Fusion Transcript in Tomato," *Science* 293: 287-289 (2001); Lucas et al., "Selective Trafficking of KNOTTED1 Homeodomain Protein and its mRNA Through Plasmodesmata," *Science* 270:1980-1983 (1995); Ruiz-Medrano et al., "Phloem Long-Distance Transport of CmNACP-mRNA: Implications for Supracellular Regulation in Plants," *Development* 126:4405-4419 (1999); Haywood et al., "Plasmodesmata: Pathways for Protein and Ribonucleoprotein Signaling," *Plant Cell Supplement* 303-325 (2002))

Mechanisms of transport. One important issue is to determine how RNAs can be recognized and delivered to specific sites in the plant body. Models established in animal systems may apply for phloem transport as well. Transported RNAs contain elements or structures in their RNA sequence that are recognized by RNA binding proteins (RBP). These recognition motifs are designated "zip codes."

Zip codes can be short segments with a defined nucleotide sequence (Chan et al, "Fatvg Encodes a New Localized RNA that Uses a 25-Nucleotide Element (FVLE1) to Localize to the Vegetal Cortex of *Xenopus* Oocytes," *Development* 126: 4943-4953 (1999)), repeated short signals, such as in the case of Vg1 or β-actin mRNA (Deshler et al., "Localization of *Xenopus* Vg1 mRNA by Vera Protein and the Endoplasmic Reticulum," *Science* 276: 1128-1131 (1997); Kislauskis et al., "Sequences Responsible for Intracellular Localization of β-Actin Messenger RNA Also Affect Cell Phenotype," *J. Cell Biol.* 127:441-451 (1994)), or stem-loop structures (Serano et al., "Small Predicted Stem-Loop Structure Mediates Oocyte Localization of *Drosophila* K10 Mrna," *Development* 121: 3809-3818 (1995); Chartrand et al., "Structural Elements Required For the Localization of ASH1 mRNA and of a Green Fluorescent Protein Reporter Particle In vivo," *Curr Biol* 9: 333-336. (1999); Ramos et al., "RNA Recognition by a Staufen Double-Stranded RNA-Binding Domain," *EMBO J.* 19:997-1009 (2000)). ASH1 mRNA of yeast is a stem-loop zip code element that lies in both the coding region (E1, E2) and in the 3' UTR (E3) (Gonzalez et al., "ASH I mRNA Localization in Yeast Involves Multiple Secondary Structural Elements and Ashl Protein Myelin Basis Protein mRNA," *J. Cell Biol.* 138:1077-1087 (1997)). ASH1 protein acts as a determinant to induce specific cell fates. Consequently, its localization in the cell is critical.

Localized mRNAs can contain more than one zip code that may have overlapping functions, or act in sequential targeting steps. Various maternal transcripts in *Drosophila* and *Xenopus* oocytes are localized through sequential events (Lasko, "RNA Sorting in *Drosophila*," *FASEB J.* 13:421-433 (1999); Zhou et al., "Localization of Xcat-2 RNA, a Putative Germ Plasm Component, to the Mitochondrial Cloud in *Xenopus* Stage I Oocytes," *Development* 122:2947-2953 (1996)). For example, the cell-fate determinant bicoid of *Drosophila* harbors a localization element in the 3' UTR with a modular architecture. Bicoid mRNA undergoes several sequential transport steps, each involving different, partially overlapping regions in the highly structured 3' UTR.

Zip Code Proteins. The cell interprets the information in a localization zip code via specific mRNA-binding proteins called zip code proteins. Although more than twenty-five zip codes have been characterized, zip-code-binding proteins are known for fewer than half. There are several examples of these types in animals: ZBP-1 (actin zip-code-binding protein) binds to the β-actin localization element in chicken fibroblasts. The *Xenopus* Vg1RBP (Vg1-mRNA-binding protein) is a homolog of ZBP-1 that recognizes the Vg1 mRNA zip code (Deshler et al., "A Highly Conserved RNA-Binding Protein for Cytoplasmic mRNA Localization in Vertebrates," *Curr. Biol.* 8:489-496 (1998); Havin et al., "RNA- Binding Protein Conserved in Both Microtubule- and Microfilament-Based RNA Localization," *Genes Devel.* 12:1593-1598 (1998)). She2 is a zip code protein that binds to the stem-loop-containing zip codes of yeast ASH1 mRNA (Bohl et al., "She2p, A Novel RNA-Binding Protein Tethers ASH1 mRNA to the Myo4p Myosin Motor via She3p," *EMBO J.* 19:5514-5524 (2000); Long et al., "She2p is a Novel RNA-Binding Protein that Recruits the Myo4p/She3p Complex to ASH1 mRNA," *EMBO J.* 19:6592-6601 (2000)). The *Drosophila* Staufen (Stau) protein is involved in localization of three transcripts (bcd, osk, and prospero) at three different stages of embryogenesis (Jansen, "mRNA Localization: Message on the Move," *Nat. Rev. Mol. Cell. Biol.* 2:247-256 (2001)). Homologs of *Drosophila* Stau in other animal species, suggest a common mechanism for deciphering zip codes during mRNA localization. These protein/RNA interactions occur within the cell to regulate the delivery of key mRNAs for translation at specific sites.

Protein escorts. Whereas there is solid evidence that mRNAs are transported long distances in the plant, very little information is available on the mechanism of this transport. Relying on the animal model for subcellular movement of RNAs, it is becoming clear that RNA transport in plants is facilitated by escort or chaperone proteins. Numerous opportunities for protein interaction in transporting and targeting ribonucleoprotein complexes (RNPs) are clearly illustrated in a model described Lucas et al., "Selective Trafficking of KNOTTED1 Homeodomain Protein and its mRNA Through Plasmodesmata," *Science* 270:1980-1983 (1995) (see Haywood et al., "Plasmodesmata: Pathways for Protein and Ribonucleoprotein Signaling," *Plant Cell Supplement* 303-325 (2002)). The cell-to-cell transport of plant and viral RNPs involves delivery to the plasmodesmata (PD), modification of the PD microchannel, and partial unfolding of the protein or RNP complex. Movement through the PD could potentially involve chaperones, SEL (size exclusion limit)-recognition proteins, receptors, docking proteins, and transport proteins. There are numerous examples of proteins associated with cell-to-cell trafficking via the PD (Aoki et al., "A Subclass of Plant Heat Shock Cognate 70 Chaperones Carries a Motif that Facilitates Trafficking Through Plasmodesmata," *Proc. Natl. Acad. Sci. USA* 99:16342-16347 (2002); Lee et al., "Selective Trafficking of Non-Cell-Autonomous Proteins Mediated by NtNCAPP1," *Science* 299:392-396 (2003)). Transport proteins like sucrose transporter-1 and CmPP16 facilitate movement of RNAs from companion cells to sieve elements to deliver RNAs into the phloem (Kühn et al., "Macromolecular Trafficking Indicated by Localization and Turnover of Sucrose Transporters in Enucleate Sieve Elements," *Science* 275:1298-1300 (1997); Xoconostle-Cazares et al., "Plant Paralog to Viral Movement Protein that Potentiates Transport of mRNA into the Phloem," *Science* 283:94-98 (1999)). SUT1 mRNA actually moves through the phloem translocation stream (Haywood et al., "Plasmodesmata: Pathways for Protein and Ribonucleoprotein Signaling," *Plant Cell Supplement* 303-325 (2002)). Putative zip code proteins, RNA-binding proteins in the phloem, may then deliver such signal RNAs to their site of activity in a specific organ. Viral movement proteins work in this way to enhance the transport of viral RNAs from cell to cell via the PD (Friedrich, "The Spread of Tobacco Mosaic Virus Infection: Insights into the Cellular Mechanism of RNA Transport," *Cell Mol. Life. Sci.* 59:58-82 (2002); Fujiwara et al., "Cell-to-Cell Trafficking of Macromolecules Through Plasmodesmata Potentiated by the Red Clover Necrotic Mosaic Virus Movement Protein," *Plant Cell* 5:1783-1794 (1993); Lough et al., "Cell-to-Cell Movement of Potexviruses: Evidence for a Ribonucleoprotein Complex Involving the Coat Protein and First Triple Gene Block Protein," *Mol. Plant. Microbe Interact.* 13:962-974 (2000)).

Fate of delivered RNA. Another mechanism for sorting mobile RNAs in plants as they reach terminal regions of the phloem is a recognition or surveillance field for screening movement into specific organs like the shoot or root apical meristem. It appears that plants control the exit of macromolecules from the phloem stream. Phloem-mobile endogenous RNA is trafficked selectively into the shoot apex. Support for this idea was obtained with studies that showed only specific phloem RNAs were detected in the apices of heterografted plants. RNAs that code for KNOX proteins of tomato moved across a graft in an acropetal direction to accumulate in the shoot apical meristems and leaf primordia of wild-type plants (Kim et al., "Developmental Changes Due to Long-Distance Movement of a Homeobox Fusion Transcript in Tomato," *Science* 293:287-289 (2001)). Accumulation of these mRNAs was correlated with the phenotype of the gain-of-function mutant in wild-type scions. Further evidence is provided by the fact that viruses are prevented from invading cells of the apical meristem (Foster et al., "A Surveillance System Regulates Selective Entry of RNA into the Shoot Apex," *Plant Cell* 14: 1497-1508 (2002)). Most viruses and long-distance post-transcriptional gene silencing (PTGS) signals are excluded from the shoot apex. These observations suggest the existence of an underlying filtering system. This surveillance system may regulate signaling and protect the shoot apex, in particular the cells that give rise to reproductive structures, from viral invasion. Despite data that support the existence of this surveillance system, very little is known about the molecular mechanisms that regulate this dynamic process. The most likely site for RNA surveillance is in the region between the protophloem and the meristem with a relay system through the PD (Lucas et al., "RNA as a Long-Distance Information Macromolecule in Plants," *Nat. Rev. Mol. Cell. Biol.* 2:849-857 (2001)). The information relay may occur through a mobile ligand/membrane receptor system in conjunction with symplasmic movement through the cell.

The present invention is directed to overcoming these and other deficiencies in the art.

SUMMARY OF THE INVENTION

The present invention relates to isolated nucleic acid molecules which encode a BEL transcription factor from potato (*Solanum tuberosum* L.) and the amino acid sequences encoded by such nucleic acid molecules.

Another aspect of the present invention pertains to host cells, DNA constructs, expression vectors, transgenic plants, and transgenic plant seeds containing the isolated nucleic acid molecules of the present invention.

The present invention is also directed to a method for enhancing tuber development in a plant. This method includes transforming a tuberous plant with a first DNA construct including a first nucleic acid molecule encoding a BEL transcription factor or a KNOX transcription factor, and a first operably linked promoter and first 3' regulatory region, whereby tuber development in the plant is enhanced.

A further aspect of the present invention relates to a method for enhancing growth in a plant. This method includes transforming a plant with a DNA construct including a nucleic acid molecule encoding a BEL transcription factor from *Solanum tuberosum* and an operably linked promoter and 3' regulatory region, whereby growth in the plant is enhanced.

Yet another aspect of the present invention relates to a method for regulating flowering in a plant. This method includes transforming a plant with a DNA construct including a nucleic acid molecule encoding a BEL transcription factor from *Solanum tuberosum* and an operably linked promoter and 3' regulatory region, whereby flowering in the plant is regulated.

The present invention relates to transcription factors which can be used to enhance tuber formation, to enhance growth, or to regulate flowering in a plant. In particular, accelerating tuber growth in field plants shortens the time for field cultivation. It can also be used to shorten the timing of a "late" potato variety to produce an earlier harvest. Many desirable breeding lines of potato produce tubers too late in the growing season or with too low a yield. The method of the present invention circumvents these problems, even under noninductive conditions. Enhanced tuberization also has applications for producing food in space under a research initiative directed by NASA (Food and Crop Systems Research, NASA's Advanced Life Support Program). Potato tubers are also being designed as biostorage organs for the production of pharmaceuticals or bioproducts. Enhanced tuber growth would be advantageous in these systems. Moreover, enhancement of growth in plants or regulation of flowering in plants can be used to produce an earlier harvest of plants/flowers.

The present invention also relates to a method of screening a biomolecule for its ability to assist in mediating long-distance movement of a mobile RNA in a plant. This method involves providing a biomolecule and providing a mobile RNA of a plant. The biomolecule is contacted with the mobile RNA. A determination is made as to whether contacting the biomolecule with the mobile RNA is effective in yielding a biomolecule/mobile RNA complex. The presence of a biomolecule/mobile RNA complex indicates that the biomolecule is able to assist in mediating long-distance movement of the mobile RNA in the plant.

The present invention can be used to increase understanding of the mechanisms by which plants coordinate the perception of, and response to, environmental cues to control development. For example, the isolated nucleic acid molecules of the present invention can be used to investigate the role of RNA transport in mediating the photoperiodic response of tuber formation. The rationale for this objective is supported by preliminary data indicating that mRNAs encoding two key transcription factors (TFs) that interact to regulate gene expression and coordinate plant growth move through the plant's vascular system.

BRIEF DESCRIPTION OF THE DRAWINGS

FIGS. 3A-F show the localization of POTH1 mRNA in potato plants as revealed by in situ hybridization. The presence of POTH1 mRNA is indicated by an orange/brown stain under dark-field microscopy. All micrographs are of equal magnification. Size bar=300 μm. FIG. 3A shows a longitudinal section through a vegetative shoot apex, probed with antisense POTH1. AP=apical meristem; L=leaf lamina; OL=older leaf lamina. Asterisks indicate leaf primordia (beneath AP) and procambium (to left of AP). FIG. 3B shows unswollen stolon apex, antisense POTH1. AP=apical meristem; P=procambium; asterisk=lamina of young leaf; V=perimedullary parenchyma associated with vascular tissue; X=xylem element. FIG. 3C shows unswollen stolon apex, sense POTH1. FIG. 3D shows swollen stolon apex, antisense POTH1. AP=apical meristem; P=procambium; V=perimedullary parenchyma and vascular tissue; L=lamina of young leaf. FIG. 3E shows swollen stolon, subapical longitudinal section, basal to section in 3D, antisense POTH1. IC=inner cortex; V=perimedullary parenchyma and vascular tissue; PI=pith. FIG. 3F shows swollen stolon, subapical section, sense POTH1.

FIG. 4A shows total RNA (5 μg) from shoot tips of wild-type (WT) and independent transgenic lines, potato subsp. *andigena* 15, 18, 20, 29, and 11 that were hybridized to a $^{32}$P-labeled POTH1 probe with the ELK or homeodomain deleted. In FIG. 4B, membranes were stripped and hybridized with $^{32}$P-labeled 1.2 kb wheat 18S rRNA to ascertain equal loading and transfer. In FIGS. 4C-F, three plants each of wild-type and overexpression lines, potato subsp. *andigena* 15, 18, 20, 29, and 11 were examined. Standard error is indicated for each mean. In FIG. 4C, plant height and in FIG. 4D, internode length were examined for 75-day old plants. In FIG. 4E, petiole length and in FIG. 4F, the terminal leaflet length was measured for the sixth expanded leaf of 84-day old plants.

FIGS. 5A-Q show the phenotype of the leaves of POTH1 overexpression lines. FIG. 5A shows that the overall size and shape of leaves from the andigena intermediate and severe overexpression lines, line 20 and line 15, respectively, have been altered compared to wild-type leaves (WT). In FIG. 5B, wild-type leaflets (WT) have a prominent mid-vein (mv) and pinnate venation pattern. The potato subsp. *andigena* intermediate overexpression mutant (line 20) has a mouse-ear shape, a shortened mid-vein, and palmate venation pattern. FIG. 5C shows the shoot tip of WT potato subsp. *andigena* line. FIG. 5D shows the severe mutant, potato subsp. *andigena* line 15, which has a mouse-ear leaf phenotype and shortened petioles causing leaves to cluster closely to the stem. The bars in FIGS. 5C and D are 5 mm. In FIG. 5E, the rachis and associated leaflets were detached from the petiole of a wild-type (WT) and a representative sense line (19), to show a slight increase in the proliferation of leaflets. FIG. 5F shows a cross-section through a wild-type leaf showing the arrangement of cell layers: e=epidermis; sp=spongy parenchyma; pp=palisade parenchyma. Size bar=50 μm. FIG. 5G shows a cross-section through a potato subsp. *andigena* line 15 leaf after treatment with GA$_3$ showing an intermediate level of cell organization. Bar=50 μm. FIG. 5H shows a cross-section through a potato subsp. *andigena* line 15 leaf showing that the cell layers lack a palisade parenchyma layer. Size bar=50 μm. FIG. 5I shows a wild-type leaf from potato subsp. *andigena* showing the morphology of a compound leaf In FIGS. 5J and K, the compound leaf structure is shown for the overexpression mutant, potato subsp. *andigena* line 15. Shoot tips were treated with either 10 μM GA$_3$ in 0.002% (v/v) ethanol (FIG. 5J) or with 0.002% (v/v) ethanol alone (FIG. 5K). Terminal leaflets from compound leaves of wild-type plants (FIG. 5L), GA$_3$-treated line 15 (FIG. 5M), and untreated line 15 (FIG. 5N) are shown. The mid-vein is marked with an arrow in FIG. 5M. Note that the morphology and venation of the GA$_3$-treated leaf (FIGS. 5J and M) is more similar to the wild-type leaf (FIGS. 5I and L) than to the potato subsp. *andigena* line 15 untreated leaf (FIGS. 5K and N). Bars in FIGS. 5I through 5K=1.0 mm. The second expanded leaf was used for the leaf samples in FIGS. 5F through 5N. FIG. 5O is a wild-type leaf from *Solanum tuberosum* cv. FL-1607 ('FL-1607') showing the morphology of a compound leaf In FIGS. 5P-Q, the compound leaf structure is shown for the overexpression mutant, 'FL-1607' line 5. Shoot tips were treated with either 10 μM GA$_3$ in 0.002% (v/v) ethanol (FIG. 5P) or with 0.002% (v/v) ethanol alone (FIG. 5Q). The mid-vein is marked with an arrow in FIG. 5P. Note that the morphology of the GA$_3$-treated leaf (FIG. 5P) is more similar to the wild-type leaf (FIG. 5O) than to 'FL-1607' line 5 control leaf (FIG. 5Q).

In FIG. 7A, 5 μg of total RNA from the shoot tips of wild-type lines (designated 2, 9, and 10) and the overexpression lines, potato subsp. *andigena* 11, 15, and 18 were hybridized with a 1.2-kb fragment of the potato GA 20-oxidase1 cDNA, StGA20ox1 (Carrera et al., "Feedback Control and Diurnal Regulation of Gibberellin 20-oxidase Transcript Levels in Potato," *Plant Physiol.* 119:765-773 (1999), which is hereby incorporated by reference in its entirety). In FIG. 7B, the membrane was stripped and reprobed with 18S wheat rRNA to ascertain equal loading and efficient transfer.

FIG. 9A shows selection on a nutrient carbon medium minus histidine, leucine, tryptophan, and adenine. The pAD plasmid provides leucine selection, the pBD plasmid (pBridge) provides tryptophan selection, and histidine and adenine selection are activated from the host strain (AH109) chromosomal DNA. The asterisk (*) designation indicates yeast growth with both plasmids transformed together, whereas the pAD plasmids (designated 5, 11, 13, 14, 22, 29, 30) are transformed alone (no growth). SIR4, a transcriptional activator of yeast, is used as a positive control and pBHD is POTH1 in pBridge alone. FIG. 9B shows that POTH1 interacts with all seven BELs as determined by a quantitative yeast two-hybrid assay. LacZ induction in the yeast strain AH 109 was assayed in transformed yeast cultures using a quantitative yeast β-galactosidase assay method (Pierce Chemical Company). For each pair, the dark bars on the left represent the pAD or pBHD plasmid alone transformed into yeast. The white bars on the right in each pair represent both plasmids (pAD and pBHD) transformed together. The standard error of the mean is represented by error bars. FIG. 9C shows immunoprecipitates of the in vitro binding of POTH1 to BEL proteins of potato. $^{35}$S-labeled GAD: POTH1 fusion protein and the three BEL1 proteins (p11Z-5, -13, and -30) were synthesized in separate in vitro transcription/translation reactions (lanes 2, 3, 6, and 9, respectively). Each of the three BEL1 proteins were incubated with the GAD:POTH1 protein and immunoprecipitated with anti-GAD antibodies (lanes 5, 8, and 11). None of the three BEL proteins bound to the GAD protein alone (lanes 4, 7, and 10). Labeled proteins were visualized by autoradiography after separation by SDS-PAGE. Molecular size markers are shown on the right.

FIGS. 1A-B show a deletion analysis of the binding regions of POTH1 and a potato BEL1-like protein using the yeast two-hybrid system. In FIG. 10A, deletion constructs of POTH1 in pBridge were tested for expression in the yeast strain AH109 and cotransformed with the full-length BEL cDNA, StBEL-05, in pGAL4 to test for interaction. In FIG. 10B, deletion constructs of StBEL-05 in pGAL4 were cotransformed with the full-length cDNA of POTH1 in pBridge. Interaction was verified with both nutritional selection and β-galactosidase activity. The white box indicates the homeodomain. The gray box indicates the putative protein/protein interaction region (for POTH1, this is the conserved KNOX domain, for StBEL5, the BELL domain). The black boxes are conserved sequences identified in the BEL proteins (see FIG. 13A) and the diagonal hatched boxes in POTH1 represent the ELK domain. The numbers in parentheses represent the amino acids of the full-length sequence included in each construct.

Ten μg of total RNA from stolons were loaded per lane. Stolons were harvested from the photoperiod-responsive potato species, *Solanum demissum*, 1, 2, 4, or 7 days after the plants were transferred to short-day conditions. A gene-specific probe for each BEL cDNA was used. A probe for the 18S ribosomal RNA was used to verify equal loading of the RNA samples (bottom panels).

Figure 12:
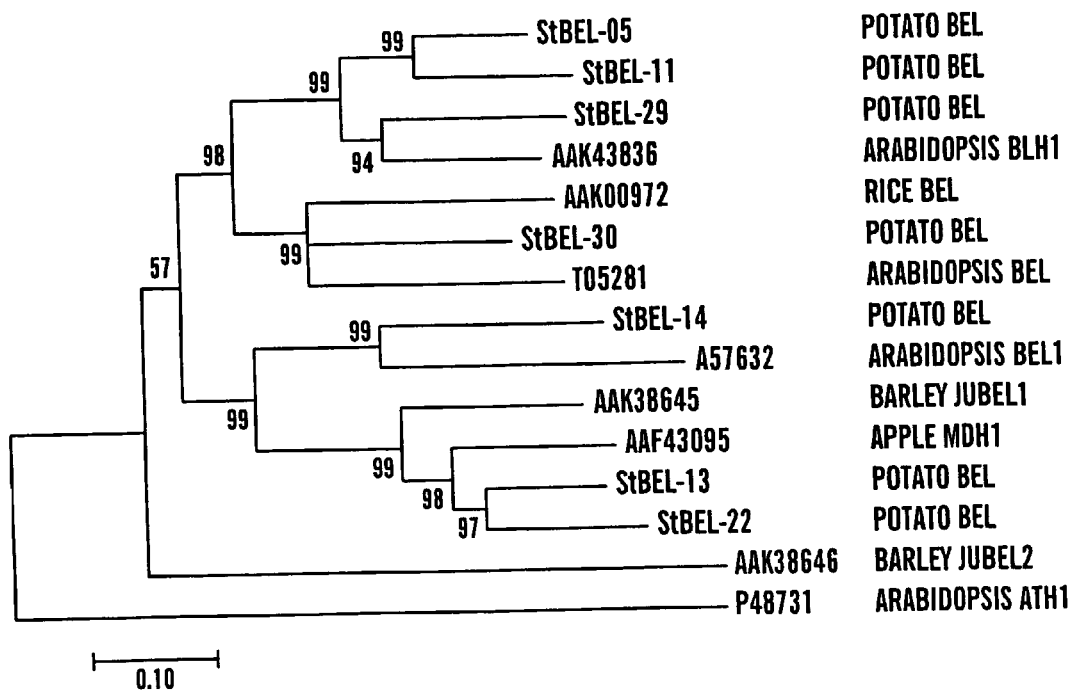

FIG. 12 shows the phylogenetic tree of the BEL1-like proteins of potato (*Solanum tuberosum* L.). The amino acid sequence of seven potato BEL-like proteins was analyzed and compared to BEL proteins of plants. These data were organized into a phylogenetic tree with the ME-Boot program of the MEGA package (version 1.0) and the neighbor-joining program (Saitou and Nei, 1987). The numbers listed at the branching points are boot-strapping values which indicate the level of significance (%) for the separation of two branches. The length of the branch line indicates the extent of difference according to the scale at the lower left-hand side. Databank accession numbers are listed on the dendrogram and the common name of the species is listed in the right-hand column.

Figure 13A:
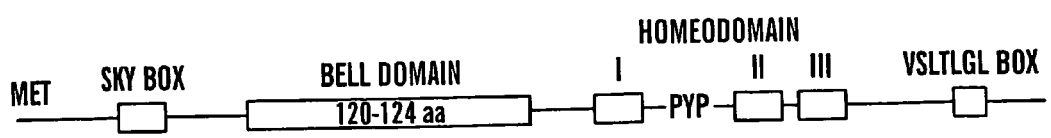

FIG. 13A shows a schematic of the amino acid sequence of the BEL1-like proteins of potato. Boxed regions represent conserved sequences identified by aligning all seven BELs. Helices I, II, and III of the homeodomain are designated. The proline-tyrosine-proline (PYP) loop extension is located between helices I and II. For clarity in labeling, the sequence is not drawn to scale.

Figure 13B:
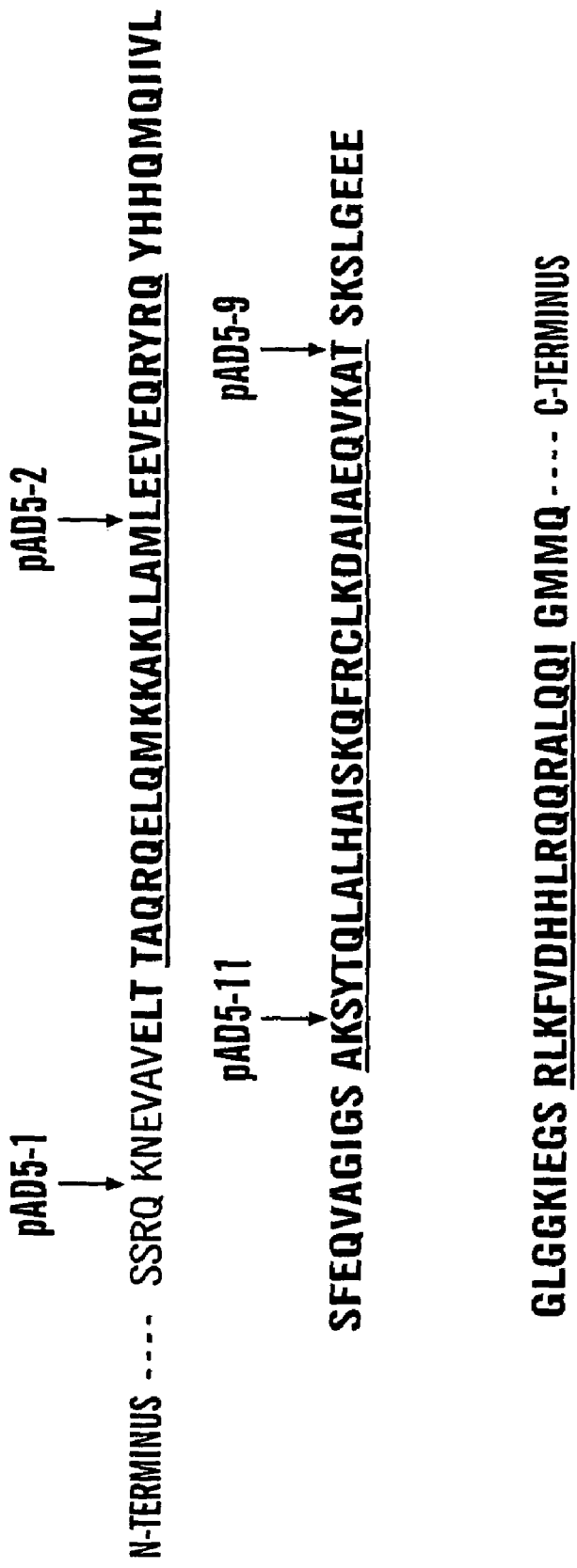
Figures 14A, 14B, 14C:
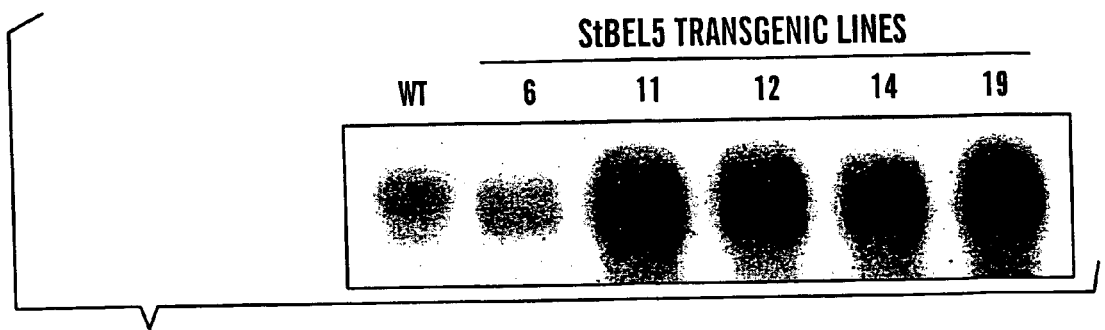

FIG. 13B shows predicted helices of the putative protein-binding region (BELL domain) of the BEL1 protein StBEL-05 (SEQ ID NO: 2). The bold letters represent amino acids conserved in other plant BEL1 proteins based on a BLAST analysis of StBEL-05. The underlined portion of the sequence represents a predicted α-helix. A consensus for the prediction of the sequence structure was derived by using three software programs for amino acid sequence analysis: sspal, ssp, and nnssp. Four deletion constructs from FIG. 14B are designated with arrows. Construct pAD5-1 contains aa 230 through 653 of pAD-05 (interaction with POTH1), and pAD5-2 contains aa 257 through 653 of pAD-05 (no interaction). Construct pAD5-11 consists of aa 1 through 286 of pAD-05 (no interaction), and pAD5-9 consists of aa 1 through 315 (interaction with POTH1).

Figure 13C:
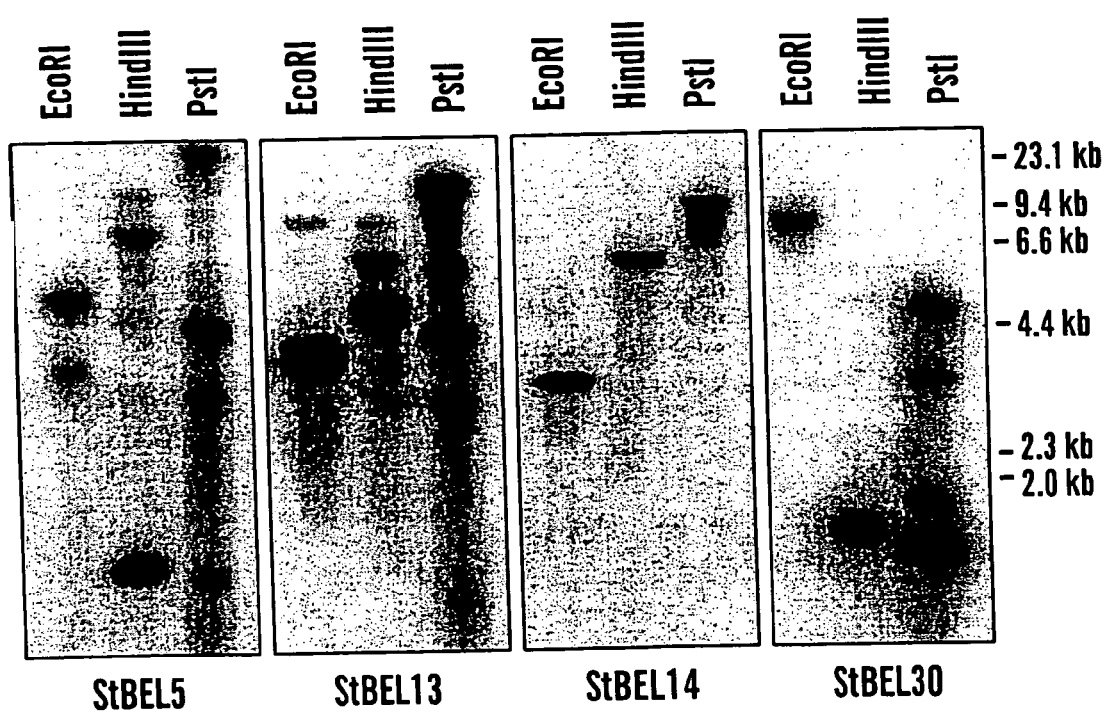

FIG. 13C is a Southern blot analysis of BEL-like genes of potato. Genomic DNA (10 μg per lane) was digested with EcoRI, HindIII, and PstI. Each blot was hybridized with a $^{32}$P-labeled gene-specific probe from each of the four StBEL cDNAs. DNA size markers in kilobases are indicated on the right.

FIGS. 14A-C show in vitro tuberization of transgenic plants that overexpress sense transcripts of StBEL-05. Northern blot analysis for the accumulation of mRNA for StBEL-05 was performed by using 10 μg of total RNA/lane from vegetative meristems of in vitro plantlets and gene-specific probes for StBEL-05 (see FIG. 14A). Equal loading of RNA samples was verified by visualizing ethidium bromide-stained rRNA bands with UV light. The rate of tuberization (days to tuberize) was determined by the first appearance of tubers from among twenty-four replicates (see FIG. 14B). The number of tubers was scored after 2 weeks of LD conditions (0 d), and after 7 (7 d) and 14 days (14 d) of SD conditions (see FIG. 14B). Tubers were harvested and weighed after 21 days (see FIG. 14C) from the StBEL-05 overexpression (24 plants each) and wild-type lines (35 plants). Cultured transgenic plants of *Solanum tuberosum* ssp. *andigena* were grown on a Murashige and Skoog medium with 6% sucrose under a long-day photoperiod (16 hours of light, 8 hours of dark) in a growth chamber for two weeks. For tuber induction, plants were transferred to a Murashige and Skoog medium supplemented with 6% sucrose and evaluated daily for tuber formation under a short-day photoperiod (8 hours of light, 16 hours of dark) in the growth chamber until tubers formed. All numbered lines were verified as transgenic by using PCR with transgene-specific primers. Control plants were both nontransgenic (WT) and transgenic (StBEL-05 line 6).

Figure 15:
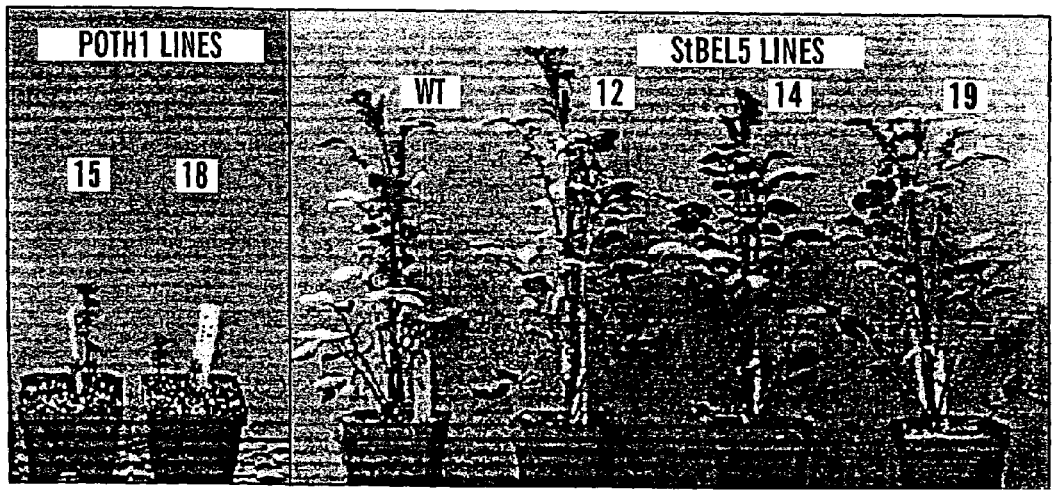

FIG. 15 shows overexpression mutant lines for the potato KNOX gene, POTH1 (lines 15 and 18), and for the BEL1-like protein, StBEL-05 (lines 12, 14, and 19). These StBEL-05 sense lines had a leaf phenotype similar to wild-type plants (WT). These are 8-week plants grown under long-day conditions (16 hours of light, 8 hours of dark) in the greenhouse supplemented with high pressure sodium HID lamps. The StBEL-05 plants ranged in height from 34 to 39 cm, whereas, the POTH1 lines were 7 to 10 cm in height.

Figures 16A, 16B:
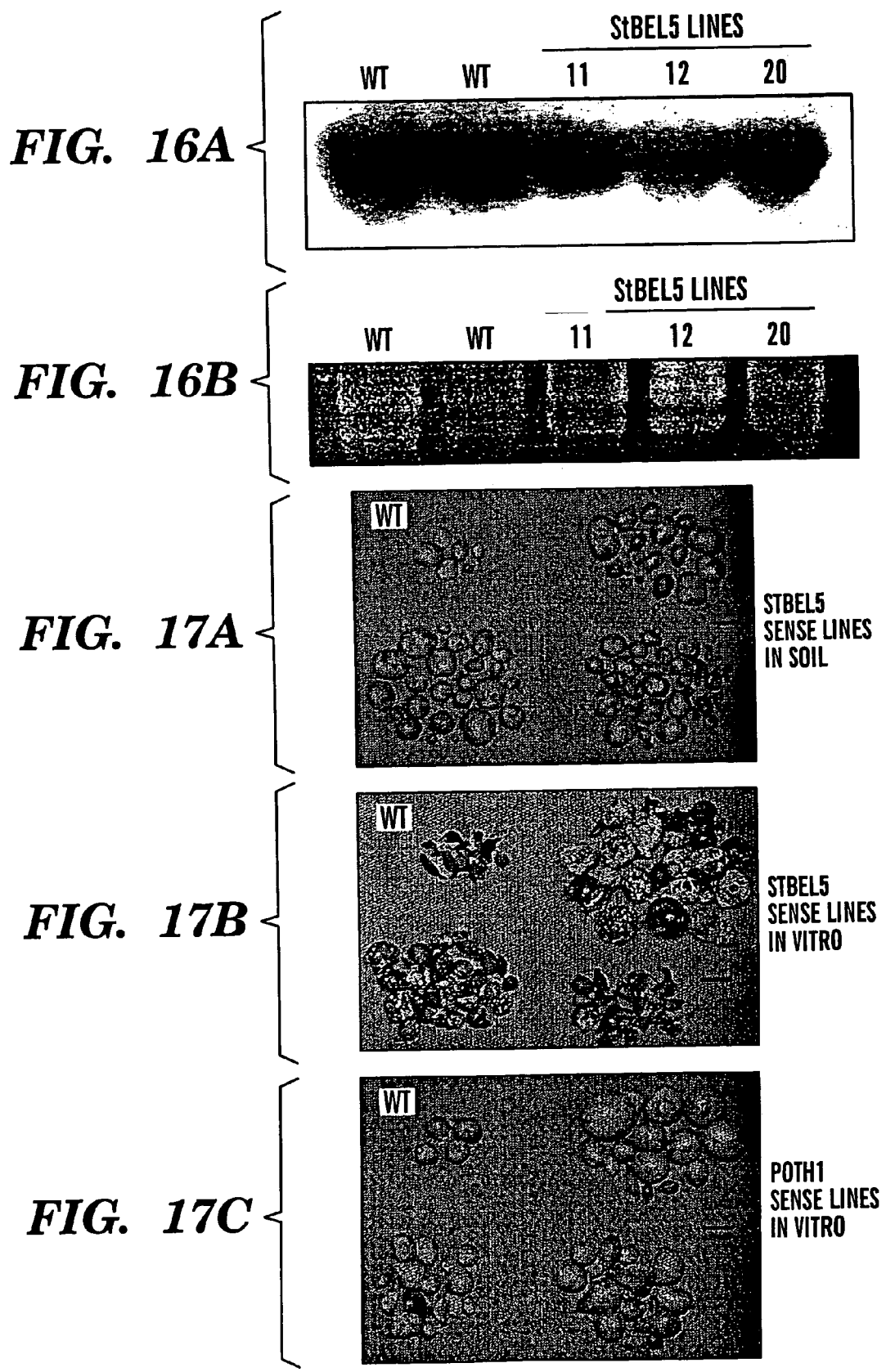

FIGS. 16A-B are a Northern blot analysis of the accumulation of the mRNA of the GA 20-oxidase1 gene of potato (Carerra et al., "Feedback Control and Diurnal Regulation of Gibberellin 20-oxidase Transcript Levels in Potato," *Plant Physiol.* 119:765-773 (1999), which is hereby incorporated by reference in its entirety) in wild-type plants and sense lines 11, 12, and 20 of StBEL-05 (FIG. 16A). Total RNA was extracted from the 2.0 mm distal tip of stolons from plants grown under LD conditions (16 hours of light, 8 hours of dark). Wild-type RNA (WT) was extracted from two separate pools. Ten μg of total RNA were loaded per lane. A gene-specific probe for GA 20-oxidase1 was used for hybridization. All three StBEL-05 lines exhibited enhanced tuber formation. Ethidium bromide-stained rRNA is visualized as a loading control (FIG. 16B).

FIG. 17A shows tubers harvested from independent lines of StBEL-05 transgenic plants (*Solanum tuberosum* spp. *andigena*) grown in soil under a short-day photoperiod. Plants were grown under long days (LD) (16 hours of light, 8 hours of dark) in 10 cm pots until they reached the 16-leaf stage and then transferred to short days. After 14 days under short days, tubers from three plants per independent line were harvested and photodocumented. Tuber numbers and yields increased by at least threefold in these StBEL-05 lines relative to control plants. Starting from the upper left-hand corner and proceeding clockwise are tubers harvested from control plants (WT) and from each of the StBEL-05 overexpression lines 14, 19, and 12. Other than the increase in the rate of tuber formation, the phenotype of these sense lines was similar to wild-type. Reference bar is equivalent to 1.0 cm.

FIG. 17B shows tubers from the same StBEL-05 lines from FIG. 17A harvested after 21 days of culture in vitro under inductive conditions of a short-day photoperiod (8 hours of light, 16 hours of dark) and 6% sucrose in the media. Tubers from 35 control plants and from 25 plants of the StBEL-05 lines are displayed in the same order as shown in FIG. 17A. Tuber yield per plant of line 14 was sixteenfold greater than wild-type. The tubers showed an intense purple color, which is the result of anthocyanin accumulation characteristic of this subspecies. Reference bar is equivalent to 1.0 cm.

FIG. 17C shows tuber production for stolons from overexpression lines of POTH1. Excised stolon tips from plants grown under LD conditions were grown in vitro in the dark in media supplemented with 8% sucrose. Tubers were harvested after 35 days of culture. Starting from the upper left-hand corner and proceeding clockwise are tubers harvested from control plants (WT) and from each of the POTH1 overexpression lines 11, 18, and 20. Twelve stolon tips per independent line were evaluated for tuber production. Reference bar is equivalent to 1.0 cm.

Figure 17D:
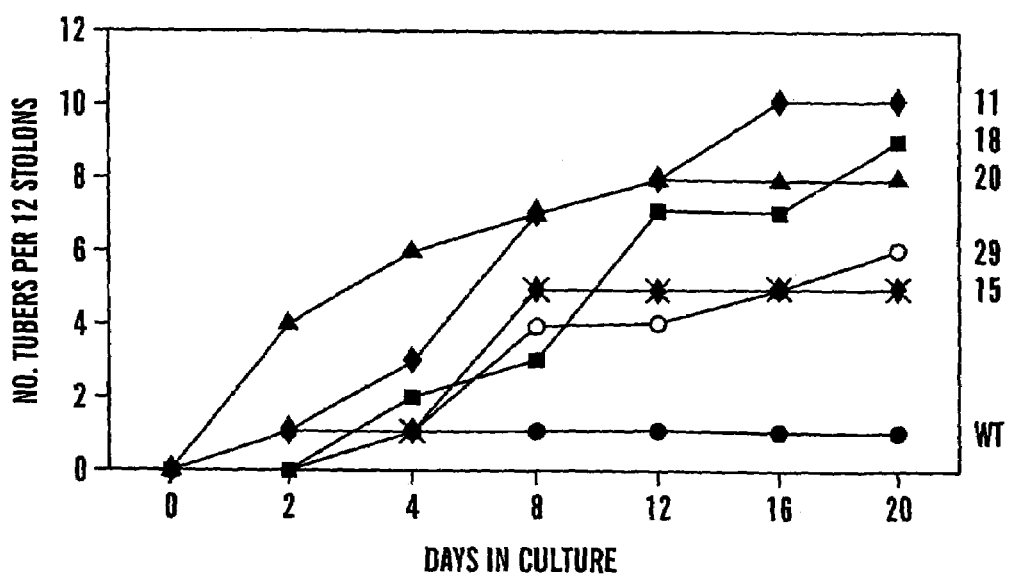

FIG. 17D shows the rate of tuberization for stolons from overexpression lines 11, 18, 20, 29, and 15 of POTH1 and from wild-type plants (WT). Excised stolon tips (approximately 1.5 cm in length) from plants grown under long-day conditions were grown in vitro in the dark in media supplemented with 8% (w/v) sucrose and monitored for 20 days.

Figure 18A:
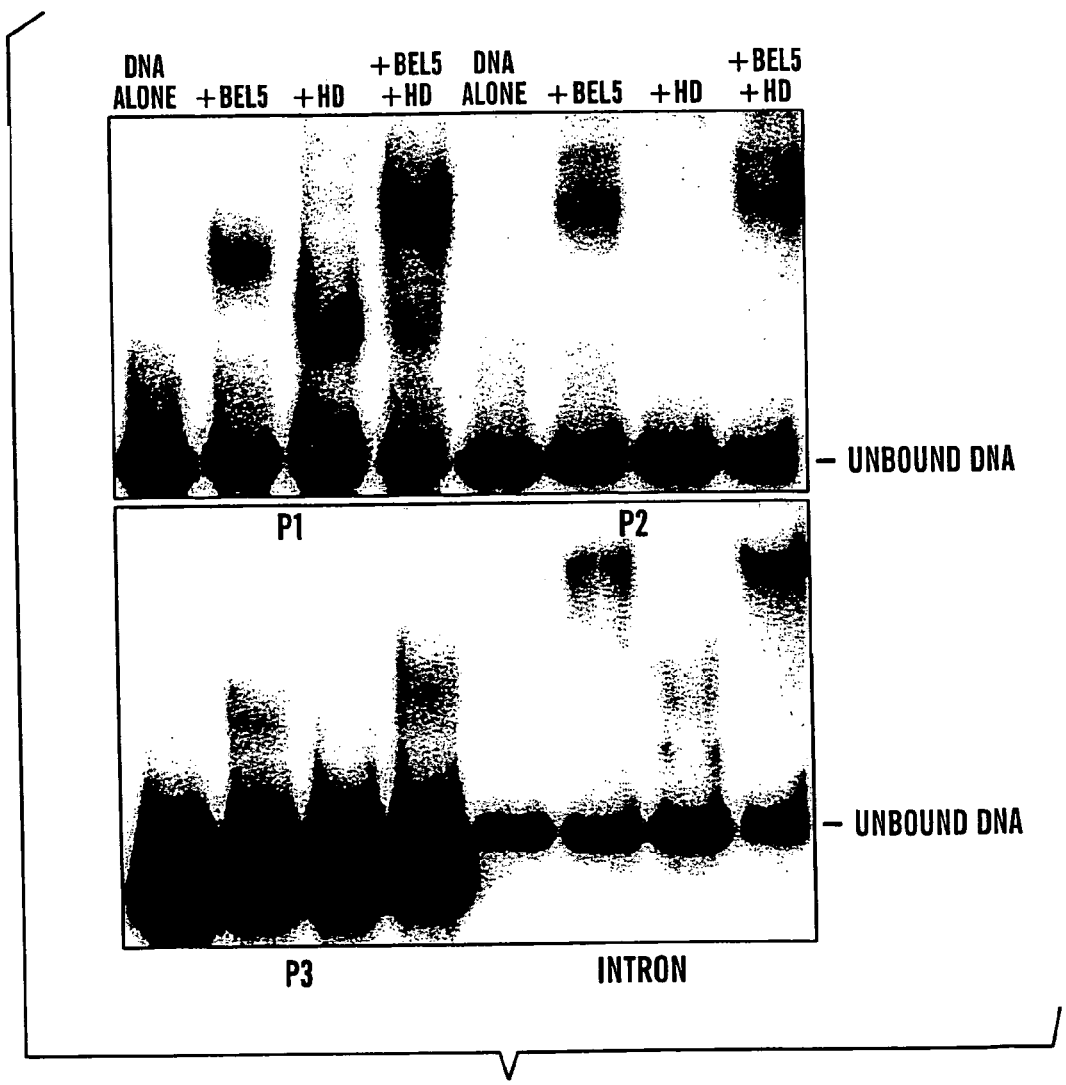
Figure 18B:
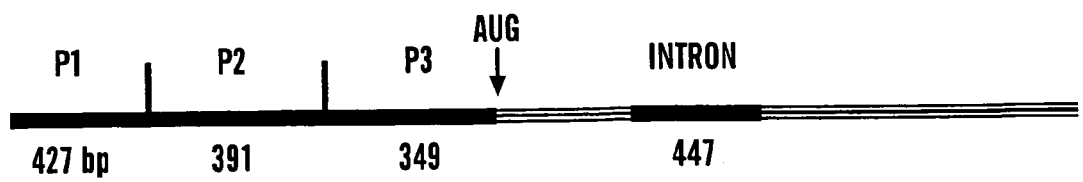

FIGS. 18A-B show gel mobility shift assays (FIG. 18A) for the binding of two transcription factors of potato, POTH1 (HD) and StBEL-05, to regions of the GA20 oxidase1 promoter and the first intron (FIG. 18B). Each DNA probe is tested for binding in four sets: DNA alone, with StBEL-05 only, with POTH1 (HD) only, and with both StBEL-05 and POTH1. The two proteins appear to bind in tandem to the P1 region. Two-hundred ng of purified protein and $^{32}$P-labeled DNA fragments were used in each binding reaction. The protein/DNA mix was run on a nondenaturing polyacrylamide gel. These results are representative of several replications. The GA20 ox1 promoter was provided by Salome Prat, Barcelona.

Figure 19:
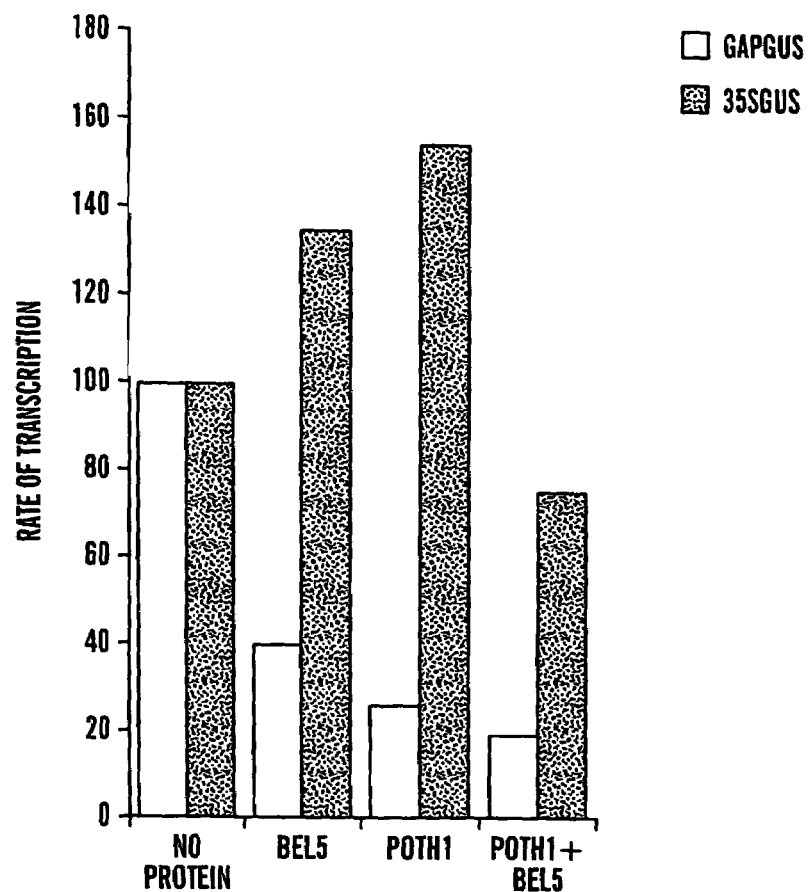

FIG. 19 shows the effect of binding two transcription factors to the GA20 oxidase1 promoter on the rate of transcription. The potato GA20 oxidase1 promoter (1170 bp) plus an enhancer was fused to a GUS marker (GAPGUS, gray bars). The two transcription factors, POTH1 and StBEL-05, were cloned and expressed in separate protein expression vectors. All constructs were transformed into tobacco protoplasts through electroporation. Whereas, repression of transcription was affected by each TF alone, expression of the proteins in tandem resulted in the greatest repression of transcription. Activity of the 35 SGUS construct (black bars) was used as a baseline control. The "no protein" protoplasts are designated as 100% transcriptional activity. All activities are calculated in relation to a luciferase internal control.

Figure 20:
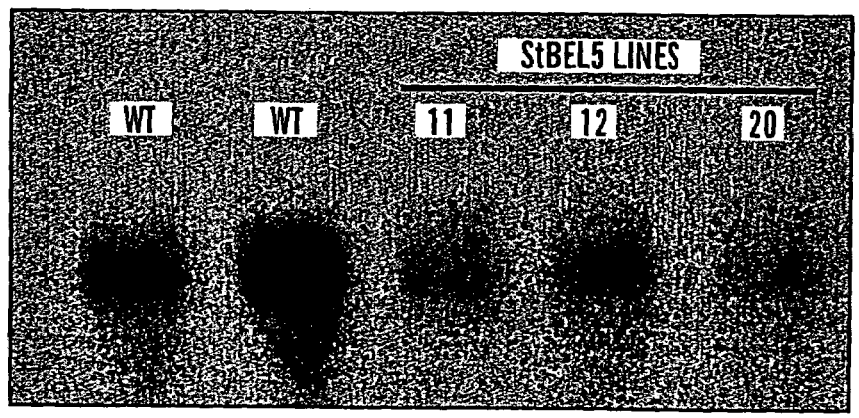

FIG. 20 shows GA20 oxidase1 mRNA accumulation in stolon tips of plants grown under long-day conditions. Ten µg of total RNA was probed with a $^{32}$P-fragment specific for the potato GA20 oxidase1 cDNA. These StBEL-05 lines all exhibited enhanced tuber formation.

Figure 21A:
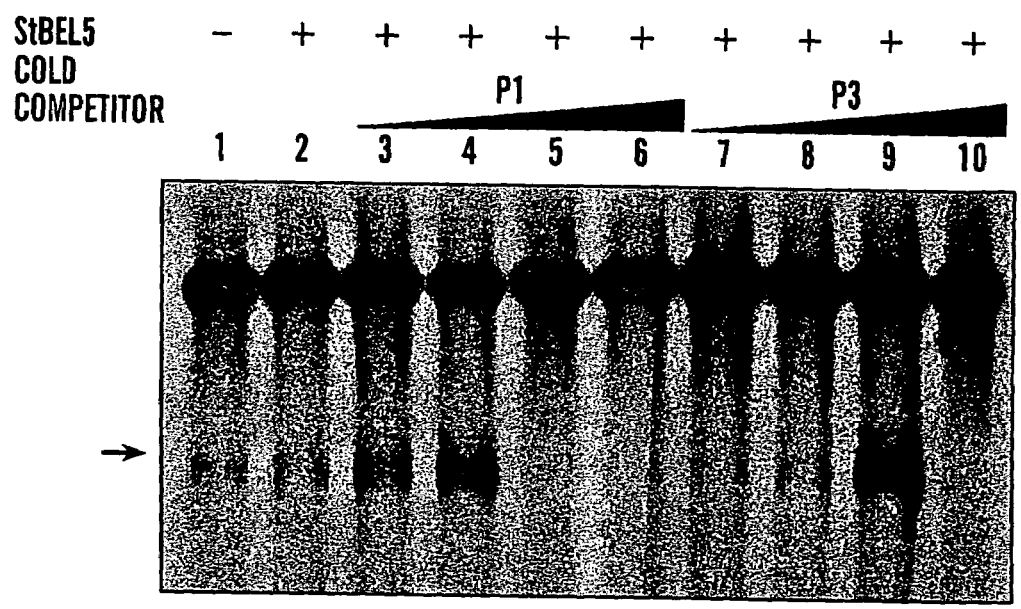
Figure 21B:
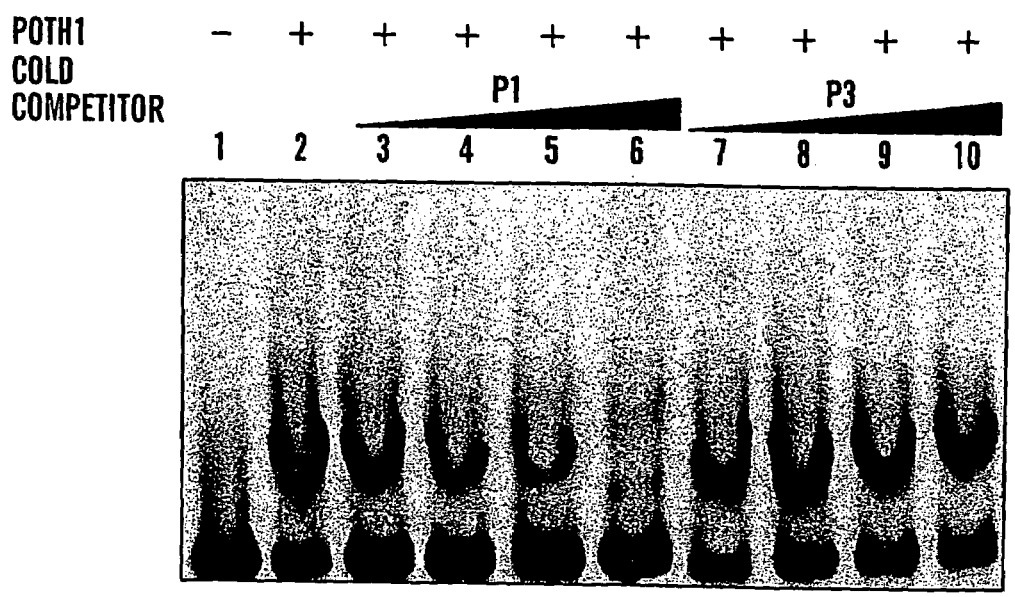

FIGS. 21A-B show a competition gel-retardation assay of P1 with cold P1 or P3 in the presence of StBEL-05 (FIG. 21A) or POTH1 (FIG. 21B). Lane 1 is labeled P1 alone, lane 2 is the labeled P1 with either StBEL-05 (FIG. 21A) or POTH1 (FIG. 21B). Increased amounts (10×, 25×, 50×, 100×) of unlabeled P1 or P3 were added to lanes 3 to 6 and 7 to 10, respectively. The DNA-protein complexes are indicated with arrowheads.

Figure 22:
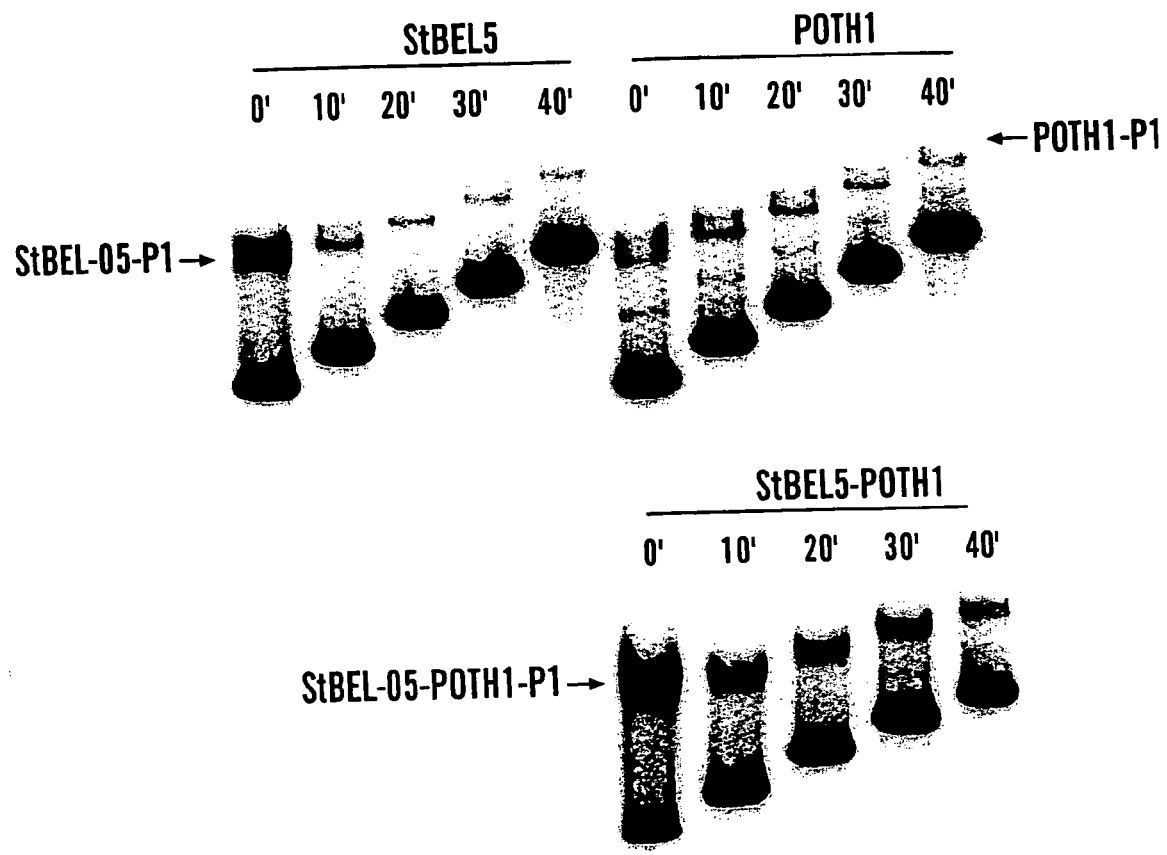

FIG. 22 shows a dissociation rate analysis of StBEL-05-P1, POTH1-P1, and StBEL-05-POTH1-P1 complexes. Labeled P1 was incubated on ice for 30 minutes with recombinant proteins, as indicated on the top. Then a 500-fold molar excess of unlabeled P1 was added and aliquots analyzed by gel mobility shift assay after the indicated time. The arrows show the DNA-protein complexes.

Figure 23A:
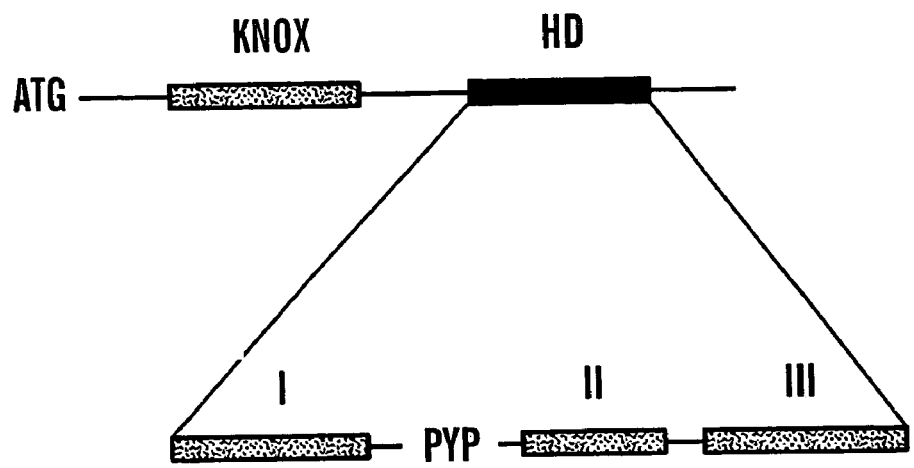
Figure 23B:
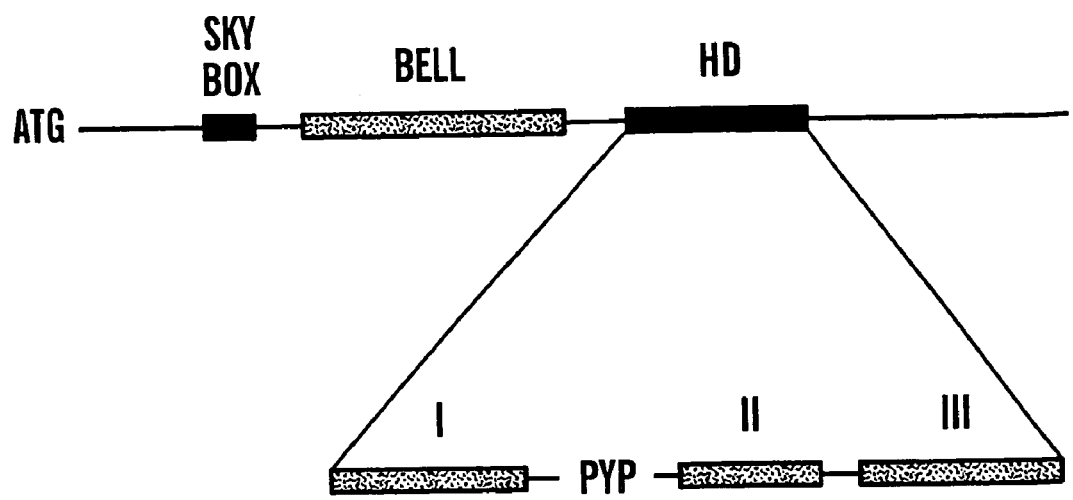

FIGS. 23A-B show the protein structures of POTH1 (FIG. 23A) and StBEL-05 (FIG. 23B). Conserved regions are labeled. These include the protein-binding regions for POTH1, KNOX I and KNOX II, and for StBEL-05, the Sky box and the BELL domains. The DNA-binding domains (HD) consisting of three helices and the characteristic proline-tyrosine-proline TALE are also designated. POTH1 is 345 aa in length, whereas StBEL-05 is 688 aa. The schematics of protein structure presented here are not drawn to scale to enhance visual clarity.

FIGS. 24A-C show schematics of constructs (FIG. 24A) and the repression effect of StBEL-05 and POTH1 on the ga20ox1 promoter (FIG. 24B) and on the 35S CaMV promoter (FIG. 24C). The construct with the LUC gene under the control of the cauliflower mosaic virus (CaMV) 35S promoter was used as an internal control. Each transfection was performed three times. Relative GUS-LUC activity was calculated with reporter alone set as 100%. Data are means±SE.

Figure 25A:
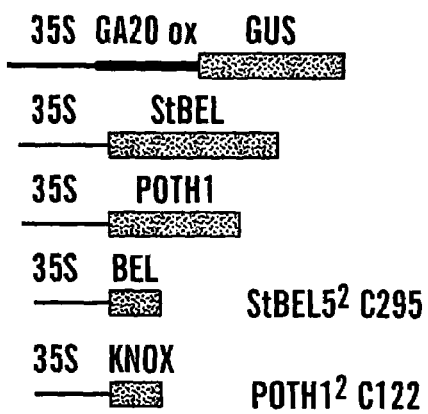
Figure 25B:
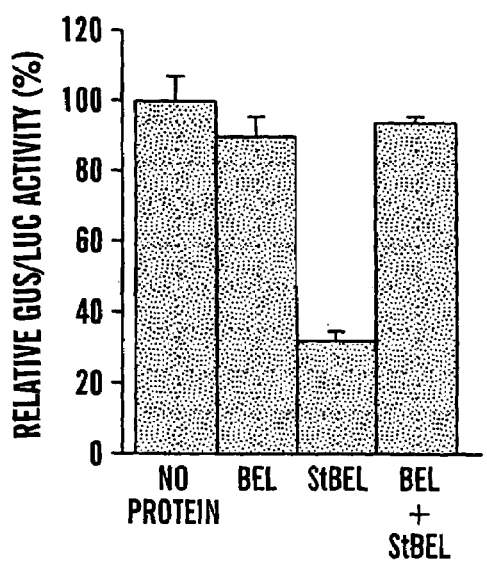
Figure 25C:
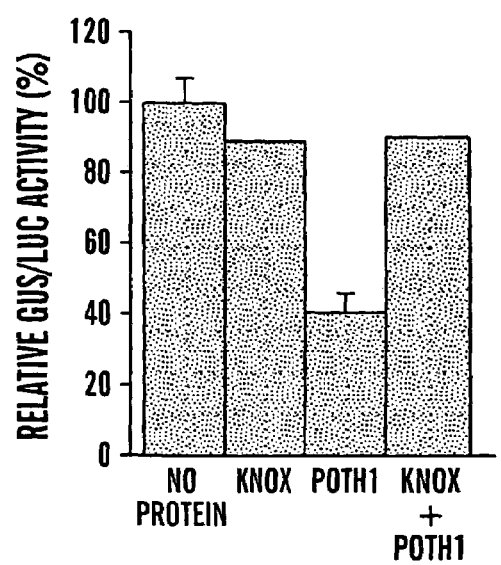

FIGS. 25 A-C show schematics of constructs (FIG. 25A) and the effect of dominant negative constructs of either StBEL-05 or POTH1 on the repression activity of StBEL-05 (FIG. 25B) or POTH1 (FIG. 25C), respectively. The construct with the LUC gene under the CaMV 35S promoter was used as a control. Each transfection was performed three times. Relative GUS-LUC activity was calculated with reporter alone set as 100%. Data are means±SE.

Figure 26A:
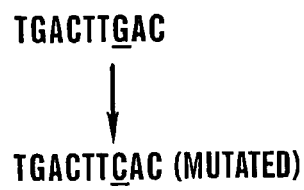
Figure 26B:
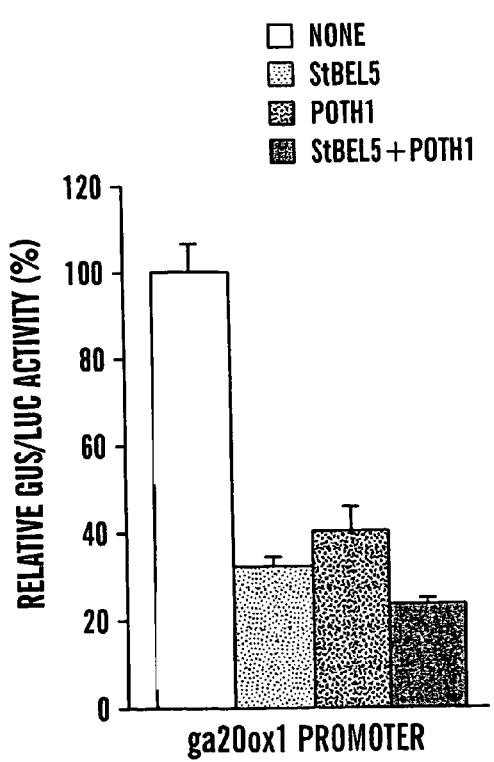
Figure 26C:
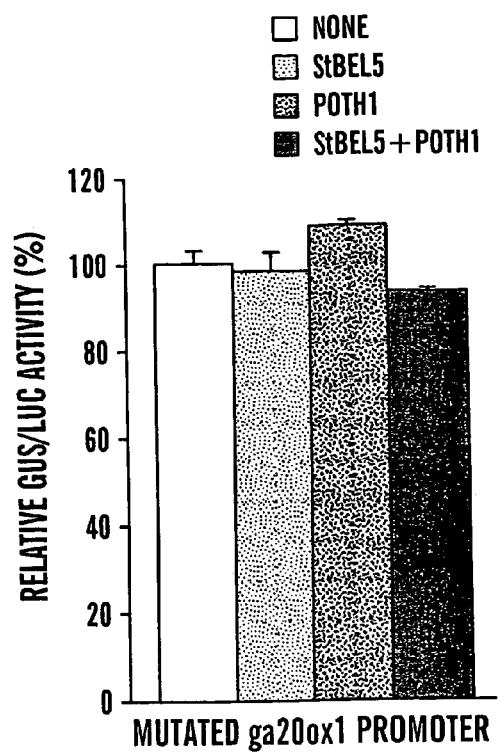

FIGS. 26A-C show a schematic of the mutated base in a 9-bp motif (FIG. 26A) and that mutation in the StBEL-05-POTH1 heterodimer binding site deprived the ga20ox1 promoter of its response to StBEL-05 and POTH1 repression (FIGS. 26B-C). The construct with the LUC gene under the CaMV 35S promoter was used as control. Each transfection was performed three times. Relative GUS-LUC activity was calculated with reporter alone set as 100%. Data are means±SE.

Figure 27:
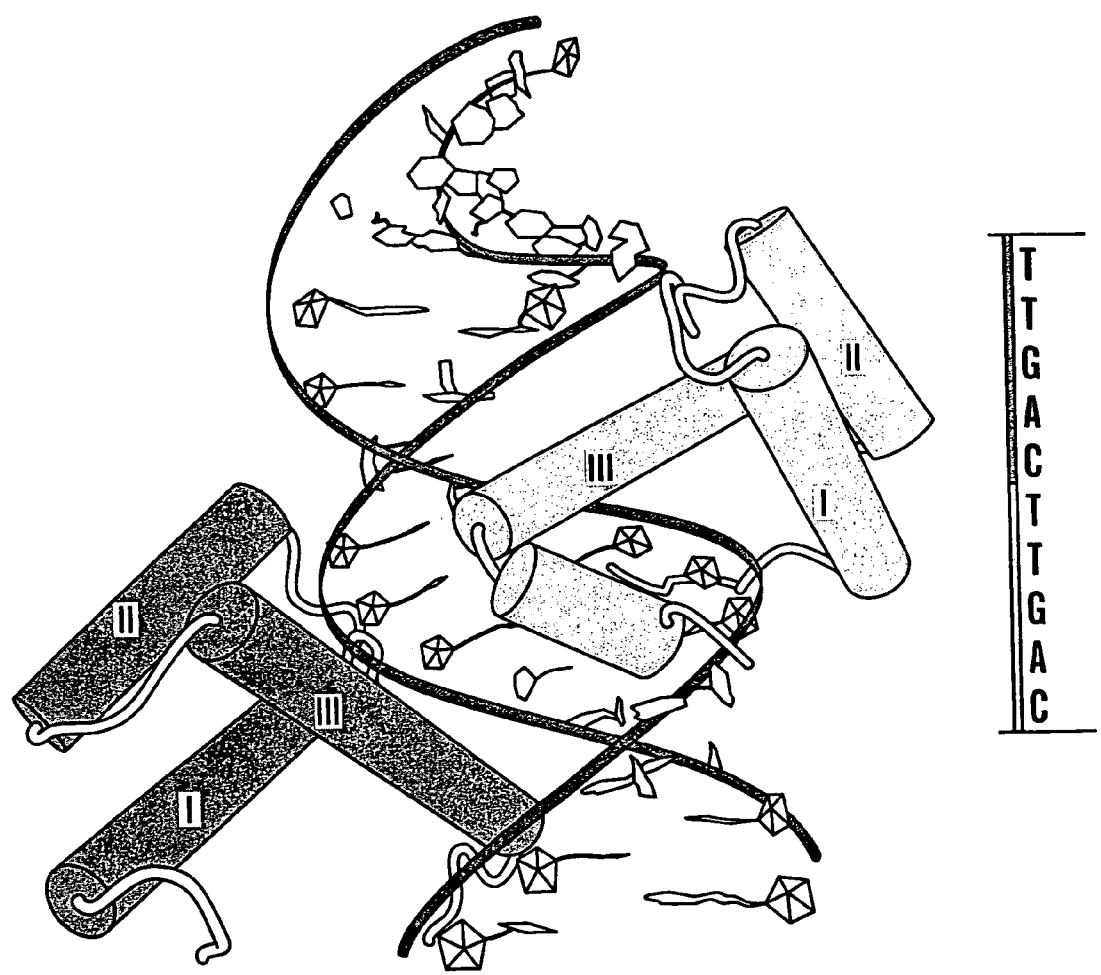

FIG. 27 shows a model of BEL/KNOX binding to target DNA. Light grey=StBEL-05 homeodomain; dark grey=POTH1 homeodomain. The three helices are indicated as I, II, or III. The schematics of protein structure presented here are not drawn to scale to enhance visual clarity. The third helix of the homeodomains of both POTH1 and StBEL-05 fit in the major groove of the DNA double helix.

Figure 28:
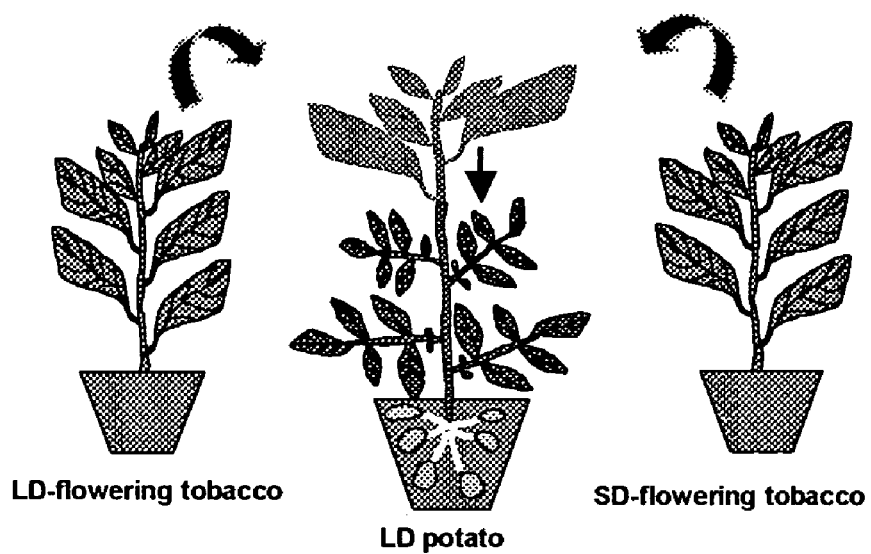

FIG. 28 is a schematic showing transmission of a flowering signal across a graft union to induce tuber formation. Scions from either LD- or SD-flowering tobacco plants grown under inductive conditions were grafted onto potato stock plants grown under noninductive conditions (LD) for tuber formation. After several days, tubers formed on the LD potato stocks.

Figure 29:
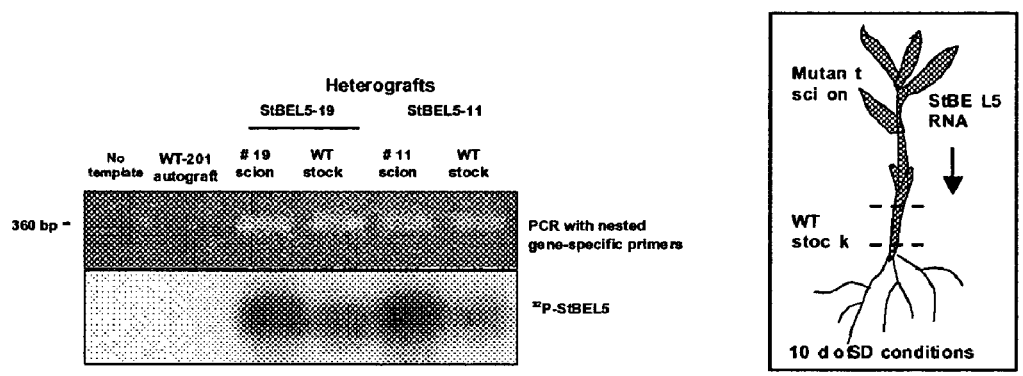

FIG. 29 shows that StBEL5 mRNA moves through a graft union in a basipetal direction Scions of mutant lines 19 and 11 that overexpressed StBEL5 were grafted onto wild-type stocks (right). Heterografts were cultured in vitro for 10 d under SD conditions (8 h light, 16 h dark). RNA was extracted and detected by RT-PCR with nested gene-specific primers and a non-plant DNA primer specific for the transgenic transcripts. Left: Ethidium bromide-stained PCR product of expected size (360 bp) (top). Autoradigraph (30 min exposure) of the PCR products hybridized with a $^{32}$P-labeled StBEL5 cDNA fragment (bottom).

Figure 30:
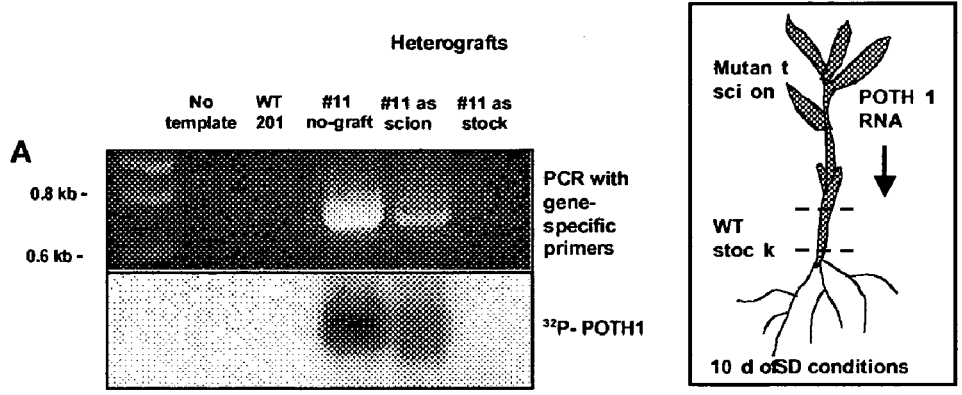

FIG. 30 shows that POTH1 mRNA also moves unidirectionally. Using grafts with tissue culture plants and RT-PCR with nested gene specific primers (GSP), we demonstrate that RNA for POTH1 moves across a graft union toward the base of the plant (#11 as scion). The same RNA does not move upward towards the apex (#11 as stock). Line 11 is a transgenic potato line that overexpresses POTH1 mRNA. The #11 no-graft sample is a positive control. WT RNA was sampled for both heterografts. PCR was done twice off cDNA template made from RNA and reverse transcriptase. Two different GSPs for POTH1 were used with a non-plant DNA primer specific for the transgenic RNA of line 11. A) Ethidium bromide-stained PCR products of expected size (750 bp) B) Autoradiograph (one hr exposure) of the PCR products in panel A hybridized with a $^{32}$P-labeled POTH1 cDNA fragment.

Figure 31:
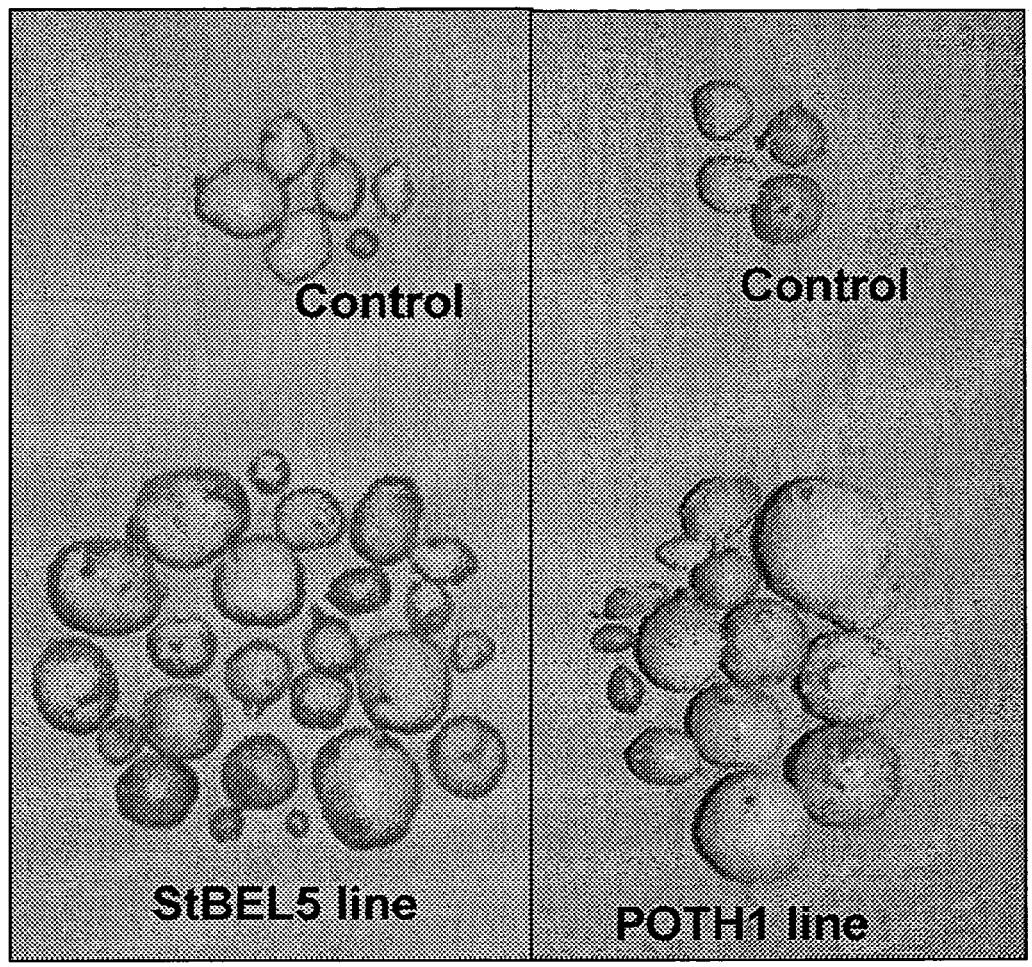

FIG. 31 is a schematic showing that tuber yields are enhanced in StBEL5 and POTH1 overexpression lines. Both are representative of several similar high-yielding lines.

Figure 32:
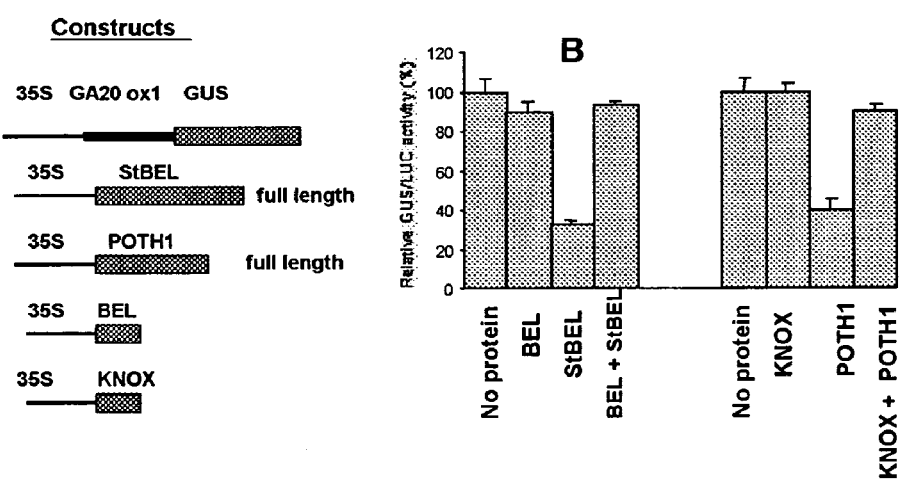

FIG. 32 shows dominant negative constructs containing amino-terminal protein binding domains of StBEL5 or POTH1 (designated BEL and KNOX, respectively, in FIG. 32A) blocked the repression activity of StBEL5 or POTH1, respectively (FIG. 32B).

Figure 33:
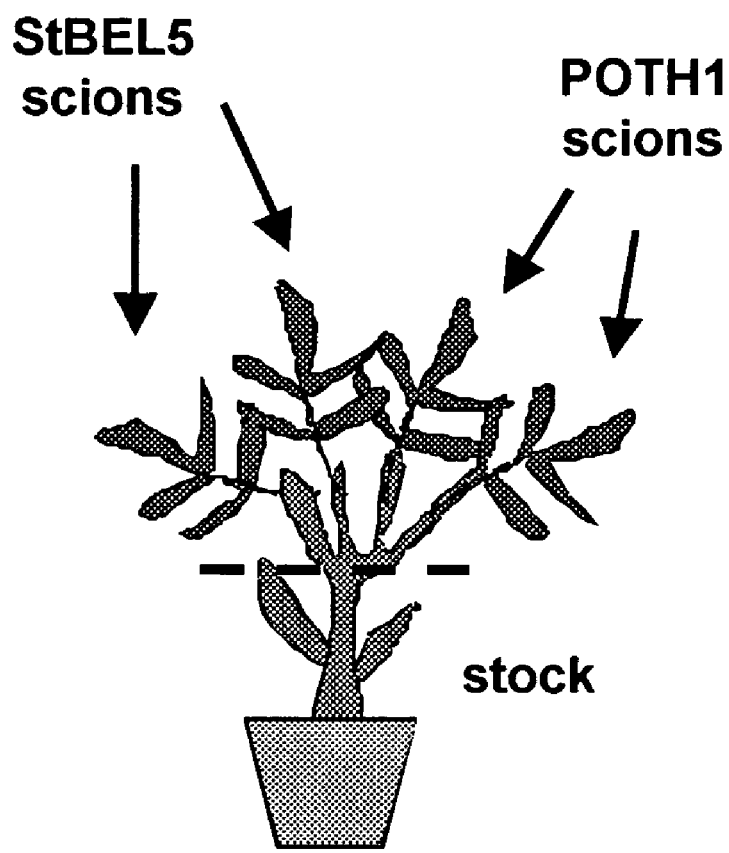

FIG. 33 is a schematic show potato heterografts using StBEL5 and POTH1 scions.

Figure 34:
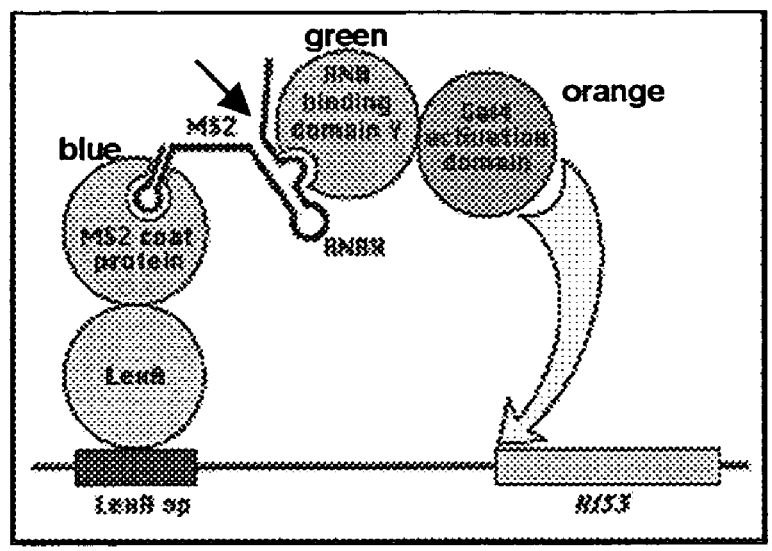

FIG. 34 is a schematic showing the three-hybrid protocol, which consists of the interaction of three hybrid molecules to identify RBPs. One is the hybrid RNA molecule (black arrow) produced off the pIIIA/MS2-1 plasmid. One part of the hybrid RNA binds to the MS2 coat protein (blue) and the other RNA part (cloned fragments) will bind to the putative RBP (green) fused to the activation domain of GAL4 (orange). This interaction results in the activation of the selectable markers for LEU, HIS, ADE, and lacZ.

Figure 35:
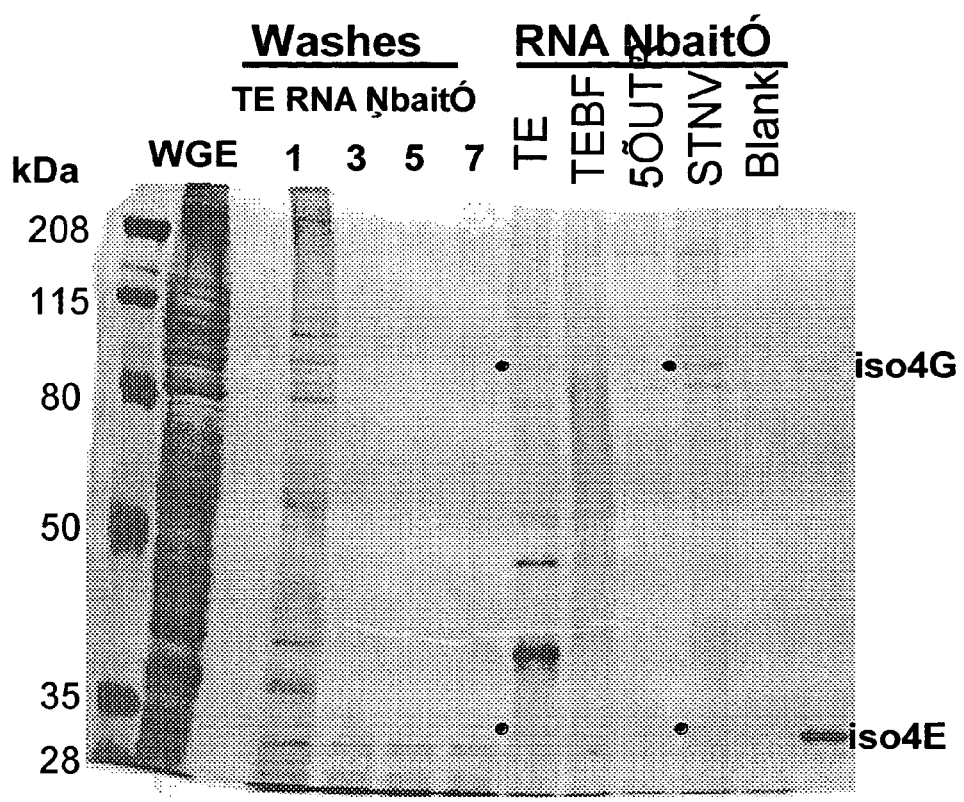

FIG. 35 shows RNA binding proteins (silver stained). Total wheat germ extract (WGE) was incubated with biotinylated RNA linked to streptavidin beads. After seven low salt washes (TE washes shown) bound protein was eluted with SDS gel loading buffer. Proteins bound to indicated bait RNAs are shown. Dots indicate proteins that co-migrate with eIFiso4G and eIFiso4E. Purified factors are in far right lane.

FIG. 36 shows StBEL5 RNA accumulation in *Solanum tuberosum* andigena. LD stands for long-day and SD stands for short-day growing conditions.

Figure 37:
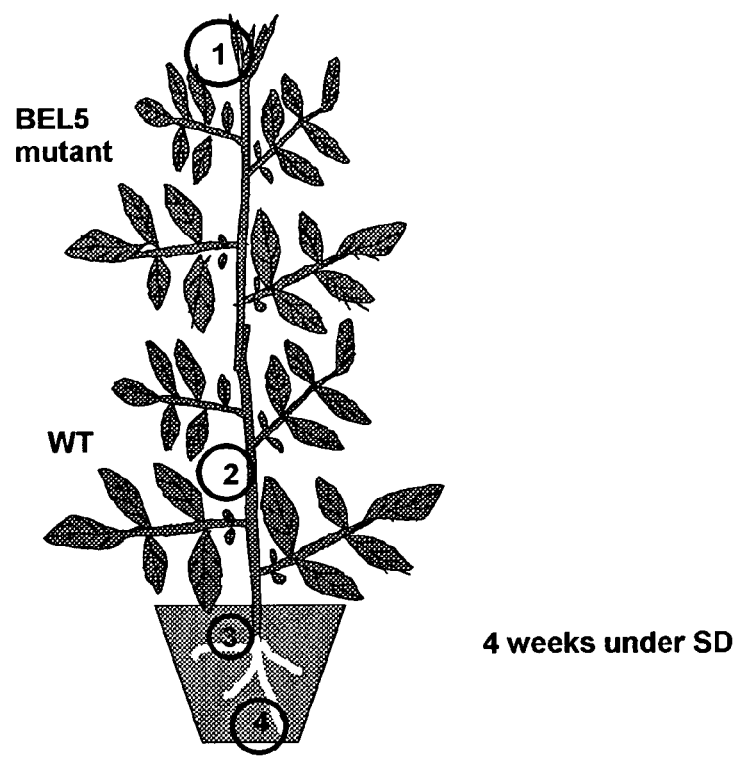

FIG. 37 is a diagram of a heterografted plant showing how StBEL5 RNA movement affects plant growth.

Figure 38:
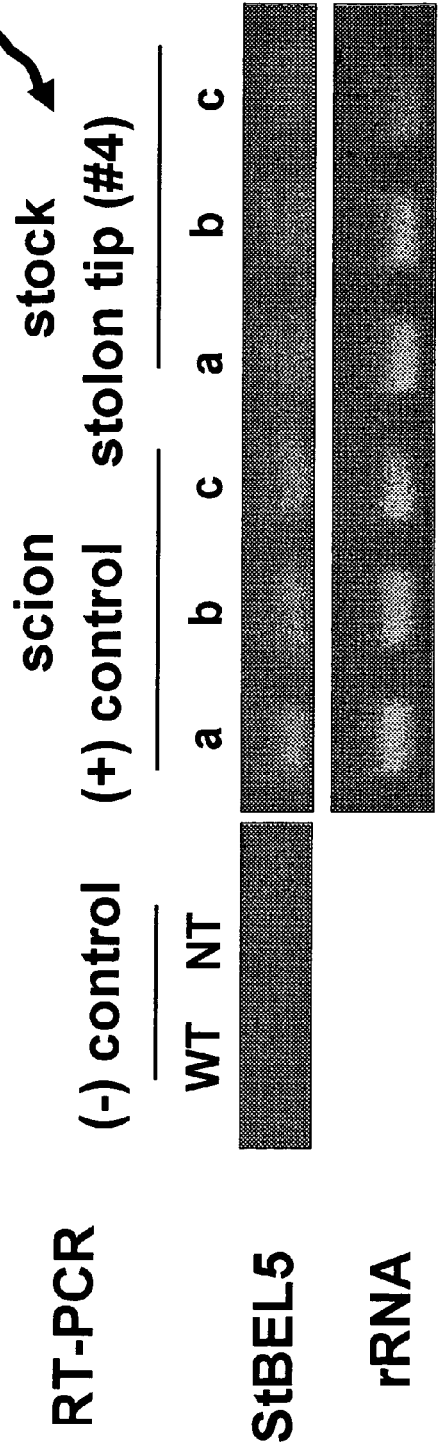

FIG. 38 is a table and RT-PCR results showing tuber yields from heterografts with overexpressers of StBEL5 and *S. tuberosum* ssp. *andigena* WT lines. The means are from three plants each grown under short day conditions (8 hr light, 16 hr dark) for 30 days. Plants for each of these three graft types formed no tubers under long day conditions (8 hr light plus 1 hr night-break). Verification of the presence of transported RNA is shown in the RT-PCR products in the lower panel. RNA was extracted and detected by RT-PCR with nested gene-specific primers and a non-plant DNA primer specific for the transgenic transcripts in stolons of WT stock plants. RNA extracted from sample #4 from FIG. 37 was used in these RT-PCR reactions.

DETAILED DESCRIPTION OF THE INVENTION

The present invention relates to nucleic acid molecules encoding BEL transcription factors from potato (*Solanum tuberosum* L.). BEL transcription factor is a general term used herein to mean a member of the BEL-1-like family of transcription factors, which includes a BELL domain (Bellaoui et al., "The *Arabidopsis* BELL1 and KNOX TALE Homeodomain Proteins Interact Through a Domain Conserved Between Plants and Animals," *Plant Cell* 13(11):2455-70 (2001), which is hereby incorporated by reference in its entirety) and which regulates growth, in particular, floral development.

In a first embodiment, the BEL transcription factor from *Solanum tuberosum* is identified herein as StBEL-05 and is encoded by a nucleic acid molecule having a nucleotide sequence of SEQ ID NO:1 as follows:

```
   1 catgcagaga taaaaatata gatcagtctg acaagaaggc aacttctcaa agcttagaga
  61 gctaccaccc gaagatagac agttagttac atgtactgtt atagataaaa ggagaaatcc
 121 gaagaagaaa gaattttttt tgcagatatg tactatcaag gaacctcgga taatactaat
 181 atacaagctg atcatcaaca acgtcataat catgggaata gtaataataa taatattcag
 241 acactttatt tgatgaaccc taacaattat atgcaaggct acactacttc tgacacacag
 301 cagcagcagc agttactttt cctgaattct tcaccagcag caagcaacgc gctttgccat
 361 gcgaatatac aacacgcgcc gctgcaacag cagcactttg tcggtgtgcc tcttccggca
 421 gtaagtttgc acgatcagat caatcatcat ggactttttac agcgcatgtg aacaaccaa
 481 gatcaatctc agcaggtgat agtaccatcg tcgacggggg tttctgccac gtcatgtggc
 541 gggatcacca cggacttggc gtctcaattg gcgtttcaga ggccgattcc gacaccacaa
 601 caccgacagc agcaacaaca gcaaggcggt ctatctctaa gcctttctcc tcagctacaa
 661 cagcaaatta gtttcaataa caatatttca tcctcatcac caaggacaaa taatgttact
 721 attaggggaa cattagatgg aagttctagc aacatggttt taggctctaa gtatctgaaa
 781 gctgcacaag agcttcttga tgaagttgtt aatattgttg gaaaaagcat caaaggagat
 841 gatcaaaaga aggataattc aatgaataaa gaatcaatgc ctttggctag tgatgtcaac
 901 actaatagtt ctggtggtgg tgaaagtagc agcaggcaga aaaatgaagt tgctgttgag
 961 cttacaactg ctcaaagaca agaacttcaa atgaaaaaag ccaagcttct tgccatgctt
1021 gaagaggtgg agcaaaggta cagacagtac catcaccaaa tgcaaataat tgtattatca
1081 tttgagcaag tagcaggaat tggatcagcc aaatcataca ctcaattagc tttgcatgca
1141 atttcgaagc aattcagatg cctaaaggat gcaattgctg agcaagtaaa ggcgacgagc
1201 aagagtttag gtgaagagga aggcttggga gggaaaatcg aaggctcaag actcaaattt
1261 gtggaccatc atctaaggca acaacgcgcg ctgcaacaga taggaatgat gcaaccaaat
```

-continued

```
1321 gcttggagac cccaaagagg tttacctgaa agagctgtct ctgtccttcg tgcttggctt
1381 ttcgagcatt ttcttcatcc ttacccaaag gattcagaca aaatcatgct tgctaagcaa
1441 acggggctaa caaggagcca ggtgtctaac tggttcataa atgctcgagt tcgattatgg
1501 aagccaatgg tagaagaaat gtacttggaa gaagtgaaga atcaagaaca aaacagtact
1561 aatacttcag gagataacaa aaacaaagag accaatataa gtgctccaaa tgaagagaaa
1621 catccaatta ttactagcag cttattacaa gatggtatta ctactactca agcagaaatt
1681 tctacctcaa ctatttcaac ttcccctact gcaggtgctt cacttcatca tgctcacaat
1741 ttctccttcc ttggttcatt caacatggat aatactacta ctactgttga tcatattgaa
1801 aacaacgcga aaaagcaaag aaatgacatg cacaagtttt ctccaagtag tattctttca
1861 tctgttgaca tggaagccaa agctagaaca tcatcaaata aagggtttac taatccttta
1921 atggcagcat acgcgatggg agattttgga aggtttgatc ctcatgatca acaaatgacc
1981 gcgaattttc atggaaataa tggtgtctct cttactttag gacttcctcc ttctgaaaac
2041 ctagccatgc cagtgagcca acaaaattac cttctaatg acttgggaag taggtctgaa
2101 atggggagtc attacaatag aatgggatat gaaaacattg attttcagag tgggaataag
2161 cgatttccga ctcaactatt accagatttt gttacaggta atctaggaac atgaatacca
2221 gaaagtctcg tattgatagc tgaaaagata aaaggaagtt agggatactc ttatattgtg
2281 tgaggccttc tggcccaagt cggaggaccc aatttgatac aacctatcat aggagaaaag
2341 aagtggagac taaattaaag taacaaaatt ttaaagcaca cttttctagta tatatacttc
2401 ttttttttat agtatagaaa agaagagatt ttgtgcttta gtgtatagat agagtctact
2461 tagtataggt tatacttcta gttccttgag aagattgata caactagtag tattttttt
2521 cttttgggtt ggcttggagt actattttaa gttattggaa actagctata gtaaatgttg
2581 taaagttgtg atattgttcc tctcaatttg catataattt gaatattttt gtacctacta
2641 gctagtctct aaattatgtt tccattgctt gtaattgcaa ttttatttga attttgtgct
2701 atcattatta gattagcaaa aaaaaaaaaa aaaaa
```

The nucleic acid sequence corresponding to SEQ ID NO:1 encodes a BEL transcription factor isolated from *Solanum tuberosum* identified herein as StBEL-05, which has a deduced amino acid sequence corresponding to SEQ ID NO:2 as follows:

```
Met Tyr Tyr Gln Gly Thr Ser Asp Asn Thr Asn Ile Gln Ala Asp His
 1               5                  10                  15

Gln Gln Arg His Asn His Gly Asn Ser Asn Asn Asn Ile Gln Thr
            20                  25                  30

Leu Tyr Leu Met Asn Pro Asn Asn Tyr Met Gln Gly Tyr Thr Thr Ser
        35                  40                  45

Asp Thr Gln Gln Gln Gln Leu Leu Phe Leu Asn Ser Ser Pro Ala
    50                  55                  60

Ala Ser Asn Ala Leu Cys His Ala Asn Ile Gln His Ala Pro Leu Gln
65                  70                  75                  80

Gln Gln His Phe Val Gly Val Pro Leu Pro Ala Val Ser Leu His Asp
                85                  90                  95

Gln Ile Asn His His Gly Leu Leu Gln Arg Met Trp Asn Asn Gln Asp
            100                 105                 110
```

-continued

```
Gln Ser Gln Gln Val Ile Val Pro Ser Ser Thr Gly Val Ser Ala Thr
            115                 120                 125
Ser Cys Gly Gly Ile Thr Thr Asp Leu Ala Ser Gln Leu Ala Phe Gln
        130                 135                 140
Arg Pro Ile Pro Thr Pro Gln His Arg Gln Gln Gln Gln Gln Gln Gly
145                 150                 155                 160
Gly Leu Ser Leu Ser Leu Ser Pro Gln Leu Gln Gln Ile Ser Phe
                165                 170                 175
Asn Asn Asn Ile Ser Ser Ser Pro Arg Thr Asn Asn Val Thr Ile
                180                 185                 190
Arg Gly Thr Leu Asp Gly Ser Ser Asn Met Val Leu Gly Ser Lys
            195                 200                 205
Tyr Leu Lys Ala Ala Gln Glu Leu Leu Asp Glu Val Val Asn Ile Val
            210                 215                 220
Gly Lys Ser Ile Lys Gly Asp Asp Gln Lys Lys Asp Asn Ser Met Asn
225                 230                 235                 240
Lys Glu Ser Met Pro Leu Ala Ser Asp Val Asn Thr Asn Ser Ser Gly
                245                 250                 255
Gly Gly Glu Ser Ser Arg Gln Lys Asn Glu Val Ala Val Glu Leu
                260                 265                 270
Thr Thr Ala Gln Arg Gln Glu Leu Gln Met Lys Lys Ala Lys Leu Leu
            275                 280                 285
Ala Met Leu Glu Glu Val Glu Gln Arg Tyr Arg Gln Tyr His His Gln
            290                 295                 300
Met Gln Ile Ile Val Leu Ser Phe Glu Gln Val Ala Gly Ile Gly Ser
305                 310                 315                 320
Ala Lys Ser Tyr Thr Gln Leu Ala Leu His Ala Ile Ser Lys Gln Phe
                325                 330                 335
Arg Cys Leu Lys Asp Ala Ile Ala Glu Gln Val Lys Ala Thr Ser Lys
                340                 345                 350
Ser Leu Gly Glu Glu Glu Gly Leu Gly Gly Lys Ile Glu Gly Ser Arg
            355                 360                 365
Leu Lys Phe Val Asp His His Leu Arg Gln Gln Arg Ala Leu Gln Gln
            370                 375                 380
Ile Gly Met Met Gln Pro Asn Ala Trp Arg Pro Gln Arg Gly Leu Pro
385                 390                 395                 400
Glu Arg Ala Val Ser Val Leu Arg Ala Trp Leu Phe Glu His Phe Leu
                405                 410                 415
His Pro Tyr Pro Lys Asp Ser Asp Lys Ile Met Leu Ala Lys Gln Thr
                420                 425                 430
Gly Leu Thr Arg Ser Gln Val Ser Asn Trp Phe Ile Asn Ala Arg Val
            435                 440                 445
Arg Leu Trp Lys Pro Met Val Glu Glu Met Tyr Leu Glu Glu Val Lys
            450                 455                 460
Asn Gln Glu Gln Asn Ser Thr Asn Thr Ser Gly Asp Asn Lys Asn Lys
465                 470                 475                 480
Glu Thr Asn Ile Ser Ala Pro Asn Glu Glu Lys His Pro Ile Ile Thr
                485                 490                 495
Ser Ser Leu Leu Gln Asp Gly Ile Thr Thr Thr Gln Ala Glu Ile Ser
            500                 505                 510
Thr Ser Thr Ile Ser Thr Ser Pro Thr Ala Gly Ala Ser Leu His His
            515                 520                 525
Ala His Asn Phe Ser Phe Leu Gly Ser Phe Asn Met Asp Asn Thr Thr
```

```
                    530             535               540
Thr Thr Val Asp His Ile Glu Asn Asn Ala Lys Lys Gln Arg Asn Asp
545                 550                 555                 560

Met His Lys Phe Ser Pro Ser Ser Ile Leu Ser Ser Val Asp Met Glu
                565                 570                 575

Ala Lys Ala Arg Glu Ser Ser Asn Lys Gly Phe Thr Asn Pro Leu Met
                580                 585                 590

Ala Ala Tyr Ala Met Gly Asp Phe Gly Arg Phe Asp Pro His Asp Gln
            595                 600                 605

Gln Met Thr Ala Asn Phe His Gly Asn Asn Gly Val Ser Leu Thr Leu
        610                 615                 620

Gly Leu Pro Pro Ser Glu Asn Leu Ala Met Pro Val Ser Gln Gln Asn
625                 630                 635                 640

Tyr Leu Ser Asn Asp Leu Gly Ser Arg Ser Glu Met Gly Ser His Tyr
                645                 650                 655

Asn Arg Met Gly Tyr Glu Asn Ile Asp Phe Gln Ser Gly Asn Lys Arg
                660                 665                 670

Phe Pro Thr Gln Leu Leu Pro Asp Phe Val Thr Gly Asn Leu Gly Thr
            675                 680                 685
```

The BEL transcription factor has a molecular mass of approximately 75.7 kDa. StBEL05, isolated from *Solanum tuberosum*, has a single open reading frame ("ORF") of 2067 bp, extending between nucleotides 148-2214.

In a second embodiment, the BEL transcription factor from *Solanum tuberosum* is identified herein as StBEL-11 and is encoded by a nucleic acid molecule having a nucleotide sequence of SEQ ID NO:3 as follows:

```
   1 atgactttca ggtctagtct tccactagac ctccgtgaaa tttcaacaac aaatcatcaa
  61 gttggaatac tatcatcatc accattacca tcaccaggaa caaataccaa taatatcaat
 121 catactcgag gattagggc atcatcatct ttttcgattt ctaatgggat gatattgggt
 181 tctaagtacc taaaagttgc acaagatctt cttgatgaag ttgttaatgt tggaaaaaac
 241 atcaaattat cagatggctt agagagtggt gcaaaggaga acacaaatt ggacaatgaa
 301 ttaatatctt tggctagtga tgatgttgaa agcagcagcc aaaaaaatag tggtgttgaa
 361 cttacaacag ctcaaagaca agaacttcaa atgaagaaag ccaagcttgt tagcatgctt
 421 gatgaggtgg atcaaggta tagacaatac catcaccaaa tgcaaatgat tgcaacatca
 481 tttgagcaaa caacaggaat tggatcatca aaatcataca cacaacttgc tttgcacaca
 541 atttcaaagc aatttagatg tttaaaagat gcaatttctg ggcaaataaa ggacactagc
 601 aaaactttag gggaagaaga aaacattgga ggcaaaattg aaggatcaaa gttgaaattt
 661 gtggatcatc atttacgcca acaacgtgca ctacaacaat tagggatgat gcaaaccaat
 721 gcatggaagc ctcaaagagg tttgccagaa agagcggttt cagttctccg cgcttggctt
 781 ttcgagcatt ttcttcatcc gtatcccaaa gattcagata aaatcatcct tgctaagcaa
 841 acagggctaa caaggagcca ggtatcaaat tggtttataa atgctagagt tagactatgg
 901 aagccaatgg tagaagaaat gtacatggaa gaagtgaaga aaaacaatca agaacaaaat
 961 attgagccta ataacaatga aattgttggc tcaaaatcaa gtgttccaca agagaaatta
1021 ccaattagta gcaatattat tcataatgct ctccaaatg atatttctac ttccaccatt
1081 tcaacatctc cgacgggtgg cggcggttcg attccgactc agacggttgc aggtttctcc
1141 ttcattaggt cattaaacat ggagaacatt gatgatcaaa ggaacaacaa aaaggcaaga
1201 aatgagatgc aaaattgttc aactagtact attctctcaa tggaaagaga atcataaat
```

```
                             -continued
1261  aaagttgtgc aagatgagac aatcaaaagt gaaaagttca acaacacaca aacaagagaa 1321  tgttactctc taatgactcc aaattacaca atggatgatc aatttggaac aaggttcaat 1381  aatcaaaatc atgaacaatt ggcaacaaca acaactttc atcaaggaaa tggtcatgtt 1441  tctcttactt tagggcttcc accaaattct gaaaaccaac acaattacat tggattggaa 1501  aatcattaca atcaacctac acatcatcca aatattagct atgaaaacat tgattttcag 1561  agtggaaagc gatacgccac tcaactatta caagattttg tttcttgatg atatatataa 1621  tttgcaggta aatcagcttg aaattacatc atgacaggtc ttgaataaaa gaagggagt 1681  tgagatttag tgatcatata aatatgtata ggtagaaatt ttagttagta tatataggtt 1741  atacttctag tttcttaatg aagatacaag ttttgttgtt atttttgtat tgaggtaact 1801  agctagcttg gattatttaa agttggtgca tgcaactaaa gaagaagaaa aaataatcta 1861  tatatgcaaa ctacagtata ttgtaaattt tgtgcttc
```

The nucleic acid sequence corresponding to SEQ ID NO:3 encodes a BEL transcription factor isolated from *Solanum tuberosum* identified herein as StBEL-11, which has a deduced amino acid sequence corresponding to SEQ ID NO:4 as follows:

```
Met Thr Phe Arg Ser Ser Leu Pro Leu Asp Leu Arg Glu Ile Ser Thr
 1               5                   10                  15

Thr Asn His Gln Val Gly Ile Leu Ser Ser Pro Leu Pro Ser Pro
            20                  25                  30

Gly Thr Asn Thr Asn Ile Asn His Thr Arg Gly Leu Gly Ala Ser
        35                  40                  45

Ser Ser Phe Ser Ile Ser Asn Gly Met Ile Leu Gly Ser Lys Tyr Leu
        50                  55                  60

Lys Val Ala Gln Asp Leu Leu Asp Glu Val Val Asn Val Gly Lys Asn
65                  70                  75                  80

Ile Lys Leu Ser Asp Gly Leu Glu Ser Gly Ala Lys Glu Lys His Lys
                85                  90                  95

Leu Asp Asn Glu Leu Ile Ser Leu Ala Ser Asp Val Glu Ser Ser
            100                 105                 110

Ser Gln Lys Asn Ser Gly Val Glu Leu Thr Thr Ala Gln Arg Gln Glu
        115                 120                 125

Leu Gln Met Lys Lys Ala Lys Leu Val Ser Met Leu Asp Glu Val Asp
        130                 135                 140

Gln Arg Tyr Arg Gln Tyr His His Gln Met Gln Met Ile Ala Thr Ser
145                 150                 155                 160

Phe Glu Gln Thr Thr Gly Ile Gly Ser Ser Lys Ser Tyr Thr Gln Leu
                165                 170                 175

Ala Leu His Thr Ile Ser Lys Gln Phe Arg Cys Leu Lys Asp Ala Ile
            180                 185                 190

Ser Gly Gln Ile Lys Asp Thr Ser Lys Thr Leu Gly Glu Glu Glu Asn
        195                 200                 205

Ile Gly Gly Lys Ile Glu Gly Ser Lys Leu Lys Phe Val Asp His His
        210                 215                 220

Leu Arg Gln Gln Arg Ala Leu Gln Gln Leu Gly Met Met Gln Thr Asn
225                 230                 235                 240

Ala Trp Lys Pro Gln Arg Gly Leu Pro Glu Arg Ala Val Ser Val Leu
                245                 250                 255
```

-continued

```
Arg Ala Trp Leu Phe Glu His Phe Leu His Pro Tyr Pro Lys Asp Ser
            260                 265                 270
Asp Lys Ile Ile Leu Ala Lys Gln Thr Gly Leu Thr Arg Ser Gln Val
            275                 280                 285
Ser Asn Trp Phe Ile Asn Ala Arg Val Arg Leu Trp Lys Pro Met Val
            290                 295                 300
Glu Glu Met Tyr Met Glu Glu Val Lys Lys Asn Asn Gln Glu Gln Asn
305                 310                 315                 320
Ile Glu Pro Asn Asn Asn Glu Ile Val Gly Ser Lys Ser Ser Val Pro
                325                 330                 335
Gln Glu Lys Leu Pro Ile Ser Ser Asn Ile Ile His Asn Ala Ser Pro
            340                 345                 350
Asn Asp Ile Ser Thr Ser Thr Ile Ser Thr Ser Pro Thr Gly Gly Gly
            355                 360                 365
Gly Ser Ile Pro Thr Gln Thr Val Ala Gly Phe Ser Phe Ile Arg Ser
    370                 375                 380
Leu Asn Met Glu Asn Ile Asp Asp Gln Arg Asn Asn Lys Lys Ala Arg
385                 390                 395                 400
Asn Glu Met Gln Asn Cys Ser Thr Ser Thr Ile Leu Ser Met Glu Arg
                405                 410                 415
Glu Ile Ile Asn Lys Val Val Gln Asp Glu Thr Ile Lys Ser Glu Lys
            420                 425                 430
Phe Asn Asn Thr Gln Thr Arg Glu Cys Tyr Ser Leu Met Thr Pro Asn
            435                 440                 445
Tyr Thr Met Asp Asp Gln Phe Gly Thr Arg Phe Asn Asn Gln Asn His
    450                 455                 460
Glu Gln Leu Ala Thr Thr Thr Phe His Gln Gly Asn Gly His Val
465                 470                 475                 480
Ser Leu Thr Leu Gly Leu Pro Pro Asn Ser Glu Asn Gln His Asn Tyr
            485                 490                 495
Ile Gly Leu Glu Asn His Tyr Asn Gln Pro Thr His His Pro Asn Ile
            500                 505                 510
Ser Tyr Glu Asn Ile Asp Phe Gln Ser Gly Lys Arg Tyr Ala Thr Gln
            515                 520                 525
Leu Leu Gln Asp Phe Val Ser
530                 535
```

The BEL transcription factor has a molecular mass of approximately 59 kDa. StBEL-11, isolated from *Solanum tuberosum*, has a single open reading frame ("ORF") of 1608 bp, extending between nucleotides 1-1608.

In a third embodiment, the BEL transcription factor from *Solanum tuberosum* is identified herein as StBEL-13 and is encoded by a nucleic acid molecule having a nucleotide sequence of SEQ ID NO:5 as follows:

```
  1  ggggagcgag tggttccgac aaggtatggt aatgggtgga ggtgcaagta
 51  gtcaacaatt gggatatgca aaaaatcata ctcctaatgt ggcggagtcc
101  atgcaacttt ttctaatgaa tccacaacca aggtcacctt ctccatctcc
151  tcctaattca acttcttcta cgcttcacat gttgttacca aacccatcat
201  ctacttcaac acttcaaggg tttcctaatc cggccgaagg atctttcggt
251  caattcatta catggggaa tggaggagca agtgctgcca cagccaccca
301  tcatctcaat gcccagaatg aaatcggagg agtaaacgtt gtagaaagtc
351  aaggcctatc tctatccttg tcttcttcgt tacagcacaa ggcggaggaa
```

```
-continued
 401   ttacaaatga gcggagaagc tggaggaatg atgttcttca atcaaggagg 451   gtctagtact tccgggcagt atcgatacaa gaatttgaat atgggtggat 501   caggagtaag cccaaacatt catcaagtcc atgttgggta tgggtcatca 551   ttaggagtgg tcaatgtgtt gaggaattcc aaatacgcga aagctgccca 601   agaactactg gaagaattct gcagtgttgg aagaggtaaa ttgaagaaga 651   ctaacaacaa agcagcagcc aataaccctat atacgaaccc tagtggcgct 701   aacaatgaag cttcttcaaa agatgttcct actttgtccg ctgctgatag 751   aattgagcat cagagaagga aggtcaaact tttatctatg gttgatgagg 801   tagataggag gtacaatcat tactgtgaac aaatgcagat ggttgtaaat 851   tcgtttgatt tagtgatggg tttcggcaca gcagttccct acacagcact 901   tgcacagaag gcaatgtcaa gacatttcag gtgtttaaag gatgcaatag 951   gagcacaatt gaagcagagt tgtgagttat taggagagaa agatgcagga 1001   aattcgggat tgactaaagg agaaactccg aggcttaaga tgcttgaaca 1051   aagtttgagg caacaaaggg cgtttcacca aatgggaatg atggaacaag 1101   aagcttggag accacaaaga ggcttacctg aacgttctgt caacatttta 1151   agagcttggc ttttgagca ttttctacac ccgtatccaa gtgatgctga 1201   taaacatctg ttggcaagac agactggtct ctccagaaat caggtatcaa 1251   attggttcat taatgctagg gttcggttgt ggaaacccat ggtagaagat 1301   atgtatcaac aagaagccaa agatgaagat ggagatggag atgagaagag 1351   ccaaagccaa aacagtggca ataacataat tgcacaaaca ccaacgccta 1401   atagcctgac taacacttca tctactaata tgacgacgac aacagcccct 1451   acaactacga cagctctagc tgctgcagag acaggaacag ctgccactcc 1501   cataactgtt acctcaagca aaagatccca aatcaatgcc acggatagtg 1551   acccttcact tgtagcaatc aattccttct ctgaaaacca agctactttt 1601   ccgaccaaca ttcatgatcc cgacgattgc cgtcgcggca acttatccgg 1651   tgacgacggg accaccacac atgatcatat ggggtccacc atgataaggt 1701   ttgggaccac tgctggtgac gtgtcactca ccttagggtt acgacatgca 1751   ggaaatttac cagagaatac tcatttcttt ggttaattaa tacgtatttt 1801   ccccatagta attaattaaa actgaatttg cttgagctca tcataattta 1851   tgcattgctt tttgttataa gaaattccat aaattagctt tgtgttaaaa 1901   aaaaaaaaaa aaaaaaaaa
```

The nucleic acid sequence corresponding to SEQ ID NO:5 encodes a BEL transcription factor isolated from *Solanum tuberosum* identified herein as StBEL-13, which has a deduced amino acid sequence corresponding to SEQ ID NO:6 as follows:

```
Met Val Met Gly Gly Gly Ala Ser Ser Gln Gln Leu Gly Tyr Ala Lys
 1               5                  10                 15

Asn His Thr Pro Asn Val Ala Glu Ser Met Gln Leu Phe Leu Met Asn
            20                  25                 30

Pro Gln Pro Arg Ser Pro Ser Pro Ser Pro Pro Asn Ser Thr Ser Ser
            35                  40                 45

Thr Leu His Met Leu Leu Pro Asn Pro Ser Ser Thr Ser Thr Leu Gln
        50                  55                 60

Gly Phe Pro Asn Pro Ala Glu Gly Ser Phe Gly Gln Phe Ile Thr Trp
 65                 70                  75                 80

Gly Asn Gly Gly Ala Ser Ala Ala Thr Ala Thr His His Leu Asn Ala
                85                  90                 95

Gln Asn Glu Ile Gly Gly Val Asn Val Val Glu Ser Gln Gly Leu Ser
            100                 105                110

Leu Ser Leu Ser Ser Ser Leu Gln His Lys Ala Glu Glu Leu Gln Met
            115                 120                125

Ser Gly Glu Ala Gly Gly Met Met Phe Phe Asn Gln Gly Gly Ser Ser
            130                 135                140

Thr Ser Gly Gln Tyr Arg Tyr Lys Asn Leu Asn Met Gly Gly Ser Gly
145                 150                 155                160

Val Ser Pro Asn Ile His Gln Val His Val Gly Tyr Gly Ser Ser Leu
            165                 170                175

Gly Val Val Asn Val Leu Arg Asn Ser Lys Tyr Ala Lys Ala Ala Gln
            180                 185                190

Glu Leu Leu Glu Glu Phe Cys Ser Val Gly Arg Gly Lys Leu Lys Lys
            195                 200                205

Thr Asn Asn Lys Ala Ala Ala Asn Asn Pro Asn Thr Asn Pro Ser Gly
            210                 215                220

Ala Asn Asn Glu Ala Ser Ser Lys Asp Val Pro Thr Leu Ser Ala Ala
225                 230                 235                240

Asp Arg Ile Glu His Gln Arg Lys Val Lys Leu Leu Ser Met Val
            245                 250                255

Asp Glu Val Asp Arg Arg Tyr Asn His Tyr Cys Glu Gln Met Gln Met
                260                 265                 270

Val Val Asn Ser Phe Asp Leu Val Met Gly Phe Gly Thr Ala Val Pro
            275                 280                 285

Tyr Thr Ala Leu Ala Gln Lys Ala Met Ser Arg His Phe Arg Cys Leu
        290                 295                 300

Lys Asp Ala Ile Gly Ala Gln Leu Lys Gln Ser Cys Glu Leu Leu Gly
305                 310                 315                 320

Glu Lys Asp Ala Gly Asn Ser Gly Leu Thr Lys Gly Glu Thr Pro Arg
                325                 330                 335

Leu Lys Met Leu Glu Gln Ser Leu Arg Gln Arg Ala Phe His Gln
            340                 345                 350

Met Gly Met Met Glu Gln Glu Ala Trp Arg Pro Gln Arg Gly Leu Pro
            355                 360                 365

Glu Arg Ser Val Asn Ile Leu Arg Ala Trp Leu Phe Glu His Phe Leu
    370                 375                 380

His Pro Tyr Pro Ser Asp Ala Asp Lys His Leu Leu Ala Arg Gln Thr
```

```
            385                 390                 395                 400
Gly Leu Ser Arg Asn Gln Val Ser Asn Trp Phe Ile Asn Ala Arg Val
                405                 410                 415

Arg Leu Trp Lys Pro Met Val Glu Asp Met Tyr Gln Gln Glu Ala Lys
            420                 425                 430

Asp Glu Asp Gly Asp Gly Asp Glu Lys Ser Gln Ser Gln Asn Ser Gly
                435                 440                 445

Asn Asn Ile Ile Ala Gln Thr Pro Thr Pro Asn Ser Leu Thr Asn Thr
            450                 455                 460

Ser Ser Thr Asn Met Thr Thr Thr Thr Ala Pro Thr Thr Thr Thr Ala
465                 470                 475                 480

Leu Ala Ala Ala Glu Thr Gly Thr Ala Ala Thr Pro Ile Thr Val Thr
                485                 490                 495

Ser Ser Lys Arg Ser Gln Ile Asn Ala Thr Asp Ser Asp Pro Ser Leu
                500                 505                 510

Val Ala Ile Asn Ser Phe Ser Glu Asn Gln Ala Thr Phe Pro Thr Asn
            515                 520                 525

Ile His Asp Pro Asp Asp Cys Arg Arg Gly Asn Leu Ser Gly Asp Asp
            530                 535                 540

Gly Thr Thr Thr His Asp His Met Gly Ser Thr Met Ile Arg Phe Gly
545                 550                 555                 560

Thr Thr Ala Gly Asp Val Ser Leu Thr Leu Gly Leu Arg His Ala Gly
                565                 570                 575

Asn Leu Pro Glu Asn Thr His Phe Phe Gly
                580                 585
```

The BEL transcription factor has a molecular mass of approximately 64.5 kDa. StBEL-13, isolated from *Solanum tuberosum*, has a single open reading frame ("ORF") of 1759 bp, extending between nucleotides 26-1784.

In a fourth embodiment, the BEL transcription factor from *Solanum tuberosum* is identified herein as StBEL-14 and is encoded by a nucleic acid molecule having a nucleotide sequence of SEQ ID NO:7 as follows:

```
  1 aaccnaaaaa agagatcgaa ttcggcacga gtgatcatgg tccttcgtct
 51 tctaagaaca ttattagtga acaattttac caacatggta gtcatgaaaa
101 tatgttgaca acaacaacta ctcatcatga tgatcatcaa ggctcgtggc
151 atcacgataa taacagaaca ttacttgttg atgatccatc tatgagatgt
201 gttttcccct tgtgaaggaa tgaaaggcca agtcatggac tttcattatc
251 tctttgttcc tcaaatccat caagtattgg tttacaatct tttgaactta
301 gacatcaaga tttgcaacaa ggattaatac atgatggatt tttgggtaaa
351 tctacaaata tacaacaagg gtattttcat catcatcatc aagttaggga
401 ctcgaaatat ttaggtccgq ctcaagagtt gctcagtgag ttctgtagtc
451 tcggaataaa gaagaataat gatcattctt cttcaaaagt acttctaaag
501 caacatgaga gtactgctag tacttcaaaa agcaacttt tacagtctct
551 tgaccttttg gaacttcaaa aaagaaagac aaaattgctt caaatgcttg
601 aagaggtgga tagaaggtac aagcattatt gtgatcaaat gaaggctgtt
651 gtatcatcat ttgaagcagt ggctggaaat ggagcagcaa caqtttactc
701 agccttagca tcaagggcta tgtcaaggca ttttagatgt ttaagagatg
751 gaattgtggc acaaattaag gccacaaaaa tggctatggg agaaaaagac
801 agtactagta ctcttattcc tggttcaaca agaggtgaaa caccaagact
```

```
 851 cagacttctt gatcaaactt taaggcaaca aaaggctttc caacagatga
 901 atatgatgga gactcatcca tggagaccgc aacgtggtct cccagaaaga
 951 tcagtctccg ttctccgcgc ttggctcttt gaacactttc ttcacccgta
1001 cccaagtgat gttgataaac acattttaqc tcqccaaact ggtctttcaa
1051 gaagccaggt gtctaattgg ttcattaatg caagggtaag gctatqgaag
1101 ccaatggtgg aagaaatgta cttagaagaa acaaaagaag aagaaaatgt
1151 tggatctcca gatggatcaa aagccctaat tgatgacatg acaattcatc
1201 aatcacacat tgatcatcat caagctgatc aaaagccaaa tcttgtaaga
1251 attgactctg aatgcatatc ttccatcata aatcatcaac ctcatgagaa
1301 aaatgatcaa aactatggag taattagagg tggagatcaa tcgtttggcg
1351 cgattgagct agatttttca acaaatattg cttatggtac tagtggtggt
1401 gaccatcatc atcatggaqq gggtgtttct ttaacattgg gattacaaca
1451 acatggtgga agtqgtggat catcaatggg gttaactaca ttttcatcac
1501 aaccatctca taatcaaagt tcactttttt atccaagaga tgatgatcaa
1551 gttcaatatt catcactttt ggatagtgaa atcaqaatt tgccatatag
1601 aaaccttgat gggggcacaa cttcttcatq atttggctgg ttaaaaaatg
1651 acagagattc ttcattttgg accttattat atactctaat tttaatatat
1701 attggtgatg aatgatgata aaaaaaaaaa aaaaaaaaa aaaaaaaaaa
1751 aaaaaaaaaa acctcgancc cggtcgactn tanancccta tagngagtcg
1801 tnttnctgca nanatctntg aatcgtaaat nctgaaaaac cccgcaagtt
1851 cacttcaact gngcatcgng cnccatctca atttctttca tttatncatc
1901 gttttgcctt nttttatgta actatnctcc tntaagtttc aatcttggcc
1951 atgtaacctn tqatctntaa aatttttttaa atqactanaa ttaatgccca
2001 tnttttttt ggacctaaat tnttcatqaa aatntnttnc nagggcttnt
2051 tcaaaanctt tggacttntt cnccanaggt ttggtcaagt ntccaatcaa
2101 ggt
```

The nucleic acid sequence corresponding to SEQ ID NO:7 encodes a BEL transcription factor isolated from *Solanum tuberosum* identified herein as StBEL-14, which has a deduced amino acid sequence corresponding to SEQ ID NO:8 as follows:

```
Met Val Asn His Gln Leu Gln Asn Phe Glu Thr Asn Pro Glu Met Tyr
 1               5                  10                  15

Asn Leu Ser Ser Thr Thr Ser Ser Met Asp Gln Met Ile Gly Phe Pro
            20                  25                  30

Pro Asn Asn Asn Pro His His Val Leu Trp Lys Gly Asn Phe Pro
        35                  40                  45

Asn Lys Ile Asn Gly Val Asp Asp Asp His Gly Pro Ser Ser Ser
     50                  55                  60

Lys Asn Ile Ile Ser Glu Gln Phe Tyr Gln His Gly Ser His Glu Asn
 65                  70                  75                  80

Met Leu Thr Thr Thr Thr Thr His His Asp Asp His Gln Gly Ser Trp
```

-continued

```
                85                  90                  95
His His Asp Asn Asn Arg Thr Leu Leu Val Asp Asp Pro Ser Met Arg
            100                 105                 110

Cys Val Phe Pro Cys Glu Gly Asn Glu Arg Pro Ser His Gly Leu Ser
        115                 120                 125

Leu Ser Leu Cys Ser Ser Asn Pro Ser Ser Ile Gly Leu Gln Ser Phe
    130                 135                 140

Glu Leu Arg His Gln Asp Leu Gln Gln Gly Leu Ile His Asp Gly Phe
145                 150                 155                 160

Leu Gly Lys Ser Thr Asn Ile Gln Gln Gly Tyr Phe His His His His
                165                 170                 175

Gln Val Arg Asp Ser Lys Tyr Leu Gly Pro Ala Gln Glu Leu Leu Ser
            180                 185                 190

Glu Phe Cys Ser Leu Gly Ile Lys Lys Asn Asn Asp His Ser Ser Ser
        195                 200                 205

Lys Val Leu Leu Lys Gln His Glu Ser Thr Ala Ser Thr Ser Lys Lys
    210                 215                 220

Gln Leu Leu Gln Ser Leu Asp Leu Leu Glu Leu Gln Lys Arg Lys Thr
225                 230                 235                 240

Lys Leu Leu Gln Met Leu Glu Glu Val Asp Arg Arg Tyr Lys His Tyr
                245                 250                 255

Cys Asp Gln Met Lys Ala Val Val Ser Ser Phe Glu Ala Val Ala Gly
            260                 265                 270

Asn Gly Ala Ala Thr Val Tyr Ser Ala Leu Ala Ser Arg Ala Met Ser
        275                 280                 285

Arg His Phe Arg Cys Leu Arg Asp Gly Ile Val Ala Gln Ile Lys Ala
    290                 295                 300

Thr Lys Met Ala Met Gly Glu Lys Asp Ser Thr Ser Thr Leu Ile Pro
305                 310                 315                 320

Gly Ser Thr Arg Gly Glu Thr Pro Arg Leu Arg Leu Leu Asp Gln Thr
                325                 330                 335

Leu Arg Gln Gln Lys Ala Phe Gln Gln Met Asn Met Met Glu Thr His
            340                 345                 350

Pro Trp Arg Pro Gln Arg Gly Leu Pro Glu Arg Ser Val Ser Val Leu
        355                 360                 365

Arg Ala Trp Leu Phe Glu His Phe Leu His Pro Tyr Pro Ser Asp Val
    370                 375                 380

Asp Lys His Ile Leu Ala Arg Gln Thr Gly Leu Ser Arg Ser Gln Val
385                 390                 395                 400

Ser Asn Trp Phe Ile Asn Ala Arg Val Arg Leu Trp Lys Pro Met Val
                405                 410                 415

Glu Glu Met Tyr Leu Glu Glu Thr Lys Glu Glu Asn Val Gly Ser
            420                 425                 430

Pro Asp Gly Ser Lys Ala Leu Ile Asp Asp Met Thr Ile His Gln Ser
        435                 440                 445

His Ile Asp His His Gln Ala Asp Gln Lys Pro Asn Leu Val Arg Ile
    450                 455                 460

Asp Ser Glu Cys Ile Ser Ser Ile Ile Asn His Gln Pro His Glu Lys
465                 470                 475                 480

Asn Asp Gln Asn Tyr Gly Val Ile Arg Gly Asp Gln Ser Phe Gly
                485                 490                 495

Ala Ile Glu Leu Asp Phe Ser Thr Asn Ile Ala Tyr Gly Thr Ser Gly
            500                 505                 510
```

```
Gly Asp His His His Gly Gly Val Ser Leu Thr Leu Gly Leu
515                 520                 525

Gln Gln His Gly Gly Ser Gly Gly Ser Ser Met Gly Leu Thr Thr Phe
    530             535                 540

Ser Ser Gln Pro Ser His Asn Gln Ser Ser Leu Phe Tyr Pro Arg Asp
545             550                 555                 560

Asp Asp Gln Val Gln Tyr Ser Ser Leu Leu Asp Ser Glu Asn Gln Asn
                565             570                 575

Leu Pro Tyr Arg Asn Leu Asp Gly Gly Thr Thr Ser Ser
            580                 585
```

The BEL transcription factor has a molecular mass of approximately 64.8 kDa. StBEL-14, isolated from *Solanum tuberosum*, has a single open reading frame ("ORF") of 1768 bp, extending between nucleotides 85-1852.

In a fifth embodiment, the BEL transcription factor from *Solanum tuberosum* is identified herein as StBEL-22 and is encoded by a nucleic acid molecule having a nucleotide sequence of SEQ ID NO:9 as follows:

```
   1 acgagcgttt atgagacagc cgggttgttg tctgaaatgt tcaattttca gacaacatcc
  61 acggctgcaa ctgaattgtt gcagaatcaa ttgtcaaata actatagaca cccgaatcaa
 121 cagccacatc atcaacctcc gaccagggag tggtttggta acagacaaga gatcgtagtt
 181 ggtggaagtt tgcaggtaac atttggggat acaaaagatg atgtgaatgc gaaggtatta
 241 ttgagtaacc gtgatagtgt aactgattat tatcagcgtc aacacaatca agtaccaagt
 301 ataaataccg cggagtccat gcaactttt cttatgaatc cacaaccaag ttcaccatca
 361 caatctactc cttcaactct tcatcaaggg ttttctagcc cggtcggagg gcattttagt
 421 caattcatgt gtggaggagc aagtacttct tcaaatccaa ttggaggagt aaatgtgatt
 481 gatcaagggc aaggtctttc attgtccttg tcatctactt tacaacattt ggaagcatcc
 541 aaagtggaag atttgaggat gaatagtgga ggagaaatgt tgttttcaa tcaagaaagt
 601 caaaatcatc ataatattgg ttttgggtca tcactaggac tagtcaatgt gttgaggaat
 661 tcaaagtatg tcaaagcaac acaagagttg ttggaagagt tttgttgtgt tgggaagggt
 721 caattgttca agaaaatcaa caaagtttc aggaataaca acacaagtac atcacccatt
 781 attaaccctc gtggaagtaa taacaataat tcatcttctt caaaggctat tatccctcct
 841 aatttgtcaa ctgcagagag acttgatcat caaagaagga aggtcaaact tttatccatg
 901 cttgatgagg tagagaaaag atacaaccac tattgtgaac aaatgcagat ggtagtaaac
 961 tcattcgatc tagtgatggg ttttggagct gcagttcctt acacagcact agcacagaaa
1021 gccatgtcta ggcatttcaa gtgtttaaaa gatggcgtgg cggcgcaatt gaagaagaca
1081 tgtgaggcac taggtgaaaa agatgcaagc agtagttcag gactgactaa aggagaaaca
1141 ccaaggctta aggtgcttga acaaagcttg aggcaacaaa gagcttttca acaaatggga
1201 atgatggaac aagaagcttg gaggccacaa agaggattgc ctgaacgatc tgtcaatatt
1261 ttaagagctt ggcttttcga acatttctta catccgtatc caagtgatgc agataagcat
1321 cttttggcac gacagactgg tctctccaga aaccaggtag caaactggtt cataaatgcg
1381 agggtgagat tgtggaaacc catggtagaa gaaatgtatc aaagagaggt taatgaagat
1441 gatgttgatg acatgcaaga aaaccaaaac agtacaaata cacaaatacc aacgcctaat
1501 attattatta caaccaattc taacattaca gaaacaaaat cagctgccac tgccacaatt
1561 gcttcagaca aaaaacccca aatcaatgtc tctgaaattg acccttcaat tgtcgcaatg
1621 aatacacatt attcttcctc tatgccaact caattaacca atttccccac tattcaagat
```

-continued

```
1681 gagtccgacc acatcttata tcgccgcagt ggagcggaat atgggaccac aaatatggct 1741 agtaattctg aaattggatc caacatgata acatttggga ccactacggc tagtgatgtt 1801 tcacttacct taggactgcg ccatgcgggt aatttacctg agaatactca tttttccggt 1861 taattaagat agtgtattca aacactgcta cataaattat gattttatat atatatatat 1921 tgtcatccga ttagtttat
```

The nucleic acid sequence corresponding to SEQ ID NO:9 encodes a BEL transcription factor isolated from *Solanum tuberosum* identified herein as StBEL-22, which has a deduced amino acid sequence corresponding to SEQ ID NO:10 as follows:

```
Thr Ser Val Tyr Glu Thr Ala Gly Leu Leu Ser Glu Met Phe Asn Phe
 1               5                  10                  15

Gln Thr Thr Ser Thr Ala Ala Thr Glu Leu Leu Gln Asn Gln Leu Ser
                 20                  25                  30

Asn Asn Tyr Arg His Pro Asn Gln Gln Pro His His Gln Pro Pro Thr
             35                  40                  45

Arg Glu Trp Phe Gly Asn Arg Gln Glu Ile Val Val Gly Gly Ser Leu
     50                  55                  60

Gln Val Thr Phe Gly Asp Thr Lys Asp Val Asn Ala Lys Val Leu
 65                  70                  75                  80

Leu Ser Asn Arg Asp Ser Val Thr Asp Tyr Tyr Gln Arg Gln His Asn
                 85                  90                  95

Gln Val Pro Ser Ile Asn Thr Ala Glu Ser Met Gln Leu Phe Leu Met
                100                 105                 110

Asn Pro Gln Pro Ser Ser Pro Ser Gln Ser Thr Pro Ser Thr Leu His
            115                 120                 125

Gln Gly Phe Ser Ser Pro Val Gly Gly His Phe Ser Gln Phe Met Cys
    130                 135                 140

Gly Gly Ala Ser Thr Ser Ser Asn Pro Ile Gly Gly Val Asn Val Ile
145                 150                 155                 160

Asp Gln Gly Gln Gly Leu Ser Leu Ser Leu Ser Ser Thr Leu Gln His
                165                 170                 175

Leu Glu Ala Ser Lys Val Glu Asp Leu Arg Met Asn Ser Gly Gly Glu
            180                 185                 190

Met Leu Phe Phe Asn Gln Glu Ser Gln Asn His His Asn Ile Gly Phe
        195                 200                 205

Gly Ser Ser Leu Gly Leu Val Asn Val Leu Arg Asn Ser Lys Tyr Val
    210                 215                 220

Lys Ala Thr Gln Glu Leu Leu Glu Glu Phe Cys Cys Val Gly Lys Gly
225                 230                 235                 240

Gln Leu Phe Lys Lys Ile Asn Lys Val Ser Arg Asn Asn Thr Ser
                245                 250                 255

Thr Ser Pro Ile Ile Asn Pro Ser Gly Ser Asn Asn Asn Ser Ser
            260                 265                 270

Ser Ser Lys Ala Ile Ile Pro Pro Asn Leu Ser Thr Ala Glu Arg Leu
        275                 280                 285

Asp His Gln Arg Arg Lys Val Lys Leu Leu Ser Met Leu Asp Glu Val
    290                 295                 300

Glu Lys Arg Tyr Asn His Tyr Cys Glu Gln Met Gln Met Val Val Asn
305                 310                 315                 320
```

-continued

```
Ser Phe Asp Leu Val Met Gly Phe Gly Ala Ala Val Pro Tyr Thr Ala
            325                 330                 335
Leu Ala Gln Lys Ala Met Ser Arg His Phe Lys Cys Leu Lys Asp Gly
            340                 345                 350
Val Ala Ala Gln Leu Lys Lys Thr Cys Glu Ala Leu Gly Glu Lys Asp
            355                 360                 365
Ala Ser Ser Ser Ser Gly Leu Thr Lys Gly Glu Thr Pro Arg Leu Lys
    370                 375                 380
Val Leu Glu Gln Ser Leu Arg Gln Gln Arg Ala Phe Gln Gln Met Gly
385                 390                 395                 400
Met Met Glu Gln Glu Ala Trp Arg Pro Gln Arg Gly Leu Pro Glu Arg
            405                 410                 415
Ser Val Asn Ile Leu Arg Ala Trp Leu Phe Glu His Phe Leu His Pro
            420                 425                 430
Tyr Pro Ser Asp Ala Asp Lys His Leu Leu Ala Arg Gln Thr Gly Leu
            435                 440                 445
Ser Arg Asn Gln Val Ala Asn Trp Phe Ile Asn Ala Arg Val Arg Leu
    450                 455                 460
Trp Lys Pro Met Val Glu Met Tyr Gln Arg Glu Val Asn Glu Asp
465                 470                 475                 480
Asp Val Asp Asp Met Gln Glu Asn Gln Asn Ser Thr Asn Thr Gln Ile
            485                 490                 495
Pro Thr Pro Asn Ile Ile Ile Thr Thr Asn Ser Asn Ile Thr Glu Thr
            500                 505                 510
Lys Ser Ala Ala Thr Ala Thr Ile Ala Ser Asp Lys Lys Pro Gln Ile
            515                 520                 525
Asn Val Ser Glu Ile Asp Pro Ser Ile Val Ala Met Asn Thr His Tyr
    530                 535                 540
Ser Ser Ser Met Pro Thr Gln Leu Thr Asn Phe Pro Thr Ile Gln Asp
545                 550                 555                 560
Glu Ser Asp His Ile Leu Tyr Arg Arg Ser Gly Ala Glu Tyr Gly Thr
            565                 570                 575
Thr Asn Met Ala Ser Asn Ser Glu Ile Gly Ser Asn Met Ile Thr Phe
            580                 585                 590
Gly Thr Thr Thr Ala Ser Asp Val Ser Leu Thr Leu Gly Leu Arg His
            595                 600                 605
Ala Gly Asn Leu Pro Glu Asn Thr His Phe Ser Gly
            610                 615                 620
```

The BEL transcription factor has a molecular mass of approximately 67.3 kDa. StBEL-22, isolated from *Solanum tuberosum*, has a single open reading frame ("ORF") of 1863 bp, extending between nucleotides 1-1863.

In a sixth embodiment, the BEL transcription factor from *Solanum tuberosum* is identified herein as StBEL-29 and is encoded by a nucleic acid molecule having a nucleotide sequence of SEQ ID NO:11 as follows:

```
  1 caagggcttt cacttagcct gtcctcgtcc cagcagccgg ggtttgggaa cttcacggcg
 61 gcgcgtgagc ttgtttcttc gccttcgggt tcggcttcag cttcagggat acaacaacaa
121 caacagcaac aacagagtat tagtagtgtg cctttgagtt ctaagtacat gaaggctgca
181 caagagctac ttgatgaagt tgtaaatgtt ggaaaatcaa tgaaaagtac taatagtact
241 gatgttgttg ttaataatga tgtcaagaaa tcgaagaata tgggcgatat ggacggacag
301 ttagacggag ttggagcaga caaagacgga gctccaacaa ctgagctaag tacaggggag
361 agacaagaaa ttcaaatgaa gaaagcaaaa cttgttaaca tgcttgacga ggtggagcag
```

-continued

```
 421 aggtatagac attatcatca ccaaatgcag tcagtgatac attggttaga gcaagctgct
 481 ggcattggat cagcaaaaac atatacagca ttggctttgc agacgatttc gaagcaattt
 541 aggtgtctta aggacgcgat aattggtcaa atacgatcag caagccagac gttaggcgaa
 601 gaagatagtt tgggagggaa gattgaaggt tcaaggctta aatttgttga taatcagcta
 661 agacagcaaa gggctttgca acaattggga atgatccagc ataatgcttg gagacctcag
 721 agaggattgc ccgaacgagc tgtttctgtt cttcgcgctt ggcttttga acatttcctc
 781 catccttatc ccaaggattc agacaaaatg atgctagcaa aacaaacagg actaactagg
 841 agtcaggtgt cgaattggtt catcaatgct cgagttcgtc tttggaagcc aatggtggaa
 901 gagatgtact tggaagagat aaaagaacac gaacagaatg ggttgggtca agaaaagacg
 961 agcaaattag gtaacagaa cgaagattca acaacatcaa gatccattgc tacacaagac
1021 aaaagccctg gttcagatag ccaaaacaag agttttgtct caaaacagga caatcatttg
1081 cctcaacaca accctgcttc accaatgccc gatgtccaac gccacttcca taccctatc
1141 ggtatgacca tccgtaatca gtctgctggt ttcaacctca ttggatcacc agagatcgaa
1201 agcatcaaca ttactcaagg gagtccaaag aaaccgagga acaacgagat gttgcattca
1261 ccaaacagca ttccatccat caacatggat gtaaagccta acgaggaaca aatgtcgatg
1321 aagtttggtg atgataggca ggacagagat ggattctcac taatgggagg accgatgaac
1381 ttcatgggag gattcggagc ctatcccatt ggagaaattg ctcggtttag caccgagcaa
1441 ttctcagcac catactcaac cagtggcaca gtttcactca ctcttggcct accacataac
1501 gaaaacctct caatgtctgc aacacaccac agtttccttc caattccaac acaaaacatc
1561 caaattggaa gtgaaccaaa tcatgagttt ggtagcttaa acacaccaac atcagctcac
1621 tcaacatcaa gcgtctatga accttcaac attcagaaca gaaagaggtt cgccgcaccc
1681 ttgttaccag attttgttgc ctgatcacaa aaacaaaaac aggttttggc aacagacaaa
1741 cttctgtcgc taaacaagga catgatttag cgacagataa cttcagtcgc taacttagcg
1801 actgaaaact tctgtcgcta agcatgaaca tgtattagcg acatacagta tgcaactgta
1861 tgtcactaaa caagaacatg atgaattagt gacggacaac ttctgtcgct aaacaacaaa
1921 aaaaaatcca tgttttagta tattgtttct cattctatca tatcatggta gtgtaaagaa
1981 tcaagaaaca agttttacat agtaacagtc tttatacatt ggagatgaag aaccatttaa
2041 gttcttcaaa atagatagat tttctaggtt acttctanaa gatatatata tggttgaggg
2101 tttgtatatt aaaaaaaaaa aaaaaaaa
```

The nucleic acid sequence corresponding to SEQ ID NO:11 encodes a BEL transcription factor isolated from *Solanum tuberosum* identified herein as StBEL-29, which has a deduced amino acid sequence corresponding to SEQ ID NO:12 as follows:

```
Gln Gly Leu Ser Leu Ser Leu Ser Ser Gln Gln Pro Gly Phe Gly
 1               5                  10                  15

Asn Phe Thr Ala Ala Arg Glu Leu Val Ser Ser Pro Ser Gly Ser Ala
                20                  25                  30

Ser Ala Ser Gly Ile Gln Gln Gln Gln Gln Gln Gln Ser Ile Ser
            35                  40                  45

Ser Val Pro Leu Ser Ser Lys Tyr Met Lys Ala Ala Gln Glu Leu Leu
```

-continued

```
                50                  55                  60
Asp Glu Val Val Asn Val Gly Lys Ser Met Lys Ser Thr Asn Ser Thr
 65                  70                  75                  80

Asp Val Val Asn Asn Asp Val Lys Lys Ser Lys Asn Met Gly Asp
                 85                  90                  95

Met Asp Gly Gln Leu Asp Gly Val Gly Ala Asp Lys Asp Gly Ala Pro
                100                 105                 110

Thr Thr Glu Leu Ser Thr Gly Glu Arg Gln Glu Ile Gln Met Lys Lys
                115                 120                 125

Ala Lys Leu Val Asn Met Leu Asp Glu Val Glu Gln Arg Tyr Arg His
            130                 135                 140

Tyr His His Gln Met Gln Ser Val Ile His Trp Leu Glu Gln Ala Ala
145                 150                 155                 160

Gly Ile Gly Ser Ala Lys Thr Tyr Thr Ala Leu Ala Leu Gln Thr Ile
                165                 170                 175

Ser Lys Gln Phe Arg Cys Leu Lys Asp Ala Ile Ile Gly Gln Ile Arg
                180                 185                 190

Ser Ala Ser Gln Thr Leu Gly Glu Glu Asp Ser Leu Gly Gly Lys Ile
            195                 200                 205

Glu Gly Ser Arg Leu Lys Phe Val Asp Asn Gln Leu Arg Gln Gln Arg
        210                 215                 220

Ala Leu Gln Gln Leu Gly Met Ile Gln His Asn Ala Trp Arg Pro Gln
225                 230                 235                 240

Arg Gly Leu Pro Glu Arg Ala Val Ser Val Leu Arg Ala Trp Leu Phe
                245                 250                 255

Glu His Phe Leu His Pro Tyr Pro Lys Asp Ser Asp Lys Met Met Leu
            260                 265                 270

Ala Lys Gln Thr Gly Leu Thr Arg Ser Gln Val Ser Asn Trp Phe Ile
        275                 280                 285

Asn Ala Arg Val Arg Leu Trp Lys Pro Met Val Glu Glu Met Tyr Leu
290                 295                 300

Glu Glu Ile Lys Glu His Glu Gln Asn Gly Leu Gly Gln Glu Lys Thr
305                 310                 315                 320

Ser Lys Leu Gly Glu Gln Asn Glu Asp Ser Thr Thr Ser Arg Ser Ile
                325                 330                 335

Ala Thr Gln Asp Lys Ser Pro Gly Ser Asp Ser Gln Asn Lys Ser Phe
            340                 345                 350

Val Ser Lys Gln Asp Asn His Leu Pro Gln His Asn Pro Ala Ser Pro
        355                 360                 365

Met Pro Asp Val Gln Arg His Phe His Thr Pro Ile Gly Met Thr Ile
370                 375                 380

Arg Asn Gln Ser Ala Gly Phe Asn Leu Ile Gly Ser Pro Glu Ile Glu
385                 390                 395                 400

Ser Ile Asn Ile Thr Gln Gly Ser Pro Lys Lys Pro Arg Asn Asn Glu
                405                 410                 415

Met Leu His Ser Pro Asn Ser Ile Pro Ser Ile Asn Met Asp Val Lys
            420                 425                 430

Pro Asn Glu Glu Gln Met Ser Met Lys Phe Gly Asp Asp Arg Gln Asp
        435                 440                 445

Arg Asp Gly Phe Ser Leu Met Gly Gly Pro Met Asn Phe Met Gly Gly
    450                 455                 460

Phe Gly Ala Tyr Pro Ile Gly Glu Ile Ala Arg Phe Ser Thr Glu Gln
465                 470                 475                 480
```

-continued

```
Phe Ser Ala Pro Tyr Ser Thr Ser Gly Thr Val Ser Leu Thr Leu Gly
                485                 490                 495

Leu Pro His Asn Glu Asn Leu Ser Met Ser Ala Thr His His Ser Phe
            500                 505                 510

Leu Pro Ile Pro Thr Gln Asn Ile Gln Ile Gly Ser Glu Pro Asn His
        515                 520                 525

Glu Phe Gly Ser Leu Asn Thr Pro Thr Ser Ala His Ser Thr Ser Ser
    530                 535                 540

Val Tyr Glu Thr Phe Asn Ile Gln Asn Arg Lys Arg Phe Ala Ala Pro
545                 550                 555                 560

Leu Leu Pro Asp Phe Val Ala
                565
```

The BEL transcription factor has a molecular mass of approximately 56.2 kDa. StBEL-29, isolated from *Solanum tuberosum*, has a single open reading frame ("ORF") of 1704 bp, extending between nucleotides 1-1704.

In a seventh embodiment, the BEL transcription factor from *Solanum tuberosum* is identified herein as StBEL-30 and is encoded by a nucleic acid molecule having a nucleotide sequence of SEQ ID NO:13 as follows:

```
   1 atctccaagt aaaaaggtta ttgagaaaag taacacagat ggcgacttat tttcctagtc
  61 caaacaatca aagagatgct gatcagacat ttcaatattt taggcaatct ttgcctgagt
 121 cttattcaga agcttcaaat gctccagaaa acatgatggt attcatgaac tattcttctt
 181 ctggggcata ttcagatatg ttgacgggta cttcccaaca acaacacaac tgcatcgata
 241 tcccatctat aggagccacg cctttcaaca catcccaaca agaaatattg tcaaatcttg
 301 gaggatcgca gatggggatt caggattttt cttcatggag agatagcaga aatgagatgc
 361 tagctgataa tgtctttcaa gttgcacaaa atgtgcaggg tcaaggatta tccctcagtc
 421 ttggctccaa tataccatct ggaattggaa tttcacatgt ccaatctcag aatcctaacc
 481 aaggtggcgg ttttaacatg tcctttggag atggtgataa ttcccaacca aagaacaaa
 541 gaaatgcaga ttatttcct ccggataatc ctggaaggga cttggatgct atgaaagggt
 601 ataattctcc atatggtacg tcgagtattg caaggaccat tcccagctcg aagtatttga
 661 aagcagctca atatttgctt gatgaggttg ttagtgtcag aaaggccatc aaggagcaaa
 721 attctaagaa agagttgaca aaggattcca gagagtctga tgtggactcg aaaaatatat
 781 catcagatac tcctgcaaat gggggttcaa atcctcatga gtccaaaaac aaccaaagtg
 841 aactttcacc taccgagaag caagaagtgc agaacaaact ggccaaactt ctgtcaatgc
 901 tggatgagat tgatagaagg tacagacaat attatcatca gatgcaaata gtggtttcat
 961 catttgatgt ggtagctgga gaaggagcag ctaaaccata cacagctctt gctctccaga
1021 caatttcccg acacttccgt tgcttgcgtg atgcaatctg cgatcagatt cgagcatcac
1081 gaagaagtct tggagagcaa gatgcttcag aaaacagcaa agcgattgga atatcacgcc
1141 tgcgttttgt ggatcatcat attagacagc agagagccct gcagcagctt ggtatgatgc
1201 aacaacatgc ctggaggcct cagaggggat tgcctgaaag ctctgtttca gttttgcgtg
1261 cttggctctt tgagcacttt cttcatccct acccgaaaga ttctgacaaa attatgctag
1321 caaggcaaac tggcttaacg agaagtcagg tatcaaattg gttcataaat gcacgggtgc
1381 gtctttggaa acccatggtt gaggaaatgt acaagaaga ggctggtgat gctaaaatag
1441 actcaaattc ttcatcggat gttgccccca gacttgcaac aaaagactca aagttgaag
1501 aagaggaga attgcaccag aatgcagctt cagaatttga gcagtacaat agtggccaaa
1561 tcctggagtc aaaatctaac catgaagctg atgtagaaat ggagggagca agtaatgcag
```

-continued

```
1621 aaactcaaag tcaatctgga atggaaaacc aaacaggcga acccctgcct gctatggata 1681 attgcaccct ttttcaggac gcatttgttc aaagcaacga tagattctca gaatttggta 1741 gttttggaag tggaaatgta ctacccaatg gagtttcact tacattgggg ctgcagcaag 1801 gtgaaggaag caacctacct atgtccatcg aaactcacgt tagttatgta ccattaaggg 1861 cagatgacat gtatagtaca gcacctacta ctatggtccc tgaaacagca gaattcaact 1921 gcttggattc tgggaatagg cagcaaccat tttggctcct accatctgct acatgatttt 1981 gtatgtgttg tagaattaaa ctgcaagttt tgagtacatc aacattcatc ttcaaaaaaa 2041 aaaaaaaaaa aaaaaaaaaa aaaaa
```

The nucleic acid sequence corresponding to SEQ ID NO:13 encodes a BEL transcription factor isolated from *Solanum tuberosum* identified herein as StBEL-30, which has a deduced amino acid sequence corresponding to SEQ ID NO:14 as follows:

```
Met Ala Thr Tyr Phe Pro Ser Pro Asn Asn Gln Arg Asp Ala Asp Gln
  1               5                  10                  15

Thr Phe Gln Tyr Phe Arg Gln Ser Leu Pro Glu Ser Tyr Ser Glu Ala
             20                  25                  30

Ser Asn Ala Pro Glu Asn Met Met Val Phe Met Asn Tyr Ser Ser Ser
         35                  40                  45

Gly Ala Tyr Ser Asp Met Leu Thr Gly Thr Ser Gln Gln Gln His Asn
     50                  55                  60

Cys Ile Asp Ile Pro Ser Ile Gly Ala Thr Pro Phe Asn Thr Ser Gln
 65                  70                  75                  80

Gln Glu Ile Leu Ser Asn Leu Gly Gly Ser Gln Met Gly Ile Gln Asp
                 85                  90                  95

Phe Ser Ser Trp Arg Asp Ser Arg Asn Glu Met Leu Ala Asp Asn Val
            100                 105                 110

Phe Gln Val Ala Gln Asn Val Gln Gly Gln Gly Leu Ser Leu Ser Leu
            115                 120                 125

Gly Ser Asn Ile Pro Ser Gly Ile Gly Ile Ser His Val Gln Ser Gln
    130                 135                 140

Asn Pro Asn Gln Gly Gly Gly Phe Asn Met Ser Phe Gly Asp Gly Asp
145                 150                 155                 160

Asn Ser Gln Pro Lys Glu Gln Arg Asn Ala Asp Tyr Phe Pro Pro Asp
                165                 170                 175

Asn Pro Gly Arg Asp Leu Asp Ala Met Lys Gly Tyr Asn Ser Pro Tyr
            180                 185                 190

Gly Thr Ser Ser Ile Ala Arg Thr Ile Pro Ser Ser Lys Tyr Leu Lys
            195                 200                 205

Ala Ala Gln Tyr Leu Leu Asp Glu Val Val Ser Val Arg Lys Ala Ile
    210                 215                 220

Lys Glu Gln Asn Ser Lys Lys Glu Leu Thr Lys Asp Ser Arg Glu Ser
225                 230                 235                 240

Asp Val Asp Ser Lys Asn Ile Ser Ser Asp Thr Pro Ala Asn Gly Gly
                245                 250                 255

Ser Asn Pro His Glu Ser Lys Asn Asn Gln Ser Glu Leu Ser Pro Thr
            260                 265                 270

Glu Lys Gln Glu Val Gln Asn Lys Leu Ala Lys Leu Leu Ser Met Leu
```

-continued

```
            275                 280                 285
Asp Glu Ile Asp Arg Arg Tyr Arg Gln Tyr Tyr His Gln Met Gln Ile
        290                 295                 300

Val Val Ser Ser Phe Asp Val Val Ala Gly Glu Gly Ala Ala Lys Pro
305                 310                 315                 320

Tyr Thr Ala Leu Ala Leu Gln Thr Ile Ser Arg His Phe Arg Cys Leu
                325                 330                 335

Arg Asp Ala Ile Cys Asp Gln Ile Arg Ala Ser Arg Arg Ser Leu Gly
            340                 345                 350

Glu Gln Asp Ala Ser Glu Asn Ser Lys Ala Ile Gly Ile Ser Arg Leu
        355                 360                 365

Arg Phe Val Asp His His Ile Arg Gln Gln Arg Ala Leu Gln Gln Leu
    370                 375                 380

Gly Met Met Gln Gln His Ala Trp Arg Pro Gln Arg Gly Leu Pro Glu
385                 390                 395                 400

Ser Ser Val Ser Val Leu Arg Ala Trp Leu Phe Glu His Phe Leu His
                405                 410                 415

Pro Tyr Pro Lys Asp Ser Asp Lys Ile Met Leu Ala Arg Gln Thr Gly
            420                 425                 430

Leu Thr Arg Ser Gln Val Ser Asn Trp Phe Ile Asn Ala Arg Val Arg
        435                 440                 445

Leu Trp Lys Pro Met Val Glu Glu Met Tyr Lys Glu Glu Ala Gly Asp
    450                 455                 460

Ala Lys Ile Asp Ser Asn Ser Ser Asp Val Ala Pro Arg Leu Ala
465                 470                 475                 480

Thr Lys Asp Ser Lys Val Glu Glu Arg Gly Glu Leu His Gln Asn Ala
                485                 490                 495

Ala Ser Glu Phe Glu Gln Tyr Asn Ser Gly Gln Ile Leu Glu Ser Lys
            500                 505                 510

Ser Asn His Glu Ala Asp Val Glu Met Glu Gly Ala Ser Asn Ala Glu
        515                 520                 525

Thr Gln Ser Gln Ser Gly Met Glu Asn Gln Thr Gly Glu Pro Leu Pro
    530                 535                 540

Ala Met Asp Asn Cys Thr Leu Phe Gln Asp Ala Phe Val Gln Ser Asn
545                 550                 555                 560

Asp Arg Phe Ser Glu Phe Gly Ser Phe Gly Ser Gly Asn Val Leu Pro
                565                 570                 575

Asn Gly Val Ser Leu Thr Leu Gly Leu Gln Gln Gly Glu Gly Ser Asn
            580                 585                 590

Leu Pro Met Ser Ile Glu Thr His Val Ser Tyr Val Pro Leu Arg Ala
        595                 600                 605

Asp Asp Met Tyr Ser Thr Ala Pro Thr Thr Met Val Pro Glu Thr Ala
    610                 615                 620

Glu Phe Asn Cys Leu Asp Ser Gly Asn Arg Gln Gln Pro Phe Trp Leu
625                 630                 635                 640

Leu Pro Ser Ala Thr
                645
```

The BEL transcription factor has a molecular mass of approximately 71 kDa. StBEL-30, isolated from *Solanum tuberosum*, has a single open reading frame ("ORF") of 1938 bp, extending between nucleotides 39-1976.

Fragments of the above BEL transcription factors are encompassed by the present invention.

Suitable fragments can be produced by several means. In one method, subclones of the genes encoding the BEL transcription factors of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein, fragments of a BEL transcription factor encoding gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for a BEL transcription factor being produced. Alternatively, subjecting a full length BEL transcription factor to high temperatures and pressures will produce fragments. These fragments can then be separated by conventional procedures (e.g., chromatography, SDS-PAGE).

Another example of suitable fragments of the nucleic acids of the present invention are fragments of the genes which have been identified as conserved ("con") regions of the proteins, or alternatively, those portions of nucleotide sequences that have been identified as variable ("var") regions. Conserved regions in accordance with the present invention include the homeodomain region (including the proline-tyrosine-proline loop between helices I and II), the amino-terminal SKY box, the BELL domain, and the carboxy-terminal VSLTLGL-box (SEQ ID NO:15), as described in Examples 20-32, below. Thus, one embodiment of the present invention relates to an isolated nucleic acid molecule encoding a protein having at least 85%, preferably 90%, similarity to the homeodomain region, the amino-terminal SKY box, the BELL domain, and the carboxy-terminal VSLTLGL-box (SEQ ID NO:15) in either SEQ ID NO:2, SEQ ID NO:4, SEQ ID NO:6, SEQ ID NO:8, SEQ ID NO:10, SEQ ID NO:12, or SEQ ID NO:14 by basic BLAST using default parameters analysis. Sequences identified using DNAStar Mega alignment program as either variable or conserved in a gene can be amplified using standard PCR methods using forward and reverse primers designed to amplify the region of choice and which include a restriction enzyme sequence to allow ligation of the PCR product into a vector of choice. Combinations of amplified conserved and variable region sequences can be ligated into a single vector to create a "cassette" which contains a plurality of DNA molecules in one vector.

Mutations or variants of the above polypeptides or proteins are encompassed by the present invention. Variants may be made by, for example, the deletion or addition of amino acids that have minimal influence on the properties, secondary structure, and hydropathic nature of a polypeptide or protein. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Also suitable as an isolated nucleic acid molecule according to the present invention is a nucleic acid molecule having a nucleotide sequence that is at least 55% similar, preferably at least 80% similar, and most preferably, at least 90% similar, to the nucleotide sequence of SEQ ID NO:1, SEQ ID NO:3, SEQ ID NO:5, SEQ ID NO:7, SEQ ID NO:9, SEQ ID NO:11, or SEQ ID NO:13 by basic BLAST using default parameters analysis.

Suitable nucleic acid molecules are those that hybridize to a nucleic acid molecule comprising a nucleotide sequence of SEQ ID NO:1, SEQ ID NO:3, SEQ ID NO:5, SEQ ID NO:7, SEQ ID NO:9, SEQ ID NO:11, or SEQ ID NO:13 under stringent conditions. For the purposes of defining the level of stringency, reference can conveniently be made to Sambrook et al., *Molecular Cloning: a Laboratory Manual*, 2$^{nd}$ Edition, Cold Spring Harbor, N.Y., Cold Spring Harbor Laboratory Press, at 11.45 (1989). An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at ≧45° C. for 2-3 hours. An example of high stringency conditions includes 0.1-1× SSC/0.1% w/v SDS at 60° C. for 1-3 hours. The skilled artisan is aware of various parameters which may be altered during hybridization and washing and which will either maintain or change the stringency conditions. Other examples of high stringency conditions include: 4-5×SSC/0.1% w/v SDS at 54° C. for 1-3 hours and 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

The precise conditions for any particular hybridization are left to those skilled in the art because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure.

A BEL transcription factor of the present invention is preferably produced in purified form (e.g., at least about 80%, more preferably 90% pure) by conventional techniques. For example, a BEL transcription factor of the present invention may be secreted into the growth medium of recombinant host cells. To isolate the BEL transcription factor, a protocol involving a host cell such as *Escherichia coli* may be used, in which protocol the *E. coli* host cell carrying a recombinant plasmid is propagated, homogenized, and the homogenate is centrifuged to remove bacterial debris. The supernatant is then subjected to sequential ammonium sulfate precipitation. The fraction containing the BEL transcription factor of the present invention is subjected to gel filtration in an appropriately sized dextran or polyacrylamide column to separate the proteins or polypeptides. If necessary, the protein fraction may be further purified by high performance liquid chromatography ("HPLC").

The present invention relates to a DNA construct that contains a DNA molecule encoding for a BEL transcription factor. This involves incorporating one or more of the nucleic acid molecules of the present invention, or a suitable portion thereof, into host cells using conventional recombinant DNA technology. Generally, this involves inserting the nucleic acid molecule into an expression system to which the nucleic acid molecule is heterologous (i.e. not normally present). The expression system contains the necessary elements for the transcription and translation of the inserted protein-coding sequences.

The present invention also relates to an expression vector containing a nucleic acid molecule encoding a BEL transcription factor of the present invention. The nucleic acid molecules of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for transformation. The selection of a vector will depend on the preferred transformation technique and target cells for transfection.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/−or KS +/−(see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), pCB201, and any derivatives thereof. Any appropriate vectors now known or later described for genetic transformation are suitable for use with the present invention. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Thus, certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used. A constitutive promoter is a promoter that directs expression of a gene throughout the development and life of an organism. An inducible promoter is a promoter that is capable of directly or indirectly activating transcription of one or more DNA sequences or genes in response to an inducer. In the absence of an inducer, the DNA sequences or genes will not be transcribed or will only be minimally transcribed.

The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Other examples of some constitutive promoters that are widely used for inducing expression of transgenes include the nopoline synthase (NOS) gene promoter, from *Agrobacterium tumefaciens*, (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), the enhanced CaMV35S promoter ("enh CaMV35S"), the figwort mosaic virus full-length transcript promoter ("FMV35S"), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter derived from the cellular elongation factor 1α gene.

Bacterial host cell strains and expression vectors may be chosen which inhibit the action of the promoter unless specifically induced. In certain operations, the addition of specific inducers is necessary for efficient transcription of the inserted nucleic acid. For example, the lac operon is induced by the addition of lactose or IPTG (isopropylthio-beta-D-galactoside). A variety of other operons, such as trp, pro, etc., are under different controls.

Other examples of some inducible promoters, induced, for examples by a chemical agent, such as a metabolite, growth regulator, herbicide or phenolic compound, or a physiological stress/physical means, such as cold, heat, salt, toxins, or through the action of a pathogen or disease agent such as a virus or fungus, include a glucocorticoid-inducible promoter (Schena et al., *Proc. Natl. Acad. Sci.* 88:10421-5 (1991), which is hereby incorporated by reference in its entirety), the heat shock promoter ("Hsp"), IPTG or tetracycline ("Tet on" system), the metallothionine promoter, which is activated by heavy metal ions, and hormone-responsive promoters, which are activated by treatment of certain hormones. A host cell containing an inducible promoter may be exposed to an inducer by externally applying the inducer to the cell. In addition, "tissue-specific" promoters can be used, which are promoters that function in a tissue specific manner to regulate the gene of interest within selected tissues of the host. Examples of such tissue specific promoters include seed, flower, or root specific promoters as are well known in the field (e.g., U.S. Pat. No. 5,750,385 to Shewmaker et al., which is hereby incorporated by reference in its entirety). Promoters of the nucleic acid construct of the present invention may be either homologous (derived from the same species as the host cell) or heterologous (derived from a different species than the host cell).

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

The constructs of the present invention also include an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known in the art. Virtually any 3' regulatory region known to be operable in the host cell of choice would suffice for proper expression of the coding sequence of the nucleic acid of the present invention.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A nucleic acid molecule of the preset invention, promoter of choice, an appropriate 3' regulatory region, and, if desired, a reporter gene, can be incorporated into a vector-expression system to contain a nucleic acid of the present invention, or a suitable fragment thereof, using standard cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology*, John Wiley & Sons, New York, N.Y., which are hereby incorporated by reference in their entirety. The transcriptional and translational elements are operably linked to the nucleic acid molecule of the present invention or a fragment thereof, meaning that the resulting vector expresses the BEL transcription factor when placed in a suitable host cell.

Once an isolated DNA molecule encoding a BEL transcription factor has been cloned into an expression vector, it is ready to be incorporated into a host cell. Such incorporation can be carried out by the various forms of transformation noted above, depending upon the vector/host cell system. Recombinant molecules can be introduced into cells via transformation, particularly transduction, conjugation, mobilization, or electroporation. The nucleic acid sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like.

Thus, the present invention also relates to a host cell incorporating one or more of the isolated nucleic acid molecules of the present invention. In one embodiment, the isolated nucleic acid molecule is heterologous to the host cell. Such incorporation can be carried out by the various forms of transformation noted above, depending upon the vector/host system, and using the various host cells described above.

Methods of transformation may result in transient or stable expression of the DNA under control of the promoter. Preferably, the nucleic acid of the present invention is stably inserted into the genome of the host cell as a result of the transformation, although transient expression can serve an important purpose.

One approach to transforming host cells with a nucleic acid molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression, because the population of cells is very high (on the order of $10^6$). To deliver DNA inside protoplasts, several methodologies have been proposed, but the most common are electroporation (Fromm et al., *Proc. Natl. Acad. Sci. USA* 82:5824-5828 (1985), which is hereby incorporated by reference in its entirety) and polyethylene glycol (PEG) mediated DNA uptake (Krens et al., *Nature* 296:72-74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the nucleic acid molecule of the present invention into a host cell is fusion of protoplasts with other entities, either minicells, cells, lysosomes, or other fusible lipid-surfaced bodies that contain the chimeric gene (Fraley, et al., *Proc. Natl. Acad. Sci. USA* 76:3348-52 (1979), which is hereby incorporated by reference in its entirety).

Stable transformants are preferable for the methods of the present invention. An appropriate method of stably introducing the nucleic acid molecule into plant cells is to infect a plant cell with *Agrobacterium tumefaciens* or *Agrobacterium rhizogenes* previously transformed with a DNA construct of the present invention. Under appropriate conditions known in the art, the transformed plant cells are grown to form shoots or roots, and develop further into plants.

Plant tissues suitable for transformation include without limitation, floral buds, leaf tissue, root tissue, meristems, zygotic and somatic embryos, megaspores, callus, protoplasts, tassels, pollen, embryos, anthers, and the like. The means of transformation chosen is that most suited to the tissue to be transformed.

Suitable plants include dicots and monocots. Monocots suitable for the present invention include Gramineae (e.g., grass, corn, grains, bamboo, sugar cane), Liliaceae (e.g., onion, garlic, asparagus, tulips, hyacinths, day 111y, and aloes), Iridaceae (e.g., iris, gladioli, freesia, crocus, and *watsonia*), and Orchidacea (e.g., orchid). Examples of dicots suitable for the present invention include Salicaceae (e.g., willow, and poplar), Ranunculaceae (e.g., *Delphinium, Paeonia, Ranunculus, Anemone, Clematis*, columbine, and marsh marigold), Magnoliaceae (e.g., tulip tree and *Magnolia*), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, wisteria, lupine, black locust, and acacia), Malvaceae (e.g., cotton, okra, and mallow), Umbelliferae (e.g., carrot, parsley, parsnips, and hemlock), Labiatae (e.g., mint, peppermints, spearmint, thyme, sage, and lavender), Solanaceae (e.g., potato, tomato, pepper, eggplant, tobacco, henbane, atropa, physalis, *datura*, and *Petunia*), Cucurbitaceae (e.g., melon, squash, pumpkin, and cucumber), Compositae (e.g., sunflower, endive, artichoke, lettuce, safflower, aster, marigold, dandelions, sage brush, *Dalia, Chrysanthemum*, and *Zinna*), and Rubiaceae (e.g., coffee).

After transformation, the transformed plant cells can be selected and regenerated. Preferably, transformed cells are first identified using a selection marker simultaneously introduced into the host cells along with the DNA construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Any known antibiotic-resistance marker can be used to transform and select transformed host cells in accordance with the present invention. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of a compound identifiable are suitable. The most widely used reporter gene for gene fusion experiments has been uidA, a gene from *Escherichia coli* that encodes the β-glucuronidase protein, also known as GUS (Jefferson et al., *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. It is known that practically all plants can be regenerated from cultured cells or tissues. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures*, Vol. 1: (MacMillan Publishing Co., New York, 1983); and Vasil I. R. (ed.), *Cell Culture and Somatic Cell Genetics of Plants*, Acad. Press, Orlando, Vol. 1, 1984, and Vol. III (1986), which are hereby incorporated by reference in their entirety.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds or propagules (e.g., cuttings) are recovered from the transgenic plants. The seeds can then be planted in the soil and cultivated using conventional procedures to produce transgenic plants.

The present invention is also directed to a method for enhancing tuber development in a plant. This method includes transforming a tuberous plant with a first DNA construct including a first nucleic acid molecule encoding a BEL transcription factor or a KNOX transcription factor, and a first operably linked promoter and first 3' regulatory region, whereby tuber development in the plant is enhanced.

Suitable BEL transcription factors include BEL transcription factors from potato, as described above. Other suitable BEL transcription factors include, but are not limited to, those from tobacco, tomato (see, e.g., GenBank Accession Nos. AF375964, AF375965, and AF375966), *Arabidopsis*, rice, barley, apple, and bago (*Gnetum gnemon*).

As used herein, a KNOX transcription factor is encoded by a Knotted-like homeobox (knox) gene and includes a KNOX domain. KNOX transcription factors regulate growth, in particular, leaf architecture and meristem growth. KNOX transcription factors have been isolated from several plant species (reviewed in Reiser et al., "Knots in the Family Tree: Evolutionary Relationships and Functions of knox Homeobox Genes," *Plant Mol. Biol.* 42:151-166 (2000), which is hereby incorporated by reference in its entirety) and can be divided into two classes based on expression patterns and sequence similarity (Kerstetter et al., "Sequence Analysis and Expression Patterns Divide the Maize knotted1-like Homeobox Genes into Two Classes," *Plant Cell* 6:1877-1887 (1994), which is hereby incorporated by reference in its entirety). Class I knox genes have high similarity to the maize knotted1 (kn1) homeodomain and generally have a meristem-specific mRNA expression pattern. Class II knox genes usually have a more widespread expression pattern. Knox genes are members of the three amino acid loop extension (TALE) superclass of homeobox genes (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997), which is hereby incorporated by reference in its entirety). Knox genes share conserved regions outside of the homeodomain including the MEINOX and ELK domains.

Suitable KNOX transcription factors include, but are not limited to, POTH1, POTH15, POTH2, H09, NTH Types (1, 9, 15, 20, 22) (Nishamura et al., *Plant J.* 18:337-347 (1999), which is hereby incorporated by reference in its entirety), those from *Arabidopsis*, maize, barley, tobacco, tomato, pea, cabbage, *Ipomoea, Helianthus, Medicago*, and Dendrobium.

In one embodiment, the KNOX transcription factor is POTH1 and is encoded by a nucleic acid molecule having a nucleotide sequence of SEQ ID NO:16 as follows:

```
   1 gagtttctct cccttttaaa aaagaaaaaa aaaacacaac acccacttca aatatcaaac
  61 aaatttctca tttgattatt tctaagtgat ttacactact ttgtattttt gtttgttttt
 121 ttttagatat atatatggat gatgaaatgt atggtttttca ttcaacaaga gacgattacg
 181 cggataaagc tttgatgtca ccggagaatt tgatgatgca aactgagtac aacaatttcc
 241 acaactatac caactcgtcc atcttgactt ctaatccgat gatgtttgga tccgatgata
 301 ttcaattatc atcggaacaa actaattctt tcagtactat gactcttcaa aataatgata
 361 atatttatca aattagaagt ggaaattgtg gcggaggcag tggcagtggt ggtagcagta
 421 aggatcataa tgataataac aataataatg aagattatga tgaagatggt tcaaatgtta
 481 tcaaggctaa aatcgtctca catccttatt atcctaaatt actcaacgct tatattgatt
 541 gccaaaaggt tggagcacca gcgggtatag taaatctgct ggaagaaata aggcaacaaa
 601 ctgattttcg taaaccaaac gctacttcta tatgtatagg agctgatcct gaacttgatg
 661 agtttatgga aacgtattgt gatatattgt tgaagtataa gtccgatctg tctaggcctt
 721 ttgatgaagc aacaacgttc ctcaacaaga ttgaaatgca actaggtaat ctttgcaaag
 781 atgatggtgg tgtatcatca gatgaggagt taagttgtgg tgaggcagat gcatcaatga
 841 gaagtgagga taatgaactc aaagatagac tcctacgtaa gtttggaagt catttaagta
 901 gtctaaagtt ggaattttca aagaaaaaga agaaagggaa gctaccaaaa gaggcaaggc
 961 aaatgttact tgcatggtgg gatgatcact ttagatggcc ttaccctacg gaggctgata
1021 agaattcact agcagaatca acaggacttg atccaaagca gatcaacaat tggtttataa
1081 atcaaaggaa gagacattgg aaaccatcag agaatatgca gttagctgtt atggataatc
1141 taagctctca gttcttctca tcagatgatt gagtttgaat ggaaattgtg aaaatactgc
1201 tcttcatttc tctttttatt atatataata tataaatagt atattttgg gaaagaaaga
1261 agttatttta ttaatcaaaa tctctataaa taatggtaga gattaattaa tgttgaattc
1321 ttcttgatca tgtaaatatt caatctagct aattgtcaaa attaatgctt acctaaaaaa
1381 aaa
```

The cDNA (Genbank Accession # U65648) includes an open reading frame of 1035 nt coding for a 345-residue protein estimated to have a mass of 37.95 kDa having an amino acid sequence corresponding to SEQ ID NO:17 as follows:

```
Met Asp Asp Glu Met Tyr Gly Phe His Ser Thr Arg Asp Asp Tyr Ala
 1               5                  10                  15

Asp Lys Ala Leu Met Ser Pro Glu Asn Leu Met Met Gln Thr Glu Tyr
            20                  25                  30

Asn Asn Phe His Asn Tyr Thr Asn Ser Ser Ile Leu Thr Ser Asn Pro
            35                  40                  45

Met Met Phe Gly Ser Asp Asp Ile Gln Leu Ser Ser Glu Gln Thr Asn
        50                  55                  60

Ser Phe Ser Thr Met Thr Leu Gln Asn Asn Asp Asn Ile Tyr Gln Ile
65                  70                  75                  80

Arg Ser Gly Asn Cys Gly Gly Gly Ser Gly Ser Gly Gly Ser Ser Lys
                85                  90                  95

Asp His Asn Asp Asn Asn Asn Asn Glu Asp Tyr Asp Glu Asp Gly
            100                 105                 110

Ser Asn Val Ile Lys Ala Lys Ile Val Ser His Pro Tyr Tyr Pro Lys
            115                 120                 125

Leu Leu Asn Ala Tyr Ile Asp Cys Gln Lys Val Gly Ala Pro Ala Gly
    130                 135                 140

Ile Val Asn Leu Leu Glu Glu Ile Arg Gln Gln Thr Asp Phe Arg Lys
145                 150                 155                 160

Pro Asn Ala Thr Ser Ile Cys Ile Gly Ala Asp Pro Glu Leu Asp Glu
                165                 170                 175

Phe Met Glu Thr Tyr Cys Asp Ile Leu Leu Lys Tyr Lys Ser Asp Leu
            180                 185                 190

Ser Arg Pro Phe Asp Glu Ala Thr Thr Phe Leu Asn Lys Ile Glu Met
            195                 200                 205

Gln Leu Gly Asn Leu Cys Lys Asp Asp Gly Gly Val Ser Ser Asp Glu
    210                 215                 220

Glu Leu Ser Cys Gly Glu Ala Asp Ala Ser Met Arg Ser Glu Asp Asn
225                 230                 235                 240

Glu Leu Lys Asp Arg Leu Leu Arg Lys Phe Gly Ser His Leu Ser Ser
            245                 250                 255

Leu Lys Leu Glu Phe Ser Lys Lys Lys Lys Gly Lys Leu Pro Lys
            260                 265                 270

Glu Ala Arg Gln Met Leu Leu Ala Trp Trp Asp Asp His Phe Arg Trp
    275                 280                 285

Pro Tyr Pro Thr Glu Ala Asp Lys Asn Ser Leu Ala Glu Ser Thr Gly
    290                 295                 300

Leu Asp Pro Lys Gln Ile Asn Asn Trp Phe Ile Asn Gln Arg Lys Arg
305                 310                 315                 320

His Trp Lys Pro Ser Glu Asn Met Gln Leu Ala Val Met Asp Asn Leu
                325                 330                 335

Ser Ser Gln Phe Phe Ser Ser Asp Asp
            340                 345
```

In accordance with the present invention, the BEL or KNOX transcription factor may be expressed throughout the plant to achieve enhanced tuber development (see Examples below). Alternatively, the BEL or KNOX transcription factor may be expressed in an organ-specific manner. This is beneficial when, for example with POTH1, expression throughout the plant results in dwarf transgenic plants with altered leaf morphology. In these circumstances, specific expression in the stolon, for example, may be desirable.

In one embodiment of this method of the present invention, the tuberous plant is transformed with one or more DNA constructs which include nucleic acid molecules encoding both a BEL transcription factor and a KNOX transcription factor. Alternatively, a plant expressing one or more of a BEL transcription factor or a KNOX transcription factor may be transformed with a DNA construct including a nucleic acid molecule encoding only one of a BEL transcription factor or a KNOX transcription factor.

Tuberous plants suitable for use in this method of the present invention include potato, dahlia, caladium, Jerusalem artichoke (*Helianthus tuberosus*), yam (*Dioscorea alta*), sweet potato (*Impomoea batatus*), cassaya (*Manihot esculenta*), tuberous begonia, cyclamen, and other *solanum* species (e.g., wild potato).

Another aspect of the present invention relates to a method of enhancing growth in a plant. This method includes transforming a plant with a DNA construct including a nucleic acid molecule encoding a BEL transcription factor from *Solanum tuberosum* and an operably linked promoter and 3' regulatory region, whereby growth in the plant is enhanced.

Suitable plants which may be transformed in this method of the present invention include Gramineae (e.g., grass, corn, grains, bamboo, sugar cane), Liliaceae (e.g., onion, garlic, asparagus, tulips, hyacinths, day lily, and aloes), Iridaceae (e.g., iris, gladioli, freesia, crocus, and *watsonia*), Orchidacea (e.g., orchid), Salicaceae (e.g., willow, and poplar), Ranunculaceae (e.g., *Delphinium, Paeonia, Ranunculus, Anemone, Clematis*, columbine, and marsh marigold), Magnoliaceae (e.g., tulip tree and *Magnolia*), Cruciferae (e.g., mustards, cabbage, cauliflower, broccoli, brussel sprouts, kale, kohlrabi, turnip, and radish), Rosaceae (e.g., strawberry, blackberry, peach, apple, pear, quince, cherry, almond, plum, apricot, and rose), Leguminosae (e.g., pea, bean, peanut, alfalfa, clover, vetch, redbud, broom, wisteria, lupine, black locust, and acacia), Malvaceae (e.g., cotton, okra, and mallow), Umbelliferae (e.g., carrot, parsley, parsnips, and hemlock), Labiatae (e.g., mint, peppemmints, spearmint, thyme, sage, and lavender), Solanaceae (e.g., potato, tomato, pepper, eggplant, tobacco, henbane, atropa, physalis, *datura*, and *Petunia*), Cucurbitaceae (e.g., melon, squash, pumpkin, and cucumber), Compositae (e.g., sunflower, endive, artichoke, lettuce, safflower, aster, marigold, dandelions, sage brush, *Dalia, Chrysanthemum,* and *Zinna*), and Rubiaceae (e.g., coffee). In one particular embodiment, the plant transformed is a solanaceous species.

Yet another embodiment of the present invention relates to a method of regulating flowering in a plant. This method includes transforming a plant with a DNA construct including a nucleic acid molecule encoding a BEL transcription factor from *Solanum tuberosum* and an operably linked promoter and 3' regulatory region, whereby flowering in the plant is regulated. BEL TFs play a role in flowering as described in Smith et al., "Competence to Respond to Floral Inductive Signals Requires the Homeobox Genes PENNYWISE and POUND-FOOLISH," *Curr. Biol.* 14(9):812-817 (2004), which is hereby incorporated by reference in its entirety.

Suitable plants in accordance with this method of the present invention are described above.

The BEL transcription factors from *Solanum tuberosum* of the present invention appear to play a diverse role in plant growth by regulating the development of both reproductive and vegetative meristems. Accordingly, they can be used in the methods for enhancing growth or regulating flowering of the present invention. In particular, the BEL transcription factors of the present invention are involved in regulating photoperiodic responses in potato (tuberization), and BEL transcription factors have previously been identified as contributing to flower development (Müller et al., "In vitro Interactions Between Barley TALE Homeodomain Proteins Suggest a Role for Protein-Protein Associations in the Regulation of Knox Gene Function," *Plant J.* 27:13-23 (2001); Mondrusan et al., "Homeotic Transformation of Ovules into Carpel-Like Structures in *Arabidopsis*," *Plant Cell* 6:333-349 (1994); Reiser et al., "The BELL1 Gene Encodes a Homeodomain Protein Involved in Patterns Formation in the *Arabidopsis* Ovule Primordium," *Cell* 83:735-742 (1995), which are hereby incorporated by reference in their entirety) and are present in numerous photoperiodic flowering species (e.g., rice, tobacco, morning glory, *Arabidopsis*), thus it appears that they contribute to regulating flower induction in many plants.

The present invention also relates to a method of screening a biomolecule for its ability to assist in mediating long-distance movement of a mobile RNA in a plant. This method involves providing a biomolecule and providing a mobile RNA of a plant. The biomolecule is contacted with the mobile RNA. A determination is made as to whether contacting the biomolecule with the mobile RNA is effective in yielding a biomolecule/mobile RNA complex. The presence of a biomolecule/mobile RNA complex indicates that the biomolecule is able to assist in mediating long-distance movement of the mobile RNA in the plant.

Suitable biomolecules for use in this method can include, for example, proteins, polypeptides, and/or ribonucleoproteins.

Suitable mobile RNAs for use in this method can include RNAs that encode the various POTH1 and/or BEL transcription factors described herein. Mobile RNA can be full length, including the 5'- and 3'-untranslated regions ("UTRs"). Other examples of particular mobile RNAs can include those that correspond to either of the UTRs of the isolated nucleic acid molecules (encoding a BEL and/or KNOX transcription factor) of the present invention.

In one embodiment, the 3'-UTR corresponds to nucleotide bases 2215 to 2735 of SEQ ID NO:1 (StBEL-05) (GenBank Accession No. AF406697) and has a nucleotide sequence of SEQ ID NO:28 as follows:

ataccagaaagtctcgtattgatagct-
gaaaagataaaaggaagttagggatactcttatattgtgtgaggccttctggc
ccaagtcggaggacccaatttgata-
caacctatcataggagaaaagaagtggagactaaattaaagtaacaaaatttta
aagcacactttctagtatatatact-
tcttttttttatagtatagaaaagaagagattttgtgctttagtgtatagatagagtcta
cttagtataggttatacttctagttcct-
tgagaagattgatacaactagtagtatttttttctttgggttggcttggagtacta ttt-
taagttattggaaactagctatag-
taaatgttgtaaagttgtgatattgttcctctcaatttgcatataatttgaaatattttg
tacctactagctagtctctaaattat-
gtttccattgcttgtaattgcaattttatttgaattttgtgctatcattattagattagcaa
aaaaaaaaaaaaaaaa In one embodiment, the 3'-UTR corresponds to nucleotide bases 1609 to 1898 of SEQ ID NO:3 (StBEL-11) (GenBank Accession No. AF406698) and has a nucleotide sequence of SEQ ID NO:29 as follows:

tgatatatataatttgcaggtaaat-
cagcttgaaattacatcatgacaggtcttgaataaaagaaggggagttgagattta
gtgatcatataaatatgtataggta-
gaaattttagttagtatatataggttatacttctagtttcttaatgaagatacaagttttg
ttgttatttttgtattgaggtaac-
tagctagcttggattatttaaagttggt-
gcatgcaactaaagaagaagaaaaaataatc tatatatgcaaactacagtatattg-
taaattttgtgcftc In one embodiment, the 3'-UTR corresponds to nucleotide bases 1707 to 1840 of SEQ ID NO:5 (StBEL-13) (GenBank Accession No. AF406699) and has a nucleotide sequence of SEQ ID NO:30 as follows:

ttaatacgtattttccccatagtaat-
taattaaaactgaatttgcttgagctcatcataatttatgcattgcttttttgttataagaa
attccataaattagctttgtgttaaaaaaaaaaaaaaaaaaaaaaa In one embodiment, the 3'-UTR corresponds to nucleotide bases 1602 to 1731 of SEQ ID NO:7 (StBEL-14) (GenBank Accession No. AF406700) and has a nucleotide sequence of SEQ ID NO:31 as follows:

tggctggttaaaaaatgacagagattct-
tcattttggaccttattatatactctaatttaatatatattggtgatgaatgatg
ataaaaaaaaaaaaaaaaaaaaaaaaaaaaaaaaaaaaaaaaa In one embodiment, the 3'-UTR corresponds to nucleotide bases 1864 to 1939 of SEQ ID NO:9 (StBEL-22) (GenBank Accession No. AF406701) and has a nucleotide sequence of SEQ ID NO:32 as follows:

ttaagatagtgtattcaaacactgcta-
cataaattatgattttatatatatatattgtcatccgattagtttat

In one embodiment, the 3'-UTR corresponds to nucleotide bases 1705 to 2128 of SEQ ID NO:11 (StBEL-29) (GenBank Accession No. AF406702) and has a nucleotide sequence of SEQ ID NO:33 as follows:

tcacaaaaacaaaaacaggttttggcaa-
cagacaaacttctgtcgctaaacaaggacatgatttagcgacagataactt
cagtcgctaacttagcgactgaaaact-
tctgtcgctaagcatgaacatgtattagcgacatacagtatgcaactgtatgt cac-
taaacaagaacatgatgaattagtgacg-
gacaacttctgtcgctaaacaacaaaaaaaatccatgttttagtatatt
gtttctcattctatcatatcatggtagt-
gtaaagaatcaagaaacaagttttacatagtaacagtctttatacattggagatg
aagaaccatttaagttcttcaaaata-
gatagattttctaggttacttctanaagatatatatatggttgagggtttgtatattaa
aaaaaaaaaaaaaaa In one embodiment, the 3'-UTR corresponds to nucleotide bases 1977 to 2065 of SEQ ID NO:13 (StBEL-30) (GenBank Accession No. AF406703) and has a nucleotide sequence of SEQ ID NO:34 as follows:

ttttgtatgtgttgtagaattaaactg-
caagttttgagtacatcaacattcatcttcaaaaaaaaaaaaaaaaaaaaaaaa
aaaaaaa Suitable plants in accordance with this method of the present invention are as described above. In a particular embodiment, the plant can be either a short-day-flowering plant or a long-day-flowering plant. Suitable short-day-flowering plants can include, for example, cotton, chrysanthemum, poinsettia, rice, orchid, soybean, strawberry, tobacco, and morning glory. Suitable long-day-flowering plants can include, for example, *Arabidopsis*, sugar beet, radish, spinach, winter barley, red clover, oat, tobacco, and wheat.

In one embodiment of this method of the present invention, the long-distance movement is through phloem tissue of the plant in a basipetal direction. In another embodiment of this method, the long-distance movement is through phloem tissue of the plant in an acropetal direction.

EXAMPLES

Example 1

Amplification of Potato Homeobox Fragment for Use as Probe

Two primers, Primer 1 (5'-AAGAAGAAGAAGAAAGG-GAA) (SEQ ID NO:18) and Primer 2 (5'-ATGAACCAGT-TGTTGAT) (SEQ ID NO:19) were designed based on comparison of the homeobox regions of five class I homeobox genes (KN1, KNAT1, KNAT2, OSH1, and SBH1) to correspond to the most highly conserved portions of the homeobox, and were synthesized at the DNA Synthesis Facility at Iowa State University. Template DNA was prepared from a mass in vivo excision of a 4-day axillary bud tuber λZAP®II cDNA library (Stratagene, La Jolla, Calif.) from potato cv. Superior. The potato homeobox fragment was amplified using an annealing temperature of 45° C. and cloned into the pCR2.1 vector of the TA Cloning® Kit (Invitrogen, Carlsbad, Calif.).

Example 2

Library Screening and Sequence Analysis

The early tuberization stage library was constructed as described in Kang et al., "A Novel MADS-box Gene of Potato (*Solanum tuberosum* L.) Expressed During the Early Stages of Tuberization," *Plant Mol. Biol.* 31: 379-386 (1996), which is hereby incorporated by reference in its entirety. Screening of 400,000 pfu was accomplished using 100 ng of $^{32}$P-labeled PCR-generated probe in 50% formamide (50% deionized formamide, 6×SSC, 3.4×Denhardt's solution, 25 mM sodium phosphate buffer, pH 7.0, 120 μg/ml denatured salmon sperm DNA, 0.4% SDS) at 42° C. for 48 hours. Membranes were washed with 2×SSC/0.1% SDS, at 25° C. for 5 minutes; then twice with 2×SSPE/0.1% SDS, at 65° C. for 20 minutes.

POTH1 was sequenced at the Nucleic Acid Sequencing Facility at Iowa State University. Sequence analyses performed included BLAST (Altschul et al., "Basic Local Alignment Search Tool," *J. Mol. Biol.* 215:403-410 (1990), which is hereby incorporated by reference in its entirety) and GAP (Genetics Computer Group (GCG), Madison, Wis.).

Example 3

RNA Isolation and Northern Blot Analysis

Total RNA was isolated (Dix et al., "In vivo Transcriptional Products of the Chloroplast DNA of *Euglena gracilis*," *Curr. Genet.* 7:265-273 (1983), which is hereby incorporated by reference in its entirety) from potato (*Solanum tuberosum* L.) plants grown in the greenhouse at 20 to 25° C. under 16 hours of light. Total RNA was enriched for poly (A)+ RNA by separation over an oligo-dT column and northern gel electrophoresis was performed using methyl mercury as a denaturant. Ethidium bromide staining under UV light was used to ascertain equal gel loading and efficient transfer to nylon membranes. The Genius™ nonradioactive nucleic acid labeling and detection system (Roche Biochemicals, Indianapolis, Ind.) was used. Fifteen ng/ml of digoxygenin-UTP-labeled antisense RNA probe in 50% formamide was hybridized to filters at 55° C. overnight. Membranes were washed twice for 5 minutes in 2×SSC, 0.1% SDS at 25° C., and then washed twice for 15 minutes in 0.1×SSC, 0.1% SDS at 68° C. The membranes were then incubated 30 minutes in blocking solution:maleic acid buffer pH 7.5 (1:10), 30 minutes in anti-digoxygenin-alkaline-phosphatase conjugate:maleic acid buffer (1:10,000), washed twice for 15 minutes in maleic acid buffer, and equilibrated 5 minutes in detection buffer before addition of disodium 3-[4-metho xyspiro {1,2-dioxetane-3, 2'-[5'-chloro]tricyclo [3.3.1.1$^{3,7}$]decan}-4-yl] phenyl phosphate (CSPD) substrate solution. Membranes were exposed to film for 30 to 45 minutes at 25° C.

Example 4

In Situ Hybridization Analysis

Preparation of Tissue Samples and In Situ Hybridizations were performed as described in Cañas et al., "Nuclear Localization of the *Petunia* MADS Box Protein FBP1," *Plant J.* 6:597-604 (1994), which is hereby incorporated by reference in its entirety. Digoxygenin-UTP-labeled RNA probes, both sense and antisense, were transcribed with RNA polymerases according to instructions (Roche Biochemicals, Indianapolis, Ind.), and hydrolyzed using 0.2 M sodium carbonate and 0.2 M sodium bicarbonate at 65° C. for 51 minutes. Unincorporated nucleotides were removed over a Sephadex G-50 column.

For immunological detection, the slides were incubated in buffer 1 (1% blocking solution, 100 mM Tris pH 7.5, 150 mM NaCl) for one hour, then equilibrated with buffer 2 (100 mM Tris pH 7.5, 150 mM NaCl, 0.5% BSA, and 0.3% Triton X-100). Tissue sections were then incubated with anti-digoxygenin-alkaline-phosphatase conjugate diluted 1:1000 in buffer 2 in a humidified box for two hours, then washed three times for 20 minutes in 100 mM Tris pH 7.5, 150 mM NaCl. The tissue sections were equilibrated in buffer 3 (100 mM Tris pH 9.5, 100 mM NaCl, 50 mM $MgCl_2$) for 10 minutes, then incubated in 3.2 µg/ml 5-bromo-4-chloro-3-indolyl-phosphate (BCIP):6.6 µg/ml nitro-blue tetrazolium salt (NBT) in buffer 3 in a humidified box for 13 hours (above-ground tissues) or 7 hours (underground tissues). Accumulation of POTH1 mRNA was visualized as an orange/brown stain under dark field illumination. Sections were viewed and photodocumented using the dark field mode on the Leitz Orthoplan light microscope.

Example 5

35S-POTH1 Transformation of Potato Plants

The full length POTH1 cDNA was cloned into the binary vector, pCB201 (Xiang et al., "A Mini Binary Vector Series for Plant Transformation," *Plant Mol. Biol.* 40:711-718 (1999), which is hereby incorporated by reference in its entirety) between the CaMV 35S promoter and the nos terminator. Two potato cultivars, *Solanum tuberosum* ssp. *andigena* and cv. FL-1607, were transformed by the *Agrobacterium tumefaciens* (strain GV2260) mediated leaf-disk transformation method (Liu et al., "Transformation of *Solanum Brevidens* Using *Agrobacterium Tumefaciens*," *Plant Cell Reports* 15:196-199 (1995), which is hereby incorporated by reference in its entirety). A total of thirty independent transgenic lines from *andigena* and twenty independent transgenic lines from 'FL-1607' were screened for insertion of the transgene and accumulation of POTH1 mRNA. Five independent transgenic lines of *S. tuberosum* spp. *andigena* and 4 lines of *S. tuberosum* cv. FL-1607 that showed high levels of POTH1 mRNA accumulation were selected for further analysis. Untransformed tissue culture plants were used as controls.

Example 6

Nucleic Acid Hybridizations

Genomic DNA was isolated using the cetyltrimethylammonium bromide (CTAB) mini-plant DNA extraction method (Doyle et al., "A Rapid DNA Isolation Procedure for Small Quantities of Fresh Leaf Tissue," *Phytochem. Bull.* 19:11-15 (1987), which is hereby incorporated by reference in its entirety). DNA (10 µg) was digested with Hind III or Xba I (Promega, Madison, Wis.), and gel electrophoresis was performed. DNA was denatured and blotted according to the methods described by Kolomiets et al., "A Leaf Lipoxygenase of Potato Induced Specifically by Pathogen Infection," *Plant Physiol.* 124:1121-1130 (2000), which is hereby incorporated by reference in its entirety. Total RNA was isolated with TriPure Isolation Reagent (Roche Biochemicals, Indianapolis, Ind.) and gel electrophoresis was performed using 10 mM methyl mercury (II) hydroxide as a denaturant. For hybridization with STGA20ox1, shoot tip samples were collected at the same time of day to avoid variations due to diurnal regulation. Probes were labeled with [α-$^{32}$P]dCTP (RadPrime DNA Labeling System, Gibco BRL, Gaithersburg, Md.). POTH1 probes were generated by using the 730 nt EcoR I fragment of POTH1 from the pCR2.1 vector (Invitrogen, Carlsbad, Calif.) with the ELK and homeodomains deleted. The 1.5 kb EcoR I-Xho I fragment of StGA20ox1 cDNA (Carrera et al., "Feedback Control and Diurnal Regulation of Gibberellin 20-oxidase Transcript Levels in Potato," *Plant Physiol.* 119:765-773 (1999), which is hereby incorporated by reference in its entirety) was provided by Salome Prat (Barcelona, Spain). All membranes were hybridized at 42° C. for 70 hours in 50% formamide. The membranes were rinsed in 2×SSC/0.1% SDS, at 25° C., followed by 1×SSC/0.1% SDS for 0-20 minutes at 65° C., then 0.1×SSC/0.1% SDS for 20-30 minutes at 65° C. Film was exposed for 4 to 7 days.

Example 7

Light Microscopy

Leaf tissue was fixed in 2% glutaraldehyde, 2% paraformaldehyde in 0.1M sodium phosphate buffer pH 7.0 at 4° C. for 72 hours, dehydrated in a graded ethanol series, and embedded in LR White resin (Electron Microscopy Sciences, Ft. Washington, Pa.). One µm thick sections were cut on an ultramicrotome (Reichert/Leica, Deerfield, Ill.) and stained with 1% toludine blue. Sections were viewed and photodocumented using bright field microscopy.

Example 8

GA Analysis

Three replicates of shoot tips down to the sixth expanded leaf (10 g each), were harvested in liquid nitrogen and frozen at −80° C. The tissue was ground with 80% methanol (MeOH) and incubated at 4° C. overnight. [$2H_2$]-GA internal standards were added in the following amounts in ng/g fwt:

$GA_1$:1, $GA_8$:10, $GA_{19}$:10, $GA_{20}$:20, and $GA_{53}$:5. The extract was filtered through Highflo Supercel and washed with 80% MeOH. After evaporation of the MeOH in vacuo, 0.5 M $Na_2HPO_4$ was added to bring the pH to about 8.5, followed by addition of 20 mL of hexane. The flask was mixed well and the hexanes were evaporated off in vacuo. The solution was than acidified to pH 3-3.5 with glacial $CH_3COOH$ (acetic acid) and incubated for 15 minutes. The sample was then filtered through polyvinylpolypyrrolidone (PVPP) and washed with 0.2% acetic acid. The eluate was loaded onto a prepared Baker SPE ($C_{18}$) cartridge and washed with 0.2% acetic acid. The sample was eluted off the column with 7 mL of 80% MeOH, evaporated to dryness, and dissolved in 1 mL 100% MeOH. The MeOH-insoluble precipitate was removed by centrifugation and the supernatant was evaporated to dryness, redissolved in 0.8 mL 0.2% acetic acid, and filtered through a 45 µm filter. A one mL loop was used to load the sample onto the $C_{18}$ HPLC column (Econosphere: Phenomenex, Torrance, Calif.) run with the following 0.2% acetic acid to acetonitrile gradient: 5%-20% over 2 minutes; 20-35% over 15 minutes; 35-75% over 15 minutes. Fractions for the following GAs were taken as follows: 10-14.3 minutes for $GA_8$; 15.3-17.45 minutes for $GA_1$; 23-27 minutes for $GA_{19}$ and $GA_{20}$; 27-29.3 minutes for $GA_{53}$. Fractions were collected separately and methylated with diazomethane in ether. Samples were dried, redissolved in 1 mL ethyl acetate, and partitioned against water. The aqueous phase was partitioned against another 1 mL of ethyl acetate and the ethyl acetate fractions were combined. The samples were dried and placed under high vacuum over $P_2O_5$. The samples were dissolved in 2 µL dry pyridine and 10 µL BSTFA [bis(trimethylsilyl)trifluoro-acetamide] with 1% TMCS (trimethylchlorosilane) (Sylon BFT: Pierce, Rockford, Ill.) and heated at 80° C. for 20 minutes. Samples were analyzed by GC-SIM on a GC-MS (HewlettPackard 5890 GC+5970B MS) with a 15 m Zebron ZB1 column (Phenomenex, Torrance, Calif.). The carrier gas, He, was set at a flow rate of approximately 35 cm/sec. The initial column temperature was 60° C. for one minute and then increased at a rate of 30° C./minute to 240° C., and then to 290° C. at a rate of 4° C./minute. The injector temperature was 225° C. and the temperature of the detector was 300° C. Concentrations of $GA_{53}$, $GA_{19}$, $GA_{20}$, $GA_1$, and $GA_8$ were determined by calculating the area of the peaks, 448/450, 434/436, 418/420, 506/508, and 594/596, respectively, at the correct Kovats retention indices. Reference spectra were obtained from Gaskin et al., "GC-MS of the Gibberellins and Related Compounds: Methodology and a Library of Spectra," Bristol UK: Cantock's Enterprises (1991), which is hereby incorporated by reference in its entirety. Cross-ion corrections were calculated according to the following formula where: $R_1$=% endogenous ion in final; $R_2$=% heavy ion in final; $A_1$=% endogenous ion in natural unlabelled sample; $A_2$=% heavy ion in natural unlabelled sample; B=heavy isotope internal standard.

Amount of natural compound $(A) =$ $$\frac{[R1]}{[R2 \times A1 - R1 \times A2]} \times \text{Amount of } B \text{ added}$$

Example 9

In Vitro Tuberization

Cuttings of transgenic and control plants were placed in Murashige-Skoog (MS) media plus 6% sucrose (Konstantinova et al., "Photoperiodic Control of Tuber Formation in Potato *Solanum Tuberosum* ssp. *Andigena* in vivo and in vitro," *Russian J. Plant Physiol.* 46:763-766 (1999), which is hereby incorporated by reference in its entirety). After 2 weeks under long days (16 hours of light, 8 hours of dark) to promote rooting, plants were cultured separately under either long or short day (8 hours of light, 16 hours of dark) conditions. Plants were examined for tuber activity (percentage of plants that produced either swollen stolons or tubers) and the number of tubers were counted.

Example 10

Results: Isolation and Characterization of POTH1

An early stage tuber cDNA library (Kang et al., "Nucleotide Sequences of Novel Potato (*Solanum tuberosum* L.) MADS-box cDNAs and Their Expression in Vegetative Organs," *Gene* 166:329-330 (1995), which is hereby incorporated by reference in its entirety) from *Solanum tuberosum* 'Superior' was screened for members of the homeobox gene family. PCR primers were designed from the consensus sequence of the homeoboxes of the class I genes kn1 from maize (Vollbrecht et al., "The Developmental Gene Knotted-1 is a Member of a Maize Homeobox Gene Family," *Nature* 350:241-243 (1991), which is hereby incorporated by reference in its entirety), KNAT1 and KNAT2 from *Arabidopsis* (Lincoln et al., "A Knotted1-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994), which is hereby incorporated by reference in its entirety), OSH1 from rice (Matsuoka et al., "Expression of a Rice Homeobox Gene Causes Altered Morphology of Transgenic Plants," *Plant Cell* 5:1039-1048 (1993), which is hereby incorporated by reference in its entirety), and SBH1 from soybean (Ma et al., "Identification of a Homeobox-Containing Gene With Enhanced Expression During Soybean (*Glycine max* L.) Somatic Embryo Development," *Plant Mol. Biol.* 24:465-473 (1994), which is hereby incorporated by reference in its entirety). A mass excision of the tuber cDNA library was performed, and this DNA was used as the PCR template. A band corresponding to the expected size of 158 nt was purified, cloned, and sequenced. This potato homeobox fragment was 87% identical to the conserved positions of the consensus sequence created from the five class I genes, and was used as a probe to screen the cDNA library. Library screening resulted in the isolation of a truncated, 1053-nt homeobox cDNA from the library, which was used as a probe to screen the library again. Three clones were isolated, and the full-length 1383-nt potato homeobox cDNA, POTH1, was selected for further study. The cDNA (Genbank Accession # U65648) includes an open reading frame of 1035 nt coding for a 345-residue protein estimated to have a mass of 37.95 kDa. It contains a 134-nt 5'-untranslated region, and a 216-nt 3'-untranslated region, including the poly-A tail. The coding sequence of the protein includes the 97-aa MEINOX domain, the 22-aa ELK domain, and the 64-aa homeodomain.

To identify proteins with similarity to POTH1, a BLAST analysis (Altschul et al., "Basic Local Alignment Search Tool," *J. Mol. Biol.* 215:403-410 (1990), which is hereby incorporated by reference in its entirety), was performed on the protein sequence and GAP analysis (Wisconsin Package Version 9.1, Genetics Computer Group (GCG), Madison, Wis.) was used to determine percent similarity. POTH1 shares 86% similarity with the homeodomain of KN1, classifying it as a class I homeobox protein (Kerstetter et al., "Sequence Analysis and Expression Patterns Divide the Maize Knotted1-like Homeobox Genes Into Two Classes," *Plant Cell* 6:1877-1887 (1994), which is hereby incorporated by reference in its entirety). However, over the entire protein sequence, POTH1 shares only 51% similarity with KN1. The five proteins with the most similarity to POTH1 include TKN3 from tomato (U76408), NTH22 of tobacco (Nishimura et al., "The Expression of Tobacco Knotted1-type Class 1 Homeobox Genes Correspond to Regions Predicted by the Cytohistological Zonation Model," *Plant J.* 18: 337-347 (1999), which is hereby incorporated by reference in its entirety), PKN2 of *Ipomoea nil* (AB016000), KNAT2 of *Arabidopsis* (Lincoln et al., "A Knotted1-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994), which is hereby incorporated by reference in its entirety) and NTH15 of tobacco (Tamaoki et al., "Ectopic Expression of a Tobacco Homeobox Gene, NTH15, Dramatically Alters Leaf Morphology and Hormone Levels in Transgenic Tobacco," *Plant Cell Physiol.* 38:917-927 (1997), which is hereby incorporated by reference in its entirety) with 94, 88, 73, 69, and 56% similarity overall, respectively. As expected, relatively high levels of conservation were observed in the homeodomains (97 to 83%) and in the MEINOX domains (95 to 63%) of this group.

Example 11

Results: Southern Analysis

Figure 1:
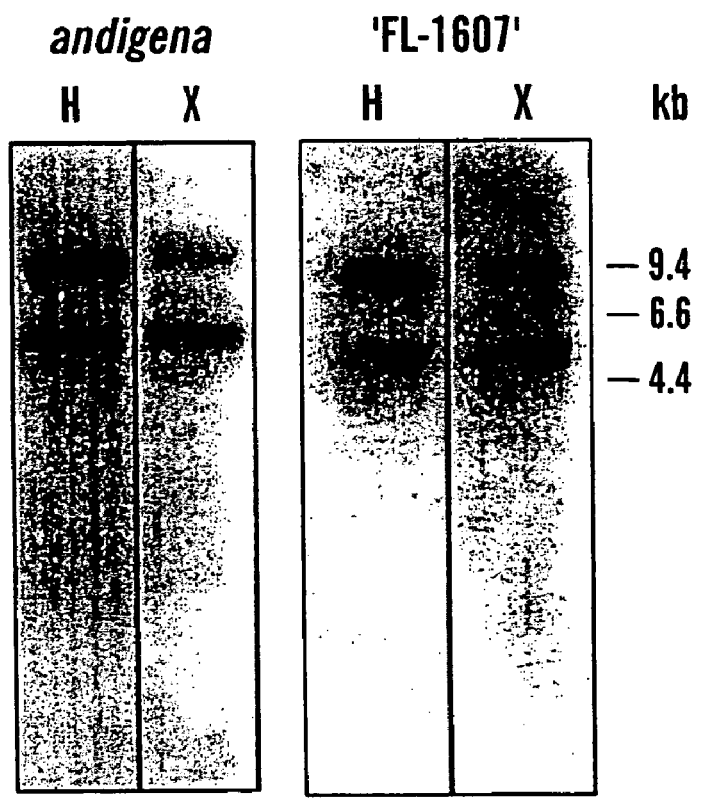
FIG. 1 shows Southern hybridization of POTH1. Genomic DNA (10 μg) was digested with the restriction enzymes, Hind III (H) or Xba I (X) and hybridized to a $^{32}$P-labeled POTH1 probe which did not include the ELK or homeodomain. There is a restriction site for Hind III within the coding sequence of POTH1. Size markers in kb are shown on the right.

To study the complexity of the POTH1 gene family in the tetraploid potato genome, Southern analysis was performed. Genomic DNA from both *S. tuberosum* cv. FL-1607 and spp. *andigena* was digested with Hind III and Xba I. For both species, only two bands hybridized to a gene-specific probe for POTH1 (FIG. 1), indicating that POTH1 is a member of a small gene family. A Hind III site is located within the cDNA sequence of POTH1.

Example 12

Results: Accumulation of POTH1 mRNA

Figure 2:
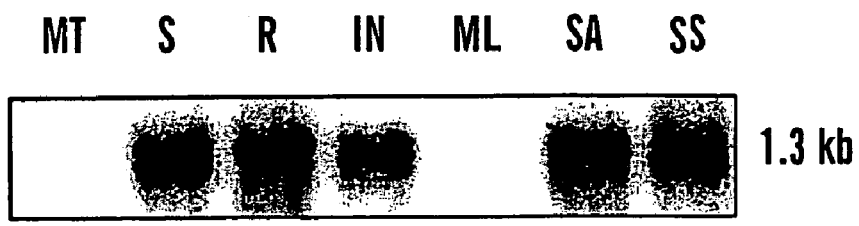
FIG. 2 shows POTH1 mRNA accumulation in various organs of the potato plants. Poly(A)-enriched RNA (5 μg in each lane) was hybridized to a digoxygenin-rUTP-labeled POTH1 RNA antisense probe with the ELK and homeodomain deleted. MT, mature tuber; S, stem; R, root; IN, inflorescence; ML, mature leaf; SA, shoot apex; SS, swollen stolon apex. Equal loading of intact poly(A)+ RNA in each lane was confirmed by ethidium bromide staining. The hybridizing bands are approximately 1.3 kb in length.

Northern blot analysis was used to determine the pattern of POTH1 mRNA accumulation in various organs of potato (FIG. 2). Poly(A)+ enriched RNA samples were hybridized with a digoxygenin-UTP labeled 780-nt RNA antisense probe with the conserved ELK region, homeobox region, and poly-A tail deleted. A single band, approximately 1.3 kb in length, representing POTH1 mRNA, was present in RNA extracted from stem, root, inflorescence, shoot apex, and swollen stolon apex (FIG. 2, lanes 2, 3, 4, 6, and 7, respectively). POTH1 transcripts were not detected in either mature leaf or mature tuber RNA (FIG. 2, lanes 1 and 5). Equal loading and the quality of the RNA loaded were ascertained via ethidium bromide staining. This autoradiograph was representative of several replicate hybridization blots.

To determine more precisely the location of POTH1 mRNA accumulation, in situ hybridization was performed on vegetative meristems of potato (FIG. 3). The potato SAM is comprised of two tunica layers, which divide anticlinally to produce the epidermis and contribute to lateral organs such as leaves, and three corpus layers, which divide both periclinally and anticlinally to contribute to lateral organ and stem development (Esau, "The Stem: Primary State of Growth. In Wiley, eds., *Anatomy of Seed Plants*, 2nd Edition New York: pp. 243-294 (1977); Sussex, "Morphogenesis in *Solanum Tuberosum* L.: Apical Structure and Developmental Pattern of the Juvenile Shoot," *Phytomorphology* 5:253-273 (1955), which are hereby incorporated by reference in their entirety). POTH1 mRNA accumulates in the two tunica and three corpus layers of the SAM, the leaf primordia, the procambium, and the lamina of young leaves (FIG. 3A). Lower levels of POTH1 transcript can also be detected in the developing leaflets of an older leaf (FIG. 3A, OL). A slightly lower level of POTH1 transcript can be detected in the central zone of the SAM, where initials divide less rapidly than adjacent cells.

Potato plants produce underground stems that grow horizontally, called stolons (Jackson, "Multiple Signaling Pathways Control Tuber Induction in Potato," *Plant Physiol*. 119: 1-8 (1999), which is hereby incorporated by reference in its entirety). Under optimum conditions, the subapical region of the stolon tip will begin to swell and eventually develop into a tuber. A nontuberizing stolon will elongate with most of its growth occurring in the tunica and corpus layers. The greatest concentration of POTH1 signal can be detected in the apical meristem of the elongating stolon (FIG. 3B). Expression levels are also high in the lamina of the youngest leaf, the procambium, and the perimedullary parenchyma associated with the vascular tissue (FIG. 3B). Differentiation of the procambium into mature vascular tissue is marked by the appearance of xylem elements (Esau, "The Stem: Primary State of Growth. In Wiley, eds., *Anatomy of Seed Plants*, 2nd Edition New York: pp. 243-294 (1977), which is hereby incorporated by reference in its entirety), and POTH1 transcript accumulates in this differentiated tissue as well (FIG. 3B). No signal is detected in an elongating stolon tip hybridized with a sense POTH1 probe (FIG. 3C).

The apex of a tuberizing stolon, visibly swollen in FIG. 3D, continues to accumulate POTH1 mRNA in the apical meristem, the procambium, the lamina of new leaves, and the perimedullary parenchyma, but the signal is less intense than in the elongating stolon apical meristem (FIG. 3B). In the subapical portion of the swollen stolon tip (FIG. 3E), where rapid radial expansion is occurring (Xu et al., "Cell Division and Cell Enlargement During Potato Tuber Formation," *J Exp. Bot.* 49:573-582 (1998), which is hereby incorporated by reference in its entirety), POTH1 signal is detected, especially in the perimedullary parenchyma, associated with the vascular tissue. There is some signal as well in the pith and inner cortex (FIG. 3E). FIG. 3F is the sense probe control corresponding to the section in FIG. 3E. Similar results were observed with sense probe controls in each section examined. The data presented in FIG. 3 is representative of several independent replications. Because FIGS. 3A-D are longitudinal sections through various apices at the same magnification, the location of labeled tissues is similar from one apex to the next.

Example 13

Results: The Overexpression of POTH1 in Transgenic Potato Plants

Figure 4A:
FIGS. 4A-F show POTH1 mRNA accumulation in transgenic potato plants and the evaluation of leaf and stem traits in POTH1 overexpression lines.
Figure 4B:

To determine the effect of POTH1 overexpression on the development of potato, the full-length POTH1 sequence was placed under the control of the CaMV 35S promoter in the binary vector, pCB201 (Xiang et al., "A Mini Binary Vector Series for Plant Transformation," *Plant Mol. Biol.* 40:711-718 (1999), which is hereby incorporated by reference in its entirety). To examine the role of POTH1 in tuberization, two cultivars of potato (*Solanum tuberosum* cv. FL-1607 and *S. tuberosum* ssp. *andigena*) were selected for transformation. *Andigena* plants are photoperiod sensitive, tuberizing only under short-day conditions (Carrera et al., "Changes in GA 20-oxidase Gene Expression Strongly Affect Stem Length, Tuber Induction and Tuber Yield of Potato Plants," *Plant J.* 22:1-10 (2000), which is hereby incorporated by reference in its entirety), whereas 'FL-1607' plants tuberize under both long- and short-day photoperiods. A total of thirty independent transgenic lines from *andigena* and twenty independent transgenic lines from 'FL-1607' were generated and screened for increased POTH1 mRNA expression. Among 10 sense lines of *andigena* and 15 lines of 'FL-1607' that showed high levels of POTH1 mRNA accumulation, five independent transgenic lines of *andigena* and 4 lines of 'FL-1607' were chosen for further analysis. An aberrant phenotype was observed only in those lines with detectable levels of POTH1 mRNA from total RNA samples. Two transgenic lines, *andigena* lines 15 and 18 had the highest levels of POTH1 mRNA accumulation (FIG. 4A), whereas *andigena* lines 11, 20, and 29 had intermediate levels of POTH1 mRNA (FIG. 4A). Similar high levels of POTH1 accumulation were observed in 'FL-1607' overexpression lines that exhibited mutant phenotypes. Equivalent loading of RNA samples was verified by using an 18S rRNA probe from wheat (FIG. 4B).

Example 14

Results: Phenotype of POTH1 Overexpression Lines

Figure 4C:
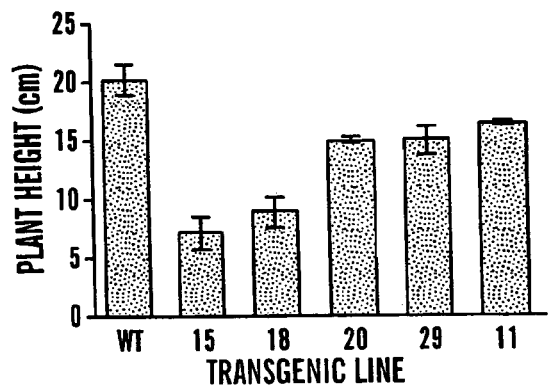
Figure 4D:
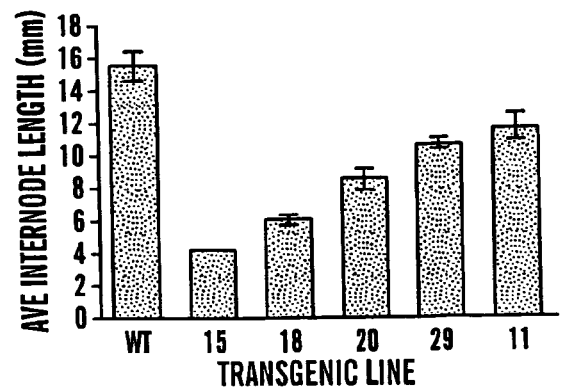
Figure 4E:
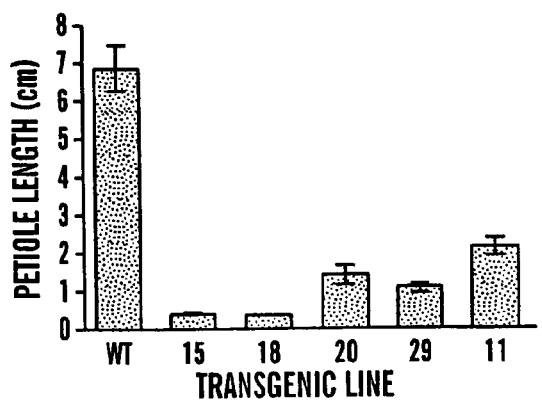
Figure 4F:
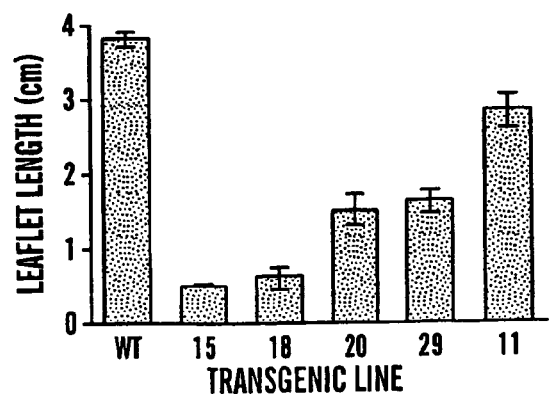

Overexpression of POTH1 resulted in a phenotype characterized by a reduction in plant height and leaf size (FIGS. 4C-F). Lines with the most abundant POTH1 RNA levels had the greatest reduction in overall height. The height of potato subsp. *andigena* lines 15 and 18 was reduced by at least 64% compared with wild-type plants (FIG. 4C). Transgenic lines with an intermediate phenotype (*andigena* lines 20, 29, and 11) showed a 20 to 25% reduction in plant height (FIG. 4C). The decrease in plant height was due to a corresponding decrease in internode elongation (FIG. 4D). The average internode length of the severe mutant, *andigena* line 15, was 4.0 mm compared to 16 mm for wild-type *andigena* plants. The same pattern was observed for petiole and leaflet length (FIGS. 4E and 4F) with the severe phenotypes displaying the greatest reduction in size. Among the five sense lines, petiole length was reduced by 70 to 96%, whereas leaflet length was reduced by 29 to 87% compared to wild-type. The sixth expanded leaf from the shoot apex was used to measure petiole and terminal leaflet length. Similar results were seen for 'FL-1607' overexpression lines.

Transgenic plants that overexpressed POTH1 also exhibited malformed leaves. The overall size of the leaflets was greatly reduced and they were rounded, curved, and wrinkled (FIGS. 5A-B). Wild-type leaflets have an ovate form and display pinnate venation with a prominent mid-vein (FIG. 5B, left). In the overexpression mutants, the midvein is less prominent and the most severe phenotypes exhibited a 'mouse-ear' leaf phenotype (FIGS. 5B-D). The leaflets are heart-shaped with a shortened mid-vein. In addition, there has been a switch from pinnate to palmate venation (FIG. 5B). The phyllotaxy is not altered in overexpression lines, although, compared with wild-type plants (FIG. 5C), the leaves are clustered closer to the stem due to shortened petioles (FIG. 5D). In tomato, the dominant mutations, Mouse-ear (Me) and Curl (Cu), were caused by a change in the spatial and temporal expression of the tomato knox gene TKn2/LeT6 (Parnis et al., "The Dominant Developmental Mutants of Tomato, Mouse-ear and Curl, are Associated With Distinct Modes of Abnormal Transcriptional Regulation of a Knotted Gene," *Plant Cell* 9:2143-2158 (1997); Chen et al., "A Gene Fusion at a Homeobox Locus: Alterations in Leaf Shape and Implications for Morphological Evolution," *Plant Cell* 9:1289-1304 (1997), which are hereby incorporated by reference in their entirety). Overexpression of kn1 (Hareven et al., "The Making of a Compound Leaf: Genetic Manipulation of Leaf Architecture in Tomato," *Cell* 84:735-744 (1996), which is hereby incorporated by reference in its entirety) in tomato caused up to a six-fold increase in the level of leaf compoundness resulting in a leaf bearing 700-2000 leaflets. Such a marked increase in the level of compoundness was not observed in POTH1 overexpression lines. Increased proliferation of leaflets from sense lines, however, was common (compare wild-type and line 19 leaflets in FIG. 5E).

To determine whether POTH1 overexpression affected the leaf at the cellular level, leaf cross-sections of the severe mutant, potato subsp. *andigena* line 15, were examined. Wild-type leaves consist of a palisade parenchyma layer on the adaxial side and a spongy parenchyma layer on the abaxial side (FIG. 5F). The cells of the palisade layer are aligned in a vertical orientation and are tightly packed, whereas the spongy parenchyma cells are more loosely arranged (FIG. 5F). In leaves of potato subsp. *andigena* line 15, the palisade parenchyma layer is absent and the spongy parenchyma cells are more closely packed (FIG. 5H). Overall cell size in the leaves of *andigena* line 15 is reduced by about one half.

Many of the traits of the phenotypes observed in POTH1 overexpression lines were similar to GA-deficient mutants. These similarities included decreased plant height, decreased internode length, and darker green coloration of the leaves (van den Berg et al., "Morphology and [$^{14}$C]Gibberellin A$_{12}$ Metabolism in Wild-Type and Dwarf *Solanum Tuberosum* ssp. *Andigena* Grown Under Long and Short Photoperiods," *J. Plant Physiol.* 146:467-473 (1995), which is hereby incorporated by reference in its entirety). Because of this, exogenous GA$_3$ was applied to determine whether the overexpression lines were responsive to GA treatment. The shoot apex of overexpression lines was sprayed to runoff with 10 µM GA$_3$ in 0.002% (v/v) ethanol or with 0.002% (v/v) ethanol alone. Application of GA$_3$ not only caused plants with a severe phenotype to increase in height, but also partially rescued the leaf morphology of both severe and intermediate phenotypes. Palisade and spongy parenchyma organization is partially rescued in leaves from line 15 treated with GA$_3$ (FIG. 5G). The compound leaf structure of the of the potato subsp. *andigena* wild-type leaf is shown in FIG. 5I. The GA$_3$-treated leaf (FIG. 5J) of the severe mutant, line 15, is more similar in morphology to the wild-type leaf (FIG. 5K). Leaflets are more ovate in form rather than the typical mouse-ear shape. Wild-type leaves have a prominent mid-vein (FIG. 5L), whereas the mid-vein (FIG. 5M, arrow) is more prominent in the mutant GA$_3$-treated leaf than in the mutant untreated leaf (FIG. 5N). The compound leaf structure of the 'FL-1607' wild-type leaf is shown in FIG. 5O. The GA$_3$-treated leaf (FIG. 5P) of the severe mutant, 'FL-1607' line 5, is more similar in morphology to the wild-type leaf than to the mutant control leaf (FIG. 5Q). Leaflets are more ovate in form rather than the typical 'mouse-ear' shape. The mid-vein (arrow) is more prominent in the GA$_3$-treated leaf (FIG. 5P) than in the mutant leaf (FIG. 5Q).

Figure 6:
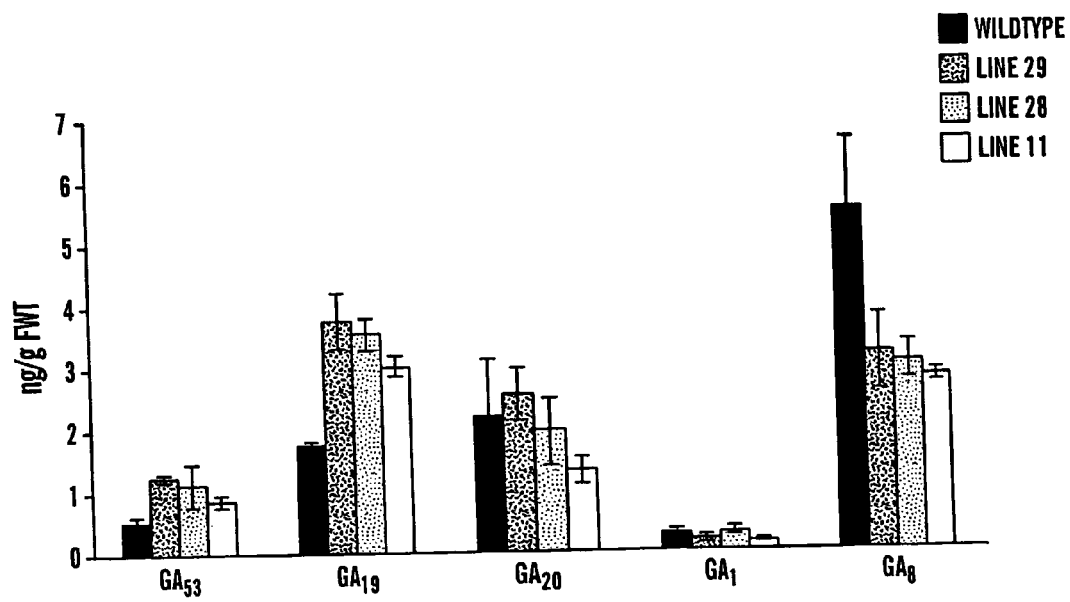
FIG. 6 shows the levels of intermediates in the GA biosynthetic pathway. GAs were extracted from shoot tips down to the sixth expanded leaf from wild-type and potato subsp. *andigena* POTH1 overexpression lines 29, 20, and 11. GAs were separated by HPLC and levels were measured by gas chromatography-mass spectrometry (GC-MS). GA$_{53}$, GA$_{19}$, and GA$_{20}$ are precursors to GA$_1$, the physiologically active GA, whereas GA$_8$ is the inactive metabolite. GA$_{53}$ and GA$_{19}$ levels increased, whereas GA$_{20}$, GA$_1$, and GA$_8$ levels decreased in POTH1 overexpression lines. Measurements are the average of three replications. Standard error is indicated for each mean. Concentrations of GA$_{53}$, GA$_{19}$, GA$_{20}$, GA$_1$ and GA$_8$ were determined by calculating the area of the peaks at the correct Kovats retention indices (KRI) at 448/450 (KRI=2,497), 434/436 (2,596), 418/420 (2,482), 506/508 (2,669), and 594/596 (2,818), respectively.

To determine whether GA biosynthesis was disrupted in POTH1 overexpression lines, levels of intermediates in the GA biosynthesis pathway in potato (van den Berg et al., "Metabolism of Gibberellin A12 and A12-aldehyde and the Identification of Endogenous Gibberellins in Potato (*Solanum tuberosum* ssp. *andigena*) Shoots," *J. Plant Physiol.* 146:459-466 (1995), which is hereby incorporated by reference in its entirety) were measured. Levels of the intermediates $GA_{53}$ and $GA_{19}$ increased in POTH1 overexpression lines, whereas $GA_1$ and $GA_8$ levels decreased (FIG. 6). In potato subsp. *andigena* lines 29 and 20, $GA_{53}$ and $GA_{19}$ levels increased approximately 2-fold compared with wild-type lines (FIG. 6). The levels of $GA_1$ and $GA_8$ present in potato subsp. *andigena* overexpression lines were approximately one-half that of wild-type levels (FIG. 6). Accumulation of $GA_{53}$ and $GA_{19}$ with a concomitant decrease in $GA_1$ and $GA_8$ indicates that the GA biosynthetic pathway is blocked at the oxidation of $GA_{19}$ to $GA_{20}$, leading to a decrease in the levels of bioactive $GA_1$. Similar patterns of accumulation for GA intermediates were also observed for potato subsp. *andigena* sense line 15 (in *andigena* line 15, $GA_{53}$ and $GA_{19}$ levels increased 4.8× and 2.1×, respectively, compared to wild-type).

Figure 7A:
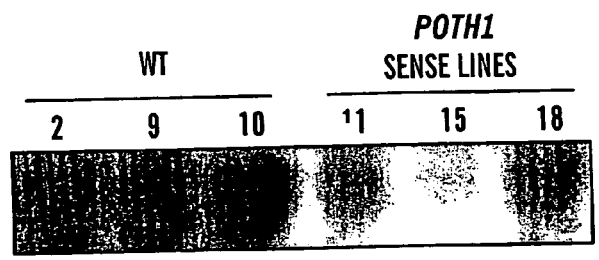
FIGS. 7A-B show the accumulation of mRNA for GA 20-oxidase1 in transgenic plants that overexpress the potato knox gene, POTH1.
Figure 7B:
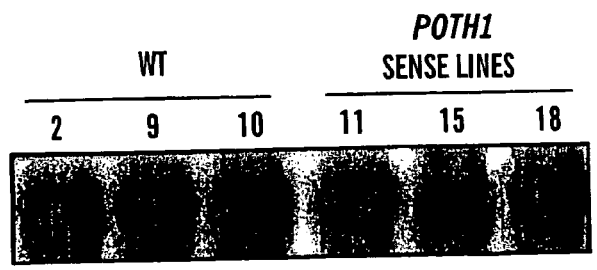

Overexpression lines were deficient in bioactive GAs, but were responsive to the exogenous application of $GA_3$. This indicates that GA biosynthesis is inhibited in the overexpression lines. In addition, accumulation of $GA_{53}$ and $GA_{19}$, with a decrease in $GA_{20}$, $GA_1$, and $GA_8$ (FIG. 6), indicates that the activity of the biosynthetic gene, GA 20-oxidase, may be suppressed. GA 20-oxidase catalyzes the oxidation of carbon 20 of $GA_{53}$ to $GA_{44}$ to $GA_{19}$ to $GA_{20}$. The enzyme GA 3-oxidase then converts $GA_{20}$ to the active $GA_1$ (Hedden et al., "Gibberellin Biosynthesis: Enzymes, Genes and Their Regulation," *Annu. Rev. Plant Physiol. Plant Mol. Biol.* 48:431-460 (1997), which is hereby incorporated by reference in its entirety). To determine whether POTH1 overexpression causes a change in GA 20-oxidase mRNA levels, RNA blot analysis was performed using one of the potato genes encoding GA 20-oxidase, StGA20ox1, as a probe (Carrera et al., "Feedback Control and Diurnal Regulation of Gibberellin 20-oxidase Transcript Levels in Potato," *Plant Physiol.* 119:765-773 (1999), which is hereby incorporated by reference in its entirety). In the overexpression lines, StGA20ox1 mRNA levels were reduced substantially compared to levels in wild-type lines (FIG. 7).

GA is involved in regulating cell growth in a tuberizing stolon (Xu et al., "The Role of Gibberellin, Abscisic Acid, and Sucrose in the Regulation of Potato Tuber Formation in vitro," *Plant Physiol.* 117:575-584 (1998), which is hereby incorporated by reference in its entirety) and in contributing to the control of the photoperiodic response of tuber formation (Martinez-Garcia et al., "The Interaction of Gibberellins and Photoperiod in the Control of Potato Tuberization," *J. Plant Growth Regul.* 20:377-386 (2001), which is hereby incorporated by reference in its entirety). Because levels of active GAs were reduced in transgenic plants, an in vitro tuberization assay (Konstantinova et al., "Photoperiodic Control of Tuber Formation in Potato *Solanum Tuberosum* ssp. *Andigena* in vivo and in vitro," *Russian J. Plant Physiol.* 46:763-766 (1999), which is hereby incorporated by reference in its entirety) was used to determine the effect of POTH1 overexpression on tuberization. After 2 weeks under a 16 hour light/8 hour dark photoperiod to induce rooting, plants were cultured on 6% (w/v) sucrose under either an 8 hour light/16 hour dark (inductive) or 16 hour light/8 hour dark (noninductive) photoperiod. After 10 days, the overexpression lines had 60 to 82% and 19 to 68% tuber activity under short and long days, respectively, compared to 0% activity for wild-type plants (Table 1).

TABLE 1

In vitro tuberization of POTH1 overexpression lines. *S. tuberosum* spp. *andigena* transgenics were placed on Murashige-Skoog media supplemented with 6% sucrose under either short-day (SD) or long-day (LD) conditions. At least 12 plants per line were monitored for total number of tubers that formed and tuber activity (percentage of plants that produced either swollen stolons or tubers). Numbers in parentheses are the average number of tubers produced per plant.

| | # tubers (tubers/plant) | | % tuber activity | | |
|---|---|---|---|---|---|
| line | 14 d SD | 14 d LD | line | 10 d SD | 10 d LD |
| control | 1 (.08) | 1 (.06) | control | 0 | 0 |
| 1200-29 | 21 (1.4) | 14 (.88) | 1200-29 | 60 | 40 |
| 1200-11 | 13 (.72) | 22 (1.2) | 1200-11 | 78 | 68 |
| 1200-15 | 17 (1.5) | 2 (.12) | 1200-15 | 82 | 19 |
| 1200-18 | 12 (.86) | 8 (.57) | 1200-18 | 79 | 43 |
| line | 21 d SD | 21 d LD | | | |
| control | (0.66) | (0.43) | | | |
| 1200-29 | (1.70) | (1.25) | | | |
| 1200-11 | (0.88) | (1.30) | | | |
| 1200-15 | (2.30) | (0.38) | | | |
| 1200-18 | (1.50) | (0.86) | | | |

Tuber activity was calculated as the percentage of plants that formed either a swollen stolon or a tuber. At 14 days, overexpression lines produced an average of 0.7 to 1.5 tubers per plant under short days, whereas wild-type plants produced an average of 0.08 tubers per plant (Table 1). Similar results were observed under long days and after 21 days in culture (Table 1). Overall, the POTH1 overexpression lines could produce more tubers in less time than controls and apparently, also overcome the negative effects of a long-day photoperiod on tuber formation. The potato cv FL-1607 overexpression lines also exhibited increased tuber activity under both photoperiods.

Example 15

Discussion: POTH1 Has a Widespread mRNA Expression Pattern

Isolated from an early stage tuber cDNA library, POTH1 is a homeobox gene belonging to the knox gene family. It contains the conserved homeodomain, ELK, and MEINOX domains. The homeodomain contains the invariant residues, PYP, between helices 1 and 2, making it a member of the TALE superclass. Because of its close sequence match with the KN1 homeodomain, POTH1 is classified as a knox class I homeobox gene.

Even though POTH1 is classified as a class I knox gene, it has a more widespread mRNA expression pattern than other class I genes. POTH1 is expressed in actively growing organs, but not in mature leaves or tubers. Unlike the mRNA expression pattern of kn1 which is limited to corpus cells of the apical meristem (Jackson et al., "Expression of Maize KNOTTED1 Related Homeobox Genes in the Shoot Apical Meristem Predicts Patterns of Morphogenesis in the Vegetative Shoot," *Development* 120:405-413 (1994), which is hereby incorporated by reference in its entirety), in situ hybridization showed that POTH1 mRNA accumulates in the meristematic and indeterminate cells of the SAM, determinate leaf primordia, the expanding lamina of new leaves, and developing leaflets of older leaves. The expression pattern of POTH1 mRNA in the unswollen stolon is similar to that seen in the shoot apical meristem. Signal was highest in undetermined, meristematic cells, but was also detected in the lamina of young leaves and the vascular tissue of the stem. Once tuberization has been initiated, the signal becomes less intense at the stolon apex, but is present in the vascular tissue in the subapical portion of the stolon. At this stage of tuberization, elongation of the meristem has stopped, and rapid, radial expansion occurs in the subapical region (Reeve et al., "Anatomy and Compositional Variation Within Potatoes I. Developmental Histology of the Tuber," *Amer. Pot. J.* 46:361-373 (1969), which is hereby incorporated by reference in its entirety).

Most class I knox genes have a more limited pattern of mRNA expression, restricted to undifferentiated cells of the meristem (Reiser et al., "Knots in the Family Tree: Evolutionary Relationships and Functions of Knox Homeobox Genes," *Plant Mol. Biol.* 42:151-166 (2000), which is hereby incorporated by reference in its entirety). Members of the tobacco knox family have distinct expression patterns within the SAM. NTH15 and NTH1 are expressed throughout the corpus, NTH20 is expressed in the peripherary zone, and NTH9 is expressed in the rib zone of the SAM (Nishimura et al., "The Expression of Tobacco Knotted1-type Class1 Homeobox Genes Correspond to Regions Predicted by the Cytohistological Zonation Model," *Plant J.* 18: 337-347 (1999), which is hereby incorporated by reference in its entirety). The tomato knox class I genes, TKn1 and TKn2/LeT6, have a expression pattern similar to POTH1 with transcripts detectable in meristematic and differentiated cells. Expression of TKn2/LeT6 was detected in the corpus of the meristem, developing leaf primordial leaflet primordia and margins, and the vascular cells of the leaf (Chen et al., "A Gene Fusion at a Homeobox Locus: Alterations in Leaf Shape and Implications for Morphological Evolution," *Plant Cell* 9:1289-1304 (1997); Janssen et al., "Overexpression of a Homeobox Gene, LeT6, Reveals Indeterminate Features in the Tomato Compound Leaf," *Plant Physiol.* 117: 771-786 (1998), which are hereby incorporated by reference in their entirety). This expanded expression pattern in tomato has been attributed to the differences in compound leaf development compared to simple leaf development and the expansion of undifferentiated tissues to include developing leaflets. Potato is unique because it forms compound leaves from the vegetative shoot apical meristem above ground, but forms simple, scale leaves from the stolon meristem below ground (Sussex, "Morphogenesis in *Solanum Tuberosum* L.: Apical Structure and Developmental Pattern of the Juvenile Shoot," *Phytomorphology* 5:253-273 (1955), which is hereby incorporated by reference in its entirety). Expression of POTH1 is detected in young leaves that arise from both the shoot apical and stolon meristems. This indicates that POTH1 mRNA expression alone is not the determining factor for the development of compound leaves in potato. In the shoot or stolon meristem, the activity of POTH1 may be regulated differently through interaction with partner proteins specific for shoot or stolon meristem development.

Example 16

Discussion: Phenotype of POTH1 Overexpression Transgenic Lines

Overexpression of POTH1 resulted in altered leaf morphology, dwarfism, and increased rates of in vitro tuberization. Leaves were small, wrinkled, and curved. Both severe and intermediate phenotypes were characterized by a 'mouse-ear' leaf phenotype. Leaves were heart-shaped with a decreased midvein and palmate venation. The petioles were reduced in length resulting in leaves clustering closer to the stems. Overexpression lines exhibited dwarfism as a result of reduced internode length. The severity of the phenotype was correlated with the greatest levels of POTH1 sense transcript accumulation. Cross-sections of leaves revealed that the mesophyll cell organization was disrupted with the palisade parenchyma layer missing in POTH1 overexpression lines. The tightly packed cells were about half the size of the wild-type cells. A similar disruption in leaf parenchyma cell layers was observed in sense mutants of KNAT1 and KNAT2 (Chuck et al., "KNAT1 Induces Lobed Leaves With Ectopic Meristems When Overexpressed in *Arabidopsis*," *Plant Cell* 8:1277-1289 (1996); Frugis et al., "Overexpression of KNAT1 in Lettuce Shifts Leaf Determinate Growth to a Shoot-like Indeterminate Growth Associated With an Accumulation of Isopentenyl-type Cytokinins," *Plant Physiol.* 126:1370-1380 (2001); Pautot et al., "KNAT2: Evidence for a Link Between Kknotted-like Genes and Carpel Development," *Plant Cell* 13:1719-1734 (2001), which are hereby incorporated by reference in their entirety). Because class I knox genes are implicated in maintaining the undifferentiated state of cells (Chan et al., "Homeoboxes in Plant Development," *Biochim. Biophys. Acta* 1442:1-19 (1998), which is hereby incorporated by reference in its entirety), disruption in leaf architecture is likely a result of a defect in the normal differentiation program.

Based on overexpression phenotypes, POTH1 and NTH22 of tobacco (Nishimura et al., "Over-Expression of Tobacco Knotted1-type Class1 Homeobox Genes Alter Various Leaf Morphology," *Plant Cell Physiol.* 41:583-590 (2000), which is hereby incorporated by reference in its entirety) appear to have similar functions that overlap, but are distinct from, the class I knox genes, kn1, NTH15, OSH1, and KNAT1. Like overexpression of POTH1 in potato and NTH22 in tobacco, overexpression of kn1, NTH15, OSH1, KNAT1 in tobacco or *Arabidopsis* (Sinha et al., "Overexpression of the Maize Homeo Box Gene, KNOTTED-1, Causes a Switch From Determinate to Indeterminate Cell Fates," *Genes Dev.* 7:787-795 (1993); Sato et al., "Abnormal Cell Divisions in Leaf Primordia Caused by the Expression of the Rice Homeobox Gene OSH1 Lead to Altered Morphology of Leaves in Transgenic Tobacco," *Mol. Gen. Genet.* 251:13-22 (1996); Tamaoki et al., "Ectopic Expression of a Tobacco Homeobox Gene, NTH15, Dramatically Alters Leaf Morphology and Hormone Levels in Transgenic Tobacco," *Plant Cell Physiol.* 38:917-927 (1997); Chuck et al., "KNAT1 Induces Lobed Leaves With Ectopic Meristems When Overexpressed in *Arabidopsis*," *Plant Cell* 8:1277-1289 (1996); Lincoln et al., "A Knotted1-like Homeobox Gene in *Arabidopsis* is Expressed in the Vegetative Meristem and Dramatically Alters Leaf Morphology When Overexpressed in Transgenic Plants," *Plant Cell* 6:1859-1876 (1994), which are hereby incorporated by reference in their entirety) resulted in dwarfism, decreased internode elongation, shortened petioles, and small deformed leaves. Additional phenotypes, including ectopic meristem formation, loss of apical dominance, and delayed senescence, however, were not observed in POTH1 or NTH22 overexpression transgenic lines. Whereas there seems to be some redundancy in function between different members of the knox gene family, (for example, regulation of GA biosynthesis), POTH1 is not likely to have an identical function to kn1, NTH15, or OSH1. Rather, these genes are likely to have different subsets of target genes, which is reflected in their differences in homeodomain sequence (83 to 86% match to POTH1's homeodomain, compared to a 98% match for NTH22).

Example 17

Discussion: Ectopic Expression of POTH1 Results in GA Deficiency

Similar to the knox genes NTH15 of tobacco and OSH1 of rice, the results above indicate that POTH1 is a negative regulator of GA biosynthesis. POTH1 overexpression transgenic lines share many phenotypes with GA-deficient mutants including dwarfism, decreased internode elongation, and darker leaf coloration (van den Berg et al., "Morphology and [$^{14}$C]Gibberellin $A_{12}$ Metabolism in Wild-Type and Dwarf *Solanum Tuberosum* ssp. *Andigena* Grown Under Long and Short Photoperiods," *J. Plant Physiol.* 146:467-473 (1995), which is hereby incorporated by reference in its entirety). Exogenous application of $GA_3$ partially rescued the aberrant leaf phenotype indicating that overexpression lines were responsive to GA. Levels of the bioactive GA, $GA_1$, were reduced in overexpression lines, whereas intermediates prior to $GA_{20}$ in the pathway accumulated. Additionally, the mRNA levels of a key GA biosynthetic enzyme, GA 20-oxidase1, were reduced in overexpression lines. When NTH15 and OSH1 were overexpressed in tobacco, the levels of the hormones, auxin, cytokinin, abscisic acid, and GA were altered. $GA_1$ levels were reduced to 1.4% and 0.4-3.5% of controls in intermediate 35S-NTH15 and severe or mild 35S-OSH1 transgenics, respectively (Kusaba et al., "Alteration of Hormone Levels in Transgenic Tobacco Plants Overexpressing the Rice Homeobox Gene OSH1," *Plant Physiol.* 116: 471-476 (1998); Tamaoki et al., "Ectopic Expression of a Tobacco Homeobox Gene, NTH15, Dramatically Alters Leaf Morphology and Hormone Levels in Transgenic Tobacco," *Plant Cell Physiol.* 38:917-927 (1997), which are hereby incorporated by reference in their entirety). In tobacco, NTH15 affects plant growth by negatively regulating GA levels by suppressing the transcription of the tobacco GA 20-oxidase gene through a direct interaction with regulatory elements (Sakamoto et al., "KNOX Homeodomain Protein Directly Suppresses the Expression of a Gibberellin Biosynthetic Gene in the Tobacco Shoot Apical Meristem," *Genes Dev.* 15:581-590 (2001), which is hereby incorporated by reference in its entirety).

POTH1 overexpression lines exhibited an increase in both the rate of tuberization and the total number of tubers formed under both short- and long-day photoperiods. These sense lines appear to have the capacity to overcome the negative effects of a long-day photoperiod on tuberization in vitro. Enhanced tuberization can be partially attributed to the decrease in $GA_1$ levels caused by POTH1 suppression of GA 20-oxidase1. Pytochrome B (PHYB) and GAs are involved in inhibiting tuberization under long-day photoperiods. A long-day photoperiod is sensed by the leaves and an inhibitory signal mediated by PHYB is transmitted from the leaves to the stolons to inhibit tuberization (Jackson, "Multiple Signaling Pathways Control Tuber Induction in Potato," *Plant Physiol.* 119:1-8 (1999), which is hereby incorporated by reference in its entirety). GA activity is regulated by light, decreasing under short-day photoperiods (Railton et al., "Effects of Daylength on Endogenous Gibberellins in Leaves of *Solanum Andigena* I. Changes in Levels of Free Acidic Gibberellin-like Substances," *Physiol. Plant.* 28:88-94 (1973), which is hereby incorporated by reference in its entirety) and is involved in the photoperiodic control of stolon growth. High levels of GA in the stolon tip favor elongation of stolon meristems, whereas decreasing levels are required for initiation of tuberization (Xu et al., "The Role of Gibberellin, Abscisic Acid, and Sucrose in the Regulation of Potato Tuber Formation in vitro," *Plant Physiol.* 117:575-584 (1998), which is hereby incorporated by reference in its entirety). GA 20-oxidase is a key enzyme in the GA biosynthetic pathway. In potato, the GA 20-oxidase genes are regulated by $GA_1$ feedback inhibition, blue light, and PHYB (Jackson et al., "Regulation of Transcript Levels of a Potato Gibberellin 20-Oxidase Gene by Light and Phytochrome B," *Plant Physiol.* 124:423-430 (2000), which is hereby incorporated by reference in its entirety). Whereas PHYB antisense plants were able to form tubers under both long- and short-day photoperiods (Jackson et al., "Phytochrome B Mediates the Photoperiodic Control of Tuber Formation in Potato," *Plant J.* 9:159-166 (1996), which is hereby incorporated by reference in its entirety), transgenic antisense andigena plants with suppressed levels of GA 20-oxidase1 (StGA20ox1) were not able to overcome the negative effects of photoperiod on tuberization in soil-grown plants (Carrera et al., "Changes in GA 20-oxidase Gene Expression Strongly Affect Stem Length, Tuber Induction and Tuber Yield of Potato Plants," *Plant J.* 22:1-10 (2000), which is hereby incorporated by reference in its entirety). While the experiments described above involved an in vitro assay rather than soil grown plants, Konstantinova et al., "Photoperiodic Control of Tuber Formation in Potato *Solanum Tuberosum* ssp. *Andigena* in vivo and in vitro," *Russian J. Plant Physiol.* 46:763-766 (1999), which is hereby incorporated by reference in its entirety, demonstrated that an in vitro assay for tuber formation is a reliable method for ascertaining the effect of photoperiod on tuberization in a photoperiod responsive cultivar. While it is possible that GA levels are not reduced sufficiently in antisense GA 20-oxidase1 plants, an additional signal may be involved in the long-day-photoperiod inhibition of tuberization. This indicates that in addition to reducing GA levels, POTH1 overexpression may enhance tuberization under long days by overcoming the effects of other negative regulators.

Example 18

Discussion: Regulation of POTH1 Activity During Development

Overexpression of POTH1 potentially regulates development in the SAM and in underground stolons through a reduction in bioactive GA levels in vegetative meristems. Whereas GA levels are high in the elongating unswollen stolon and decrease in swollen stolons (Xu et al., "The Role of Gibberellin, Abscisic Acid, and Sucrose in the Regulation of Potato Tuber Formation in vitro," *Plant Physiol.* 117:575-584 (1998), which is hereby incorporated by reference in its entirety), POTH1 mRNA accumulates in both unswollen and swollen stolons. If POTH1 is a negative regulator of GA synthesis, how can its expression mediate a decrease in GA levels in the swollen stolon leading to tuberization, but not in the elongating unswollen stolon tip? With other TFs, an interaction with a partner protein can regulate development by affecting the binding of the homeodomain(s) to the DNA of a target gene. In Antirrhinum, for example, formation of a ternary complex consisting of the MADS box proteins, SQUA, DEF, and GLO, greatly increases DNA binding compared to SQUA homodimers or DEF/GLO heterodimers alone (Egea-Cortines et al., "Ternary Complex Formation Between the MADS-box Proteins SQUAMOSA, DEFICIENS and GLOBOSA is Involved in the Control of Floral Architecture in *Antirrhinum majus,*" *EMBO J.* 18:5370-5379 (1999), which is hereby incorporated by reference in its entirety). The interaction of HOX proteins with PBC proteins in animals modulates the affinity of the HOX proteins for specific DNA binding sites (Chang et al., "Meis Proteins are Major in vivo DNA Binding Partners for Wild-Type but not Chimeric Pbx Proteins," *Mol. Cell. Biol.* 17:5679-5687 (1997), which is hereby incorporated by reference in its entirety). HOX homodimers have different DNA binding sites than HOX-PBC heterodimers (Mann et al., "Extra Specificity From Extradenticle: the Partnership Between HOX and PBX/EXD Homeodomain Proteins," *Trends Genet.* 12:258-262 (1996), which is hereby incorporated by reference in its entirety) indicating that the target gene (and function) is dependent on protein-protein interactions. Additionally, HOX-PBC complexes can be activators or repressors of transcription depending on the cell-type and the presence of a third interacting partner (Saleh et al., "Cell Signaling Switches HOX-PBX Complexes From Repressors to Activators of Transcription Mediated by Histone Deacetylases and Histone Acetyltransferases," *Mol. Cell. Biol.* 20:8623-8633 (2000), which is hereby incorporated by reference in its entirety). With the formation of different combinations of heterodimers and ternary complexes, the potential to regulate growth by interacting with different target genes is greatly increased.

It is clear that the interaction of KNOX proteins with other proteins is an important mechanism for regulating development. Protein-protein interactions between BEL-type TFs and KNOX proteins have been reported in barley (Müller et al., "In vitro Interactions Between Barley TALE Homeodomain Proteins Suggest a Role for Protein-protein Associations in the Regulation of Knox Gene Function," *Plant J.* 27:13-23 (2001), which is hereby incorporated by reference in its entirety) and *Arabidopsis* (Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety). Homodimerization of KNOX proteins of barley (Müller et al., "In vitro Interactions Between Barley TALE Homeodomain Proteins Suggest a Role for Protein-protein Associations in the Regulation of Knox Gene Function," *Plant J.* 27:13-23 (2001), which is hereby incorporated by reference in its entirety) and rice (Nagasaki et al., "Functional Analysis of the Conserved Domains of a Rice KNOX Homeodomain Protein, OSH15," *Plant Cell* 13:2085-2098 (2001), which is hereby incorporated by reference in its entirety) has also been demonstrated. Sakamoto et al., "The Conserved KNOX Domain Mediates Specificity of Tobacco KNOTTED1-type Homeodomain Proteins," *Plant Cell* 11: 1419-1431 (1999), which is hereby incorporated by reference in its entirety, showed by expressing chimeric proteins in transgenic tobacco plants that the region of the MEINOX domain (designated KNOX2) involved in protein interaction was more important than the homeodomain in determining the severity of the mutant phenotype. By using a yeast two-hybrid library screen, as described in Examples 20-32, below, seven unique proteins were isolated from potato stolons that interact with POTH1. These seven proteins are homeobox genes of the BEL1-like family and members of the TALE superclass. Whereas POTH1 has a widespread mRNA expression pattern, the seven potato BELs have a differential pattern of expression. It is possible that POTH1 interacts with one BEL protein to negatively regulate GA levels in the tuberizing stolon, but interacts with a different BEL partner in the elongating stolon or SAM. Overexpression of one of the POTH1-interacting proteins, StBEL-05, enhances tuberization under both long- and short-day photoperiods; but unlike POTH1 overexpression, leaf morphology is not altered (see below). In a tandem complex with a specific BEL partner, POTH1 could activate transcription of a set of target genes in one organ or set of cells and with another partner suppress those same genes in a different organ.

Example 19

Figure 8:
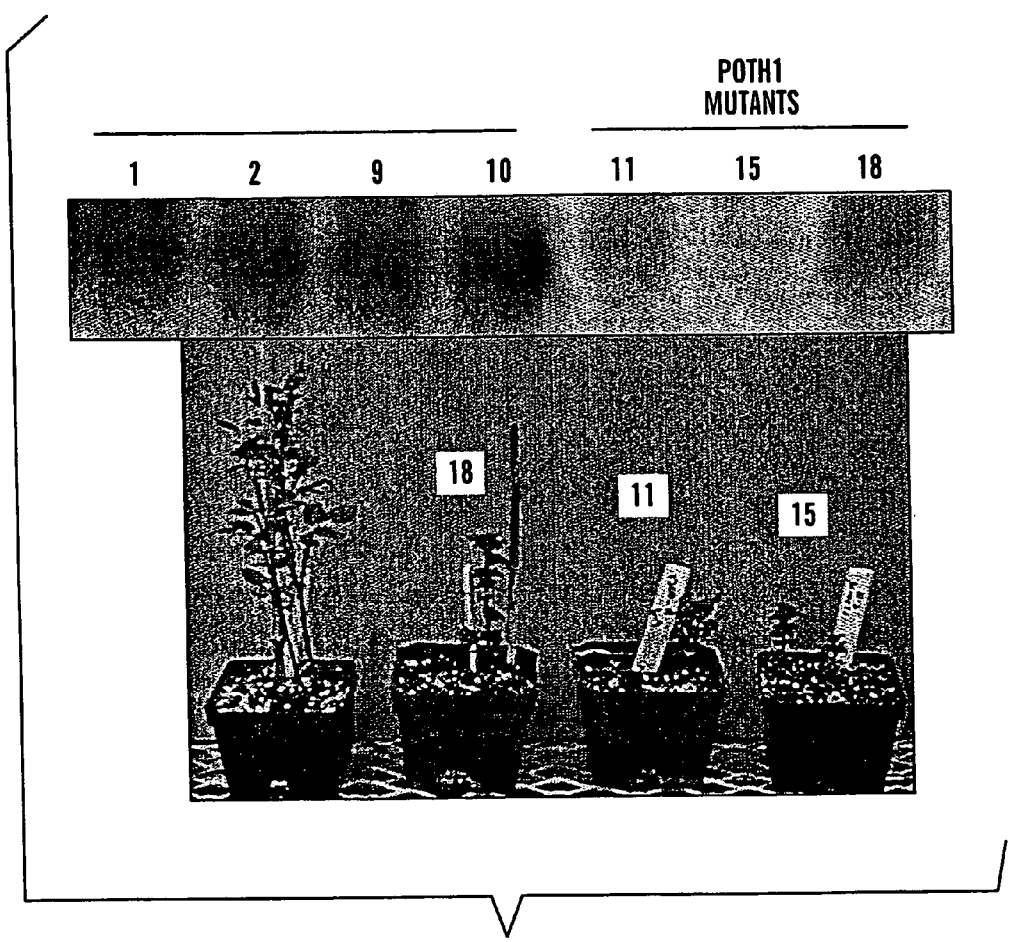
FIG. 8 shows GA 20-oxidase1 mRNA accumulation in shoot tips of POTH1 overexpressers (plants #11, 15, and 18) with a severe phenotype (dwarf with small, curled leaves). Total RNA (10 μg in each lane) was hybridized to $^{32}$P-labeled GA 20-oxidase1 (Carrera et al., "Feedback Control and Diurnal Regulation of Gibberellin 20-oxidase Transcript Level in Potato," *Plant Physiol.* 119:765-773 (1999), which is hereby incorporated by reference) probe. Standard procedures for RNA blot hybridization were used. The plants shown are 8 weeks old. These same plants had reduced levels of GA$_{20}$ and GA$_1$ and increased levels of GA$_{53}$ and GA$_{19}$.

Overexpression of POTH1 Negatively Regulates GA Levels and Affects Vegetative Morphology To further examine the function of POTH1, transformed potato plants (*Solanum tuberosum* spp. andigena) that overexpressed POTH1 mRNA were analyzed. For these experiments, the full-length cDNA sequence of POTH1 in a sense orientation driven by the CaMV-35S promoter in the binary vector, pCB201 (Xiang et al., "A Mini Binary Vector Series for Plant Transformation," *Plant Mol. Biol.* 40:711-718 (1999), which is hereby incorporated by reference in its entirety) was used. The accumulation of the POTH1 mRNA was tightly correlated with a change in phenotype. These overexpressing lines were characterized by distorted, smaller leaves, and dwarfism (FIG. 8). The mutant leaf traits are designated "mouse-ear" or "curled" phenotype as reported previously in other knox mutants (Parnis et al., "The Dominant Developmental Mutants of Tomato, Mouse-Ear and Curl, Are Associated with Distinct Modes of Abnormal Transcriptional regulation of a knotted Gene," *Plant Cell* 9:2143-2158 (1997); Tamaoki et al., "Ectopic Expression of a Tobacco Homeobox Gene, NTH15, Dramatically Alters Leaf Morphology and Hormone Levels in transgenic Tobacco," *Plant Cell Physiol.* 38:917-927 (1997), which are hereby incorporated by reference in their entirety). Application of $GA_3$ produced a partial reversal of the leaf phenotype and completely rescued the dwarf phenotype (see above).

Because of the similarity of this POTH1 phenotype to those reported in tobacco (Tanaka-Ueguchi et al., "Overexpression of a Tobacco Homeobox Gene, NTH15, Decreases the Expression of a Gibberellin Biosynthetic Gene Encoding GA 20-oxidase," *Plant J.* 15:391-400 (1998); Tamaoki et al., "Transgenic Tobacco Over-Expressing a Homeobox Gene Shows a Developmental Interaction Between Leaf Morphogenesis and Phyllotaxy," *Plant Cell Physiol.* 40:657-557 (1999), which are hereby incorporated by reference in their entirety), the effect of GA 20-oxidase mRNA accumulation in these POTH1 overexpressers was examined. GA 20-oxidase is a key biosynthetic enzyme in the GA pathway, catalyzing the conversion of $GA_{53}$ to $GA_{20}$ via $GA_{44}$ and $GA_{19}$ (Hedden et al., "Gibberellin Biosynthesis: Enzymes, Genes and Their Regulation," *Ann. Rev. Plant Physiol. Plant Mol. Biol.* 48:431-460 (1997), which is hereby incorporated by reference in its entirety). Using a probe for the potato GA 20-oxidase1 gene (Carrera et al., "Feedback Control and Diurnal Regulation of Gibberellin 20-oxidase Transcript Level in Potato," *Plant Physiol.* 119:765-773 (1999), which is hereby incorporated by reference in its entirety), a reduction in GA 20-oxidase1 mRNA in shoots of the most severe mutant phenotypes was observed (FIG. 8). Both internode length and overall plant height were reduced approximately threefold in these mutant plants relative to controls. In addition, in a biochemical analysis performed in collaboration with Dr. Peter Davies, Cornell University, the levels of $GA_{53}$ and $GA_{19}$ increased, whereas the levels of $GA_{20}$ and $GA_1$ decreased in shoot tips of these plants. These results indicate that POTH1 is a negative regulator of GA biosynthesis and that it plays a role in controlling vegetative pattern formation.

Example 20

Two-Hybrid Selection and Deletion Analysis

The Matchmaker two-hybrid system (Clontech, CA) was used for the yeast two-hybrid screen. Yeast transformation and plasmid rescue into DH5-a *E. coli* cells were according to the manufacturer's instructions. Full-length POTH1 was cloned into the pBridge (Clontech, CA) vector and used as bait to screen the potato (*S. tuberosum* 'Desireé') stolon cDNA library in pAD-GAL4-2.1 (Stratagene, Calif.). Positive interactions were confirmed by cotransforming yeast strain AH109 with each purified pAD plasmid and pBridge:POTH1 and plating on -leucine/-tryptophan (transformation control) and -leucine/-tryptophan/-histidine/-adenine (selection) nutrient medium. Induction of the AH109 reporter gene, lacZ, was measured with a yeast β-galactosidase assay kit (Pierce Chemicals). β-galactosidase activity (FIG. 9B) was determined from a known density of yeast cells and calculated as $1000 \times OD_{420}$/time of color reaction (minutes)×volume of yeast culture (ml)×$OD_{600}$.

The StBEL-05 deletion constructs were amplified by PCR, then cloned into the vector, pGAD, in-frame with the GAL4 activation domain. POTH1 deletion constructs were amplified by PCR, and cloned into pBridge (Clontech) in-frame with the GAL4 binding domain. Sequencing of selected cDNAs and constructs was performed at the Iowa State University DNA Facility. For deletion analysis, modified constructs of POTH1 were cloned into the pBridge vector for fusion with the DNA-binding domain of GAL4 (FIG. 10A). For StBEL-05, constructs were cloned into the pGAD vector for fusion with the activating domain of GAL4 (FIG. 10B). Deletion constructs were made from both the amino and carboxy termini. These mutants were then tested for interaction in the yeast two-hybrid system by cotransforming into yeast strain AH109 with the corresponding full-length partner (StBEL-05 in pGAL4 or POTH1 in pBridge). All constructs were sequenced to verify that they were in-frame. Positive interactions were verified for lacZ induction by using a β-galactosidase assay (Pierce Chemical Company). For POTH1, seven deletion constructs were tested (FIG. 10A). For the BEL TFs, a fusion construct of StBEL-05 (653 aa of StBEL-05 sequence) and nine deletion constructs were tested (FIG. 10B).

GenBank accession numbers for StBEL-05, -11, -13, -14, -22, -29, and -30 are AF406697, AF406698, AF406699, AF406700, AF406701, AF406702, AF406703, respectively.

Example 21

In Vitro Binding Assay

In vitro binding experiments were performed as described by Ni et al., "PIF3, a Phytochrome-Interacting Factor Necessary for Normal Photoinduced Signal Transduction, is a Novel Basic Helix-Loop-Helix Protein," *Cell* 95:657-667 (1998), which is hereby incorporated by reference in its entirety. The full-length sequence for POTH1 was cloned into a pET17b/GAD fusion cassette and transcribed under the control of the T7 promoter. The BEL cDNAs were cloned into pGEM11Z vectors and were transcribed under the control of the T7 promoter. $^{35}$S-methionine labeled bait and prey proteins were synthesized using the TnT in vitro transcription-translation kit (Promega) according to the manufacturer's protocols. Each 50 µl TnT reaction contained 2.0 µg of template plasmid DNA and 20 µmol (20 µCi) of labeled $^{35}$S-methionine. The POTH1:GAD/BEL complex was immunoprecipitated with anti-GAD antibodies (Santa Cruz Biotechnology, CA). The proteins from the pellet (one-half the fraction) and for the prey (one-fourth of the reaction volume) were resolved on a 10% SDS-PAGE gel and visualized by autoradiography.

Example 22

Hybridization Blot Analysis

Total RNA was extracted from various organs of *Solanum tuberosum* ssp. *andigena* plants grown under a long-day photoperiod by using TRI REAGENT® according to the manufacturer's manual (Molecular Research Center, Inc., Cincinnati, Ohio). Swollen stolons (newly formed tubers) and tubers were harvested from short-day plants. For FIG. 11B, RNA was extracted from leaves and stolons that were harvested from the photoperiod-responsive species *Solanum tuberosum* ssp. *andigena* grown under a short-day photoperiod. Total RNA was size-fractionated via electrophoresis through a 1.4% agarose gel that contained 5.0 mM methyl-mercury hydroxide and transferred onto a MagnaGraph nylon membrane (Micron Separations Inc., Westboro, Mass.). Hybridization and washing conditions were the same as described by Kolomiets et al., "Lipoxygenase is Involved in the Control of Potato Tuber Development," *Plant Cell* 13:613-626 (2001), which his hereby incorporated by reference in its entirety. For autoradiography, membranes were exposed to X-ray film with intensifying screens for three to six days at –80° C. A 1.2 kb wheat 18S ribosomal RNA probe was used to confirm uniform loading of RNA for the blots in FIG. 11A. Blots presented are representative examples of at least two independent experiments.

Example 23

Plant Transformation

Transformation and regeneration of plants was undertaken on leaf sections from *Solanum tuberosum* ssp. *andigena* line 7540 as described by Liu et al., "Transformation of *Solanum brevidens* Using *Agrobacterium tumefaciens*," *Plant Cell Reports* 15:196-199 (1995), which is hereby incorporated by reference in its entirety. These autotetraploid andigena plants, strictly photoperiodic for tuberization, were obtained from the Institut für Pflanzenbau und Pflanzenzüchtung, Braunchsweig, Germany. The sense constructs were made from a 2.0 kb fragment from the StBEL-05 cDNA and cloned into the binary vector pCB201 (Xiang et al., "A Mini Binary Vector Series for Plant Transformation," *Plant Mol Biol* 40:711-718 (1999), which is hereby incorporated by reference in its entirety) driven by the constitutive CaMV-35S promoter. Constructs were checked by using PCR with clone-specific primers. Positive recombinants were transferred to the *Agrobacterium tumefaciens* strain GV2260 by using the procedure of direct transformation (An et al., Binary vectors. in *Plant Mol. Biol. Manual*, pp. A3:1-19, Kluwer Academic, Belgium (1988), which is hereby incorporated by reference in its entirety). Control plants in the tuberization study were *andigena* plants regenerated in vitro. Functional transformants were identified by PCR analysis of genomic DNA and by detection of the accumulation of sense transcripts of StBEL-05 in shoot tip samples. From among these positives, the seven independent transformants (lines 7, 11, 12, 14, 16, 19, and 20 for StBEL-05) used in this study were selected on the basis of abundant accumulation of sense mRNA in shoot tips. Quantitative analysis of cytokinins was performed by using liquid chromatography as described above. Three replicate 200 mg (fresh wt) samples of shoot tips down to the fourth visible expanded leaf were collected, frozen in liquid nitrogen, lyophilized, and analyzed.

Example 24

Evaluation of Tuber Formation

For in vitro tuberization, cultured transgenic plants were grown on a Murashige and Skoog medium with 6.0% sucrose under a long-day photoperiod (16 hours of light, 8 hours of dark) in a growth chamber for two weeks and then transferred to a short-day photoperiod (8 hours of light, 16 hours of dark) in the same growth chamber. For tuber induction, plants were evaluated daily for tuber formation. Soil-grown plants were grown in 10-cm pots under long days (16 hours of light, 8 hours of dark) in the greenhouse supplemented with high pressure sodium HID lamps until they reached the 16-leaf stage and then transferred to short days in the growth chamber. After 14 days under short days, plants were evaluated for tuber formation.

Example 25

Results: Isolation of Potato KNOX Interactive Proteins

Figure 9A:
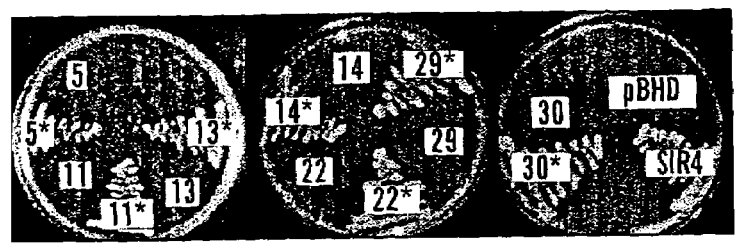
FIGS. 9A-C show the specific interaction of POTH1 with seven BEL1-like proteins of potato.
Figure 9B:
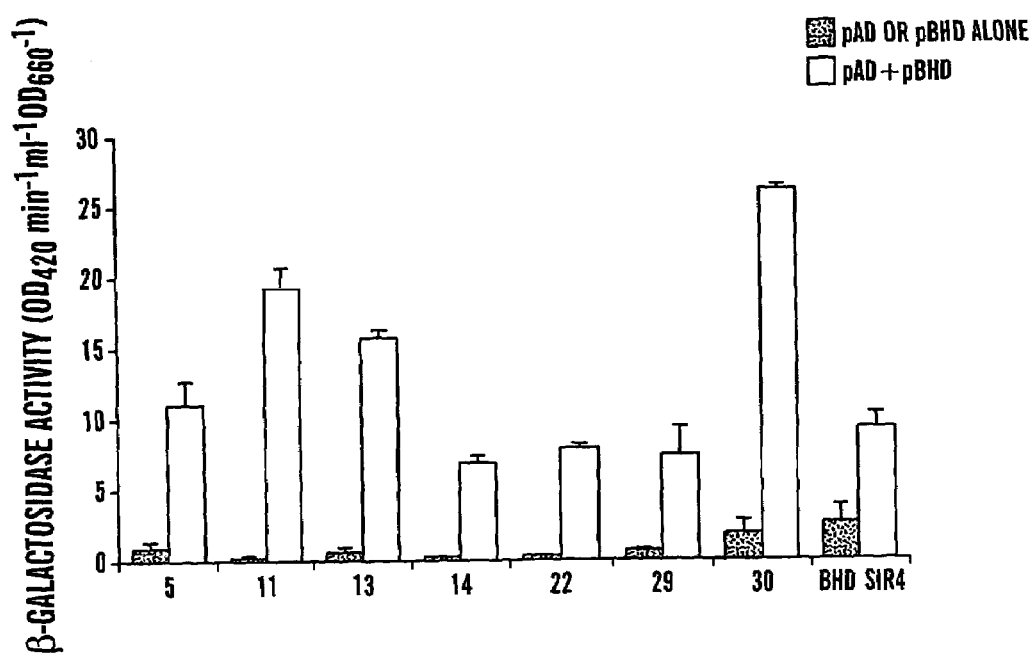
Figure 9C:
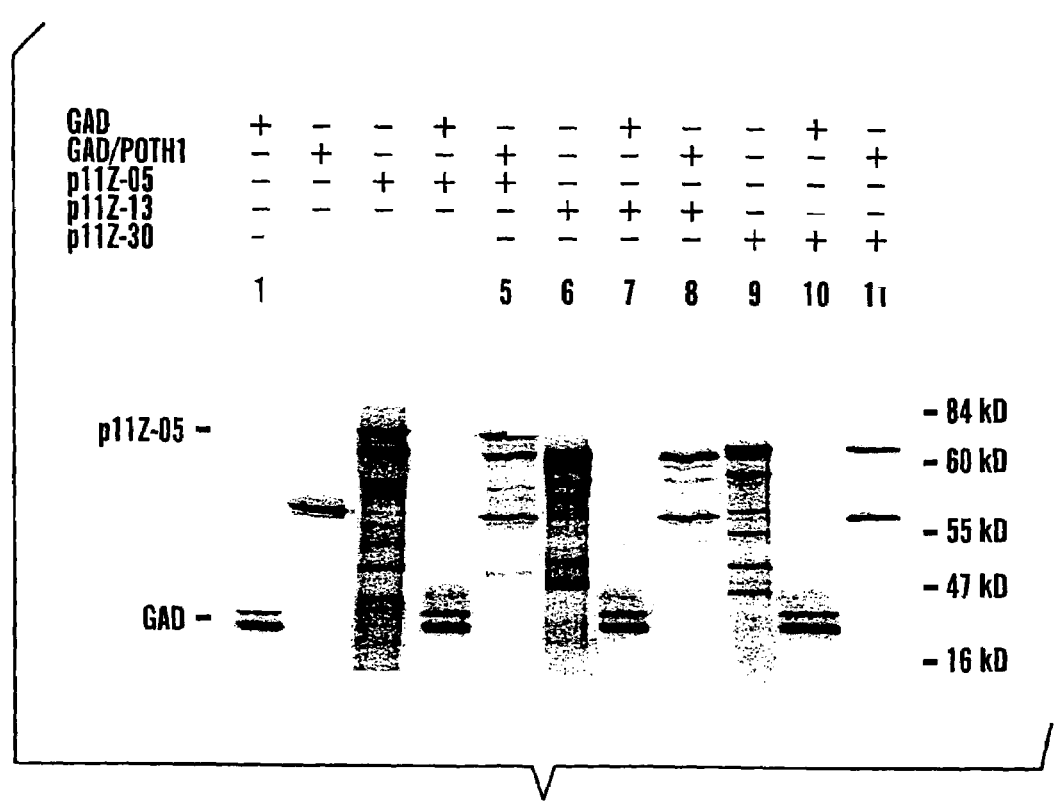

Making use of the two-hybrid selection system in yeast, approximately $10^6$ transformants from a stolon cDNA library of potato were screened using POTH1 in the GAL4-binding domain vector, pBridge (Clontech), as bait. Thirty-eight positive clones that grew on selective media were identified. Of the 38 that were sequenced, 23 clones could be grouped into seven unique genes encoding different members of the TALE superclass of transcription factors (Chan et al., "Homeoboxes in Plant Development," *Biochim Biophys Acta* 1442: 1-19 (1998), which is hereby incorporated by reference in its entirety). All seven, designated StBEL-05, -11, -13, -14, -22, -29, and -30 (GenBank accession numbers AF406697, AF406698, AF406699, AF406700, AF406701, AF406702, AF406703, respectively) showed selective interaction when tested in the yeast system both for nutritional markers and for lacZ activation (FIGS. 9A and 9B). Interaction occurred also when the prey cDNAs were cloned into pBridge and transformed with POTH1 in a GAL4-activation domain vector. As a test for autoactivation, the pAD transformants (5, 11, 13, 14, 22, 29, 30) did not grow on -histidine, -adenine, and -leucine medium and the pBD transformant did not grow on -histidine, -tryptophan, and -adenine medium. In vitro binding experiments verified the results of the two-hybrid selection. POTH1 pulled down three representative StBEL proteins with divergent sequence similarity in the BELL domain (5, 13, and 30) and synthesized by in vitro transcription/translation in immunoprecipitation assays (FIG. 9C).

Example 26

Results: The Proteins that Interact with the Potato KNOX Protein are Members of the BEL Family of Transcription Factors A phylogenetic analysis of the sequences of the seven interacting proteins identified them as members of the BEL1-like family of transcription factors (FIG. 12). These seven can be organized into four subgroups based on amino acid sequence similarity. Three clones (StBEL-05, -11, and -29) had 60-69% similarity to each other overall and two other clones had a 78% match (StBEL-13 and -22). These two groups range in similarity to the others from 45-53% and a third (StBEL-30) has about 51% similarity to the others. The sequence similarity of StBEL-14 to the other six ranged from 45 to 56%. The amino acid sequence of StBEL-05 has overall 56% similarity to BLH1 of *Arabidopsis* that interacts with KNAT1 (GenBank accession number AAK43836), StBEL-13 matches an apple BEL (Dong et al., "MDH1: an Apple Homeobox Gene Belonging to the BEL1 Family," *Plant Mol Biol* 42:623-633 (2000), which is hereby incorporated by reference in its entirety, GenBank accession number AAF43095) at 74% similarity, and StBEL-30 matches another *Arabidopsis* BEL (GenBank accession number T05281) at 59% similarity. The close match of all seven to the conserved homeodomain and the presence of the proline-tyrosine-proline (P-Y-P) loop between helices I and II (FIG. 13A) distinguish these novel proteins as BEL types in the TALE superclass (Bürglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997), which is hereby incorporated by reference in its entirety). The homeodomain region is nearly identical among these seven (FIG. 13A, encompassing helices I, II, and III). Other regions of conserved sequence identity are shown schematically in FIG. 13A. These include the amino-terminal SKY box consisting of 20 aa (from ser-207 to lys-226 in StBEL-05), the 120-aa domain starting at leu-272 of the StBEL-05 sequence, and the carboxy-terminal VSLTLGL-box (SEQ ID NO: 15) beginning at val-620. Three α-helices were predicted from the conserved 120-aa region of the BEL protein StBEL-05 (underlined sequence of FIG. 13B). Among the seven BELs, the percent similarity of the amino acid sequence in this conserved 120-aa domain ranged from 58 to 90%. Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by referenced in its entirety, referred to this region as the BELL domain.

The deduced lengths of the seven original cDNAs are 688 aa for StBEL-05, 535 aa for StBEL-11, 586 aa for StBEL-13, 589 aa for StBEL-14, 620 aa for StBEL-22, 567 aa for StBEL-29, and 645 aa for StBEL-30. Five'-RACE was used to verify the full-length of StBEL-05, -13, -14 and -30. For blot hybridizations, a representative clone from each of the four subgroups (StBEL-05, -13, -14, and -30) was used. Southern blot analysis revealed that these genes are unique and belong to small gene subfamilies, based on the complexity of bands detected by gene-specific probes from each of the cDNAs (FIG. 13C).

Example 27

Results: Patterns of mRNA Accumulation for the Potato BELs

Figure 11A:
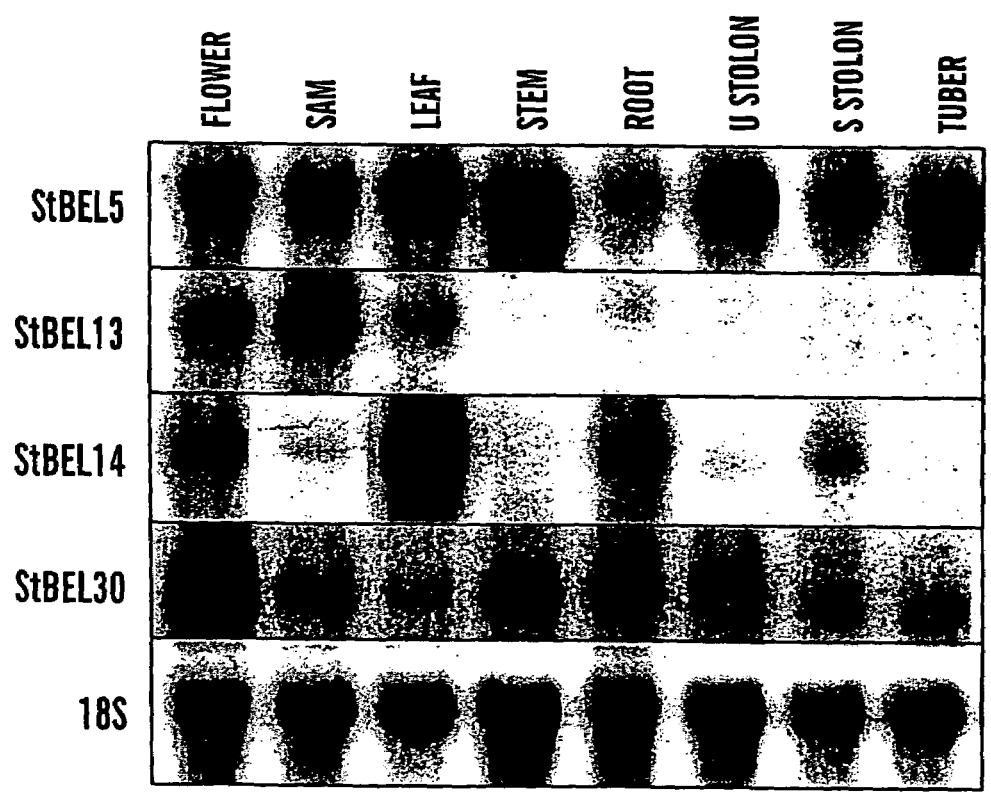
FIG. 11A shows a Northern blot analysis of the accumulation of mRNA for four BEL1-like cDNAs (StBEL-05, -13, -14, and -30) in potato organs. Ten μg of total RNA from flowers, shoot tips (SAM), leaves, stems, roots, unswollen stolons (U stolon), swollen stolons (S stolon), and tubers were loaded per lane. Swollen stolons represent an early stage of tuber formation. A probe for the 18S ribosomal RNA was used to verify equal loading of RNA samples (bottom panel).
Figure 11B:
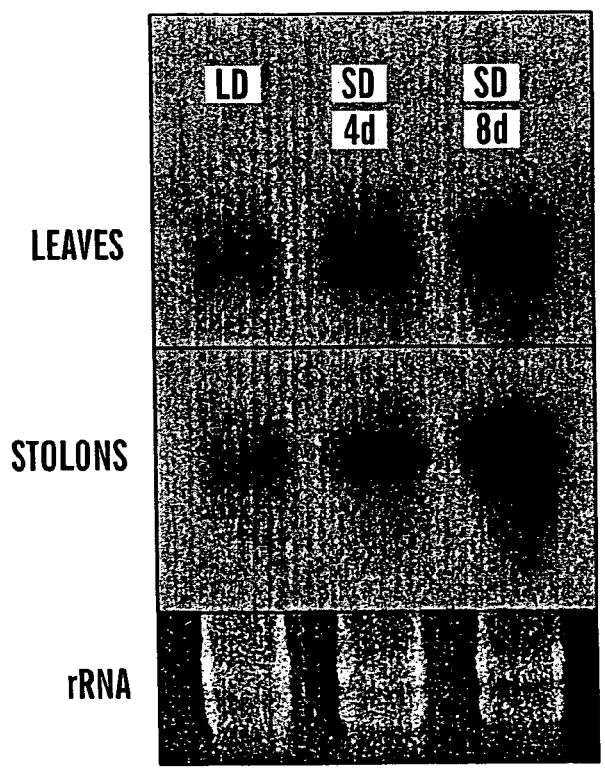
FIG. 11B shows a Northern blot analysis of the accumulation of the mRNA of StBEL-05 in leaves and stolons of WT plants grown under long days (LD, 16 hours of light, 8 hours of dark) and short days (SD, 8 hours of light, 16 hours of dark). Ten μg of total RNA from stolons were loaded per lane. Leaves and stolons were harvested from the photoperiod-responsive potato species, *Solanum tuberosum* ssp. *andigena*, 4 and 8 days after the plants were transferred to short-day conditions. Samples were harvested one hour after the end of the dark period. A gene-specific probe for each BEL cDNA was used. Ethidium bromide-stained ribosomal RNA is visualized as a loading control.
Figure 11C:
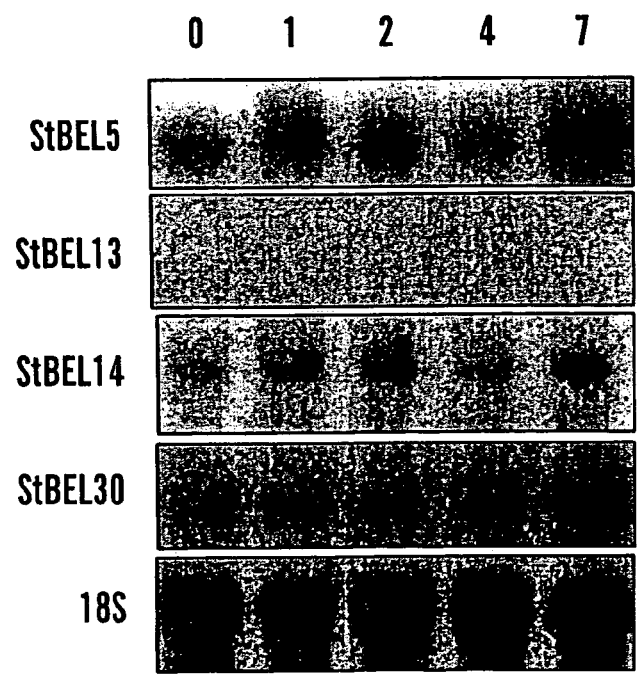
FIG. 11C shows a Northern blot analysis of the accumulation of the mRNA of potato BEL-like cDNAs (StBEL-05, StBEL-13, StBEL-14, and StBEL-30) in tuberizing stolons.

The BEL1-like gene represented by StBEL-05 exhibited mRNA accumulation in all organs examined, with the greatest levels in leaves and stems (FIG. 11A). Transcript accumulation of StBEL-11 and StBEL-29 was similar to the pattern of StBEL-05. Transcripts for StBEL-13 accumulated to the highest levels in the SAM and in fully formed flowers but were barely detectable in other organs (FIG. 11A). The autoradiographs for StBEL-13 were exposed two-times longer than the other StBELs. For StBEL-14, transcripts were detected in flowers, leaves, roots, and stolons. The greatest accumulation of StBEL-30 was in flowers with detectable levels in all organs examined. To examine more closely the dynamics of StBEL expression during tuber induction, a temporal study was undertaken for the accumulation of StBEL-05 transcripts in leaves and stolons of the photoperiod-sensitive potato species *S. tuberosum* ssp. *andigena* grown under short-day conditions. Steady-state levels of StBEL-05 mRNA increased in both leaves and stolons after exposing the plants to short-day (SD) conditions (FIG. 11B). Visible tuber formation for the plants grown under SD conditions was observed between 10 to 14 days. In this study, the accumulation of mRNA for the BEL cDNA, StBEL-05, was linked to the induction of tuber formation in the leaves and stolons of a potato species responsive to a SD photoperiod. In addition, a temporal study was undertaken for the accumulation of BEL transcripts in stolons of the photoperiod-sensitive potato species *S. demissum* grown under short-day conditions. The induction of StBEL-05, StBEL-14, and StBEL-30 expression was first detected in stolons one day after exposing the plants to short-day (SD) conditions (FIG. 11C). This increase in RNA levels remained steady through 7 days. Transcripts for StBEL-13 were not detected in stolons in any stage of development (FIG. 11C). Visible tuber formation for the plants grown under SD conditions was observed between 10 to 14 days. In this study, the accumulation of mRNA for the BEL cDNAs, StBEL-05, StBEL-14, and StBEL-30 was linked to the induction of tuber formation in the stolons of a potato species responsive to a SD photoperiod.

Example 28

Results: Determining the Protein Binding Regions in POTH1 and the BEL-Like Proteins Interaction with StBEL-05 was observed with all deletions outside the KNOX domain, with pBHD2 (missing the amino-terminus and the first 48 aa of the KNOX domain, FIG. 10A), with pBHD6 (missing the carboxy terminus and 52 aa of the carboxy-end of the KNOX domain), and with pBHD-9 (first amino-terminal 114 aa but no KNOX domain sequence). No interaction was observed with pBHD3 (missing all of the KNOX domain and the first 114 aa). Control experiments identified the first 114 aa of the N-terminus (pBHD9) as a transcriptional activator. This construct transformed alone into AH109 exhibited nutrient selection on -histidine, -tryptophan, and -adenine medium. Co-transformation of pBHD9 with an empty pGAD cassette produced transformants capable of growth on -histidine, -tryptophan, -adenine, and -leucine medium and induction of lacZ. None of the other constructs containing this domain were capable of growing on selection media without StBEL-05. Using the in vitro binding protocol, both the pBHD6 construct, containing the amino-terminal half of the KNOX domain, and the pBHD9 construct were unable to pull-down StBEL-05. When the pBDH9 construct was cloned into the pGAD vector, no interaction was observed with StBEL-05 in pBridge.

Fusion constructs of StBEL-05 that dissected the 120-aa domain (pAD5-2, -3, -4, -9, and -11) were tested because this is one of the regions that is conserved in BEL TFs from other plant species (Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety; FIG. 13B). Interaction with POTH1 was observed with all constructs that had deletions exclusively outside of the conserved 120-aa box (FIG. 10B). The only exception to this was with pAD5-9 that demonstrated an interaction and included a 43-aa deletion from the carboxy end of the 120-aa domain. Even with as little as a 27-aa deletion from the amino end of the 120-aa domain, interaction did not occur (FIG. 13B, FIG. 10B, pAD5-2). Similar to the results of Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety, deletion of the SKY box (construct pAD5-1) resulted in a 55% decrease in the induction of the lacZ marker as measured by β-galactosidase activity relative to the full-length construct, StBEL-05 (FIG. 10B).

Example 29

Results: Enhanced Tuber Formation in Transgenic Plants that Overexpress the BEL cDNA, StBEL-05

To examine the function of the potato BELs, transformed potato plants (*Solanum tuberosum* ssp. *andigena*) that over expressed StBEL-05 from a constitutive promoter were analyzed. This BEL gene was selected because of its moderate level of activity in stolons and tubers and its increase in RNA levels in response to inductive conditions for tuber formation (FIG. 11). For these experiments, a 2000-bp fragment of the coding sequence of StBEL-05 in a sense orientation driven by the CaMV-35S promoter in the binary vector pCB201 (Xiang et al., "A Mini Binary Vector Series for Plant Transformation," *Plant Mol Biol* 40:711-718 (1999), which is hereby incorporated by reference in its entirety) was used. Transformants were identified by PCR analysis of genomic DNA and by detection of the accumulation of sense transcripts of StBEL-05 in RNA samples from vegetative meristems. From among approximately twenty-five positives, four independent lines with the highest levels of StBEL-05 mRNA accumulation (FIG. 14A) were selected for evaluation of tuber formation in vitro under both inductive (SD) and noninductive (LD) conditions. The highest expressers of StBEL-05 sense transcripts (lines 11, 12, 14, and 19) exhibited tuber formation under LD conditions (FIG. 14B). Control plants (WT and line 6) produced tubers only under SD conditions. The highest overexpressers of StBEL-05 also produced more tubers than control plants over the course of this experiment and were more responsive to inductive conditions. After seven days under SD conditions, the control plants had produced no tubers, whereas the overexpression mutants (lines 11, 12, 14, and 19) had produced 10, 8, 15, and 4 tubers, respectively (FIG. 14B). After 14 days under SD, controls had increased to 6 and 4 tubers, whereas the overexpression lines had increased to 12, 14, 24, and 10 tubers, respectively. Tuber yields (fr wt) also increased in overexpression lines 12, 14, and 19 (FIG. 14C). The greatest tuber production was exhibited by lines 12 and 14 with a five- and sixteenfold increase, respectively, relative to wild-type plants (FIG. 14B, bottom panel). Tubers from the overexpression lines grew larger than controls. Select tubers from line 14 reached fresh weights of almost 700 mg, whereas the largest control tuber reached only 140 mg.

With whole plants grown in soil under SD conditions for 14 days, StBEL-05 overexpression lines produced an average of three- to fivefold more tubers per plant and more than a threefold greater tuber yield per plant than controls (Table 2).

TABLE 2

Rate of tuberization for overexpression lines of StBEL-05 under soil-grown, short-day conditions. Plants were grown in 10-cm pots under long days (16 hours of light, 8 hours of dark) until they reached the 16-leaf stage and then transferred to short days (8 hours of light, 16 hours of dark). After 14 days under short days, four plants per independent line were evaluated for tuber formation. Standard errors of the mean are shown.

| Plant line | Number tubers plant$^{-1}$ | Tuber yield plant$^{-1}$ (g) |
|---|---|---|
| Wild-type | 2.2 ± 1.4 | 1.4 ± 0.9 |
| StBEL5-12 | 8.0 ± 0.8 | 5.4 ± 1.3 |
| StBEL5-14 | 8.3 ± 0.9 | 4.6 ± 1.3 |
| StBEL5-19 | 11.5 ± 2.1 | 4.7 ± 1.4 |

Increased yields (as high as 50%) were maintained for these lines even after six weeks of growth in soil. Seven overexpressing sense lines (lines 7, 11, 12, 14, 16, 19, and 20) also exhibited tuber activity (swollen stolons or tuber formation) on soil-grown plants under LD greenhouse conditions. Five of these plants produced tubers, whereas control plants exhibited no tuber activity. In addition, the rate of tuberization for plants grown in vitro under short-day conditions for 21 days is shown in Table 3, below.

TABLE 3

Rate of tuberization for overexpression lines of StBEL-05. Plants were grown in vitro under short days in media with 6% sucrose for 21 days and scored for tuber formation. Twenty-five plants per independent line were evaluated, thirty-five for controls.

| Plant line | Number tubers plant$^{-1}$ | Tuber yield plant$^{-1}$ (mg) |
|---|---|---|
| Control | 0.4 | 18 |
| StBEL-05-12 | 0.9 | 95 |
| StBEL-05-14 | 1.3 | 292 |
| StBEL-05-19 | 0.9 | 50 |

Similar to POTH1 overexpressers (see above), these results show that the accumulation of StBEL-05 mRNA is correlated with an increased rate of tuber formation. Other than this enhanced capacity for tuberization, the StBEL-05 overexpression lines in Table 2 did not exhibit the phenotype characteristic of KNOX gene overexpressers, including extreme dwarfism and abnormal leaf morphology (FIG. 15). The abnormal phenotype of KNOX overexpressers is mediated by changes in hormone levels, specifically, a reduction in gibberellins and an increase in cytokinins (see above; Sato et al., "Abnormal Cell Divisions in Leaf Primordia Caused by the Expression of the Rice Homeobox Gene OSH1 Lead to Altered Morphology of Leaves in Transgenic Tobacco," *Mol Gen Genet.* 251:13-22 (1996); Tamaoki et al., "Ectopic Expression of a Tobacco Homeobox Gene, NTH15, Dramatically Alters Leaf Morphology and Hormone Levels in Transgenic Tobacco," *Plant Cell Physiol* 38:917-927 (1997); Frugis et al., "Overexpression of KNAT1 in Lettuce Shifts Leaf Determinate Growth to a Shoot-like Indeterminate Growth Associated With an Accumulation of Isopentenyl-type Cytokinins," *Plant Physiol* 126:1370-1380 (2001), which are hereby incorporated by reference in their entirety). With the exception of two StBEL-05 sense mutants (lines 11 and 20), the leaf and stem growth of the StBEL-05 overexpression lines was similar to wild-type plants (FIG. 15). All five StBEL-05 lines exhibited an enhanced rate of growth comparable to control plants (Table 4).

TABLE 4

Plant height (cm) and fresh weight (g) of overexpression lines of StBEL-05 under soil-grown, long-day conditions. Plants were grown in 10-cm pots under long days (16 hours of light, 8 hours of dark) and plant height was measured after 10 and 45 days. Four plants per independent line were evaluated for growth. Fresh weight of leaves and stems was measured after 45 days. Standard errors of the mean are shown.

| | Plant height (cm) | | Fresh weight (g) of |
|---|---|---|---|
| Plant Line | at 10 d | at 45 d | stem and leaves |
| Wild type | 5.3 ± 0.3 | 35.2 ± 2.2 | 18.0 ± 2.6 |
| StBEL5-11 | 7.3 ± 0.4 | 31.9 ± 3.0 | 19.6 ± 1.3 |
| StBEL5-20 | 6.3 ± 0.6 | 32.2 ± 2.0 | 10.8 ± 0.5 |
| StBEL5-12 | 7.1 ± 0.7 | 44.9 ± 0.9 | 23.3 ± 1.2 |
| StBEL5-14 | 6.2 ± 0.2 | 38.2 ± 1.2 | 29.2 ± 1.0 |
| StBEL5-19 | 7.1 ± 0.5 | 48.7 ± 1.9 | 25.5 ± 3.5 |

The average height of line 19 plants was 13.5 cm greater than control plants after 45 days. Fresh weights of leaves and stems of lines 12, 14, and 19 were 29 to 62% greater than control plants. Lines 11 and 20 exhibited a more rapid rate of growth early (10 days) and then growth rate dropped off by 45 days (Table 4). Accumulation of StBEL-05 transgenic mRNA in line 20 was equivalent to line 11. Three-month old plants from lines 11 and 20 exhibited a slight reduction in leaf size and stem height as a result of decreased apical dominance. To examine the mechanism for this reduced leaf morphology, cytokinin analysis was performed on shoot apices down to the fourth visible true leaf. Similar to POTH1 overexpressers, shoot tips of both StBEL-05 lines 11 and 20 exhibited a two- to fivefold increase in the bioactive forms of cytokinin (Table 5).

TABLE 5

Cytokinin content (picomoles g fr wt$^{-1}$) in shoot tips of POTH1 and StBEL-05 overexpression lines grown under long days (16 hours of light, 8 hours of dark) in the greenhouse. Wild-type lines are nontransformed *Solanum tuberosum* spp. *andigena*. Zeatin types include zeatin, zeatin riboside, dihydrozeatin, and dihyrozeatin riboside. Isopentenyl types include isopentenyl and isopentenyladenine. Standard error was calculated on three replicates.

| Sample | Zeatin types | Isopentenyl types |
|---|---|---|
| Wild-type | 10.5 ± 1.0 | 12.0 ± 1.5 |
| POTH1-15 | 42.5 ± 15 | 35.5 ± 7.0 |
| POTH1-29 | 34.0 ± 12 | 30.0 ± 6.0 |
| StBEL5-11 | 55.5 ± 30 | 31.5 ± 11 |
| StBEL5-20 | 30.5 ± 6.0 | 29.5 ± 6.5 |

The overall magnitude increases in the cytokinin types among the four STBEL and POTH1 mutant lines were remarkably consistent.

POTH1 sense lines had increased levels of $GA_{53}$ and $GA_{19}$ and decreased levels of $GA_{20}$ and GA1 in shoot tips, indicating a down-regulation of the biosynthetic enzyme GA 20-oxidase1 (see above). Using a probe for the potato GA 20-oxidase1 gene (Carrera et al., "Changes in GA 20-oxidase Genes Expression Strongly Affect Stem Length, Tuber Induction and Tuber Yield of Potato Plants," *Plant J.* 22:1-10 (2000), which is hereby incorporated by reference in its entirety), a reduction in GA 20-oxidase1 mRNA in shoots of the most severe mutant phenotypes for POTH1 sense lines was observed (see above, FIG. 15). To determine the effect of overexpression of the POTH1 partner, StBEL-05, RNA levels for GA 20-oxidase1 were examined in the stolons of StBEL-05 sense lines grown under long-day photoperiod conditions. All three of the StBEL-05 lines examined (lines 11, 12, and 20) exhibited a reduction in GA 20-oxidase1 mRNA in stolon tips comparable to controls (FIG. 16). No such reduction in the levels of GA 20-oxidase1 mRNA was observed in shoot tips of StBEL-05 lines grown under long days.

To determine the effect of upregulating StBEL-05 mRNA levels on POTH1 RNA accumulation, northerns were performed on total RNA extracted from StBEL-05 sense lines 12, 14, 19, and 20 using POTH1 as a probe. There were no changes in the levels of POTH1 mRNA in both shoot tips and stolon tips of these StBEL-05 lines relative to wild-type plants. These results indicate that the enhancement of tuber formation in StBEL-05 overexpression lines is not mediated by an indirect increase in POTH1 expression.

Example 30

Discussion: Seven BEL Proteins Interact with a KNOX Protein of Potato

Using a yeast two-hybrid library screen, seven unique proteins from potato stolons that interact with the knotted-like protein, POTH1, were identified. Sequence analysis revealed that these interacting proteins are from the BEL1-like family in the TALE superclass of homeodomain proteins. These proteins have conserved regions in common with other TALE proteins, including the homeodomain (comprised of three α-helices) and the proline-tyrosine-proline "TALE" (Buirglin, "Analysis of TALE Superclass Homeobox Genes (MEIS, PBC, KNOX, Iroquois, TGIF) Reveals a Novel Domain Conserved Between Plants and Animals," *Nucleic Acids Res* 25:4173-4180 (1997), which is hereby incorporated by reference in its entirety). These sequences have been implicated in DNA-binding and protein/protein interactions, respectively (Mann et al., "Extra Specificity From extradenticle: the Partnership Between HOX and PBX/EXD Homeodomain Proteins," *Trends in Genet.* 12:258-262 (1996); Passner et al., "Structure of DNA-Bound Ultrabithorax-Extradenticle Homeodomain Complex," *Nature* 397:714-719 (1999), which are hereby incorporated by reference in their entirety). A second conserved region of 120 aa just upstream from the homeodomain (designated the BELL domain by Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety) was identified among BEL proteins by using a BLAST analysis (FIG. 13B, bold letters). Sequence analysis of the predicted secondary structure of this domain reveals the presence of three putative α-helices within the 120 residues (FIG. 13B, underlined sequence). Not all BEL proteins conserve the third helix, however, including the *Arabidopsis* BEL, ATH1 (Quaedvlieg et al., "The Homeobox Gene ATH1 of *Arabidopsis* is Depressed in the Photomorphogenic Mutants cop1 and det1," *Plant Cell* 7:117-129 (1995), which is hereby incorporated by reference in its entirety) and the barley BEL, JUBEL2 (Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety). Protein interaction using the two-hybrid system demonstrated that the first 80 aa of this domain (up to QVKAT of the STBEL-05 sequence and comprising the first two predicted helices of this region) are necessary to mediate interaction with POTH1 (interaction of construct pAD5-9 with POTH1). Deletion of as little as the first 20 aa of this domain (comprising a major portion of the first predicted helix) interfered with the interaction with POTH1 (FIGS. 13B and 10B, construct pAD5-2). The results also showed that deletion of 43 aa from the carboxy-end of the 120-aa domain (see FIG. 10B, construct pAD5-9; comprising the third helical structure) did not affect protein interaction. Deletion of the two carboxyl-terminal helices in this region (construct pAD5-11) resulted in a loss of interaction. It appears that all three helical structures contribute to specific binding affinity for POTH1 but that only the amino-terminal two-thirds of the 120-aa domain are necessary for binding to occur. Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety, identified a coiled-coil region in a BEL protein of barley that was involved in the interaction with KNOX proteins. This coiled-coil domain overlaps with 48 of the 80 aa (and comprising the first helix) identified as essential for interaction to occur.

Sequence differences in this putative protein-binding region appear to contribute to the regulation of POTH1 activity by affecting binding affinity to a shared partner. In the interaction between PIF3, a basic helix-loop-helix factor, and phytochrome A and B, phytochrome B has tenfold greater binding affinity for the PIF3 partner than phytochrome A (Zhu et al., "Phytochrome B Binds With Greater Affinity Than Phytochrome A to the Basic Helix-loop-helix Factor PIF3 in a Reaction Requiring the PAS Domain of PIF3," *Proc Natl Acad Sci USA* 97:13419-13424 (2000), which is hereby incorporated by reference in its entirety). A comparison of this 120-aa domain in the potato BELs revealed that StBEL-05 (expressed ubiquitously) has a 58% similarity match to StBEL-13 (expressed predominately in the SAM and flower only) and that StBEL-13 has a 63% match to StBEL-30 in this conserved region. Such differences in sequence may mediate binding affinities to shared partners and, coupled with expression patterns, could reflect organ-specific differences in function.

Conservation in sequence among these seven proteins was also identified in two short amino acid sequence motifs, one near the carboxyl-end of the protein (VSLTLGL) (SEQ ID NO:15) and another just upstream of the BELL domain (SKY box, FIG. 13A). Both of these regions are conserved among other plant BELs. Protein interaction studies showed that the VSLTLGL (SEQ ID NO:15) box is not involved in protein interaction with POTH1 and its function remains unknown. Consistent with Bellaoui et al., "The *Arabidopsis* BELL1 and KNOX TALE Homeodomain Proteins Interact Through a Domain Conserved Between Plants and Animals," *Plant Cell* 13:2455-2470 (2001), which is hereby incorporated by reference in its entirety, it was observed that, whereas binding occurred without the 229 aa at the amino terminus of StBEL-05 (construct pAD5-1), this 229 aa sequence alone, containing the SKY box, was sufficient to mediate an interaction with POTH1 (and other class I KNOX proteins). This 229-aa sequence, however, did not interact with a class II KNOX protein. Müllller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety, identified the SKY-box sequence in the barley BEL protein to be a part of the KNOX-interacting domain. Our deletion analysis indicates that the SKY box enhances the binding affinity of StBEL-05 to KNOX partners.

Example 31

Discussion: The Protein Binding Region of POTH1

In addition to the homeodomain, KNOX TFs also contain a conserved region of approximately 100 aa, upstream from the homeodomain, known as the KNOX (MEINOX) domain, and postulated to be involved in protein/protein interaction (Bürglin, "The PBC Domain Contains a MEINOX Domain: Coevolution of Hox and TALE Homeobox Genes," *Dev Genes Evol* 208:113-116 (1998), which is hereby incorporated by reference in its entirety). Using deletion mutants in the two-hybrid yeast system, regions of amino acid sequence in the KNOX domain of the class I KNOX protein, POTH1, that are involved in an interaction with the BEL TFs have been identified. Binding to the BEL partner is mediated by the KNOX domain but is not dependent on the presence of the first half of the 120 aa KNOX region (FIG. 10A). Similar results were obtained by Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety. Sakamoto et al., "The Conserved KNOX Domain Mediates Specificity of Tobacco KNOTTED 1-type Homeodomain Proteins," *Plant Cell* 11: 1419-1431 (1999), which is hereby incorporated by reference in its entirety, showed by using chimeric proteins that the second half of the KNOX domain (designated KNOX2) of a tobacco KNOX protein (NTH15, with 63% similarity to POTH1 in the KNOX region) was most important for determining the severity of the mutant phenotype. Their results indicated that this conserved domain was even more important in determining the phenotype than the DNA-binding domain. The deletion analysis for POTH1 in the present study combined with the results of Sakamoto et al., "The Conserved KNOX Domain Mediates Specificity of Tobacco KNOTTED1-type Homeodomain Proteins," *Plant Cell* 11: 1419-1431 (1999), which is hereby incorporated by reference in its entirety, indicate that the interaction of the BEL proteins with the KNOX domain is a prominent control mechanism for mediating KNOX activity and maintaining stable development of the vegetative meristem. KNOX2 contains 18 aa that are predicted to form an α-helix and are conserved among all tobacco and potato KNOX proteins. POTH1 has a close sequence match to members of the family of KNOX proteins of tobacco (Nishimura et al., Over-expression of Tobacco Knotted1-type Class1 Homeobox Genes Alters Various Leaf Morphology," *Plant Cell Physiol* 41:583-590 (2000), which is hereby incorporated by reference in its entirety), with an overall sequence similarity ranging from 60 to 73% and an even greater match in the conserved KNOX and homeodomain regions. Using the two-hybrid system, all seven BELs of potato interacted with four other tobacco class I-type KNOX proteins. Unlike KNOX proteins of barley (Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety) and rice (Nagasaki et al., "Functional Analysis of the Conserved Domains of a Rice KNOX Homeodomain Protein, OSH15," *Plant Cell* 13:2085-2098 (2001), which is hereby incorporated by reference in its entirety), however, POTH1 did not form homodimers in vitro. Structural similarities to the MEIS domain of animal homeodomain proteins (Bürglin, "The PBC Domain Contains a MEINOX Domain: Coevolution of Hox and TALE Homeobox Genes," *Dev Genes Evol* 208:113-116 (1998), which is hereby incorporated by reference in its entirety) suggest that sequences in the KNOX domain of plants are important for interactions with other proteins (Sakamoto et al., "The Conserved KNOX Domain Mediates Specificity of Tobacco KNOTTED1-type Homeodomain Proteins," *Plant Cell* 11:1419-1431 (1999), which is hereby incorporated by reference in its entirety). These results confirm the function of this domain in an interaction with a BEL1-like protein of potato.

Example 32

Discussion: The Function of the BEL/POTH1 Interaction

Through both molecular and genetic analyses, the BEL proteins are known to function in the development of ovules. Reiser et al., "The BELL1 Gene Encodes a Homeodomain Protein Involved in Pattern Formation in the *Arabidopsis* Ovule Primordium," *Cell* 83:735-742 (1995), which is hereby incorporated by reference in its entirety, showed that BELL1 of *Arabidopsis* was involved in the pattern formation of ovule primordium. More specifically, the expression of NOZZLE (a nuclear protein and putative TF) and BELL are spatially linked and interact with other transcription factors to determine distal-proximal pattern formation during ovule development (Balasubramanian et al., "NOZZLE Links Proximal-Distal and Adaxial-Abaxial Pattern Formation During Oovule Development in *Arabidopsis thaliana,*" *Development* 129:4291-4300 (2002), which is hereby incorporated by reference in its entirety). Both NOZZLE and BELL are chalazal identity genes that share overlapping functions (Balasubramanian et al., "NOZZLE Regulates Proximal-Distal Formation, Cell Pproliferation and Early Sporogenesis During Oovule Development in *Arabidopsis thaliana,*" *Development* 127:4227-4238 (2000), which is hereby incorporated by reference in its entirety). In bell mutants, the chalazal domain undergoes altered development and growth of the integuments is replaced by irregular outgrowths (Mondrusan et al., "Homeotic Transformation of Ovules into Carpel-like Structures in *Arabidopsis,*" *Plant Cell* 6:333-349 (1994), which is hereby incorporated by reference in its entirety). Overexpression of an apple BEL gene (MDH1) in *Arabidopsis* produced plants that were dwarf, had reduced fertility, and exhibited changes in both carpel and fruit shape (Dong et al., "MDH1: an Apple Homeobox Gene Belonging to the BEL1 Family," *Plant Mol Biol* 42:623-633 (2000), which is hereby incorporated by reference in its entirety). Overall, these results support that BEL proteins function in controlling the formation of carpellate tissues and plant fertility. Overexpression of a cDNA of a barley BEL in tobacco produced plants that were dwarf and exhibited malformed leaves and reduced apical dominance (Müller et al., "In vitro Interactions Between Barley TALE Homeodomain Proteins Suggest a Role for Protein-protein Associations in the Regulation of Knox Gene Function," *Plant J* 27:13-23 (2001), which is hereby incorporated by reference in its entirety). This BEL1-like cDNA isolated from floral meristems produced a sense phenotype similar to a class I knox overexpresser (Chan et al., "Homeoboxes in Plant Development," *Biochim Biophys Acta* 1442:1-19 (1998), which is hereby incorporated by reference in its entirety). All seven of the BEL TFs in this study were isolated from stolons, a vegetative organ. Based on these results and the patterns of mRNA accumulation in potato, it appears that the BEL1 TFs of potato play a diverse role in plant growth by regulating the development of both reproductive and vegetative meristems.

Because the BEL TFs of potato and POTH1 interact, the function of one provides a clue to the function of the other. The KNOX protein of tobacco, NTH15, affects plant growth by regulating GA levels through a direct interaction with a specific motif in regulatory sequences of the GA 20-oxidase1 gene, a key GA biosynthetic enzyme (Sakamoto et al., KNOX Homeodomain Protein Directly Suppresses the Expression of a Gibberellin Biosynthesis Gene in the Tobacco Shoot Apical Meristem," *Genes Dev* 15:581-590 (2001), which is hereby incorporated by reference in its entirety). NTH15 directly suppresses the expression of GA 20-oxidase1 within specific cells of the SAM to maintain the indeterminate state of corpus cells. The knotted1-like protein of potato, POTH1, is also involved in the regulation of GA synthesis and acts as a developmental switch during tuber formation. Transgenic plants that overexpressed POTH1 had reduced levels of GA 20-oxidase1 mRNA, altered levels of GA intermediates, and exhibited a phenotype that could be partially rescued by $GA_3$ treatment (see above). These plants were dwarf and developed malformed leaves. Under both short-day (inductive conditions) and long-day (noninductive) photoperiods, POTH1 overexpressing lines produced more tubers than controls (see above). These sense lines exhibited a capacity for enhanced tuber formation. Lines that overexpressed StBEL-05 produced tubers even under LD in vitro conditions, whereas control plants produced tubers only after 10 days of SD conditions. Overall, the BEL sense lines produced more tubers at a faster rate than controls even on soil-grown plants. After 14 days of SD conditions, soil-grown StBEL-05 overexpressers exhibited a threefold increase in tuber production relative to wild-type plants (Table 2). Thus, both POTH1 and StBel-05 overexpression lines produced more tubers at a faster rate than controls (see FIGS. 17A-D). In FIG. 17D, stolon tips excised from in vitro plantlets overexpressing POTH1 that were not tuberizing were cultured. After a 20-day incubation in the dark on 8% (w/v) sucrose, stolons from all five POTH1 sense lines produced more tubers than wild-type stolons. Line 11 exhibited almost a 10-fold increase in tuber yield (262 mg stolon tip$^{-1}$) after 35 days in culture compared with wild-type plants (27 mg stolon tip$^{-1}$).

All of the above results show that that the expression of both POTH1 and its protein partner, STBEL-05, is associated with an enhanced rate of tuber formation. In addition to enhanced tuber production, select StBEL-05 lines exhibited increases in cytokinin levels and a reduction in GA 20-oxidase1 mRNA similar to POTH1 overexpression lines. This increase in cytokinin levels could explain the enhanced rate of growth for the StBEL-05 lines, although excessive accumulation may have led to the reduction in growth exhibited by mature plants of lines 11 and 20. GA is involved in regulating cell growth in a tuberizing stolon (Xu et al., "The Role of Gibberellin, Abscisic Acid, and Sucrose in the Regulation of Potato Tuber Formation in vitro," *Plant Physiol* 117:575-584 (1998), which is hereby incorporated by reference in its entirety) and in contributing to the control of the photoperiodic response of tuber formation (Jackson et al., "Control of Tuberisation in Potato by Gibberellins and Phytochrome," *B. Physiol Plant* 98:407-412 (1996), Martinez-Garcia et al., "The Interaction of Gibberellins and Photoperiod in the Control of Potato Tuberization," *J Plant Growth Regul* 20:377-386 (2001), which are hereby incorporated by reference in their entirety). Low levels of GA in the stolon tip are correlated with tuber induction (Xu et al., "The Role of Gibberellin, Abscisic Acid, and Sucrose in the Regulation of Potato Tuber Formation in vitro," *Plant Physiol* 117:575-584 (1998), which is hereby incorporated by reference in its entirety). Tuberization is also affected by cytokinin accumulation, with high levels inhibiting and moderate levels promoting tuber formation (Gális et al., "The Effect of an Elevated Cytokinin Level Using the ipt Gene and $N^6$-Benzyladenine on Single Node and Intact Potato Plant Tuberization in vitro," *J Plant Growth Regul* 14:143-150 (1995); Romanov et al., "Effect of Indole-3-Acetic Acid and Kinetin on Tuberisation Parameters of Different Cultivars and Transgenic Lines of Potato in vitro," *Plant Growth Reg* 32:245-251 (2000), which are hereby incorporated by reference in their entirety). Local accumulation of cytokinins in axillary buds of transgenic tobacco produced truncated, tuberizing lateral branches (Guivarc'h et al., "Local Expression of the ipt Gene in Transgenic Tobacco (*Nicotiana tabacum* L. cv. SR1) Axillary Buds Establishes a Role for Cytokinins in Tuberization and Sink Formation," *J Exp Bot* 53:621-629 (2002), which is hereby incorporated by reference in its entirety). Through an interaction with POTH1, the BEL protein encoded by StBEL-05 may also function to regulate hormone levels in stolons or leaves to favor the formation of tubers.

The results set forth above indicate that the physical interaction between the KNOX and BEL proteins provides a molecular basis for regulating processes of growth in the potato and that overexpression of each partner alone affects vegetative development and enhances tuber formation.

Example 33

Both POTH1 and StBEL-05 Interact to Repress Transcriptional Activity of the GA20 Oxidase1 Gene of Potato—Preliminary Results If POTH1 and StBEL physically interact and their overexpression produces transgenic plants that exhibit similar developmental pathways, it is reasonable to assume that they target the same gene. Using gel mobility shift assays (FIG. 18), it is shown that in tandem POTH1 and StBEL-05 bind to the P1 region of the GA20 oxidase1 promoter. In tandem, StBEL-05 and POTH1 had a greater binding affinity for the ga20ox1 promoter than either alone. The StBEL-05-POTH1 heterodimer bound specifically to a composite sequence T TGACTTGAC(SEQ ID NO:20) containing two adjacent TGAC cores in the P1 region. Using a transcription assay with GUS reporter driven by the ga20ox1 promoter in tobacco protoplasts, StBEL-05 and POTH1 alone suppressed the activity of the ga20ox1 promoter by more than 50%, together about 80%. The binding affinity of POTH1 and StBEL-05 represses the transcriptional activity of the promoter (FIG. 19).

Consistent with the in vitro results of StBEL/POTH1 repression of the GA20 oxidase1 promoter/GUS marker (FIG. 19), GA20 oxidase1 mRNA levels are also reduced in stolons of the StBEL-05 sense lines grown under long days (FIG. 20). This reduction in mRNA will lead to a reduction in bioactive GA and result in facilitating tuber formation. StBEL-05 mRNA levels were found to increase in both stolons and leaves of WT plants in response to the inductive conditions of short days. These results are consistent with the proposed role of GA in mediating photoperiodic responses in potato (Martinez-Garcia et al., "The Interaction of Gibberellins and Photoperiod in the Control of Potato Tuberization," *J. Plant Growth ReguL* 20:377-386 (2002), which is hereby incorporated by reference in its entirety).

These preliminary data show that POTH1 and StBEL-05 proteins interact in vitro and that overexpression of each separately, produces plants that are enhanced in their capacity to form tubers. Both proteins interact to repress the transcriptional activity of a key GA biosynthetic gene. Because expression of the BEL TFs appears to be differential, the BELs appear to act in tandem with POTH1 (or other KNOX proteins) to regulate growth differently in the various organs or cells of the potato. A more detailed description of the above experiments is provided in Examples 34-43, below.

Example 34

BEL and KNOX Interaction Mediates Transcriptional Activity of the Potato ga20ox1 Promoter—Plant Materials Tobacco 'Petit Havana' plants were maintained in Murashige and Skoog basal medium (1962) supplemented with 2% sucrose and incubated at 25° C., under 16 hour photoperiods for three to four weeks.

Example 35

BEL and KNOX Interaction Mediates Transcriptional Activity of the Potato ga20ox1 Promoter—Protein Expression and Purification in *E. coli*

Glutathione S-transferase (GST) fusion constructs were generated by introducing full-length cDNAs of StBEL-05 and POTH1 in frame with GST into the pGEX-5X-2 expression vector (Roche, Indianapolis, Ind.) and transformed into BL21 (DE3) *E. coli* cells (Stratagene, La Jolla, Calif.). Cells were grown at 30° C. until the $OD_{600}$ reached 0.6, induced with 1.0-mM isopropyl-β-D-thiogalactopyranoside, and cultured for 5 hours. The manufacturer's protocol (Roche) was followed for cell lysis and affinity purification by using glutathione sepharose 4B beads. The GST portion of the fusion protein was cleaved by Factor Xa protease (Promega, Madison, Wis.). Purified StBEL-05 and POTH1 protein were frozen in liquid $N_2$ and stored at −80° C.

Example 36

BEL and KNOX Interaction Mediates Transcriptional Activity of the Potato ga20ox1 Promoter—Gel Retardation Assay The first intron with partial flanking exon sequence (450 bp) of potato ga20ox1 and its promoter (981 bp, provided by Dr. Salomé Prat, CSIC Cantoblanco Campus, Univ. of Madrid, Spain) were used for gel mobility shift assays. Polymerase chain reaction (PCR) was used to amplify three regions of the promoter: −981 to 636 (P1), −660 to 307 (P2), and −331 to 0 (P3). About a 25-bp overlap was maintained between P1 and P2 or P2 and P3 in the chance that the protein-binding site would span the overlapped region. The first intron of this gene was amplified from potato genomic DNA by using PCR and the oligos 5'-GGATCCT-TGAAGTGGCTCTTCTCT-3' (SEQ ID NO:21) and 5'-AATCTAGAGACACTCTCTTTTTCGT-3' (SEQ ID NO:22) as primers. These primers were designed based on the site of the first intron of the tobacco GA20 oxidase gene Ntc12. The four fragments were purified on a 1.4% agarose gel and labeled with $\alpha^{32}$P-dATP using Klenow fragment. DNA-binding reactions were set up on ice in 20 μL containing 10-mM Tris-HCl (pH 7.5), 5% glycerol, 0.5-mM EDTA, 0.5-mM DTT, 0.05% NP-40, 50-mM NaCl, 50-mg·$L^{-1}$ poly (dG-dC)·poly (dG-dC) (Amersham Pharmacia Biotech, Piscataway, N.J.), 100-ng protein, and 1-fmol labeled DNA. After incubation on ice for 30 minutes, the reactions were resolved on a 6% native polyacrylamide gel in 1×TGE (Tris-Glycine-EDTA) buffer. The gel was dried and exposed to X-ray film.

In the competition assays, unlabeled double-stranded DNA fragments (10×, 25×, 50×, 100×) were incubated with the recombinant protein before the addition of the radioactive probe. The dissociation rates were determined by adding 500-fold more cold DNA fragments to the DNA-binding reactions that were being incubated on ice, and loaded onto the running gel every 10 minutes. Mutated oligos for binding sites were synthesized by the DNA Sequencing and Synthesis Facility, Iowa State University (Ames, Iowa).

Example 37

BEL and KNOX Interaction Mediates Transcriptional Activity of the Potato ga20ox1 Promoter—Transcription Assay Generation of Reporters and Effectors The cauliflowermosaic virus (CaMV) 35S promoter in pBI221 (Clontech, Palo Alto, Calif.) was replaced by an enhancer fragment (−832 to −50) of the 35S promoter plus 980 bp of the ga20ox1 promoter to generate the pGAOP::β-glucuronidase (GUS) reporter construct. With this construct, the reporter GUS transcription level is augmented but its transcription may still be affected by the ga20ox1 promoter. A CaMV 35S promoter-driven luciferase (LUC) construct 35S-LUC (obtained from Dr. Takahashi, Dept. of Biological Sciences, Graduate School of Science, Univ. of Tokyo, Japan) was used as an internal control. Effector constructs were also generated by using pBI221 vector as a backbone, with the GUS gene replaced by the full-length cDNAs of either StBEL-05 or POTH1, downstream of the CaMV 35S promoter. Truncated cDNAs that encode the N-terminal protein-binding domains of StBEL-05 or POTH1 were used to generate the dominant negative constructs, StBEL5ΔC295 and POTH1ΔC122, respectively. The reporter construct with the mutated promoter was generated by site-directed PCR mutagenesis with oligos 5'-CTATTTGACTTC*ACACGGTTATTT-3' (SEQ ID NO:23) and 5'-AAATAACCGTGTG*AAGTCAAATAG-3' (SEQ ID NO:24).

Transfection Assay

Fully expanded leaves from three- to four-week-old tobacco plants were excised and placed in $K_3$ basal media (Kao et al., "Nutritional Requirements for Growth of *Vicia hajastana* Cells and Protoplasts at a Very Low Density in Liquid Media," *Planta* 126:105-110 (1975), which is hereby incorporated by reference in its entirety) supplemented with 0.4 M sucrose, 0.25% (w-v) cellulases (Karlan Research Products, Santa *Rosa*, CA), and 0.05% (w-v) macerases (Calbiochem, La Jolla, Calif.) and incubated for overnight at 28° C. After incubation, the liberated protoplasts were filtered through sterile cheesecloth into a Babcock bottle, and centrifuged for 10 minutes at 1000 rpm. Protoplasts were collected from the bottleneck area and washed once in K3 media with 0.4 M sucrose and resuspended in K3 media containing 0.4 M glucose to a final concentration of $4 \times 10^6$ protoplasts per milliliter.

For each transfection analysis, 700 μL of tobacco protoplasts (prepared as described above) were mixed with 30 μL 2 M KCl and plasmid DNA in an electroporation cuvette with 0.4-cm electrode gap. The plasmid DNA was a mixture of 2 µg of the pGAOP::GUS reporter construct, 0.1 µg of the 35S-LUC construct as internal control, and a different combination of 2 µg of each effector plasmid. After electroporation (voltage=170 V, capacitance=125 µF, Gene Pulser Transfection Apparatus; Bio-Rad, Hercules, Calif.), 4.0 mL of Murashige and Skoog (1962) basal media was added, and the protoplasts were incubated in the dark at room temperature for 40 to 48 hours before conducting GUS and LUC activity assays. Transfections were performed three times for each effector combination.

Luciferase assays were performed by injecting 100-µL luciferase substrate (Promega, Madison, Wis.) into 20 µL of extract and measuring the emitted photons for 15 seconds in a TD-20 luminometer (Turner Designs, Sunnyvale, Calif.). Fluorometric GUS assays were performed as described (Jefferson, "Assaying Chimeric Genes in Plants: The GUS Gene Fusion System," *Plant Mol. Biol. Rep.* 5:387-405 (1987), which is hereby incorporated by reference in its entirety). A fluorescence multiwell plate reader, Fluoroskan II (MTX labs, Vienna, Va.), was used to measure GUS activity at 365 nm (excitation) and 455 nm (emission). Each sample was measured three times for both LUC and GUS activity. Relative GUS-LUC activity was calculated by dividing the ratio of GUS activity to LUC activity from different effectors with the ratio from reporter plasmid alone. Relative activities calculated from three transfection replications were presented as a mean±SE.

Example 38

Results: StBEL-05 and POTH1 Bind to the Regulatory Regions of ga20ox1

Recombinant StBEL-05 protein expressed from *E. coli* retarded the mobility of all three promoter sequences and the first intron (FIGS. 18A and B). POTH1 only formed a complex with P1. StBEL-05 and POTH1 together produced a supershifted band with P1, which had stronger signal intensity and migrated much slower than either the StBEL-05-P1 or POTH1-P1 complexes (FIG. 18A). Competition assays were performed with labeled P1 and unlabeled P1 or unlabeled P3. With increased unlabeled P1, the P1-StBEL-05 complex quickly disappeared (FIG. 21A). With unlabeled P3, however, even at a concentration 100-fold more than labeled P1, the shifted band was still present (FIG. 21A). Unlabeled P1 also reduced the P1-POTH1 complex formation, but unlabeled P3 had no effect on the P1-POTH1 complex (FIG. 21B).

Consistent with the increased signal intensity of the StBEL-05-POTH1-P1 complex, the dissociation rate of this complex was much slower than either the StBEL-05-P1 or POTHL-P1 complexes (FIG. 22). Although StBEL-05 could bind to P2, P3, and the intron fragments, there was no supershifted band formed when both StBEL-05 and POTH1 were incubated with these three DNA fragments (FIG. 18A). These results indicate that both StBEL-05 and POTH1 are required for binding to the P1 DNA fragment. Based on these results, at least two TALE homeodomain binding sites may be present in P1. To support this premise, excessive amounts of a truncated protein containing only the HD portion of StBEL-05 produced a supershifted band similar to the POTH1-StBEL-05-P1 complex. Apparently, there were two binding sites recognized by StBEL-05 in P1. No supershifted band was detected, however, when P1 was incubated with excessive amounts of full-length StBEL-05 or POTH1. This indicates that the two binding sites in P1 are in close proximity to one other and that two full-length StBEL-05 molecules cannot bind to both sites at the same time because of size constraints.

Example 39

Results: The StBEL-05-POTH1 Heterodimer Binds Specifically to the TGA(C/G)(T/A)TGAC Site Based on the *Arabidopsis* KNOX-BEL heterodimer binding site TGACAG(G/C)T (SEQ ID NO:25) (Smith et al., "Selective Interaction of Plant Homeodomain Proteins Mediates High DNA-Binding Affinity," *Proc. Natl. Acad. Sci.* 99:9579-9584 (2002), which is hereby incorporated by reference in its entirety) and the TGAC binding core confirmed for MEINOX proteins (Smith et al., "Selective Interaction of Plant Homeodomain Proteins Mediates High DNA-Binding Affinity," *Proc. Natl. Acad. Sci.* 99:9579-9584 (2002); Tejada et al., "Determinants of the DNA-Binding Specificity of the Avian Homeodomain Protein, AKR," *DNA and Cell Biol.* 18:791-804 (1999), which are hereby incorporated by reference in their entirety, one putative site, TTGACTTGAC (SEQ ID NO:20), in the potato ga2ox1 promoter P1 region was identified. Oligonucleotides with serial point mutations across this site were used as probes in gel-retardation assays in the presence of StBEL-05, POTH1, or both. Point mutations across this site did not affect the binding of either StBEL-05 or POTH1 alone, but most mutations in TGACTTGAC (SEQ ID NO:26) abolished the binding by StBEL-05-POTH1 heterodimer. Based on these results, it was deduced that the consensus sequence of the StBEL-05-POTH1 heterodimer is TGA(C/G)(T/A)TGAC (SEQ ID NO:27).

Example 40

Results: Repression of ga2ox1 Promoter Requires the Interaction of StBEL-05 and POTH1

POTH1 encodes for a 345-residue protein estimated to have a mass of 37.95 kDa. The coding sequence of the protein includes the 97-aa KNOX domain and the 64-aa homeodomain consisting of three helices (FIG. 23A). The KNOX domain of POTH1 contains two conserved regions, designated Knox I and II. StBEL-05 is 688 aa in length with an estimated mass of 75.68 kDa. The coding sequence of StBEL-05 contains the conserved sky box, BELL domain, homeodomain, and the proline-tyrosine-proline (P-Y-P) loop between helices I and II (FIG. 23B). The BELL domain is 120 aa in length and the HD of StBEL-05 is 61 aa.

When co-transfected with effector p35S::StBEL5, p35S::POTH1, or both (FIG. 24A), relative GUS-LUC activity of the pGAOP::GUS reporter construct decreased by more than half (FIG. 24B). Neither StBEL-05 nor POTH1 showed any effect on the activity of the CaMV 35S promoter (FIG. 24C). To eliminate the possibility that endogenous BEL1-like or KNOX proteins cooperatively interact with POTH1 or StBEL-05, respectively, truncated forms of StBEL-05 and POTH1, StBEL5ΔC295 and POTH1ΔC122 (FIG. 25A), were generated to use as dominant negatives in the transcription assays. StBEL5ΔC295 and POTH1ΔC122 contain the intact protein-binding domain, but lack the carboxy-terminal region including the homeodomain. StBEL5ΔC295 and POTH1ΔC122 can interact with endogenous KNOX or BEL1-like proteins, respectively. Such heterodimers are not functional due to the lack of the homeodomain from the truncated proteins. In transcription assays with pGAOP::GUS as reporter, StBEL5ΔC295 had little effect on the activity of the ga20ox1 promoter (FIG. 25B). When co-transfected with StBEL-05, StBEL5ΔC295 abolished almost all of the repression activity of StBEL-05 (FIG. 25B). POTH1ΔC122 had a similar effect on the repression activity of POTH1 (FIG. 25C).

Example 41

Results: The Binding Site in the ga20ox1 Promoter Acts as a Cis-Element for the Repression by StBEL-05-POTH1 Heterodimer To investigate whether the StBEL-05-POTH1 binding site identified through EMSA studies functions as a cis-element, a reporter construct with a point mutation in the binding site was used for the transcription assay (FIG. 26A). Constructs containing this single mutation exhibited no detectable repression of promoter activity when co-transfected with either StBEL-05, POTH1, or both (FIGS. 26B-C).

Example 42

Discussion: Cooperative Interaction Between StBEL-05 and POTH1 Mediates Binding Affinity for the ga20ox1 Promoter To regulate target gene expression, a transcription factor binds to the regulatory sequence of its target gene or interacts with another protein that does. Gel-retardation assays showed that both StBEL-05 and POTH1 bound to the promoter region of potato ga20ox1 gene, and StBEL-05 could also bind with the first intron sequence (FIGS. 18A-B). Unlabeled P3 competed with the StBEL-05-P1 complex, but not as effectively as unlabeled P1 (FIG. 21A), whereas P3 had no competition effect with the POTH1-P1 complex (FIG. 21B). These results indicated that the interaction between these two TALE HD proteins and P1 was specific and that StBEL-05 bound to P1 more strongly than to P3. It is highly likely then that P1 contains the cis element that functions with this protein complex in planta. The tobacco KNOX protein, NTH15, binds to both the promoter and the first intron of GA20 oxidase, but with higher affinity to the first intron (Sakamoto et al., "KNOX Homeodomain Protein Directly Suppresses the Expression of a Gibberellin Biosynthetic Gene in the Tobacco Shoot Apical Meristem," *Genes & Dev.* 15:581-590 (2001), which is hereby incorporated by reference in its entirety). NTH15 is not the tobacco homolog of POTH1 and this may explain the disparity in binding affinities. No BEL partners were tested for binding with the tobacco KNOX protein or the GA20 oxidase promoter.

Several consensus binding sites for KNOX proteins have been identified from either target gene promoters or in vitro binding site selection by using KNOX HD proteins from barley (Krusell et al., "DNA Binding Sites Recognized in Vitro by a Knotted Class 1 Homeodomain Protein Encoded by the Hooded Gene, K, in Barley (*Hordeum vulgare*)," *FEBS Lett.* 408:25-29 (1997), which is hereby incorporated by reference in its entirety, tobacco (Sakamoto et al., "KNOX Homeodomain Protein Directly Suppresses the Expression of a Gibberellin Biosynthetic Gene in the Tobacco Shoot Apical Meristem," *Genes & Dev.* 15:581-590 (2001), which is hereby incorporated by reference in its entirety), and rice (Nagasaki et al., "Functional Analysis of the Conserved Domains of a Rice KNOX Homeodomain Protein, OSH15," *Plant Cell* 13:2085-2098 (2001), which is hereby incorporated by reference in its entirety). Because the homeodomains, especially the third α-helix in the HD region, of these KNOX proteins are almost identical, the consensus sequences recognized by them share a core TGTCAC motif (Nagasaki et al., "Functional Analysis of the Conserved Domains of a Rice KNOX Homeodomain Protein, OSH15," *Plant Cell* 13:2085-2098 (2001), which is hereby incorporated by reference in its entirety). Two interacting TALE proteins of vertebrates, Meis1 and Pbx1, dimerize on the composite DNA sequence, TGATTGACAG (SEQ ID NO:28), containing 5'-Pbx and 3'-Meis half sites (Chang et al., "Meis Proteins are Major in Vivo DNA Binding Partners for Wild-Type But Not Chimeric Pbx Proteins," *Mol. Cell. Biol.* 7:5679-5687 (1997), which is hereby incorporated by reference in its entirety). Using random oligonucleotide selection, the consensus sequence, TGACAG(G/C)T (SEQ ID NO:25), was identified for the *Arabidopsis* BEL-KNOX heterodimeric complex (Smith et al., "Selective Interaction of Plant Homeodomain Proteins Mediates High DNA-Binding Affinity," *Proc. Natl. Acad. Sci.* 99:9579-9584 (2002), which is hereby incorporated by reference in its entirety). Because the StBEL-05-POTH1-P1 complex requires both proteins to bind the target DNA, and increased amounts of the StBEL-05 homeodomain lead to a supershifted band, this indicates that there are two closely located TALE homeodomain binding sites in the P1 region similar to the two half binding sites for Meis1 and Pbx1 (Chang et al., "Meis Proteins are Major in Vivo DNA Binding Partners for Wild-Type But Not Chimeric Pbx Proteins," *Mol. Cell. Biol.* 7:5679-5687 (1997), which is hereby incorporated by reference in its entirety). Based on these results and comparisons to the known binding motifs, a potential StBEL5-POTH1 binding site, TTGACTTGAC (SEQ ID NO:25), has been identified in the P1 fragment. Gel-retardation assays confirmed that this oligo was sufficient for binding to StBEL-05, POTH1, and StBEL5-POTH1. Mutational gel-retardation analysis of this BEL-KNOX binding site showed that the StBEL-05-POTH1 heterodimer recognizes the 9-bp sequence, TGA(C/G)(T/A)TGAC (SEQ ID NO:27), containing two TGAC cores. StBEL-05 and POTH1 could bind to either one of the TGAC cores, because serial mutations had no effect on the DNA-binding ability of StBEL-05 or POTH1.

It has been a paradox for HD proteins regarding their high level of functional specificity in directing developmental programs and their high degree of redundancy in binding site specificity. Besides the low affinity and high redundancy in binding sites, the 5-base consensus sequences recognized by HD proteins randomly show up on average once every 1.0 kb in eukaryotic genomes (Mann et al., "Extra Specificity From Extradenticle: The Partnership Between Hox and Exd-Pbx Homeodomain Proteins. *Trends Genet.* 12:258-262 (1996), which is hereby incorporated by reference in its entirety). Therefore, it is likely that interaction with other DNA-binding transcription factors is necessary for HDs to affect binding affinity and specificity. Monomeric HD proteins have modest specificity for DNA binding, but their specificity is greatly increased through cooperative binding with other DNA binding partners (Mann et al., "Extra Specificity From Extradenticle: The Partnership Between Hox and Exd-Pbx Homeodoamin Proteins. *Trends Genet.* 12:258-262 (1996), which is hereby incorporated by reference in its entirety). The gel-retardation assays also showed that StBEL-05 and POTH1 in tandem formed a complex with P1 with greater signal intensity than either POTH1-P1 or StBEL5-P1 complexes (FIG. 18A), and that the StBEL-05-POTH1-DNA complex had a much slower dissociation rate (FIG. 22). Both of these results indicate that the BEL-KNOX heterodimer has an increased binding affinity for the target site.

Example 43

Discussion: STBEL-05-POTH1 Heterodimer Mediates the Repression of the ga20ox1 Promoter The previous examples showed that both StBEL-05 and POTH1 overexpression mutants exhibited decreased ga20ox1 mRNA levels in stolons and leaves, respectively (see Examples 1-32). Gel-retardation assay results showed that these two transcription factors bound to the promoter and the first intron of ga20ox1. These results indicate that StBEL-05 and POTH1 directly represses ga20ox1 transcription by binding to the promoter region. Results from the transcription assay showed that either StBEL-05 or POTH1 alone could repress reporter gene activity by more than 50%. The fact that neither POTH1 nor StBEL-05 affected CaMV 35S promoter activity (FIG. 24C) confirmed that such repression was not due to inhibition of the general transcription machinery. Direct repression of GA20 oxidase gene transcription by the KNOX protein NTH15 has also been reported in tobacco (Sakamoto et al., "KNOX Homeodomain Protein Directly Suppresses the Expression of a Gibberellin Biosynthetic Gene in the Tobacco Shoot Apical Meristem," *Genes & Dev.* 15:581-590 (2001), which is hereby incorporated by reference in its entirety).

Although either StBEL-05 or POTH1 could repress ga20ox1 promoter in the transcription assay, the KNOX-BEL heterodimers were possibly still formed with endogenous partners to function in tobacco protoplasts. There are three lines of evidence to support this possibility. First, of the seven BEL proteins identified in potato, all seven interacted with four tobacco KNOX proteins (see above). Second, the protein binding domains of the tobacco KNOX NTHs were most important in determining the severity of transgenic plant phenotypes (Sakamoto et al., "The Conserved KNOX Domain Mediates Specificity of Tobacco KNOTTED-1 type Homeodomain Proteins," *Plant Cell* 11:1419-1431 (1999), which is hereby incorporated by reference in its entirety), implying that interaction with protein partners, most probably the BEL1-like proteins, is essential for KNOX function. Third, the identification of BEL-KNOX binding sites (Smith et al., "Selective Interaction Of Plant Homeodomain Proteins Mediates High DNA-Binding Affinity," *Proc. Natl. Acad. Sci.* 99:9579-9584 (2002), which is hereby incorporated by reference in its entirety) and the StBEL-05-POTH1 binding site in this study, further implies that the BEL-KNOX dimer is involved in the regulation of target genes. In the transcription assays, constructs of the dominant negatives, StBEL5ΔC295 or POTH1ΔC122, abolished the repression activity of StBEL-05 or POTH1, respectively (FIG. 25). Therefore, StBEL-05 or POTH1 protein alone is not sufficient for the repression of ga20ox1 promoter. The BEL-KNOX heterodimeric complex is required for repression of transcription to occur.

The results above showed that the mutated P1 binding site of the ga20ox1 promoter did not respond to StBEL-05-POTH1-mediated repression, indicating that this binding site functions as a cis-element for the StBEL-05-POTH1 heterodimer. Based on the results from gel-retardation analysis of serial mutations in this site, the mutated promoter was capable of binding with StBEL-05 or POTH1 separately, but not the StBEL-05-POTH1 heterodimer. This is further evidence that it is the BEL-KNOX heterodimer and not the individual BEL or KNOX proteins that affect repression. The interaction of StBEL-05/POTH1 to affect transcription is summarized in the model of FIG. 27. The partner proteins interact through conserved protein binding domains. For StBEL-05, this includes the two amino-terminal helices of the BELL domain and the sky box (Chen et al., "Interacting Transcription Factors From the TALE Superclass Regulate Tuber Formation," *Plant Physiol.* 132:1391-1404 (2003), which is hereby incorporated by reference in its entirety). For POTH1, this includes the KNOX domain with Knox II playing the most significant role (Sakamoto et al., "The Conserved KNOX Domain Mediates Specificity of Tobacco KNOTTED-1 type Homeodomain Proteins," *Plant Cell* 11:1419-1431 (1999), which is hereby incorporated by reference in its entirety). The sky box contributes to the tandem formation and interacts weakly with Knox I. Interaction between the respective protein binding domains and the spatial arrangement of the first two helices of the homeodomain bring the third helices of both TFs together in a major groove of the DNA helix. Specificity is then provided within the spatial constraints of the three components (StBEL-05, POTH1, and the helical groove) through recognition of the binding motif. In this case, the BEL/KNOX complex may repress transcription by interfering with the binding of critical components of the transcriptional machinery. Other BEL/KNOX complexes may affect gene expression differentially by recognizing other cis-elements as a result of slight modifications in protein structure.

The results indicate that similar to HDs in animals, collaboration of HD proteins to modulate the expression of target genes also occurs in plants. The interaction of HD proteins not only enhances their DNA-binding affinity, but also imparts another level of regulation to these complexes in fine-tuning developmental processes. It is very likely that the numerous potential BEL/KNOX protein interactions participate in a comprehensive system of regulation that coordinates plant growth.

Example 44

Investigations Involving the Use of the BEL Transcription Factor RNAs

One long-range goal is to understand the molecular mechanisms that control growth in potato. The central hypothesis of this study is that specific RNAs act as long-distance mobile signals that mediate growth responses regulated by photoperiod. This hypothesis is based on strong preliminary data that indicate that 1) KNOX/BEL partners regulate growth, 2) the KNOX/BEL heterodimer is required for mediating transcriptional activity, and 3) the RNAs of both partners move through the phloem in a basipetal (downward) direction. It is very likely that these two TFs are working together to coordinate development in potato. The mechanism of this signaling pathway can be studied using the present invention.

Specific Aims: First, determine if the full-length, translatable *RNAs of POTH1 and StBEL5 undergo long-distance transport in response to photoperiod. This question can be analyzed by quantifying RNA movement through micrografis unions using real-time RT-PCR. Movement of functional mRNA and its destination in the plant can be monitored by making GFP fusions to the above mRNAs. Second, determine the phenotype associated with the transport of POTH1 and StBEL5 RNAs. While overexpression of StBEL5 and POTH1 in transgenic lines produced a clear effect on development, it is not known if these transported RNAs are functional. The effect of mobile RNAs on organ formation can be readily assayed by using micrografts and an in vitro model system for tuber formation. Third, determine the source of transcription for POTH1 and StBEL5. To identify the cells in which these genes are transcribed, promoters can be isolated and used to drive expression of a marker gene in transgenic lines. Fourth, identify the RNA sequences of POTH1 and StBEL5 mRNAs that facilitate transport. Sequences or structures on these mRNAs that specify their movement will be determined by deletion analysis in constructs fused to reporter genes. RNA structural analysis will also be performed. Fifth, use POTH1 and StBEL5 RNAs as bait to identify RNA-binding proteins that facilitate long-distance movement. Both a 3-hybrid system in yeast and a biotinylated RNA pull-down approach can be used to select for proteins that bind to specific RNA sequences.

The present invention can be used to analyze the function and mechanism of RNA transport in plants making use of the BEL/KNOX interaction in potato as a model system. Preliminary experiments indicate that the KNOX and BEL proteins work in tandem to regulate transcription and that their mRNAs are mobile in the vascular system.

The present invention can further be used to determine if mobile RNAs act as long-distance signaling molecules that control flowering. The rationale for this objective is supported by the recent discovery that mobile RNAs act as signals to activate tuber formation in potatoes. The expected significance of this project will be inherent in the increased understanding of the mechanisms by which plants coordinate the response to environmental cues to control development. The present invention can thus be used to investigate the long-distance movement of specific mRNAs and to determine their function in the induction of flowering in response to photoperiod. Recent work with potato implicates mRNAs encoding proteins that regulate gene activity in this process. It has been hypothesized that the long-distance movement of specific RNAs acts as a signal that mediates flower induction regulated by photoperiod. This can be tested by working with the photoperiod-responsive plant, morning glory (*Pharbitis nil*), a close relative of potato. Genetic and RNA movement experiments can also be used for such testing. The present invention can thus be used to provide valuable new information on a novel mechanism for coordinating development in whole plants, and may assist in revealing entirely new mechanisms of information transfer that will affect the knowledge of plant development and facilitate crop enhancement.

Example 45

Long-Distance Transport of RNAs of BEL Transcription Factors

Various experiments can be conducted to identify proteins that may direct RNA transport by binding to the mobile RNAs of specific TALE transcription factors of potato. One such experimental procedure can involve determining whether the transcription factor signal can be transmitted across a graft union. In an eloquent grafting experiment (FIG. 28), a graft-transmissible substance was transported from the shoot tips of either long-day (LD) or short-day (SD) flowering tobacco plants to a potato stock grown under long days to induce tuber formation (Chailakyan et al., "Photoperiodism and Tuber Formation in Grafting of Tobacco onto Potato," *Dokl. Akad. Nauk. SSSR* 257:1276-1280 (1981), which is hereby incorporated by reference in its entirety). This graft-transmissible substance has not yet been identified. However, recent work reported in Kim et al., "Developmental Changes Due to Long-Distance Movement of a Homeobox Fusion Transcript in Tomato," *Science* 293:287-289 (2001), which is hereby incorporated by reference in its entirety, demonstrated that RNA from the KNOX family of transcription factors was transported through grafts of tomato plants to elicit a phenotype characteristic of the tomato KNOX overexpresser. Both the RNA and protein of KNOTTED1 (KN1 of maize) move from cell to cell via the PD (Lucas et al., "Selective Trafficking of KNOTTED1 Homeodomain Protein and its mRNA Through Plasmodesmata," *Science* 270:1980-1983 (1995), which is hereby incorporated by reference in its entirety) and cell-to-cell traffic has been reported for other transcription factors (Sessions et al., "Cell-Cell Signaling and Movement by the Floral Transcription Factors LEAFY and APETALA1," *Science* 289:779-782 (2000); Nakajima et al., "Intercellular Movement of the Putative Transcription Factor SHR in Root Patterning," *Nature* 413:307-311 (2001); Wu et al., "Modes of Intercellular Transcription Factor Movement in the *Arabidopsis* Apex," *Development* 130:3735-3745 (2003), which are hereby incorporated by reference in their entirety). Long-distance RNA transport is a well-documented but poorly understood biological phenomenon (Ruiz-Medrano et al., "Phloem Long-Distance Transport of CmNACP-mRNA: Implications for Supracellular Regulation in Plants," *Development* 126:4405-4419 (1999); Lucas et al., "Selective Trafficking of KNOTTED1 Homeodomain Protein and its mRNA Through Plasmodesmata," *Science* 270:1980-1983 (1995), which are hereby incorporated by reference in their entirety).

In considering the above tobacco/potato grafting experiment, it is important to determine what signals are graft-transmissible and identical in both potato and tobacco, and induce potato tuberization. One possible answer is the Knox and StBEL5 mRNAs. StBEL5 mRNA levels increase in stems, leaves and stolons in response to short-day conditions (Chen et al., "Interacting Transcription Factors from the TALE Superclass Regulate Tuber Formation," *Plant Physiol.* 132: 1391-1404 (2003), which is hereby incorporated by reference in its entirety). Based on preliminary experiments (FIGS. 29 and 30), Knox and BEL mRNAs of potato are transported across a graft union in a basipetal direction (towards the stolons, the site of tuber formation). Based on sequence and functional analyses, the BEL and KNOX proteins of potato and tobacco are almost identical. For example, all seven of the known BEL proteins of potato physically interacted with all five of the KNOX proteins of tobacco (Chen et al., "Interacting Transcription Factors from the TALE Superclass Regulate Tuber Formation," *Plant Physiol.* 132: 1391-1404 (2003), which is hereby incorporated by reference in its entirety). Overexpression of select Knox and BEL cDNAs enhances tuber formation (FIG. 31).

It has been determined that both POTH1 and StBEL5 have RNAs that move through a graft union. RNA for StBEL5 moves through the phloem stream towards the base of the plant and stolons (FIG. 29). Earlier work (Chen et al., "Interacting Transcription Factors from the TALE Superclass Regulate Tuber Formation," *Plant Physiol.* 132: 1391-1404 (2003), which is hereby incorporated by reference in its entirety) showed that overexpression of StBEL5 RNA produced plants that grew faster and displayed enhanced tuber formation. Here, it is shown that this mRNA is mobile and that potentially it could act as a signal to control growth in potato. Because both StBEL5 and POTH1 in tandem are necessary to affect transcription of the target gene, a key determination is whether RNA of the KNOX partner is also transported across a graft union. Data from FIG. 30 indicates that it is transported.

Preliminary experimental results have been helpful in analyzing this issue. For example, it has been found that using transgenic analysis, both of the potato TFs (the BEL and the KNOX types) affect plant growth by increasing growth and tuber production (Rosin et al., "Overexpression of a Knotted-Like Homeobox Gene of Potato Alters Vegetative Development by Decreasing GA Accumulation," *Plant Physiol.* 132: 106-117 (2003); Chen et al., "Interacting Transcription Factors from the TALE Superclass Regulate Tuber Formation," *Plant Physiol.* 132: 1391-1404 (2003), which are hereby incorporated by reference in their entirety). Overexpression of both TFs increases cytokinins and lowers GAs (Rosin et al., "Overexpression of a Knotted-Like Homeobox Gene of Potato Alters Vegetative Development by Decreasing GA Accumulation," *Plant Physiol.* 132:106-117 (2003a); Chen et al., "Interacting Transcription Factors from the TALE Superclass Regulate Tuber Formation," *Plant Physiol.* 132: 1391-1404 (2003), which are hereby incorporated by reference in their entirety) has been demonstrated. In an interaction with the target gene, it has been shown that each protein alone cannot repress transcription but must work in tandem (FIG. 32). The mRNA of both partners have been shown to be transported through a graft union in a basipetal direction (FIGS. 29-30). Under SD conditions, StBEL5 RNA accumulates in an increasing concentration gradient from the shoot tip through the stem to the stolon tip. Further, the StBEL5 RNA levels were shown to increase in the stem under a short-day photoperiod (Chen et al., "Interacting Transcription Factors from the TALE Superclass Regulate Tuber Formation," *Plant Physiol.* 132: 1391-1404 (2003), which is hereby incorporated by reference in its entirety). Based on these preliminary results, it is conceivable that the mRNAs of these transcription factors act as mobile signals that are delivered to target organs via the phloem stream. Members of the BEL and KNOX families described in this application can be used in comparative studies as a functional model to examine the mechanism of long-distance RNA transport. As described below in Examples 46-49, various experiments can be performed to analyze whether any movement of specific RNAs acts as a signal that mediates growth responses regulated by photoperiod.

Example 46

Determination of Whether the Full-Length, Translatable RNAs of POTH1 and StBEL5 Undergo Long-Distance Transport in Response to Photoperiod To determine if the full-length, translatable RNAs of POTH1 and StBEL5 undergo long-distance transport in response to photoperiod, key questions should be investigated. Such questions involve determining: (1) whether either (or both) of these full-length RNAs move through a graft union in response to a photoperiodic (SD) signal; (2) whether the RNAs of other potato BELs mobile; and (3) the direction in which these RNAs move. Below is a description of the experiments that can be performed to answer these questions.

Micrografting. For these experiments, in vitro micrografting techniques (Jinhua et al., "In Vitro Shoot Tip Grafting Improves Recovery of Cotton Plant from the Culture," *Plant Cell Tissue and Organ Culture* 57:211-213 (1999), which is hereby incorporated by reference in its entirety) can be used. Transgenic plants that constitutively overexpress full-length (including UTRs) POTH1 or one of the full-length StBELs can be used for scion and stock material and grafted with wild type (WT) stocks and scions, respectively. By alternating stock and scion material, the direction of RNA movement (FIG. 30) can be determined. In addition to StBEL5 and POTH1, full-length StBEL13 and -14 mRNA movement can be tested because of their prevalence in leaves and shoot tips. Transgenic transcripts will contain flanking non-plant sequence (nos terminator) that will be used via RT-PCR along with nested internal gene-specific primers (GSP) to identify the presence of specific transcripts (as in FIGS. 29-30). Control lines will have WT scion grafted onto WT stock material. A GFP sequence driven by the 35S promoter will be used as a negative mobility control. The transgenic GFP transcripts should not be detectable in control stocks or stolons. Grafted plants will be grown under long- and short-day conditions. Under SD conditions, a photoperiod response (stolon and tuber production) will occur within a few days.

RNA movement will be assayed in total RNA from WT stocks by using RT-PCR. To assay the effect of photoperiod on mobility, relative mRNA levels will be quantified by using the two-step real-time reverse transcription-PCR protocol (reverse transcription being a separate step from the PCR) described by B. C. Frank, Institute for Genomic Research (pga.tigr.org/sop/RT-PCR.pdf). SYBR Green I (Molecular Probes, Inc.) will be used as the detected fluorophore and 10 nM fluorescein to normalize the contents of each well. The TaqMan Reverse Transcription kit with random hexamers (Applied Biosystems) and the QuantiTect SYBR Green PCR kit (Qiagen) will be used. Standard curves will be generated from a dilution series generated from RT-PCR from RNA of one of the overexpression lines (POTH1 or StBEL5) and 18S rRNA as the endogenous control using the 18S rRNA assay kit (Applied Biosystems). Relative values for target abundance in each experimental sample will be extrapolated from the standard curve. Each assay will be performed in triplicate. Negative controls will be included for every real-time run. The Biorad icycler, which can be used for this experiment, has been routinely used with the TaqMan system for quantitation of very small amounts of viral RNA in single aphids. This approach will greatly expedite the analysis of RNA transport. RNA assays can be done with in vitro micro-grafted plants within a few days (FIGS. 29-30) compared to weeks for greenhouse grafted plants. The high humidity present under in vitro conditions ensures that virtually all grafted plants survive, in contrast to greenhouse or growth chamber conditions. RNA from three plantlets per treatment will be assayed.

Preliminary results with the RT-PCR detection produced partial cDNA fragments (FIGS. 29-30). The full-length StBEL5 and POTH1 transcripts are 2.3 and 1.2 kb long, respectively. As yet, it has not been determined whether full-length functional mRNAs are transported. To address this, two approaches can be taken: (1) Use gene-specific primers in the RT-PCR that will produce full-length cDNAs for each transcript type; and (2) Use GFP-StBEL5 (full-length) and —POTH1 (full-length) fusions (Von Arnim et al., "Cloning Vectors for the Expression of Green Fluorescent Protein Fusion Proteins in Transgenic Plants," *Gene* 221:35-43 (1998), which is hereby incorporated by reference in its entirety) expressed in the binary vector pCB201 containing the 35S promoter. These chimeric fusions will be in-frame and constitutively expressed in transgenic lines. These over-expressers will then be used as scions in heterografts to monitor RNA transport. Immunoblot analysis (using GFP antibody from BD Biosciences) of proteins from organs from wild-type stocks of these heterografts will then reveal the location of protein expression for both fusions. The size of the GFP-StBEL5 and the GFP—POTH1 fusions is approximately 100 and 66 kDa, respectively.

RNA movement in photoperiod mutants. To determine if the expression of potato genes involved in regulating photoperiod responses affects the movement of BEL and Knox mRNAs, micrografting experiments can be performed with mutant transgenic lines of phytochrome B (PHYB) and CONSTANS(CO). Modifying the levels of expression of these two genes disrupted wild-type photoperiodic responses (Martinez-Garcia et al., "Control of Photoperiod-Regulated Tuberization in Potato by the *Arabidopsis* Flowering-Time Gene CONSTANS," *Proc. Natl. Acad. Sci. USA* 199:15211-15216 (2002); Jackson et al., "Phytochrome B Mediates the Photoperiodic Control of Tuber Formation in Potato," *Plant J.* 9:159-166 (1996); Jackson et al., "Control of Tuberisation in Potato by GAs and Phytochrome B," *Physiol Plant.* 9:407-412 (1996), which are hereby incorporated by reference in their entirety). The mechanism for transmitting the photoperiod signal is constitutively activated in the PHYB mutants and blocked in the CO lines. To test for effects on mobility, scions from both StBEL5 and POTH1 full-length overexpression lines will be grafted onto to three stock lines: PHYB antisense, CO overexpression, and WT lines (similar to FIG. 33). StBEL5 and POTH1 RNA movement will be quantified by using real-time RT-PCR (described above) on RNA from stock material after 10d of LD conditions for the PHYB antisense line or under SD conditions for the CO overexpresser. Four micrografts per experiment will be performed and three will be tested for RNA mobility.

Example 47

Determination of the Phenotype Associated with the Transport of POTH1 and StBEL5 RNAs Previous heterografts were done with POTH1 and StBEL5 overexpression lines separately. Because these TFs work in tandem (FIG. 32), it would be more realistic to test dual movement in the same plant. To test this, control stock plants will be micrografted with scions of both POTH1 and StBEL5 (full-length) overexpression lines and assay for stolon and tuber formation in vitro. This is easily accomplished by using branched, in vitro stock plants. At least two shoots from each of the overexpression lines will be grafted onto WT stocks (FIG. 33). Plants will be evaluated under both long and short days in media supplemented with 6% sucrose. By monitoring plantlets daily, any changes in the rate of stolon or tuber growth can be easily ascertained within a few days (Rosin et al., "Overexpression of a Knotted-Like Homeobox Gene of Potato Alters Vegetative Development by Decreasing GA Accumulation," *Plant Physiol.* 132:106-117 (2003), which is hereby incorporated by reference in its entirety). RNA from heterografted plants will be sampled with RT-PCR to detect RNA movement. Observations will be made to determine if there is any correlation between RNA movement and tuber formation.

Example 48

Determination of the Source of Transcription for POTH1 and StBEL5

For these experiments, promoters will first be isolated from both POTH1 and StBEL5 using gene-specific primers and the Genome Walker kit (Invitrogen). Generous upstream sequence (at least, 3.0 kb in length) will be subcloned, sequenced, fused with an appropriate GUS marker, and inserted into a binary vector. Transgenic plants will be produced with this fusion vector and screened for GUS expression in various organs throughout the plant. The GUS construct will be designed with minimal POTH1 or StBEL5 sequence in the transcribed region (untranslated regions), so that the mRNA will not be transported through the plant. GUS expression will be confined to the cells in which it was transcribed. In situ hybridization revealed that POTH1 transcripts accumulate in apical meristems, leaf primordia, and vascular cambium (Rosin et al., "Overexpression of a Knotted-Like Homeobox Gene of Potato Alters Vegetative Development by Decreasing GA Accumulation," *Plant Physiol.* 132:106-117 (2003), which is hereby incorporated by reference in its entirety). Using blot hybridization, RNA was detected throughout the plant for both POTH1 and StBEL5 (Rosin et al., "Overexpression of a Knotted-Like Homeobox Gene of Potato Alters Vegetative Development by Decreasing GA Accumulation," *Plant Physiol.* 132:106-117 (2003); Chen et al., "Interacting Transcription Factors from the TALE Superclass Regulate Tuber Formation," *Plant Physiol.* 132: 1391-1404 (2003), which are hereby incorporated by reference in their entirety). Staining for GUS expression in sections from various organs will verify the location of POTH1 and StBEL5 transcription. StBEL5 RNA localization will be examined in meristems by using in situ hybridization as described in Rosin et al., "Overexpression of a Knotted-Like Homeobox Gene of Potato Alters Vegetative Development by Decreasing GA Accumulation," *Plant Physiol.* 132:106-117 (2003), which is hereby incorporated by reference in its entirety, and this profile will be compared to POTH1 accumulation. Promoter activity will be verified by careful analysis of these results, RNA hybridization, and GFP-RNA localization.

Example 49

Identification of the RNA Sequences of POTH1 and StBEL5 mRNAs that Facilitate Transport GFP fusions to monitor RNA movement. To examine the movement of RNAs for both POTH1 and StBEL5, select RNA fragments from these mRNAs will be fused to an mRNA encoding GFP in transgenic plants. The destination cells/organs of these mRNAs will be monitored by UV detection of GFP expression. A plant GFP expression vector has been constructed by the inserting the full-length S65T-GFP (Chiu et al., "Engineered GFP as a Vital Reporter in Plants," *Curr. Biol.* 6(3):325-30 (1996), which is hereby incorporated by reference in its entirety) cDNA into cloning sites of the vector carrying the CaMV 35S promoter, pCB201 (Xiang et al., "A Mini Binary Vector Series for Plant Transformation," *Plant Mol. Biol.* 40:711-717 (1999), which is hereby incorporated by reference in its entirety). This binary vector has worked very well in past experiments (Kolomiets et al., "Lipoxygenase is Involved in the Control of Potato Tuber Development," *Plant Cell* 13:613-626 (2001)); Rosin et al., "Overexpression of a Knotted-Like Homeobox Gene of Potato Alters Vegetative Development by Decreasing GA Accumulation," *Plant Physiol.* 132:106-117 (2003); Chen et al., "Interacting Transcription Factors from the TALE Superclass Regulate Tuber Formation," *Plant Physiol.* 132: 1391-1404 (2003), which are hereby incorporated by reference in their entirety). Initially, the GFP genes will be constructed with three regions from StBEL5 and POTH1 mRNAs: the full length 5' untranslated regions (UTRs), the 3' UTRs, and the coding sequences. All three of these regions will not be translatable as they will occur after the GFP stop codon and be a part of the 3' UTR of GFP. The UTRs are isolated because of their prevalence for containing zip codes. These chimeric genes will be cloned into the pCB201-S65T-GFP vector. GFP will be used with vector-derived UTRs as a negative control. The constructs will be introduced into plants using *Agrobacterium tumefaciens* LBA4404 with assistance as necessary from the Iowa State University Plant Transformation Facility.

Transgenic plants will be regenerated and screened according to conventional techniques developed in the Hannapel lab (Liu et al., "Isolation of a CONSTANS Ortholog from *Pharbitis nil* and its Role in Flowering," *Plant Physiol.* 125:1821-1830 (2001), which is hereby incorporated by reference in its entirety). High expressers will be selected and used as stocks or scions in micrografting experiments. These experiments will be repeated with large deletions in the StBEL5 and POTH1-derived sequences until sequence elements are identified that are capable of facilitating mRNA transport, and small enough (<500 nt) to serve as bait to identify RNA-binding proteins. Also, candidate transport sequences to delete will be identified by RNA sequence and structural comparisons (below).

Confocal microscopy. Tissue samples from transgenic heterografted plantlets (one graft part the GFP-RNA transgenic, the other WT) grown in vitro and collected at different stages of development will be mounted for observation in water under glass coverslips. WT tissue will be examined from heterografts to assay for the GFP tag as evidence of RNA mobility. Stolon, leaf, and shoot samples can be readily examined. The plantlets will be examined using a confocal laser-microscope (Zeiss LSM 5 Pascal). The Argon laser excitation wavelength will be 488 nm; GFP emission will be detected with the filter set for FITC (505-530 nm). If necessary, clearing techniques as described by (Wright et al., "Structural and Functional Vein Maturation in Developing Tobacco Leaves in Relation to AtSUC2 Promoter Activity," *Plant Physiol.* 131: 1555-1565 (2003), which is hereby incorporated by reference in its entirety) will be utilized for visualizing the GFP signal.

RNA structural analysis. Because there are so many distinct BEL and Knox genes present in potato (Chen et al., "Interacting Transcription Factors from the TALE Superclass Regulate Tuber Formation," *Plant Physiol.* 132: 1391-1404 (2003), which is hereby incorporated by reference in its entirety), a comparison of their RNA sequences provides a powerful tool to predict elements that facilitate transport, by identifying sequences or secondary structures that the transported mRNAs have in common. Because the RNA accumulation patterns of the various BELs are so diverse (Chen et al., "Interacting Transcription Factors from the TALE Superclass Regulate Tuber Formation," *Plant Physiol.* 132: 1391-1404 (2003), which is hereby incorporated by reference in its entirety), it is conceivable that transport determines their spatial expression differences (Kim et al., "Developmental Changes Due to Long-Distance Movement of a Homeobox Fusion Transcript in Tomato," *Science* 293:287-289 (2001), which is hereby incorporated by reference in its entirety). These patterns of accumulation will be considered when analyzing RNA structures.

To identify RNA secondary structures that may facilitate transport through the plant, a variety of RNA secondary structure prediction programs can be used, including MFOLD (Zuker, "Mfold Web Server for Nucleic Acid Folding and Hybridization Prediction," *Nucleic Acids Res.* 31: 1-10 (2003), which is hereby incorporated by reference in its entirety), STAR (finds pseudoknots) (Gultyaev et al., "The Computer Simulation of RNA Folding Pathways Using a Genetic Algorithm," *J. Mol. Biol.* 250: 37-51 (1995), which is hereby incorporated by reference in its entirety), the Vienna package, Alidot (Hofacker et al., "Automatic Detection of Conserved RNA Structure Elements in Complete RNA Virus Genomes," *Nucleic Acids Res.* 26(16):3825-36 (1998), which is hereby incorporated by reference in its entirety), and ESSA (Chetouani et al., "ESSA: An Integrated and Interactive Computer Tool for Analysing RNA Secondary Structure," *Nucleic Acids Res.* 25(17):3514-3522 (1997), which is hereby incorporated by reference in its entirety). Alidot combines sequence alignment (CLUSTALW) with folding prediction, to find the best structure shared among aligned, related sequences. These phylogenetically conserved structures are highly likely to exist and to be biologically relevant. Analyses for structural motifs present in BEL and Knox mRNAs will be performed by using Genetic Programming for RNA Motifs (bioinfo.cis.nctu.edu.tw/service/gprm/). This software (GPRM) is capable of discovering structural motifs more complicated than stem-loop structures and is designed for analysis of sets of functionally related sequences (Hu, "GPRM: A Genetic Programming Approach to Finding Common RNA Secondary Structure Elements," *Nucleic Acids Res.* 31:3446-3449 (2003), which is hereby incorporated by reference in its entirety). This information will be combined with results from the GFP fusions and the RNA/protein assays to map putative zip code elements present in select RNA sequences.

Folding programs are not perfect because many different structures can have very similar thermodynamic stability. Thus, key RNA structures will be probed directly. Rapid and well-established methods to be used include cleavage with imidazole (Guo et al., "Structure and Function of a Cap-Independent Translation Element that Functions in Either the 3' or the 5' Untranslated Region," *RNA* 6:1808-1820 (2000); Vlassov et al., "Cleavage of tRNA with Imidazole and Spermine Imidazole Constructs: A New Approach for Probing RNA Structure," *Nucleic Acids Res.* 23(16):3161-3167 (1995), which are hereby incorporated by reference in their entirety), and RNases T1, U2, V1 (Miller et al., "Alternative Tertiary Structure Attenuates Self-Cleavage of the Ribozyme in the Satellite RNA of Barley Yellow Dwarf Virus," *Nucleic Acids Res.* 19(19):5313-5320 (1991), which is hereby incorporated by reference in its entirety), and modification with kethoxal, DMS, and DEPC (Merryman et al., "Footprinting and Modification-Interference Analysis of Binding Sites on RNA," in Christopher et al., eds., *RNA: Protein Interactions: A Practical Approach*, pp. 237-253, Oxford: Oxford University Press (1998), which is hereby incorporated by reference in its entirety). The small size of the chemical agents avoids steric hindrance that may limit access of some nucleases to bases. For detection of modified bases, RT primer extension will be employed, as done previously (Guo et al., "Base-Pairing Between Untranslated Regions Facilitates Translation of Uncapped, Nonpolyadenylated Viral RNA," *Mol. Cell.* 7:1103-1109 (2001), which is hereby incorporated by reference in its entirety).

Example 50

Using POTH1 and StBEL5 RNAs as Bait to Identify RNA-Binding Proteins that Facilitate Long-Distance Movement Like RNA transport in animals, it has been hypothesized that the mobility of the RNAs for POTH1 and StBEL5 is regulated by chaperone/zip code proteins. Thus, it has been proposed that specific-proteins recognize different RNA motifs in BEL and Knox mRNAs that are targeted to different tissues. Two complementary approaches will be used to seek and identify these: yeast 3-hybrid and in vitro pull-down assays. The protein binding capacity of mRNAs for StBEL5, -13, and -14 and select Knox genes will be compared. These three BEL RNAs have been selected because of their diverse patterns of RNA accumulation (Chen et al., "Interacting Transcription Factors from the TALE Superclass Regulate Tuber Formation," *Plant Physiol.* 132: 1391-1404 (2003), which is hereby incorporated by reference in its entirety).

The 3-hybrid system. The yeast three-hybrid system (SenGupta et al., "A Three-Hybrid System to Detect RNA-Protein Interactions In Vivo," *Proc. Natl. Acad. Sci. USA* 93:8496-8501 (1996); Zhang et al., "A Conserved RNA-Binding Protein that Regulates Sexual Fates in the *C. elegans* Hermaphrodite Germ Line," *Nature* 390:477-484 (1997), which are hereby incorporated by reference in their entirety) will be the first choice for identifying putative RNA-binding proteins (RBPs) and characterizing their binding with relevant RNA fragments. This is an adaptation of the two-hybrid system but requires an RNA-protein interaction rather than a protein-protein interaction to activate gene expression (FIG. 34). This system has the advantages of (i) providing a clone of the RBP, (ii) providing in vivo binding conditions, (iii) being independent of the biological function of the RNA and RBP, and (iv) allowing rapid screening of large numbers of RNA-protein interactions. This method has been used to identify a large number of previously unknown specific RBPs in many organisms (SenGupta et al., "A Three-Hybrid System to Detect RNA-Protein Interactions In Vivo," *Proc. Natl. Acad. Sci. USA* 93:8496-8501 (1996); Zhang et al., "A Conserved RNA-Binding Protein that Regulates Sexual Fates in the *C. elegans* Hermaphrodite Germ Line," *Nature* 390:477-484 (1997), which are hereby incorporated by reference in their entirety).

As in the 2-hybrid system, the HIS3 reporter gene is activated when the appropriate interaction occurs, allowing growth of histidine auxotrophic yeast on His-minus media. In the 3-hybrid system, only those cells transformed with a gene encoding an RBP-GAL4 activation domain fusion (green and orange) that binds the bait RNA should grow on His-minus plates (Zhang et al., "A Conserved RNA-Binding Protein that Regulates Sexual Fates in the *C. elegans* Hermaphrodite Germ Line," *Nature* 390:477-484 (1997), which is hereby incorporated by reference in its entirety).

Two pAD cDNA libraries will be screened from potato directionally cloned into pAD-GAL4, one from SD leaves and one from tuberizing stolons. These high quality libraries have been previously used to isolate the BEL proteins of potato (Chen et al., "Interacting Transcription Factors from the TALE Superclass Regulate Tuber Formation," *Plant Physiol.* 132: 1391-1404 (2003), which is hereby incorporated by reference in its entirety). For the first experiment, bait RNAs identified as minimal transport (zip code-like) sequences, and negative control RNAs will be cloned into pIIIA/MS2-1. Protein/RNA interactions have been reported using bait RNAs in the range of 200 to 1600 nt in length (Rho et al., "The bI4 Group I Intron Binds Directly to Both its Protein Splicing Partners, a tRNA Synthetase and Maturase, to Facilitate RNA Splicing Activity," *RNA* 6:1882-1894 (2000); Bernstein et al., "Analyzing mRNA βprotein Complexes Using a Yeast Three-Hybrid System," *Methods* 26:123-141 (2002), which are hereby incorporated by reference in their entirety). The expression cDNA libraries will be transformed into the yeast 3-hybrid strain, L40-coat, that has already been transformed with the hybrid RNA plasmid pIIIA/MS2-1 containing the RNA fragments of either StBEL5 or POTH1. In this way, a variety of RBPs can be screened for in different organs. After confirming this system works, bait RNAs from StBEL13 and -14 and one other Knox gene, NTH15 of tobacco (provided by M. Matsuoka, University of Tsukuba, Japan), will be used. NTH15 is selected because of the plethora of information available on its function and biology (Sakamoto et al., "KNOX Homeodomain Protein Directly Suppresses the Expression of a Gibberellin Biosynthetic Gene in the Tobacco Shoot Apical Meristem," *Genes Devel.* 15:581-590 (2001); Nishimura et al., "Overexpression of Tobacco Knotted1-Type Class1 Homeobox Genes Alters Various Leaf Morphology," *Plant Cell Physiol.* 41:583-590 (2000); Sakamoto et al., "The Conserved KNOX Domain Mediates Specificity of Tobacco KNOTTED1-Type Homeodomain Proteins," *Plant Cell* 11:1419-1432 (1999); Tanaka-Ueguchi et al., "Over-Expression of a Tobacco Homeobox Gene, NTH15, Decreases the Expression of a Gibberellin Biosynthetic Gene Encoding GA 20-Oxidase," *Plant J.* 15:391-400 (1998), which are hereby incorporated by reference in their entirety). If positive interactions occur, mutant bait RNA sequences will be used that lost their ability to function, in order to seek a correlation between protein-RNA binding and zip code function. This is crucial to show that the RBP actually plays a role in RNA transport.

To minimize nonspecific activation of HIS3 expression, additional screening strategies will be taken advantage of by using 3-aminotriazole (3-AT) (Park et al., "Differential Sensitivity to 5-Fluoro-Orotic Acid as a Screen for Bait RNA-Independent False Positives in a Yeast Three-Hybrid System," *BioTechniques* 26:1102-1106 (1999); Zhang et al., "A Conserved RNA-Binding Protein that Regulates Sexual Fates in the *C. elegans* Hermaphrodite Germ Line," *Nature* 390: 477-484 (1997), which are hereby incorporated by reference in their entirety) and 5-fluoro-orotic acid (5-FOA) (Park et al., "Differential Sensitivity to 5-Fluoro-Orotic Acid as a Screen for Bait RNA-Independent False Positives in a Yeast Three-Hybrid System," *BioTechniques* 26:1102-1106 (1999), which is hereby incorporated by reference in its entirety) in the media as described in Bernstein et al., "Analyzing mRNA βprotein Complexes Using a Yeast Three-Hybrid System," *Methods* 26:123-141 (2002), which is hereby incorporated by reference in its entirety. Positive controls, pIIIA/IRE-MS2 and pAD-IRP, are to be used to optimize 3-AT concentrations to minimize false positives. Candidate RBPs will be verified by using lacZ rather than HIS as the induced gene. In this case, β-gal expression is proportional to the strength of the RBP-RNA binding that can be seen in the form of blue colonies on X-gal containing media. Thus, the binding affinities of various RBP/RNA complexes can be compared by quantifying β-gal activity to determine RBP profiles for each RNA molecule.

Occasionally, HIS3 expression can be activated in the absence of specific RNA binding (Park et al., "Differential Sensitivity to 5-Fluoro-Orotic Acid as a Screen for Bait RNA-Independent False Positives in a Yeast Three-Hybrid System," *BioTechniques* 26:1102-1106 (1999); Zhang et al., "A Conserved RNA-Binding Protein that Regulates Sexual Fates in the *C. elegans* Hermaphrodite Germ Line," *Nature* 390: 477-484 (1997), which are hereby incorporated by reference in their entirety). To weed out these transformants, 3-aminotriazole (3-AT) will be incorporated in the medium to increase selection for high HIS3 expressers (Zhang et al., "A Conserved RNA-Binding Protein that Regulates Sexual Fates in the *C. elegans* Hermaphrodite Germ Line," *Nature* 390:477-484 (1997), which is hereby incorporated by reference in its entirety). Even in the presence of 3-AT, some AD fusion proteins can nonspecifically induce HIS3 in the absence of the RNA plasmid, pIIIA/MS2-1. Thus, an improved counterselection will be used on media containing 5-fluoro-orotic acid (5-FOA) (Park et al., "Differential Sensitivity to 5-Fluoro-Orotic Acid as a Screen for Bait RNA-Independent False Positives in a Yeast Three-Hybrid System," *BioTechniques* 26:1102-1106 (1999), which is hereby incorporated by reference in its entirety) that kills cells that contain the URA3 gene (encoded by pIIIA/MS2-1). Any colonies that grow on -His, 3-AT-containing medium, but not on replica plates containing 5-FOA will be likely to encode an RBP that binds the RNA of interest. Positive controls, pIIIA/IRE-MS2 and pAD-IRP, are to be used to optimize 3-AT concentrations to minimize false positives. Candidate RBPs will be verified by using lacZ rather than HIS as the induced gene. In this case, β-gal expression is proportional to the strength of the RBP-RNA binding that can be seen in the form of blue colonies on X-gal containing media. Thus, the binding affinities of various RBP/RNA complexes can be compared by quantifying β-gal activity to determine RBP profiles for each RNA molecule.

The cDNAs for selected RBPs will then be sequenced and BLAST searched on Genbank. Mutations can also be introduced into the RBPs to map the relevant RNA-binding domains. All the necessary plasmids and yeast strains have been obtained.

Pull-downs with biotinylated RNA bait. In vitro pull-down of plant proteins will be used as a complementary approach to the three-hybrid approach. Crude protein extracts will be bound to biotinylated bait RNA that is linked to streptavidin magnetic beads. Proteins that remain bound after several low salt washes will be pulled down with a magnetic stand (Promega). Crude protein extracts will be obtained from stem, leaf, or stolon tissue. Bait RNAs, produced by in vitro transcription, will be modified at the 3' terminus by the addition of a biotin-amidocaproyl linkage and prepared by modification of the method of Von Ahsen et al. "Identification of Bases in 16S rRNA Essential for tRNA Binding at the 30S Ribosomal P Site," Science 267:234-237 (1995), which is hereby incorporated by reference in its entirety. Labeled RNA is purified on a BioRad P30 spin column to remove unincorporated biotin. Biotinylated RNAs will be bound to streptavidin magnetic beads, followed by incubation with select protein extracts. After washing to remove unbound proteins, bound protein fractions will be eluted under high salt conditions. This method has been used to identify proteins that specifically interact with a 105 nt viral sequence (TE) that mediates cap-independent translation. Many proteins bound the TE RNA but not the nonfunctional mutant RNA called TEBF (FIG. 35). This shows the advantage of the pull-down assay which reveals many proteins in an RNA binding complex even if they do not bind the RNA directly.

Pulled-down RBPs will be separated by PAGE (FIG. 35), electroblotted on to a PVDF membrane and partially microsequenced by the ISU Protein facility, as has been done previously (Suh et al., "Purification and Characterization of the 22-Kilodalton Potato Tuber Proteins," Plant Physiol. 94:40-45 (1990); Di et al., "Translational Frameshifting by Barley Yellow Dwarf Virus RNA (PAV Serotype) in Escherichia coli and in Eukaryotic Cell-Free Extracts," Mol. Plant. Microbe Interact. 6:444-452 (1993), which are hereby incorporated by reference in their entirety). This information will be used to generate primers for cloning and sequencing the RBP gene. If matches are found, clones will be requested from the TIGR Potato EST Bank or Arabidopsis Genome projects as we have done previously (Brown et al., "Three Eukaryotic Release Factor One (eRF1) Homologs from Arabidopsis thaliana Columbia (U40217, U40218, X69374, X69375)," Plant Physiol. (Plant Gene Register) 110:336 (1996), which is hereby incorporated by reference in its entirety). Approximately fifty ESTs for putative RBPs have been identified from the Potato TIGR Genome database.

Example 51

Determination of Whether Mobile RNAs Act as the Signal that Mediates Flower Induction The morning glory (Pharbitis nil) plant can be used to study whether mobile RNAs act as the signal that mediates flower induction. The SDP Pharbitis nil (P. nil) represents an excellent model for the study of photoperiodic control of floral initiation. Flower formation can be induced at a very early stage for P. nil (Imamura, "Photoperiodic Induction and the Floral Stimulus. In S Imamura, ed., Physiology of Flowering in Pharbitis nil Japanese Society of Plant Physiol., Tokyo, pp 15-28 (1967), which is hereby incorporated by reference in its entirety). This SDP can be induced to flower by a single dark period of at least 14 h just after the cotyledons have fully expanded. During the inductive dark period, a floral stimulus is produced in the cotyledons, which is subsequently exported to the apical meristem (Zeevaart, "Physiology of Flowering," Science 137:723-731 (1962), which is hereby incorporated by reference in its entirety). These physiological characteristics make P. nil an attractive model plant for research on flowering (Vince-Prue et al., "Pharbitis nil.," in AH Halevy, ed., Handbook of Flowering, Vol IV., Boca Raton, Fla.: CRC Press, pp. 47-81 (1985), which is hereby incorporated by reference in its entirety).

Strong preliminary evidence implicats select mobile RNAs in activating tuber formation in potato. Unlike P. nil, flowering in potato is not photoperiodic. Tuberization, however, is induced by SDs. P. nil is a member of the Convolvulaceae family, a very close taxonomic relative of potato. Upon sequence analyses of the potato genes involved in this system, the best matches are commonly from P. nil (e.g., Knox, Constans). Using the yeast 2-hybrid system to test protein interaction, all of the P. nil KNOX proteins interacted with the potato BEL proteins. To date, the BEL genes of P. nil have not been identified. In light of these similarities, it has been proposed that the signaling information gleaned from our tuberization model may be applied to flowering in P. nil.

One hypothesis is that the long-distance movement of specific RNAs acts as a signal that mediates flower induction regulated by photoperiod. Recent studies on signaling mechanisms in potato indicate that mobile RNAs may be involved in activating growth responses mediated by photoperiod. It is conceivable that this same mechanism is functional in floral induction. Specific questions that can be addressed using the present invention include: Are mobile RNAs the flowering signal? Does photoperiod control this movement? Is flowering in pepper and P. nil affected by overexpression of select BELs? What RNAs are present in phloem cells of SD-grown plants? Answers to these questions have the potential to elucidate one of the outstanding problems in plant biology, floral induction.

Objectives and Research Design: The first objective is to determine the effect of BEL expression and movement on flowering. Two approaches will be taken to address this question: (i) a genetic analysis by transforming P. nil and pepper plants with select BEL cDNAs of potato and (ii) grafting experiments with P. nil lines that overexpress each of three BEL genes to determine if RNA moves and what effect it has on flowering. The second objective is to monitor RNA accumulation patterns in P. nil in response to short- and long-day conditions. Patterns of RNA accumulation will be examined for Knox and BEL genes in various organs of P. nil in response to photoperiod by using conventional techniques of blot hybridization. The third objective is to analyze the 3'-untranslated RNA sequence of the BEL genes of P. nil. Making use of software for the analysis of RNA stem-loop structure, the 3'-UTRs will be examined for conserved RNA sequence that may facilitate RNA movement. The fourth objection is to identify phloem-specific RNAs. Laser capture microdissection will be used to identify and profile RNAs present in phloem cells from short-day grown plants of P. nil.

Example 52

Determination of the Effect of BEL Expression and Movement on Flowering

Genetic approach—Transformation. To address the function of these transcription factors in flowering, transgenic analysis will be used in both P. nil and pepper. Both are close relatives of potato. P. nil is induced by SDs and pepper is not. Flower production is important for fruit yield in pepper. Because of their patterns of RNA accumulation, P. nil will be transformed with BEL5, -13, and -14 of potato. The Knox gene of potato will not be used because of its adverse effects on phenotype (Rosin et al., "Overexpression of a Knotted-Like Homeobox Gene of Potato Alters Vegetative Development by Decreasing GA Accumulation," Plant Physiol. 132: 106-117 (2003), which is hereby incorporated by reference in its entirety). For the production of transgenic lines, full-length, sense fragments will be cloned into the binary vector pCB201 driven by the CaMV-35S promoter (Xiang et al., "A Mini Binary Vector Series for Plant Transformation," Plant Mol. Biol. 40:711-717 (1999), which is hereby incorporated by reference in its entirety). This vector has been used successfully with sense constructs (Kolomiets et al., "A Leaf Lipoxygenase of Potato Induced Specifically by Pathogen Infection," Plant Physiol. 124:1121-1130 (2000); Rosin et al., "Overexpression of a Knotted-Like Homeobox Gene of Potato Alters Vegetative Development by Decreasing GA Accumulation," Plant Physiol. 132:106-117 (2003), which are hereby incorporated by reference in their entirety). Positive recombinants will be transferred to the Agrobacterium tumefaciens strain GV2260 by using the procedure of direct transformation (An et al., "Binary Vectors," in Plant Mol. Biol. Manual, pp. A3:1-19, Belgium: Kluwer Academic (1988), which is hereby incorporated by reference in its entirety). Transformation for P. nil (Choisy cv. Violet) will be implemented by the methods described by Ono et al., "Agrobacterium-Mediated Transformation and Plant Regeneration of Pharbitis nil," Plant Biotech. 17:211-216 (2000), which is hereby incorporated by reference in its entirety, by using immature embryos incubated with GV2260 that contain one of the constructs. Transformed plants will be regenerated from secondary embryos. Pepper plants (Capsicum annuum L.) will be transformed and regenerated by using pepper cotyledons as explants (Li et al., "Establishment of a Highly Efficient Transformation System for Pepper (Capsicum annuum L.)," Plant Cell Rep. 21:785-788 (2003), which is hereby incorporated by reference in its entirety). Control plants will be transformed with an empty pCB201 vector. About 30 to 40 transgenic control plants are routinely regenerated to evaluate the stability of the regeneration procedure. From this experiment, identification of transgenic plants that overexpress the potato BEL TFs and determination of the effect on flowering numbers and timing can be made. Potato plants that overexpress one of the potato BEL genes exhibited increased overall vigor and enhanced flower production (Chen et al., "Interacting Transcription Factors from the TALE Superclass Regulate Tuber Formation," Plant Physiol. 132: 1391-1404 (2003), which is hereby incorporated by reference in its entirety).

Genetic approach—Transgenic plant analysis. Plants will be selected on the basis of kanamycin resistance and high expression of the transgenic mRNA. Transgenic plants will be analyzed for changes in sense RNA accumulation (using RNA blot hybridization), response to photoperiod, leaf morphology, internode length, and flower and fruit development.

Grafting experiments. Characterize the long-distance transport of the StBEL mRNAs in P. nil in response to photoperiod. Verify the direction of movement. Preliminary data indicates movement of BEL RNAs through a graft union in potato. To test for movement in P. nil and identify factors that influence it, grafting techniques (Jinhua et al., "In Vitro Shoot Tip Grafting Improves Recovery of Cotton Plant from the Culture," Plant Cell Tissue and Organ Culture 57:211-213 (1999), which is hereby incorporated by reference in its entirety) will be used. Transgenic P. nil plants that constitutively overexpress full-length (including UTRs) BEL5, -13, or -14 (from potato) will be used for scion and stock material and grafted with wild type (WT) stocks and scions, respectively. By alternating stock and scion material, the direction of RNA movement can be determined. BEL13 and -14 mRNA movement will be tested because of their prevalence in flowers and shoot tips (Table 6).

TABLE 6

3'-UTR of Potato BEL Genes

| Potato BEL gene | Length of 3'-UTR (nt) | Site of RNA accumulation |
| --- | --- | --- |
| BEL5* | 505 | ubiquitous |
| BEL29* | 406 | ubiquitous |
| BEL11* | 286 | ubiquitous |
| BEL13 | 112 | shoot tip, flower |
| BEL14 | 90 | flower, leaf |
| BEL22 | 76 | flower, leaf |
| BEL30 | 60 | ubiquitous |

*RNA accumulation induced by SD conditions (Chen et al., "Interacting Transcription Factors from the TALE Superclass Regulate Tuber Formation," Plant Physiol. 132: 1391-1404 (2003), which is hereby incorporated by reference in its entirety).

Transgenic transcripts will contain flanking non-plant sequence (nos terminator) that will be used via RT-PCR along with nested internal gene-specific primers to identify the presence of specific transcripts. Control lines will have WT scion grafted onto WT stock material. GFP sequence, driven by the 35S promoter as a negative mobility control, will be used. Grafted plants will be grown under long- and short-day conditions. Under SD conditions (long nights) with WT plants of P. nil, flowering is induced within a few days.

To assay the effect of photoperiod on mobility, relative mRNA levels will be quantified by using the two-step real-time reverse transcription-PCR protocol described by the Institute for Genomic Research (pga.tigr.org/sop/RT-PCR.pdf). SYBR Green I will be used as the detected fluorophore and 10 nM fluorescein to normalize the contents of each well. The TaqMan Reverse Transcription kit with random hexamers and the QuantiTect SYBR Green PCR kit will be used. Standard curves will be generated from a dilution series generated from RT-PCR from RNA of one of the overexpression lines (BEL5, 13, or 14) and 18S rRNA as the endogenous control. Relative values for target abundance in each sample will be extrapolated from the standard curve. Each assay will be performed in triplicate. Negative controls will be included for every real-time run. The Biorad iCycler can be used for these experiments. The TaqMan system with the Biorad iCycler has been routinely used for quantitation of very small amounts of RNA. RNA from three plants per treatment will be assayed. This approach will greatly expedite the analysis of RNA transport. Grafts have been shown to bee essentially 100% successful.

Example 53

Monitoring RNA Accumulation Patterns in *P. nil*

To study the patterns of RNA accumulation among BEL and Knox genes of *P. nil*, routine RNA blot hybridizations (Kolomiets et al., "Lipoxygenase is Involved in the Control of Potato Tuber Development," *Plant Cell* 13:613-626 (2001), which is hereby incorporated by reference in its entirety) will be performed. Patterns of accumulation in various organs under both SD and LD conditions will be studied. With these experiments, it can be determined whether accumulation of any BEL or Knox RNAs in *P. nil* is correlated with photoperiod similar to potato (Chen et al., "Interacting Transcription Factors from the TALE Superclass Regulate Tuber Formation," *Plant Physiol.* 132: 1391-1404 (2003), which is hereby incorporated by reference in its entirety). BEL cDNAs will be obtained from a λZAP library made from RNA extracted from SD leaves of *P. nil* (graciously provided by J. Zeevaart, Mich St. Univ.). Sequence from the conserved homeodomain to the poly(A)+ tail will be isolated by using PCR off plasmid DNA from the library with homeodomain primers and primers off the pBluescript vector (T3, T7, SK, KS). These PCR products will contain gene-specific sequence that may be used as probe for hybridizations and the full-length 3'-untranslated region (3'-UTR) of the RNAs may be used for various other analyses discussed herein. The length and sequence of the BEL cDNAs will make them easy to identify from among other related genes. Alternatively, cDNAs for *P. nil* BELs will be isolated by screening the library with BEL-specific probes (using conserved BEL-specific sequence).

Considerable diversity exists in the 3'-UTR of BEL RNAs from potato (Table 6). There is a positive correlation in the length of the 3'-UTR and induction by a SD photoperiod.

Example 54

Analysis of the 3-Prime Untranslated RNA Sequence of the BEL Genes of *P. nil*

Making use of software for the analysis of RNA stem-loop structure, the 3'-UTRs will be examined for conserved RNA sequences that may facilitate RNA movement for BELs of *P. nil*. In animals, the UTRs of the transcript commonly contain structures that bind to proteins that mediate movement (Kloc et al, "Mechanisms of Subcellular mRNA Localization," *Cell* 108:533-544 (2002), which is hereby incorporated by reference in its entirety). In a preliminary analysis using MFOLD, conserved stem-loop structures present in BEL5 mRNA molecules have been identified that are not present in other BEL mRNAs of potato. BEL5 mRNA has the largest 3'-UTR of any of the potato BELs (Table 6). To determine if such conserved stem-loop structures are present in BEL RNAs of *P. nil*, RNA secondary structure prediction programs will be used, like MFOLD (Zuker, "Mfold Web Server for Nucleic Acid Folding and Hybridization Prediction," *Nucleic Acids Res.* 31:1-10 (2003), which is hereby incorporated by reference in its entirety), STAR (finds pseudoknots) (Gultyaev et al., "The Computer Simulation of RNA Folding Pathways Using a Genetic Algorithm," *J. Mol. Biol.* 250: 37-51 (1995), which is hereby incorporated by reference in its entirety), and Alidot (Hofacker et al., "Automatic Detection of Conserved RNA Structure Elements in Complete RNA Virus Genomes," *Nucleic Acids Res.* 26(16):3825-36 (1998), which is hereby incorporated by reference in its entirety). Structural motifs present in the BEL mRNAs of *P. nil* will also be analyzed by using his Genetic Programming for RNA Motifs (bioinfo.cis.nctu.edu.tw/service/gprm). This software is capable of discovering structural motifs more complicated than stem-loop structures and is designed for analysis of functionally related sequences (Hu, "GPRM: A Genetic Programming Approach to Finding Common RNA Secondary Structure Elements," *Nucleic Acids Res.* 31:3446-3449 (2003), which is hereby incorporated by reference in its entirety).

Example 55

Identification of Phloem-Specific mRNAs

Laser capture microdissection (LCM) is a powerful tool that allows the isolation of selectively targeted cells from a tissue section for the analysis of gene expression profiles of individual cells (Kerk et al., "Laser Capture Microdissection of Cells from Plant Tissues," *Plant Physiol.* 132:27-35 (2003), which is hereby incorporated by reference in its entirety). This technique has been successfully used for the isolation of specific phloem cells in rice (Asano et al., "Construction of a Specialized cDNA Library from Plant Cells Isolated by Laser Capture Microdissection Toward Comprehensive Analysis of the Genes Expressed in the Rice Phloem," *Plant Journal* 32: 401-408 (2002), which is hereby incorporated by reference in its entirety), and would be a valuable analytical tool for studying photoperiod-induced phloem RNAs. Efforts will be devoted to optimizing the protocol for stems of *P. nil*.

Embedding of stem samples from plants grown under short days will be performed as described previously (Kerk et al., "Laser Capture Microdissection of Cells from Plant Tissues," *Plant Physiol.* 132:27-35 (2003), which is hereby incorporated by reference in its entirety). Sufficient phloem cells from mounted, paraffin sections will be captured by catapulting into lysis buffer. Sectioning will be optimized by using the Arcturus PixCell system (available at the Image Analysis Facility, Iowa State University). Microdissection will be performed using the Zeiss PALM system located in the Plant Sciences Institute Building (Nakazono et al., "Laser-Capture Microdissection, a Tool for the Global Analysis of Gene Expression in Specific Plant Cell Types: Identification of Genes Expressed Differentially in Epidermal Cells or Vascular Tissues of Maize," *Plant Cell* 15:583-596 (2003), which is hereby incorporated by reference in its entirety). Total RNA (30-40 ng) will be extracted from the microdissected phloem cells and the RNA will be used for the construction of a cDNA library following amplification with T7 RNA polymerase, the addition of adaptors, and two rounds of PCR amplification. RNA/cDNA quality will be monitored throughout the process. Sequence analysis of randomly chosen clones from the library will be performed to obtain a profile of expressed RNAs. In rice phloem cells, 124 different groups of related genes were identified (Asano et al., "Construction of a Specialized cDNA Library from Plant Cells Isolated by Laser Capture Microdissection: Toward Comprehensive Analysis of the Genes Expressed in the Rice Phloem," *Plant Journal* 32: 401-408 (2002), which is hereby incorporated by reference in its entirety). One RNA type found in rice, NAC1, was verified to move long distances through phloem in *Cucurbita* species (Ruiz-Medrano et al., "Phloem Long-Distance Transport of CmNACPmRNA: Implications for Supracellular Regulation in Plants," *Development* 126:4405-4419 (1999), which is hereby incorporated by reference in its entirety). No mitochondrial, chloroplast or rRNA sequence were found in the rice phloem library. In situ hybridization will be performed to determine the precise location of key RNAs. In situ RNA hybridizations (Rosin et al., "Overexpression of a Knotted-Like Homeobox Gene of Potato Alters Vegetative Development by Decreasing GA Accumulation," *Plant Physiol.* 132:106-117 (2003), which are hereby incorporated by reference in their entirety) have been routinely performed.

Long-distance transport of RNA occurs in phloem cells (Lucas et al., "Selective Trafficking of KNOTTED1 Homeodomain Protein and its mRNA Through Plasmodesmata," *Science* 270:1980-1983 (1995), which is hereby incorporated by reference in its entirety). This experimental approach will allow for identification of phloem-specific RNAs induced by SDs. Accumulation of select RNAs will be compared in stems from both SD and LD plants. Experiments are ongoing to analyze phloem RNAs in potato stems from SD plants as well, and the two profiles (SD potato and SD *P. nil*) may be compared. Identification of common RNAs in both phloem samples would be an indication that they play a role in mediating the signaling process.

Example 56

Determining Whether Mobile RNA Mediates the Control of Plant Growth in Response to a Light Signal Experiments will be performed to address the question of what RNAs are transported through potato plants in response to SD conditions. One hypothesis is that mobile RNA mediates the control of plant growth in response to a light signal. Various questions can be investigated using the methods outlined below.

Determining the presence of POTH1 and StBEL5 mRNAs in phloem sap. From previous work, it is known that RNAs for both POTH1 and StBEL5 are present in stem RNA, but it is not clear if they are present specifically in the phloem sap, which is the most likely medium for transport (Kim et al., "Developmental Changes Due to Long-Distance Movement of a Homeobox Fusion Transcript in Tomato," *Science* 293: 287-289 (2001), which is hereby incorporated by reference in its entirety). Phloem sap will be collected by using the reliable EDTA exudation technique (King et al., "Enhancement of Phloem Exudation from Cut Petioles by Chelating Agents," *Plant Physiol.* 53:96-103 (1974), which is hereby incorporated by reference in its entirety). RT-PCR will be used with gene-specific primers for RNA analysis in sap. Examinations will also be made of RNA in stem sections and the concentration gradient in the stem. If RNA is being transported, a greater proportion may be detectable in lower stems or stolon sections over time as it moves toward stolon tips. Stems will be examined from whole plants of a photoperiod-responsive cultivar grown under both long-day (noninductive) and short-day (inductive) conditions. Proximal, middle, and distal stem sections and stolon sections will be harvested at 3, 6, and 12 days. Total RNA will be extracted and northern blot hybridization performed using POTH1 and StBEL5 probes. This experiment will reveal spatial or temporal concentration gradients, if they exist, in the stem and stolon.

Determining whether these RNAs move through a graft union in response to a photoperiodic (SD) signal. For these experiments, in vitro micrografting techniques will be used (Jinhua et al., "In vitro Shoot Tip Grafting Improves Recovery of Cotton Plant from the Culture," *Plant Cell Tissue and Organ Culture* 57:211-213 (1999), which is hereby incorporated by reference in its entirety). Micrografted plantlets have been successfully grown in vitro. Transgenic plants that constitutively overexpress POTH1 or StBEL5 will be used for scion material and grafted onto wild type (WT) stocks. Both transgenic transcripts will contain flanking nonplant sequence that will be used via RT-PCR along with internal gene-specific primers to identify the presence of specific transcripts. RNA sequence of a cDNA template from both the 5- and 3-prime ends will be assayed. This technique is being tested for StBEL5 lines. Control lines will have WT scion grafted onto WT stock material. Grafted plants will be grown under long- and short-day conditions. Under SD conditions, a photoperiod response (stolon and tuber production) will occur within a few days. RNA movement will be assayed in total RNA from WT stocks by using RT-PCR. Eventually, the system may be optimized to quantify the RNA levels. The transgenic transcripts will not be detectable in control stocks or stolons. This system will greatly expedite the analysis of RNA transport. RNA assays can be done with in vitro micrografted plants within a few days compared to weeks for greenhouse grafted plants. The high humidity present under in vitro conditions insures that virtually all grafted plants survive, in contrast to greenhouse or growth chamber conditions.

Determining whether this RNA movement associated with a morphological response. The micrografted plants discussed in the previous section will be assayed for stolon and tuber formation in vitro. Plants will be evaluated under both long and short days in media supplemented with 6% sucrose. By monitoring plantlets daily, any changes in the rate of stolon or tuber growth can be easily ascertained within a few days (Rosin et al., "Suppression of a Vegetative MADS Box Gene of Potato Activates Axillary Meristem Development," *Plant Physiol.* 131 (2003), which is hereby incorporated by reference in its entirety). Observations will be made as to whether there is any correlation between RNA movement and tuber formation.

Determining the location of POTH1 and StBEL5 transcription. For these experiments, promoters from both POTH1 and StBEL5 will first be isolated using gene-specific primers and the Genome Walker kit (Invitrogen). Adequate upstream sequence (at least, 3.0 kb in length) will be sequenced and cloned as a fusion with an appropriate GUS marker and cloned into a binary vector. Transgenic plants will be produced with this fusion vector and screened for GUS expression in various organs throughout the plant. In situ hybridization revealed that POTH1 transcripts accumulate in apical meristems, leaf primordia, and vascular cambium (Rosin et al., "Suppression of a Vegetative MADS Box Gene of Potato Activates Axillary Meristem Development," *Plant Physiol.* 131 (2003), which is hereby incorporated by reference in its entirety). Using blot hybridization, RNA was detected throughout the plant for both POTH1 and StBEL5 (Rosin et al., "Suppression of a Vegetative MADS Box Gene of Potato Activates Axillary Meristem Development," *Plant Physiol.* 131 (2003); Chen et al., "Interacting Transcription Factors from the TALE Superclass Regulate Tuber Formation," *Plant Physiol.* 132: 1391-1404 (2003), which are hereby incorporated by reference in their entirety). Staining for GUS expression in sections from various organs will verify the location of POTH1 and StBEL5 transcription. StBEL5 RNA localization in meristems will be examined by using in situ hybridization and this profile will be compared to POTH1 accumulation. In this way, the following question can be addressed: Are POTH1 and StBEL5 expressed in stems? It seems highly unlikely that TFs that regulate meristem development would be transcribed in cells of mature vascular tissue.

Determining whether the tuber signal influence flowering in tobacco. To address this question, a SD-flowering tobacco line will be transformed with the same potato constructs used previously (see above). Following the same rationale, in vitro micrografting experiments will be performed with tobacco overexpressers of POTH1 and StBEL5 (used as both stock and scion) and WT tobacco plants (both LD- and SD-flowering lines) to determine if the RNAs move across graft unions and in which direction. The transgenic SD tobacco lines that overexpress POTH1 and StBEL5 will be evaluated to determine if there is a flowering phenotype. This experiment is, in effect, the reversal of that described in Chailakyan et al., "Photoperiodism and Tuber Formation in Grafting of Tobacco on to Potato," *Dokl. Akad. Nauk SSSR* 257:1276-1280 (1981), which is hereby incorporated by reference in its entirety, which showed that the tobacco flowering signal could induce tuber formation. Here, determinations will be made as to whether the tuberization signal can influence flowering in either LD- or SD-flowering lines.

Preliminary results show that mobile RNA is transported and functional, and that photoperiod affects movement. SD favors BEL5 RNA movement and LD inhibit (see FIGS. 36-38). Results also show that BEL5 RNAs move in response to photoperiod and mediated by the RNA sequence that binds to the "biomolecule" (as used herein). POTH1 moves nonselectively but in conjunction with the biomolecule.

FIG. 36 shows StBEL5 RNA accumulation in stems and stolons of potato plants grown under short day photoperiod conditions. An increasing concentration gradient for RNA accumulation is established towards the stolon tips. RNA was extracted from samples of *Solanum tuberosum* andigena plants. RNA levels were assayed using standard techniques of RNA blot hybridization and a gene-specific probe for StBEL5 labeled with radioactive ATP.

FIG. 37 is a schematic of a heterografted plant used to determine whether StBEL5 mRNA can move through a graft union in a basipetal direction. Scions of mutant lines that overexpressed StBEL5 were grafted onto wild-type stocks. Heterografts were cultured for 4 weeks under SD conditions (8 h light, 16 h dark). RNA was extracted and detected by RT-PCR with nested gene-specific primers and a non-plant DNA primer specific for the transgenic transcripts in WT stock material. RNA from sample #4 is used in the RT-PCR reactions shown in FIG. 38.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of screening a biomolecule for its ability to assist in mediating long-distance movement of a mobile RNA in a plant, said method comprising:
   providing a biomolecule;
   providing a mobile RNA encoding a BEL transcription factor;
   contacting the biomolecule with the mobile RNA under conditions effective for a biomolecule/mobile RNA complex to form; and
   determining whether said contacting is effective in yielding a biomolecule/mobile RNA complex, thereby indicating that the biomolecule is able to assist in mediating long-distance movement of the mobile RNA in the plant.

2. The method according to claim 1, wherein the biomolecule is a protein or polypeptide.

3. The method according to claim 1, wherein the biomolecule is a ribonucleoprotein.

4. The method according to claim 1, wherein BEL transcription factor is a protein or polypeptide having a molecular mass of about 56 kDa to about 76 kDa.

5. The method according to claim 1, wherein said providing a mobile RNA comprises providing the 3' untranslated region of the mobile RNA encoding a BEL transcription factor.

6. The method according to claim 1, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labiatae, Solanaceae, Cucurbitaceae, Compositae, and Rubiaceae.

7. The method according to claim 1, wherein the plant is either a short-day-flowering plant or a long-day-flowering plant.

8. The method according to claim 7, wherein the plant is a short-day-flowering plant selected from the group consisting of cotton, chrysanthemum, poinsettia, rice, orchid, soybean, strawberry, tobacco, and morning glory.

9. The method according to claim 7, wherein the plant is a long-day-flowering plant selected from the group consisting of *Arabidopsis*, sugar beet, radish, spinach, winter barley, red clover, oat, tobacco, and wheat.

10. The method according to claim 1, wherein said long-distance movement is through phloem tissue of the plant in a basipetal direction.

11. The method according to claim 1, wherein said long-distance movement is through phloem tissue of the plant in an acropetal direction.

12. The method according to claim 1, wherein the BEL transcription factor is encoded by a nucleic acid molecule having a nucleotide sequence comprising SEQ ID NO:1.

13. The method according to claim 1, wherein the BEL transcription factor comprises a polypeptide having an amino acid sequence that is at least 85% similar to a homeodomain region, a SKY box, a BELL domain, and a VSLTLGL-box in SEQ ID NO:2 by basic BLAST using default parameters analysis.

14. The method according to claim 1, wherein the BEL transcription factor is encoded by a nucleic acid molecule that hybridizes to the nucleotide sequence of SEQ ID NO:1 under stringent conditions characterized by a hybridization buffer comprising 5×SSC at a temperature of 55° C.

15. The method according to claim 1, wherein the BEL transcription factor is a protein or polypeptide comprising the amino acid sequence of SEQ ID NO:2.

16. A method of screening a biomolecule for its ability to assist in mediating long-distance movement of a mobile RNA in a plant, said method comprising:
providing a biomolecule;
providing a mobile RNA encoding a KNOX transcription factor;
contacting the biomolecule with the mobile RNA under conditions effective for a biomolecule/mobile RNA complex to form; and
determining whether said contacting is effective in yielding a biomolecule/mobile RNA complex, thereby indicating that the biomolecule is able to assist in mediating long-distance movement of the mobile RNA in the plant.

17. The method according to claim 16, wherein the KNOX transcription factor is from *Solanum tuberosum*.

18. The method according to claim 16, wherein the mobile RNA has a nucleotide sequence of SEQ ID NO:16.

19. The method according to claim 16, wherein the mobile RNA comprises a nucleic acid molecule that hybridizes to a nucleotide sequence of SEQ ID NO:16 under stringent conditions characterized by a hybridization buffer comprising 5×SSC at a temperature of 55° C.

20. The method according to claim 16, wherein the mobile RNA encodes a protein or polypeptide having an amino acid sequence of SEQ ID NO:17.

21. The method according to claim 16, wherein the plant is selected from the group consisting of Gramineae, Liliaceae, Iridaceae, Orchidaceae, Salicaceae, Ranunculaceae, Magnoliaceae, Cruciferae, Rosaceae, Leguminosae, Malvaceae, Umbelliferae, Labiatae, Solanaceae, Cucurbitaceae, Compositae, and Rubiaceae.

22. The method according to claim 16, wherein the plant is either a short-day-flowering plant or a long-day-flowering plant.

23. The method according to claim 22, wherein the plant is a short-day-flowering plant selected from the group consisting of cotton, chrysanthemum, poinsettia, rice, orchid, soybean, strawberry, tobacco, and morning glory.

24. The method according to claim 22, wherein the plant is a long-day-flowering plant selected from the group consisting of *Arabidopsis*, sugar beet, radish, spinach, winter barley, red clover, oat, tobacco, and wheat.

25. The method according to claim 16, wherein said long-distance movement is through phloem tissue of the plant in a basipetal direction.

26. The method according to claim 16, wherein said long-distance movement is through phloem tissue of the plant

UNITED STATES PATENT AND TRADEMARK OFFICE
CERTIFICATE OF CORRECTION

PATENT NO. : 7,579,150 B1  Page 1 of 1
APPLICATION NO. : 11/172023
DATED : August 25, 2009
INVENTOR(S) : Hannapel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 634 days.

Signed and Sealed this

Fourteenth Day of September, 2010

David J. Kappos
*Director of the United States Patent and Trademark Office*